US010364474B2

(12) United States Patent
Brandon et al.

(10) Patent No.: US 10,364,474 B2
(45) Date of Patent: Jul. 30, 2019

(54) MICROBIAL MARKERS AND USES THEREFOR

(71) Applicant: ImmuneXpress Pty Ltd, Boonah (AU)

(72) Inventors: Richard Bruce Brandon, Boonah (AU); Flavia Huygens, Westlake (AU)

(73) Assignee: IMMUNEXPRESS PTY LTD, Boonah, Queensland (AU)

( * ) Notice: Subject to any disclaimer, the term of this patent is extended or adjusted under 35 U.S.C. 154(b) by 0 days.

(21) Appl. No.: 14/894,304

(22) PCT Filed: May 29, 2014

(86) PCT No.: PCT/AU2014/050053
§ 371 (c)(1),
(2) Date: Nov. 25, 2015

(87) PCT Pub. No.: WO2014/190394
PCT Pub. Date: Dec. 4, 2014

(65) Prior Publication Data
US 2016/0145696 A1 May 26, 2016

(30) Foreign Application Priority Data

May 29, 2013 (AU) ................................ 2013901907
Oct. 11, 2013 (AU) ................................ 2013903914

(51) Int. Cl.
| | | |
|---|---|---|
| *C12Q 1/68* | (2018.01) | |
| *C12Q 1/6895* | (2018.01) | |
| *G16B 30/00* | (2019.01) | |
| *G16B 35/00* | (2019.01) | |
| *G16C 20/60* | (2019.01) | |
| *C12Q 1/689* | (2018.01) | |

(52) U.S. Cl.
CPC .......... *C12Q 1/6895* (2013.01); *C12Q 1/689* (2013.01); *G16B 30/00* (2019.02); *G16B 35/00* (2019.02); *G16C 20/60* (2019.02); *C12Q 2600/156* (2013.01)

(58) Field of Classification Search
None
See application file for complete search history.

(56) References Cited

U.S. PATENT DOCUMENTS 6,410,056 B1 * 6/2002 Setterstrom .......... A61K 9/1647
424/501

FOREIGN PATENT DOCUMENTS

| WO | WO 2007/083147 A2 | 7/2007 |
| WO | WO 2008/107377 A2 | 9/2008 |
| WO | WO 2010/039819 A2 | 4/2010 |
| WO | WO 2012/068642 A1 | 5/2012 |

OTHER PUBLICATIONS

Afshari et al., Bench-to-bedside review: Rapid molecular diagnostics for bloodstream infection—a new frontier? Critical Care (2012); 16: 222, 12 pages.
Bailey et al., "Identification of Equine Cecal Bacteria Producing Amines in an In Vitro Model of Carbohydrate Overload." Applied and Environmental Microbiology (2003); 69(4): 2087-2093.
Bauer and Reinhart, "Molecular diagnostics of sepsis—Where are we today'?" International Journal of Medical Microbiology (2010); 300: 411-413.
Bispo et al., "Detection and Gram Discrimination of Bacterial Pathogens from Aqueous and Vitreous Humor Using Real-Time PCR Assays." Investigative Ophthalmology & Visual Science (2011); 52(2): 873-881.
Carroll et al., "Detection of and Discrimination between Gram-Positive and Gram-Negative Bacteria in Intraocular Samples by Using Nested PCR." Journal of Clinical Microbiology (2000); 38(5): 1753-1757.
Claesson et al., "Comparison of two next-generation sequencing technologies for resolving highly complex microbiota composition using tandem variable 16S rRNA gene regions." Nucleic Acids Research (2010); 38(22): e200.
Clarridge et al., "Impact of 16S rRNA Gene Sequence Analysis for Identification of Bacteria on Clinical Microbiology and Infectious Diseases." Clinical Microbiology Reviews (2004); 17(4): 840-862.
European Patent Office, Extended European Search Report for EP 14804209.6, dated Jan. 3, 2017, 8 pages.
Ferrer et al., "Detection and Identification of Fungal Pathogens by PCR and by ITS2 and 5.8S Ribosomal DNA Typing in Ocular Infections." Journal of Clinical Microbiology (2001); 39(8): 2873-2879.
Field et al., "Molecular phylogeny of the animal kingdom." Science (1988); 239(4841): 748-753.
Gehlot et al., "Molecular diagnostics of human pathogenic *Aspergillus* species." Indian Journal of Biotechnology (2011); 10: 207-211.
Gehron et al., "Determination of the gram-positive bacterial content of soils and sediments by analysis of teichoic acid components." Journal of Microbiological Methods (1984); 2: 165-176.
Gopaul et al., "Rapid identification of *Brucella* isolates to the species level by real time PCR based single nucleotide polymorphism (SNP) analysis." BMC Microbiology (2008); 8: 86, 14 pages.
International Preliminary Report on Patentability in International Application No. PCT/AU2014/050053 dated Sep. 14, 2015, 10 pages.
International Search Report and Written Report in International Application No. PCT/AU2014/050053 dated Sep. 19, 2014, 8 pages.
Klaschik et al., "Real-Time PCR for Detection and Differentiation of Gram-Positive and Gram-Negative Bacteria." Journal of Clinical Microbiology (2002); 40(11): 4304-4307.

(Continued)

*Primary Examiner* — Katherine D Salmon

(57) ABSTRACT

Disclosed are methods for identifying and/or classifying microbes using one or more single nucleotide polymorphisms (SNPs) in 16S ribosomal RNA (16S rRNA) of prokaryotes and/or one or more SNPs in 5.8S ribosomal RNA (5.8S rRNA) of eukaryotes. Also disclosed are probes, primers and kits that are useful in those methods. Methods for the diagnosis of sepsis based upon these SNPs are also disclosed.

13 Claims, 1 Drawing Sheet
Specification includes a Sequence Listing.

(56) References Cited

OTHER PUBLICATIONS

Klausegger et al., "Gram Type-Specific Broad Range PCR Amplification for Rapid Detection of 62 Pathogenic Bacteria." Journal of Clinical Microbiology (1999); 37(2): 464-466.

Lamy et al., "What Is the Relevance of Obtaining Multiple Blood Samples for Culture? A Comprehensive Model to Optimize the Strategy for Diagnosing Bacteremia." Clinical Infectious Diseases (2002); 35: 842-850.

Lodes et al., "PCR-based rapid sepsis diagnosis effectively guides clinical treatment in patients with new onset of SIRS." Langenbecks Arch Surg (2012); 397: 447-455.

Lucignano et al., "Multiplex PCR Allows Rapid and Accurate Diagnosis of Bloodstream Infections in Newborns and Children with Suspected Sepsis." Journal of Clinical Mircobiology (2011); 49(6): 2252-2258.

Pasqualini et al., "Diagnostic Performance of a Multiple Real-Time PCR Assay in Patients with Suspected Sepsis Hospitalized in an Internal Medicine Ward." Journal of Clinical Microbiology (2012); 50(4): 1285-1288.

Pingle et al., "Multiplexed Identification of Blood-Borne Bacterial Pathogens by Use of a Novel 16S rRNA Gene PCR-Ligase Detection Reaction-Capillary Electrophoresis Assay." Journal of Clinical Microbiology (2007); 45(6): 1927-1935.

Shigemura et al., "Rapid detection and differentiation of Gram-negative and Gram-positive pathogenic bacteria in urine using TaqMan probe." Clin. Exp. Med (2005); 4: 196-201.

Silverman and Kool, "Quenched autoligation probes allow discrimination of live bacterial species by single nucleotide differences in rRNA." Nucleic Acids Research (2005); 33(15): 4978-4986.

Spiro et al., "A Bead-Based Method for Multiplexed Identification and Quantitation of DNA Sequences Using Flow Cytometry." Applied and Environmental Microbiology (2000); 66(10): 4258-4265.

Vincent et al., "Sepsis in European intensive care units: Results of the SOAP study." Crit. Care Med. (2006); 34(2): 344-353.

Weisburg et al., "16S Ribosomal DNA Amplification for Phylogenetic Study." Journal of Bacteriology (1991); 173(2): 697-703.

Yadav et al., "DNA analysis reveals genomic homogeneity and single nucleotide polymorphism in 5.8S ribosomal RNA gene spacer region among commercial cultivars of the button mushroom *Agaricus bisporus* in India." Current Science (2007); 93(10): 1383-1389.

Zarain et al., "Nested-PCR as a tool for the detection and differentiation of Gram-positive and Gram-negative bacteria in patients with sepsis-septic shock." African Journal of Microbiology Research (2012) 6(21): 4601-4607.

\* cited by examiner

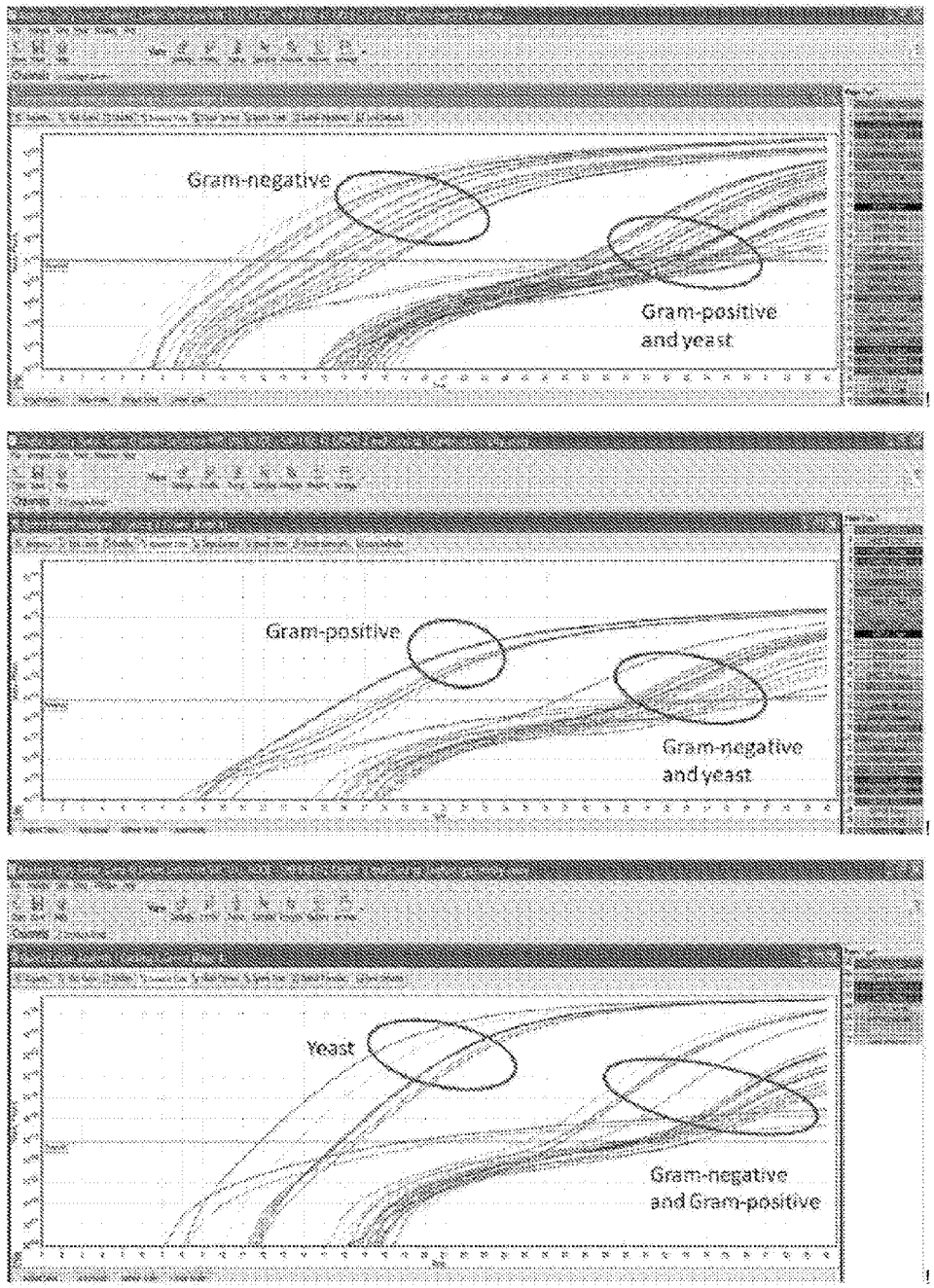

SEQUENCE LISTING

<160> NUMBER OF SEQ ID NOS: 335

<210> SEQ ID NO 1
<211> LENGTH: 1542
<212> TYPE: DNA
<213> ORGANISM: Escherichia coli

<400> SEQUENCE: 1

```
aaattgaaga gtttgatcat ggctcagatt gaacgctggc ggcaggccta acacatgcaa      60
gtcgaacggt aacaggaaga agcttgcttc tttgctgacg agtggcggac gggtgagtaa     120
tgtctgggaa actgcctgat ggagagggat aactactgga aacggtagct aataccgcat     180
aacgtcgcaa gaccaaagag ggggaccttc gggcctcttg ccatcggatg tgcccagatg     240
ggattagcta gtaggtgggg taacggctca cctaggcgac gatccctagc tggtctgaga     300
ggatgaccag ccacactgga actgagacac ggtccagact cctacgggag gcagcagtgg     360
ggaatattgc acaatgggcg caagcctgat gcagccatgc cgcgtgtatg aagaaggcct     420
tcgggttgta aagtactttc agcggggagg aagggagtaa agttaatacc tttgctcatt     480
gacgttaccc gcagaagaag caccggctaa ctccgtgcca gcagccgcgg taatacggag     540
ggtgcaagcg ttaatcggaa ttactgggcg taaagcgcac gcaggcggtt tgttaagtca     600
gatgtgaaat ccccgggctc aacctgggaa ctgcatctga tactggcaag cttgagtctc     660
gtagaggggg gtagaattcc aggtgtagcg gtgaaatgcg tagagatctg gaggaatacc     720
ggtggcgaag gcggcccct ggacgaagac tgacgctcag gtgcgaaagc gtggggagca     780
aacaggatta gataccctgg tagtccacgc cgtaaacgat gtcgacttgg aggttgtgcc     840
cttgaggcgt ggcttccgga gctaacgcgt taagtcgacc gcctggggag tacggccgca     900
aggttaaaac tcaaatgaat tgacggggc ccgcacaagc ggtggagcat gtggtttaat     960
tcgatgcaac gcgaagaacc ttacctggtc ttgacatcca cagaactttc cagagatgga    1020
ttggtgcctt cgggaactgt gagacaggtg ctgcatggct gtcgtcagct cgtgttgtga    1080
aatgttgggt taagtcccgc aacgagcgca acccttatcc tttgttgcca gcggtccggc    1140
cgggaactca aaggagactg ccagtgataa actggaggaa ggtggggatg acgtcaagtc    1200
atcatggccc ttacgaccag ggctacacac gtgctacaat ggcgcataca agagaagcg    1260
```

-continued

```
acctcgcgag agcaagcgga cctcataaag tgcgtcgtag tccggattgg agtctgcaac    1320
tcgactccat gaagtcggaa tcgctagtaa tcgtggatca gaatgccacg gtgaatacgt    1380
tcccgggcct tgtacacacc gcccgtcaca ccatgggagt gggttgcaaa agaagtaggt    1440
agcttaacct tcgggagggc gcttaccact ttgtgattca tgactggggt gaagtcgtaa    1500
caaggtaacc gtaggggaac ctgcggttgg atcacctcct ta                       1542
```

<210> SEQ ID NO 2
<211> LENGTH: 459
<212> TYPE: DNA
<213> ORGANISM: Candida albicans

<400> SEQUENCE: 2

```
ttgcttaatt gcaccacatg tgtttttctt tgaaacaaac ttgctttggc ggtgggccca     60
gcctgccgcc agaggtctaa acttacaacc aatttttat taacttgtca caccagatta    120
ttactaaata gtcaaaactt tcaacaacgg atctcttggt tctcgcatcg atgaagaacg    180
cagcgaaatg cgatacgtaa tatgaattgc agatattcgt gaatcatcga atctttgaac    240
gcacattgcg ccctctggta ttccggaggg catgcctgtt tgagcgtcgt ttctccctca    300
aaccgctggg tttggtgttg agcaatacga cttgggtttg cttgaaagac ggtagtggta    360
aggcgggatc gctttgacaa tggcttaggt ctaaccaaaa acattgcttg cggcggtaac    420
gtctaccacg tatatcttca aactttgacc tcaaatcag                           459
```

<210> SEQ ID NO 3
<211> LENGTH: 156
<212> TYPE: DNA
<213> ORGANISM: Homo sapiens

<400> SEQUENCE: 3

```
gactcttagc ggtggatcac tcggctcgtg cgtcgatgaa gaacgcagct agctgcgaga     60
attaatgtga attgcaggac acattgatca tcgacacttc gaacgcactt gcggccccgg    120
gttcctcccg gggctacgcc tgtctgagcg tcgctt                              156
```

<210> SEQ ID NO 4
<211> LENGTH: 12
<212> TYPE: DNA
<213> ORGANISM: Artificial sequence
<220> FEATURE:
<223> OTHER INFORMATION: Gram-positive 396/398 probe

<400> SEQUENCE: 4

```
gcaacgccgc gt                                                         12
```

<210> SEQ ID NO 5
<211> LENGTH: 12
<212> TYPE: DNA
<213> ORGANISM: Artificial sequence
<220> FEATURE:
<223> OTHER INFORMATION: Gram-positive 396/398 probe

<400> SEQUENCE: 5

```
gcgacgccgc gt                                                         12
```

<210> SEQ ID NO 6
<211> LENGTH: 12
<212> TYPE: DNA
<213> ORGANISM: Artificial sequence
<220> FEATURE:
<223> OTHER INFORMATION: Gram-negative 396/398 probe

```
<400> SEQUENCE: 6
gccaagtagc gt                                                        12

<210> SEQ ID NO 7
<211> LENGTH: 12
<212> TYPE: DNA
<213> ORGANISM: Artificial sequence
<220> FEATURE:
<223> OTHER INFORMATION: Gram-negative 396/398 probe

<400> SEQUENCE: 7
gccatgccgc gt                                                        12

<210> SEQ ID NO 8
<211> LENGTH: 21
<212> TYPE: DNA
<213> ORGANISM: Artificial sequence
<220> FEATURE:
<223> OTHER INFORMATION: Gram-negative and Gram-positive 396/398
      forward primer

<400> SEQUENCE: 8
actcctacgg gaggcagcag t                                              21

<210> SEQ ID NO 9
<211> LENGTH: 21
<212> TYPE: DNA
<213> ORGANISM: Artificial sequence
<220> FEATURE:
<223> OTHER INFORMATION: Gram-negative 396/398 reverse primer

<400> SEQUENCE: 9
gccagcagcy gcggtaatac g                                              21

<210> SEQ ID NO 10
<211> LENGTH: 21
<212> TYPE: DNA
<213> ORGANISM: Artificial sequence
<220> FEATURE:
<223> OTHER INFORMATION: Gram-positive 396/398 reverse primer

<400> SEQUENCE: 10
gccagcagcc gcggtaatac g                                              21

<210> SEQ ID NO 11
<211> LENGTH: 14
<212> TYPE: DNA
<213> ORGANISM: Artificial sequence
<220> FEATURE:
<223> OTHER INFORMATION: Gram-negative 278/286 probe

<400> SEQUENCE: 11
gcgatgatca gtag                                                      14

<210> SEQ ID NO 12
<211> LENGTH: 14
<212> TYPE: DNA
<213> ORGANISM: Artificial sequence
<220> FEATURE:
<223> OTHER INFORMATION: Gram-negative 278/286 probe

<400> SEQUENCE: 12
gctatgacgc ttaa                                                      14
```

```
<210> SEQ ID NO 13
<211> LENGTH: 14
<212> TYPE: DNA
<213> ORGANISM: Artificial sequence
<220> FEATURE:
<223> OTHER INFORMATION: Gram-negative 278/286 probe

<400> SEQUENCE: 13
gctttgacgc ataa                                                       14

<210> SEQ ID NO 14
<211> LENGTH: 14
<212> TYPE: DNA
<213> ORGANISM: Artificial sequence
<220> FEATURE:
<223> OTHER INFORMATION: Gram-negative 278/286 probe

<400> SEQUENCE: 14
gctatgacgg gtat                                                       14

<210> SEQ ID NO 15
<211> LENGTH: 14
<212> TYPE: DNA
<213> ORGANISM: Artificial sequence
<220> FEATURE:
<223> OTHER INFORMATION: Gram-negative 278/286 probe

<400> SEQUENCE: 15
gcaatgatca gtag                                                       14

<210> SEQ ID NO 16
<211> LENGTH: 14
<212> TYPE: DNA
<213> ORGANISM: Artificial sequence
<220> FEATURE:
<223> OTHER INFORMATION: Gram-negative 278/286 probe

<400> SEQUENCE: 16
gttttgacgt ctag                                                       14

<210> SEQ ID NO 17
<211> LENGTH: 14
<212> TYPE: DNA
<213> ORGANISM: Artificial sequence
<220> FEATURE:
<223> OTHER INFORMATION: Gram-positive 278/286 probe

<400> SEQUENCE: 17
gcaacgatgc atag                                                       14

<210> SEQ ID NO 18
<211> LENGTH: 14
<212> TYPE: DNA
<213> ORGANISM: Artificial sequence
<220> FEATURE:
<223> OTHER INFORMATION: Gram-positive 278/286 probe

<400> SEQUENCE: 18
gcaacgatgc gtag                                                       14

<210> SEQ ID NO 19
<211> LENGTH: 14
<212> TYPE: DNA
<213> ORGANISM: Artificial sequence
<220> FEATURE:
<223> OTHER INFORMATION: Gram-positive 278/286 probe
```

```
<400> SEQUENCE: 19
gccacgatac atag                                                      14

<210> SEQ ID NO 20
<211> LENGTH: 19
<212> TYPE: DNA
<213> ORGANISM: Artificial sequence
<220> FEATURE:
<223> OTHER INFORMATION: Gram-negative 278/286 forward primer

<400> SEQUENCE: 20
tgwaggaggg gattgcgtc                                                 19

<210> SEQ ID NO 21
<211> LENGTH: 19
<212> TYPE: DNA
<213> ORGANISM: Artificial sequence
<220> FEATURE:
<223> OTHER INFORMATION: Gram-negative 278/286 forward primer

<400> SEQUENCE: 21
tgtaggatga gactatatw                                                 19

<210> SEQ ID NO 22
<211> LENGTH: 19
<212> TYPE: DNA
<213> ORGANISM: Artificial sequence
<220> FEATURE:
<223> OTHER INFORMATION: Gram-negative 278/286 forward primer

<400> SEQUENCE: 22
taarrgatca gcctatgtc                                                 19

<210> SEQ ID NO 23
<211> LENGTH: 19
<212> TYPE: DNA
<213> ORGANISM: Artificial sequence
<220> FEATURE:
<223> OTHER INFORMATION: Gram-positive 278/286 forward primer

<400> SEQUENCE: 23
ttatagatgg atccgcgcy                                                 19

<210> SEQ ID NO 24
<211> LENGTH: 19
<212> TYPE: DNA
<213> ORGANISM: Artificial sequence
<220> FEATURE:
<223> OTHER INFORMATION: Gram-positive 278/286 forward primer

<400> SEQUENCE: 24
tgatggatgg acccgcggt                                                 19

<210> SEQ ID NO 25
<211> LENGTH: 17
<212> TYPE: DNA
<213> ORGANISM: Artificial sequence
<220> FEATURE:
<223> OTHER INFORMATION: Gram-negative 278/286 reverse primer

<400> SEQUENCE: 25
atgaacggcc acattgg                                                   17

<210> SEQ ID NO 26
<211> LENGTH: 17
```

```
<212> TYPE: DNA
<213> ORGANISM: Artificial sequence
<220> FEATURE:
<223> OTHER INFORMATION: Gram-negative 278/286 reverse primer

<400> SEQUENCE: 26
atgatcagtc acactgg                                                  17

<210> SEQ ID NO 27
<211> LENGTH: 17
<212> TYPE: DNA
<213> ORGANISM: Artificial sequence
<220> FEATURE:
<223> OTHER INFORMATION: Gram-negative 278/286 reverse primer

<400> SEQUENCE: 27
gtgawcggac acactgg                                                  17

<210> SEQ ID NO 28
<211> LENGTH: 21
<212> TYPE: DNA
<213> ORGANISM: Artificial sequence
<220> FEATURE:
<223> OTHER INFORMATION: Gram-positive 278/286 reverse primer

<400> SEQUENCE: 28
gtgatcggcc acactggrac t                                             21

<210> SEQ ID NO 29
<211> LENGTH: 14
<212> TYPE: DNA
<213> ORGANISM: Artificial sequence
<220> FEATURE:
<223> OTHER INFORMATION: Gram-negative 648 probe

<400> SEQUENCE: 29
ctgctgatct agag                                                     14

<210> SEQ ID NO 30
<211> LENGTH: 14
<212> TYPE: DNA
<213> ORGANISM: Artificial sequence
<220> FEATURE:
<223> OTHER INFORMATION: Gram-negative 648 probe

<400> SEQUENCE: 30
ctggaaaact tgag                                                     14

<210> SEQ ID NO 31
<211> LENGTH: 14
<212> TYPE: DNA
<213> ORGANISM: Artificial sequence
<220> FEATURE:
<223> OTHER INFORMATION: Gram-negative 648 probe

<400> SEQUENCE: 31
ctgggagact tgag                                                     14

<210> SEQ ID NO 32
<211> LENGTH: 20
<212> TYPE: DNA
<213> ORGANISM: Artificial sequence
<220> FEATURE:
<223> OTHER INFORMATION: Gram-negative 648 forward primer

<400> SEQUENCE: 32
```
taaccccgtg akgggatgga                                                  20

<210> SEQ ID NO 33
<211> LENGTH: 21
<212> TYPE: DNA
<213> ORGANISM: Artificial sequence
<220> FEATURE:
<223> OTHER INFORMATION: Gram-positive 648 forward primer

<400> SEQUENCE: 33
caaccgkgga gggtcattgg a                                                21

<210> SEQ ID NO 34
<211> LENGTH: 22
<212> TYPE: DNA
<213> ORGANISM: Artificial sequence
<220> FEATURE:
<223> OTHER INFORMATION: Gram-negative 648 reverse primer

<400> SEQUENCE: 34
tcggagagga aagtggaatt cc                                               22

<210> SEQ ID NO 35
<211> LENGTH: 22
<212> TYPE: DNA
<213> ORGANISM: Artificial sequence
<220> FEATURE:
<223> OTHER INFORMATION: Gram-positive 648 reverse primer

<400> SEQUENCE: 35
carragrgga ragtggaatt cc                                               22

<210> SEQ ID NO 36
<211> LENGTH: 19
<212> TYPE: DNA
<213> ORGANISM: Artificial sequence
<220> FEATURE:
<223> OTHER INFORMATION: Fungi 164/165 probe

<400> SEQUENCE: 36
ctcttggttc cggcatcga                                                   19

<210> SEQ ID NO 37
<211> LENGTH: 19
<212> TYPE: DNA
<213> ORGANISM: Artificial sequence
<220> FEATURE:
<223> OTHER INFORMATION: Fungi 164/165 probe

<400> SEQUENCE: 37
ctcttggttc tcgcatcga                                                   19

<210> SEQ ID NO 38
<211> LENGTH: 28
<212> TYPE: DNA
<213> ORGANISM: Artificial sequence
<220> FEATURE:
<223> OTHER INFORMATION: Fungi 164/165 forward primer

<400> SEQUENCE: 38
tatgcagtct gagttgatta tcgtaatc                                         28

<210> SEQ ID NO 39
<211> LENGTH: 29
<212> TYPE: DNA
<213> ORGANISM: Artificial sequence

```
<220> FEATURE:
<223> OTHER INFORMATION: Fungi 164/165 forward primer

<400> SEQUENCE: 39
cagaggtcta aacttacaac caatttttt                                        29

<210> SEQ ID NO 40
<211> LENGTH: 19
<212> TYPE: DNA
<213> ORGANISM: Artificial sequence
<220> FEATURE:
<223> OTHER INFORMATION: Fungi 164/165 forward primer

<400> SEQUENCE: 40
gcatttcgct gcgttcttc                                                   19

<210> SEQ ID NO 41
<211> LENGTH: 19
<212> TYPE: DNA
<213> ORGANISM: Artificial sequence
<220> FEATURE:
<223> OTHER INFORMATION: Forward primer

<400> SEQUENCE: 41
tgtaggatga gactatatw                                                   19

<210> SEQ ID NO 42
<211> LENGTH: 14
<212> TYPE: DNA
<213> ORGANISM: Artificial sequence
<220> FEATURE:
<223> OTHER INFORMATION: Probe

<400> SEQUENCE: 42
gctatgacgc ttaa                                                        14

<210> SEQ ID NO 43
<211> LENGTH: 17
<212> TYPE: DNA
<213> ORGANISM: Artificial sequence
<220> FEATURE:
<223> OTHER INFORMATION: Reverse primer

<400> SEQUENCE: 43
atgatcagtc acactgg                                                     17

<210> SEQ ID NO 44
<211> LENGTH: 19
<212> TYPE: DNA
<213> ORGANISM: Artificial sequence
<220> FEATURE:
<223> OTHER INFORMATION: Forward primer

<400> SEQUENCE: 44
tgtaggatga gactatatw                                                   19

<210> SEQ ID NO 45
<211> LENGTH: 14
<212> TYPE: DNA
<213> ORGANISM: Artificial sequence
<220> FEATURE:
<223> OTHER INFORMATION: Probe

<400> SEQUENCE: 45
gctttgacgc ataa                                                        14
```

```
<210> SEQ ID NO 46
<211> LENGTH: 17
<212> TYPE: DNA
<213> ORGANISM: Artificial sequence
<220> FEATURE:
<223> OTHER INFORMATION: Reverse primer

<400> SEQUENCE: 46
atgatcagtc acactgg                                                    17

<210> SEQ ID NO 47
<211> LENGTH: 19
<212> TYPE: DNA
<213> ORGANISM: Artificial sequence
<220> FEATURE:
<223> OTHER INFORMATION: Forward primer

<400> SEQUENCE: 47
taarrgatca gcctatgtc                                                  19

<210> SEQ ID NO 48
<211> LENGTH: 14
<212> TYPE: DNA
<213> ORGANISM: Artificial sequence
<220> FEATURE:
<223> OTHER INFORMATION: Probe

<400> SEQUENCE: 48
gctatgacgg gtat                                                       14

<210> SEQ ID NO 49
<211> LENGTH: 17
<212> TYPE: DNA
<213> ORGANISM: Artificial sequence
<220> FEATURE:
<223> OTHER INFORMATION: Reverse primer

<400> SEQUENCE: 49
gtgawcggac acactgg                                                    17

<210> SEQ ID NO 50
<211> LENGTH: 19
<212> TYPE: DNA
<213> ORGANISM: Artificial sequence
<220> FEATURE:
<223> OTHER INFORMATION: Forward primer

<400> SEQUENCE: 50
catcagatgt gcccagatg                                                  19

<210> SEQ ID NO 51
<211> LENGTH: 14
<212> TYPE: DNA
<213> ORGANISM: Artificial sequence
<220> FEATURE:
<223> OTHER INFORMATION: Probe

<400> SEQUENCE: 51
gcgacgatcc ctag                                                       14

<210> SEQ ID NO 52
<211> LENGTH: 17
<212> TYPE: DNA
<213> ORGANISM: Artificial sequence
<220> FEATURE:
<223> OTHER INFORMATION: Reverse primer
```

<400> SEQUENCE: 52
atgaccagcc acactgg                                                    17

<210> SEQ ID NO 53
<211> LENGTH: 19
<212> TYPE: DNA
<213> ORGANISM: Artificial sequence
<220> FEATURE:
<223> OTHER INFORMATION: Forward primer

<400> SEQUENCE: 53
tatcggatga acccatatg                                                  19

<210> SEQ ID NO 54
<211> LENGTH: 14
<212> TYPE: DNA
<213> ORGANISM: Artificial sequence
<220> FEATURE:
<223> OTHER INFORMATION: Probe

<400> SEQUENCE: 54
gcgacgatct ctag                                                       14

<210> SEQ ID NO 55
<211> LENGTH: 17
<212> TYPE: DNA
<213> ORGANISM: Artificial sequence
<220> FEATURE:
<223> OTHER INFORMATION: Reverse primer

<400> SEQUENCE: 55
atgaccagcc acactgg                                                    17

<210> SEQ ID NO 56
<211> LENGTH: 19
<212> TYPE: DNA
<213> ORGANISM: Artificial sequence
<220> FEATURE:
<223> OTHER INFORMATION: Forward primer

<400> SEQUENCE: 56
tattcgagcg gccgatatc                                                  19

<210> SEQ ID NO 57
<211> LENGTH: 14
<212> TYPE: DNA
<213> ORGANISM: Artificial sequence
<220> FEATURE:
<223> OTHER INFORMATION: Probe

<400> SEQUENCE: 57
cctgcgatct ctag                                                       14

<210> SEQ ID NO 58
<211> LENGTH: 17
<212> TYPE: DNA
<213> ORGANISM: Artificial sequence
<220> FEATURE:
<223> OTHER INFORMATION: Reverse primer

<400> SEQUENCE: 58
atgaccagcc acactgg                                                    17

<210> SEQ ID NO 59

```
<211> LENGTH: 19
<212> TYPE: DNA
<213> ORGANISM: Artificial sequence
<220> FEATURE:
<223> OTHER INFORMATION: Forward primer

<400> SEQUENCE: 59
tatcagatga gcctaggtc                                                  19

<210> SEQ ID NO 60
<211> LENGTH: 14
<212> TYPE: DNA
<213> ORGANISM: Artificial sequence
<220> FEATURE:
<223> OTHER INFORMATION: Probe

<400> SEQUENCE: 60
gcgacgatcc gtaa                                                       14

<210> SEQ ID NO 61
<211> LENGTH: 17
<212> TYPE: DNA
<213> ORGANISM: Artificial sequence
<220> FEATURE:
<223> OTHER INFORMATION: Reverse primer

<400> SEQUENCE: 61
atgatcagtc acactgg                                                    17

<210> SEQ ID NO 62
<211> LENGTH: 19
<212> TYPE: DNA
<213> ORGANISM: Artificial sequence
<220> FEATURE:
<223> OTHER INFORMATION: Forward primer

<400> SEQUENCE: 62
tattcgagcg gccgatatc                                                  19

<210> SEQ ID NO 63
<211> LENGTH: 14
<212> TYPE: DNA
<213> ORGANISM: Artificial sequence
<220> FEATURE:
<223> OTHER INFORMATION: Probe

<400> SEQUENCE: 63
gcgacgatca gtag                                                       14

<210> SEQ ID NO 64
<211> LENGTH: 17
<212> TYPE: DNA
<213> ORGANISM: Artificial sequence
<220> FEATURE:
<223> OTHER INFORMATION: Reverse primer

<400> SEQUENCE: 64
atgaccagcc acactgg                                                    17

<210> SEQ ID NO 65
<211> LENGTH: 19
<212> TYPE: DNA
<213> ORGANISM: Artificial sequence
<220> FEATURE:
<223> OTHER INFORMATION: Forward primer

<400> SEQUENCE: 65
```
tgwaggaggg gattgcgtc                                              19

<210> SEQ ID NO 66
<211> LENGTH: 14
<212> TYPE: DNA
<213> ORGANISM: Artificial sequence
<220> FEATURE:
<223> OTHER INFORMATION: Probe

<400> SEQUENCE: 66
gcgatgatca gtag                                                   14

<210> SEQ ID NO 67
<211> LENGTH: 17
<212> TYPE: DNA
<213> ORGANISM: Artificial sequence
<220> FEATURE:
<223> OTHER INFORMATION: Reverse primer

<400> SEQUENCE: 67
atgaacggcc acattgg                                                17

<210> SEQ ID NO 68
<211> LENGTH: 19
<212> TYPE: DNA
<213> ORGANISM: Artificial sequence
<220> FEATURE:
<223> OTHER INFORMATION: Forward primer

<400> SEQUENCE: 68
tgwaggaggg gattgcgtc                                              19

<210> SEQ ID NO 69
<211> LENGTH: 14
<212> TYPE: DNA
<213> ORGANISM: Artificial sequence
<220> FEATURE:
<223> OTHER INFORMATION: Probe

<400> SEQUENCE: 69
gcaatgatca gtag                                                   14

<210> SEQ ID NO 70
<211> LENGTH: 17
<212> TYPE: DNA
<213> ORGANISM: Artificial sequence
<220> FEATURE:
<223> OTHER INFORMATION: Reverse primer

<400> SEQUENCE: 70
atgaacggcc acattgg                                                17

<210> SEQ ID NO 71
<211> LENGTH: 19
<212> TYPE: DNA
<213> ORGANISM: Artificial sequence
<220> FEATURE:
<223> OTHER INFORMATION: Forward primer

<400> SEQUENCE: 71
ttaagggaga gtctatggg                                              19

<210> SEQ ID NO 72
<211> LENGTH: 14
<212> TYPE: DNA

```
<213> ORGANISM: Artificial sequence
<220> FEATURE:
<223> OTHER INFORMATION: Probe

<400> SEQUENCE: 72
gttttgacgt ctag                                                       14

<210> SEQ ID NO 73
<211> LENGTH: 17
<212> TYPE: DNA
<213> ORGANISM: Artificial sequence
<220> FEATURE:
<223> OTHER INFORMATION: Reverse primer

<400> SEQUENCE: 73
ttgaccgcca acactgg                                                    17

<210> SEQ ID NO 74
<211> LENGTH: 19
<212> TYPE: DNA
<213> ORGANISM: Artificial sequence
<220> FEATURE:
<223> OTHER INFORMATION: Forward primer

<400> SEQUENCE: 74
taaaggatgg ggatgcgtt                                                  19

<210> SEQ ID NO 75
<211> LENGTH: 14
<212> TYPE: DNA
<213> ORGANISM: Artificial sequence
<220> FEATURE:
<223> OTHER INFORMATION: Probe

<400> SEQUENCE: 75
ccttcgatgg atag                                                       14

<210> SEQ ID NO 76
<211> LENGTH: 17
<212> TYPE: DNA
<213> ORGANISM: Artificial sequence
<220> FEATURE:
<223> OTHER INFORMATION: Reverse primer

<400> SEQUENCE: 76
aaggtccccc acattgg                                                    17

<210> SEQ ID NO 77
<211> LENGTH: 21
<212> TYPE: DNA
<213> ORGANISM: Artificial sequence
<220> FEATURE:
<223> OTHER INFORMATION: Forward primer

<400> SEQUENCE: 77
actcctacgg gaggcagcag t                                               21

<210> SEQ ID NO 78
<211> LENGTH: 12
<212> TYPE: DNA
<213> ORGANISM: Artificial sequence
<220> FEATURE:
<223> OTHER INFORMATION: Probe

<400> SEQUENCE: 78
gcaacgccgc gt                                                         12
```

```
<210> SEQ ID NO 79
<211> LENGTH: 21
<212> TYPE: DNA
<213> ORGANISM: Artificial sequence
<220> FEATURE:
<223> OTHER INFORMATION: Reverse primer

<400> SEQUENCE: 79
gccagcagcy gcggtaatac g                                              21

<210> SEQ ID NO 80
<211> LENGTH: 21
<212> TYPE: DNA
<213> ORGANISM: Artificial sequence
<220> FEATURE:
<223> OTHER INFORMATION: Forward primer

<400> SEQUENCE: 80
actcctacgg gaggcagcag t                                              21

<210> SEQ ID NO 81
<211> LENGTH: 12
<212> TYPE: DNA
<213> ORGANISM: Artificial sequence
<220> FEATURE:
<223> OTHER INFORMATION: Probe

<400> SEQUENCE: 81
gccaagtagc gt                                                        12

<210> SEQ ID NO 82
<211> LENGTH: 21
<212> TYPE: DNA
<213> ORGANISM: Artificial sequence
<220> FEATURE:
<223> OTHER INFORMATION: Reverse primer

<400> SEQUENCE: 82
gccagcagcy gcggtaatac g                                              21

<210> SEQ ID NO 83
<211> LENGTH: 21
<212> TYPE: DNA
<213> ORGANISM: Artificial sequence
<220> FEATURE:
<223> OTHER INFORMATION: Forward primer

<400> SEQUENCE: 83
actcctacgg gaggcagcag t                                              21

<210> SEQ ID NO 84
<211> LENGTH: 12
<212> TYPE: DNA
<213> ORGANISM: Artificial sequence
<220> FEATURE:
<223> OTHER INFORMATION: Probe

<400> SEQUENCE: 84
gccatgccgc gt                                                        12

<210> SEQ ID NO 85
<211> LENGTH: 21
<212> TYPE: DNA
<213> ORGANISM: Artificial sequence
<220> FEATURE:
```

```
<223> OTHER INFORMATION: Reverse primer

<400> SEQUENCE: 85
gccagcagcy gcggtaatac g                                              21

<210> SEQ ID NO 86
<211> LENGTH: 21
<212> TYPE: DNA
<213> ORGANISM: Artificial sequence
<220> FEATURE:
<223> OTHER INFORMATION: Forward primer

<400> SEQUENCE: 86
taaccattaa actgcttgag a                                              21

<210> SEQ ID NO 87
<211> LENGTH: 14
<212> TYPE: DNA
<213> ORGANISM: Artificial sequence
<220> FEATURE:
<223> OTHER INFORMATION: Probe

<400> SEQUENCE: 87
ctgataatct agag                                                      14

<210> SEQ ID NO 88
<211> LENGTH: 22
<212> TYPE: DNA
<213> ORGANISM: Artificial sequence
<220> FEATURE:
<223> OTHER INFORMATION: Reverse primer

<400> SEQUENCE: 88
dgggagaggy agrtggaatt sg                                             22

<210> SEQ ID NO 89
<211> LENGTH: 21
<212> TYPE: DNA
<213> ORGANISM: Artificial sequence
<220> FEATURE:
<223> OTHER INFORMATION: Forward primer

<400> SEQUENCE: 89
taaccgttga actgcttggg a                                              21

<210> SEQ ID NO 90
<211> LENGTH: 14
<212> TYPE: DNA
<213> ORGANISM: Artificial sequence
<220> FEATURE:
<223> OTHER INFORMATION: Probe

<400> SEQUENCE: 90
ctggtaatct agag                                                      14

<210> SEQ ID NO 91
<211> LENGTH: 22
<212> TYPE: DNA
<213> ORGANISM: Artificial sequence
<220> FEATURE:
<223> OTHER INFORMATION: Reverse primer

<400> SEQUENCE: 91
dgggagaggy agrtggaatt sg                                             22
```

```
<210> SEQ ID NO 92
<211> LENGTH: 21
<212> TYPE: DNA
<213> ORGANISM: Artificial sequence
<220> FEATURE:
<223> OTHER INFORMATION: Forward primer

<400> SEQUENCE: 92
taactacaga actgcatttg a                                              21

<210> SEQ ID NO 93
<211> LENGTH: 14
<212> TYPE: DNA
<213> ORGANISM: Artificial sequence
<220> FEATURE:
<223> OTHER INFORMATION: Probe

<400> SEQUENCE: 93
ctgactatct agag                                                      14

<210> SEQ ID NO 94
<211> LENGTH: 22
<212> TYPE: DNA
<213> ORGANISM: Artificial sequence
<220> FEATURE:
<223> OTHER INFORMATION: Reverse primer

<400> SEQUENCE: 94
dgggagaggy agrtggaatt sg                                             22

<210> SEQ ID NO 95
<211> LENGTH: 21
<212> TYPE: DNA
<213> ORGANISM: Artificial sequence
<220> FEATURE:
<223> OTHER INFORMATION: Forward primer

<400> SEQUENCE: 95
taaccataga actgcatttg a                                              21

<210> SEQ ID NO 96
<211> LENGTH: 14
<212> TYPE: DNA
<213> ORGANISM: Artificial sequence
<220> FEATURE:
<223> OTHER INFORMATION: Probe

<400> SEQUENCE: 96
ctactattct agag                                                      14

<210> SEQ ID NO 97
<211> LENGTH: 22
<212> TYPE: DNA
<213> ORGANISM: Artificial sequence
<220> FEATURE:
<223> OTHER INFORMATION: Reverse primer

<400> SEQUENCE: 97
dgggagaggy agrtggaatt sg                                             22

<210> SEQ ID NO 98
<211> LENGTH: 21
<212> TYPE: DNA
<213> ORGANISM: Artificial sequence
<220> FEATURE:
<223> OTHER INFORMATION: Forward primer
```

<400> SEQUENCE: 98
taactacaga actgcatttg a                                              21

<210> SEQ ID NO 99
<211> LENGTH: 14
<212> TYPE: DNA
<213> ORGANISM: Artificial sequence
<220> FEATURE:
<223> OTHER INFORMATION: Probe

<400> SEQUENCE: 99
ctgactatct agag                                                      14

<210> SEQ ID NO 100
<211> LENGTH: 22
<212> TYPE: DNA
<213> ORGANISM: Artificial sequence
<220> FEATURE:
<223> OTHER INFORMATION: Reverse primer

<400> SEQUENCE: 100
dgggagaggy agrtggaatt sg                                             22

<210> SEQ ID NO 101
<211> LENGTH: 21
<212> TYPE: DNA
<213> ORGANISM: Artificial sequence
<220> FEATURE:
<223> OTHER INFORMATION: Forward primer

<400> SEQUENCE: 101
taactacaga actgcatttg a                                              21

<210> SEQ ID NO 102
<211> LENGTH: 14
<212> TYPE: DNA
<213> ORGANISM: Artificial sequence
<220> FEATURE:
<223> OTHER INFORMATION: Probe

<400> SEQUENCE: 102
ctactattct agag                                                      14

<210> SEQ ID NO 103
<211> LENGTH: 22
<212> TYPE: DNA
<213> ORGANISM: Artificial sequence
<220> FEATURE:
<223> OTHER INFORMATION: Reverse primer

<400> SEQUENCE: 103
dgggagaggy agrtggaatt sg                                             22

<210> SEQ ID NO 104
<211> LENGTH: 21
<212> TYPE: DNA
<213> ORGANISM: Artificial sequence
<220> FEATURE:
<223> OTHER INFORMATION: Forward primer

<400> SEQUENCE: 104
caacctggga actgcatttg a                                              21

<210> SEQ ID NO 105
<211> LENGTH: 14

```
<212> TYPE: DNA
<213> ORGANISM: Artificial sequence
<220> FEATURE:
<223> OTHER INFORMATION: Probe

<400> SEQUENCE: 105
ctggcaggct ggag                                                           14

<210> SEQ ID NO 106
<211> LENGTH: 22
<212> TYPE: DNA
<213> ORGANISM: Artificial sequence
<220> FEATURE:
<223> OTHER INFORMATION: Reverse primer

<400> SEQUENCE: 106
tygtagaggg gggtagaatt cc                                                  22

<210> SEQ ID NO 107
<211> LENGTH: 21
<212> TYPE: DNA
<213> ORGANISM: Artificial sequence
<220> FEATURE:
<223> OTHER INFORMATION: Forward primer

<400> SEQUENCE: 107
caacctggga actgcattcg a                                                   21

<210> SEQ ID NO 108
<211> LENGTH: 14
<212> TYPE: DNA
<213> ORGANISM: Artificial sequence
<220> FEATURE:
<223> OTHER INFORMATION: Probe

<400> SEQUENCE: 108
ctggcaggct tgag                                                           14

<210> SEQ ID NO 109
<211> LENGTH: 22
<212> TYPE: DNA
<213> ORGANISM: Artificial sequence
<220> FEATURE:
<223> OTHER INFORMATION: Reverse primer

<400> SEQUENCE: 109
tygtagaggg gggtagaatt cc                                                  22

<210> SEQ ID NO 110
<211> LENGTH: 21
<212> TYPE: DNA
<213> ORGANISM: Artificial sequence
<220> FEATURE:
<223> OTHER INFORMATION: Forward primer

<400> SEQUENCE: 110
caacctggga actgcatttg a                                                   21

<210> SEQ ID NO 111
<211> LENGTH: 14
<212> TYPE: DNA
<213> ORGANISM: Artificial sequence
<220> FEATURE:
<223> OTHER INFORMATION: Probe

<400> SEQUENCE: 111
```
ctggcaagct agag							14

<210> SEQ ID NO 112
<211> LENGTH: 22
<212> TYPE: DNA
<213> ORGANISM: Artificial sequence
<220> FEATURE:
<223> OTHER INFORMATION: Reverse primer

<400> SEQUENCE: 112
tygtagaggg gggtagaatt cc						22

<210> SEQ ID NO 113
<211> LENGTH: 21
<212> TYPE: DNA
<213> ORGANISM: Artificial sequence
<220> FEATURE:
<223> OTHER INFORMATION: Forward primer

<400> SEQUENCE: 113
caacctggga actgcatctg a							21

<210> SEQ ID NO 114
<211> LENGTH: 14
<212> TYPE: DNA
<213> ORGANISM: Artificial sequence
<220> FEATURE:
<223> OTHER INFORMATION: Probe

<400> SEQUENCE: 114
ctggcaagct tgag							14

<210> SEQ ID NO 115
<211> LENGTH: 22
<212> TYPE: DNA
<213> ORGANISM: Artificial sequence
<220> FEATURE:
<223> OTHER INFORMATION: Reverse primer

<400> SEQUENCE: 115
tygtagaggg gggtagaatt cc						22

<210> SEQ ID NO 116
<211> LENGTH: 21
<212> TYPE: DNA
<213> ORGANISM: Artificial sequence
<220> FEATURE:
<223> OTHER INFORMATION: Forward primer

<400> SEQUENCE: 116
caacctggga actgcatcca a							21

<210> SEQ ID NO 117
<211> LENGTH: 14
<212> TYPE: DNA
<213> ORGANISM: Artificial sequence
<220> FEATURE:
<223> OTHER INFORMATION: Probe

<400> SEQUENCE: 117
ctactgagct agag							14

<210> SEQ ID NO 118
<211> LENGTH: 22
<212> TYPE: DNA
<213> ORGANISM: Artificial sequence

```
<220> FEATURE:
<223> OTHER INFORMATION: Reverse primer

<400> SEQUENCE: 118
cggtagaggg tggtggaatt tc                                              22

<210> SEQ ID NO 119
<211> LENGTH: 21
<212> TYPE: DNA
<213> ORGANISM: Artificial sequence
<220> FEATURE:
<223> OTHER INFORMATION: Forward primer

<400> SEQUENCE: 119
taacttggga attgcatctg a                                               21

<210> SEQ ID NO 120
<211> LENGTH: 14
<212> TYPE: DNA
<213> ORGANISM: Artificial sequence
<220> FEATURE:
<223> OTHER INFORMATION: Probe

<400> SEQUENCE: 120
ctggttggct agag                                                       14

<210> SEQ ID NO 121
<211> LENGTH: 22
<212> TYPE: DNA
<213> ORGANISM: Artificial sequence
<220> FEATURE:
<223> OTHER INFORMATION: Reverse primer

<400> SEQUENCE: 121
tygtagaggg gggtagaatt cc                                              22

<210> SEQ ID NO 122
<211> LENGTH: 21
<212> TYPE: DNA
<213> ORGANISM: Artificial sequence
<220> FEATURE:
<223> OTHER INFORMATION: Forward primer

<400> SEQUENCE: 122
taacctagga attgcatttc a                                               21

<210> SEQ ID NO 123
<211> LENGTH: 14
<212> TYPE: DNA
<213> ORGANISM: Artificial sequence
<220> FEATURE:
<223> OTHER INFORMATION: Probe

<400> SEQUENCE: 123
ctgggtaact agag                                                       14

<210> SEQ ID NO 124
<211> LENGTH: 22
<212> TYPE: DNA
<213> ORGANISM: Artificial sequence
<220> FEATURE:
<223> OTHER INFORMATION: Reverse primer

<400> SEQUENCE: 124
ctttagggag gggtagaatt cc                                              22
```

```
<210> SEQ ID NO 125
<211> LENGTH: 21
<212> TYPE: DNA
<213> ORGANISM: Artificial sequence
<220> FEATURE:
<223> OTHER INFORMATION: Forward primer

<400> SEQUENCE: 125
caacccggga actgcgttct g                                              21

<210> SEQ ID NO 126
<211> LENGTH: 14
<212> TYPE: DNA
<213> ORGANISM: Artificial sequence
<220> FEATURE:
<223> OTHER INFORMATION: Probe

<400> SEQUENCE: 126
ctgggtgact cgag                                                      14

<210> SEQ ID NO 127
<211> LENGTH: 22
<212> TYPE: DNA
<213> ORGANISM: Artificial sequence
<220> FEATURE:
<223> OTHER INFORMATION: Reverse primer

<400> SEQUENCE: 127
tgtcagaggg aggtagaatt cc                                             22

<210> SEQ ID NO 128
<211> LENGTH: 20
<212> TYPE: DNA
<213> ORGANISM: Artificial sequence
<220> FEATURE:
<223> OTHER INFORMATION: Forward primer

<400> SEQUENCE: 128
taaccccgtg akgggatgga                                                20

<210> SEQ ID NO 129
<211> LENGTH: 14
<212> TYPE: DNA
<213> ORGANISM: Artificial sequence
<220> FEATURE:
<223> OTHER INFORMATION: Probe

<400> SEQUENCE: 129
ctgctgatct agag                                                      14

<210> SEQ ID NO 130
<211> LENGTH: 22
<212> TYPE: DNA
<213> ORGANISM: Artificial sequence
<220> FEATURE:
<223> OTHER INFORMATION: Reverse primer

<400> SEQUENCE: 130
tcggagagga aagtggaatt cc                                             22

<210> SEQ ID NO 131
<211> LENGTH: 20
<212> TYPE: DNA
<213> ORGANISM: Artificial sequence
<220> FEATURE:
<223> OTHER INFORMATION: Forward primer
```

<400> SEQUENCE: 131 taacccgtg akgggatgga          20

<210> SEQ ID NO 132
<211> LENGTH: 14
<212> TYPE: DNA
<213> ORGANISM: Artificial sequence
<220> FEATURE:
<223> OTHER INFORMATION: Probe

<400> SEQUENCE: 132
ctgccaatct agag          14

<210> SEQ ID NO 133
<211> LENGTH: 22
<212> TYPE: DNA
<213> ORGANISM: Artificial sequence
<220> FEATURE:
<223> OTHER INFORMATION: Reverse primer

<400> SEQUENCE: 133
tcggagagga aagtggaatt cc          22

<210> SEQ ID NO 134
<211> LENGTH: 21
<212> TYPE: DNA
<213> ORGANISM: Artificial sequence
<220> FEATURE:
<223> OTHER INFORMATION: Forward primer

<400> SEQUENCE: 134
caaccccaag ccagcatcta a          21

<210> SEQ ID NO 135
<211> LENGTH: 14
<212> TYPE: DNA
<213> ORGANISM: Artificial sequence
<220> FEATURE:
<223> OTHER INFORMATION: Probe

<400> SEQUENCE: 135
ctatctttct agag          14

<210> SEQ ID NO 136
<211> LENGTH: 22
<212> TYPE: DNA
<213> ORGANISM: Artificial sequence
<220> FEATURE:
<223> OTHER INFORMATION: Reverse primer

<400> SEQUENCE: 136
tagatggaga aagggaatt cc          22

<210> SEQ ID NO 137
<211> LENGTH: 21
<212> TYPE: DNA
<213> ORGANISM: Artificial sequence
<220> FEATURE:
<223> OTHER INFORMATION: Forward primer

<400> SEQUENCE: 137
caaccgtaaa attgcagttg a          21

<210> SEQ ID NO 138

```
<211> LENGTH: 14
<212> TYPE: DNA
<213> ORGANISM: Artificial sequence
<220> FEATURE:
<223> OTHER INFORMATION: Probe

<400> SEQUENCE: 138
ctgtcagtct tgag                                                         14

<210> SEQ ID NO 139
<211> LENGTH: 22
<212> TYPE: DNA
<213> ORGANISM: Artificial sequence
<220> FEATURE:
<223> OTHER INFORMATION: Reverse primer

<400> SEQUENCE: 139
cagtagaggt gggcggaatt cg                                                22

<210> SEQ ID NO 140
<211> LENGTH: 19
<212> TYPE: DNA
<213> ORGANISM: Artificial sequence
<220> FEATURE:
<223> OTHER INFORMATION: Forward primer

<400> SEQUENCE: 140
ttatagatgg atccgcgcy                                                    19

<210> SEQ ID NO 141
<211> LENGTH: 14
<212> TYPE: DNA
<213> ORGANISM: Artificial sequence
<220> FEATURE:
<223> OTHER INFORMATION: Probe

<400> SEQUENCE: 141
gcaacgatgc atag                                                         14

<210> SEQ ID NO 142
<211> LENGTH: 21
<212> TYPE: DNA
<213> ORGANISM: Artificial sequence
<220> FEATURE:
<223> OTHER INFORMATION: Reverse primer

<400> SEQUENCE: 142
gtgatcggcc acactggrac t                                                 21

<210> SEQ ID NO 143
<211> LENGTH: 19
<212> TYPE: DNA
<213> ORGANISM: Artificial sequence
<220> FEATURE:
<223> OTHER INFORMATION: Forward primer

<400> SEQUENCE: 143
ttatagatgg atccgcgcy                                                    19

<210> SEQ ID NO 144
<211> LENGTH: 14
<212> TYPE: DNA
<213> ORGANISM: Artificial sequence
<220> FEATURE:
<223> OTHER INFORMATION: Probe

<400> SEQUENCE: 144
```
gcaacgatgc gtag                                                          14

<210> SEQ ID NO 145
<211> LENGTH: 21
<212> TYPE: DNA
<213> ORGANISM: Artificial sequence
<220> FEATURE:
<223> OTHER INFORMATION: Reverse primer

<400> SEQUENCE: 145
gtgatcggcc acactggrac t                                                  21

<210> SEQ ID NO 146
<211> LENGTH: 19
<212> TYPE: DNA
<213> ORGANISM: Artificial sequence
<220> FEATURE:
<223> OTHER INFORMATION: Forward primer

<400> SEQUENCE: 146
trtgagatgg acctgcgtt                                                     19

<210> SEQ ID NO 147
<211> LENGTH: 14
<212> TYPE: DNA
<213> ORGANISM: Artificial sequence
<220> FEATURE:
<223> OTHER INFORMATION: Probe

<400> SEQUENCE: 147
gcgacgatac atag                                                          14

<210> SEQ ID NO 148
<211> LENGTH: 21
<212> TYPE: DNA
<213> ORGANISM: Artificial sequence
<220> FEATURE:
<223> OTHER INFORMATION: Reverse primer

<400> SEQUENCE: 148
gtgatcggcc acactggrac t                                                  21

<210> SEQ ID NO 149
<211> LENGTH: 19
<212> TYPE: DNA
<213> ORGANISM: Artificial sequence
<220> FEATURE:
<223> OTHER INFORMATION: Forward primer

<400> SEQUENCE: 149
taccagatgg acctgcgtt                                                     19

<210> SEQ ID NO 150
<211> LENGTH: 14
<212> TYPE: DNA
<213> ORGANISM: Artificial sequence
<220> FEATURE:
<223> OTHER INFORMATION: Probe

<400> SEQUENCE: 150
gcgacgatac atag                                                          14

<210> SEQ ID NO 151
<211> LENGTH: 21
<212> TYPE: DNA

```
<213> ORGANISM: Artificial sequence
<220> FEATURE:
<223> OTHER INFORMATION: Reverse primer

<400> SEQUENCE: 151
gtgatcggcc acactggrac t                                              21

<210> SEQ ID NO 152
<211> LENGTH: 19
<212> TYPE: DNA
<213> ORGANISM: Artificial sequence
<220> FEATURE:
<223> OTHER INFORMATION: Forward primer

<400> SEQUENCE: 152
tgatggatgg acccgcggt                                                 19

<210> SEQ ID NO 153
<211> LENGTH: 14
<212> TYPE: DNA
<213> ORGANISM: Artificial sequence
<220> FEATURE:
<223> OTHER INFORMATION: Probe

<400> SEQUENCE: 153
gccacgatgc atag                                                      14

<210> SEQ ID NO 154
<211> LENGTH: 21
<212> TYPE: DNA
<213> ORGANISM: Artificial sequence
<220> FEATURE:
<223> OTHER INFORMATION: Reverse primer

<400> SEQUENCE: 154
gtgatcggcc acactggrac t                                              21

<210> SEQ ID NO 155
<211> LENGTH: 19
<212> TYPE: DNA
<213> ORGANISM: Artificial sequence
<220> FEATURE:
<223> OTHER INFORMATION: Forward primer

<400> SEQUENCE: 155
tgmaggatgr gcccgcggc                                                 19

<210> SEQ ID NO 156
<211> LENGTH: 14
<212> TYPE: DNA
<213> ORGANISM: Artificial sequence
<220> FEATURE:
<223> OTHER INFORMATION: Probe

<400> SEQUENCE: 156
gcgacgacgg gtag                                                      14

<210> SEQ ID NO 157
<211> LENGTH: 21
<212> TYPE: DNA
<213> ORGANISM: Artificial sequence
<220> FEATURE:
<223> OTHER INFORMATION: Reverse primer

<400> SEQUENCE: 157
gcgaccggcc acactgggac t                                              21
```

<210> SEQ ID NO 158
<211> LENGTH: 19
<212> TYPE: DNA
<213> ORGANISM: Artificial sequence
<220> FEATURE:
<223> OTHER INFORMATION: Forward primer

<400> SEQUENCE: 158
tgtgggatga gcccgcggc                                                19

<210> SEQ ID NO 159
<211> LENGTH: 14
<212> TYPE: DNA
<213> ORGANISM: Artificial sequence
<220> FEATURE:
<223> OTHER INFORMATION: Probe

<400> SEQUENCE: 159
gcgacgacgg gtag                                                     14

<210> SEQ ID NO 160
<211> LENGTH: 21
<212> TYPE: DNA
<213> ORGANISM: Artificial sequence
<220> FEATURE:
<223> OTHER INFORMATION: Reverse primer

<400> SEQUENCE: 160
gtgtccggcc acactgggac t                                             21

<210> SEQ ID NO 161
<211> LENGTH: 19
<212> TYPE: DNA
<213> ORGANISM: Artificial sequence
<220> FEATURE:
<223> OTHER INFORMATION: Forward primer

<400> SEQUENCE: 161
tatgagatgg acccgcggc                                                19

<210> SEQ ID NO 162
<211> LENGTH: 15
<212> TYPE: DNA
<213> ORGANISM: Artificial sequence
<220> FEATURE:
<223> OTHER INFORMATION: Probe

<400> SEQUENCE: 162
gcgacgatgc tgtag                                                    15

<210> SEQ ID NO 163
<211> LENGTH: 21
<212> TYPE: DNA
<213> ORGANISM: Artificial sequence
<220> FEATURE:
<223> OTHER INFORMATION: Reverse primer

<400> SEQUENCE: 163
gtgatcggcc acattgggac t                                             21

<210> SEQ ID NO 164
<211> LENGTH: 21
<212> TYPE: DNA
<213> ORGANISM: Artificial sequence
<220> FEATURE:

<223> OTHER INFORMATION: Forward primer

<400> SEQUENCE: 164
actcctacgg gaggcagcag t                                              21

<210> SEQ ID NO 165
<211> LENGTH: 12
<212> TYPE: DNA
<213> ORGANISM: Artificial sequence
<220> FEATURE:
<223> OTHER INFORMATION: Probe

<400> SEQUENCE: 165
gcaacgccgc gt                                                        12

<210> SEQ ID NO 166
<211> LENGTH: 21
<212> TYPE: DNA
<213> ORGANISM: Artificial sequence
<220> FEATURE:
<223> OTHER INFORMATION: Reverse primer

<400> SEQUENCE: 166
gccagcagcc gcggtaatac g                                              21

<210> SEQ ID NO 167
<211> LENGTH: 21
<212> TYPE: DNA
<213> ORGANISM: Artificial sequence
<220> FEATURE:
<223> OTHER INFORMATION: Forward primer

<400> SEQUENCE: 167
actcctacgg gaggcagcag t                                              21

<210> SEQ ID NO 168
<211> LENGTH: 12
<212> TYPE: DNA
<213> ORGANISM: Artificial sequence
<220> FEATURE:
<223> OTHER INFORMATION: Probe

<400> SEQUENCE: 168
gcgacgccgc gt                                                        12

<210> SEQ ID NO 169
<211> LENGTH: 21
<212> TYPE: DNA
<213> ORGANISM: Artificial sequence
<220> FEATURE:
<223> OTHER INFORMATION: Reverse primer

<400> SEQUENCE: 169
gccagcagcc gcggtaatac g                                              21

<210> SEQ ID NO 170
<211> LENGTH: 21
<212> TYPE: DNA
<213> ORGANISM: Artificial sequence
<220> FEATURE:
<223> OTHER INFORMATION: Forward primer

<400> SEQUENCE: 170
caaccgkgga gggtcattgg a                                              21

```
<210> SEQ ID NO 171
<211> LENGTH: 14
<212> TYPE: DNA
<213> ORGANISM: Artificial sequence
<220> FEATURE:
<223> OTHER INFORMATION: Probe

<400> SEQUENCE: 171
ctggaaaact tgag                                                        14

<210> SEQ ID NO 172
<211> LENGTH: 22
<212> TYPE: DNA
<213> ORGANISM: Artificial sequence
<220> FEATURE:
<223> OTHER INFORMATION: Reverse primer

<400> SEQUENCE: 172
carragrgga ragtggaatt cc                                               22

<210> SEQ ID NO 173
<211> LENGTH: 21
<212> TYPE: DNA
<213> ORGANISM: Artificial sequence
<220> FEATURE:
<223> OTHER INFORMATION: Forward primer

<400> SEQUENCE: 173
caaccgkgga gggtcattgg a                                                21

<210> SEQ ID NO 174
<211> LENGTH: 14
<212> TYPE: DNA
<213> ORGANISM: Artificial sequence
<220> FEATURE:
<223> OTHER INFORMATION: Probe

<400> SEQUENCE: 174
ctgggagact tgag                                                        14

<210> SEQ ID NO 175
<211> LENGTH: 22
<212> TYPE: DNA
<213> ORGANISM: Artificial sequence
<220> FEATURE:
<223> OTHER INFORMATION: Reverse primer

<400> SEQUENCE: 175
carragrgga ragtggaatt cc                                               22

<210> SEQ ID NO 176
<211> LENGTH: 20
<212> TYPE: DNA
<213> ORGANISM: Artificial sequence
<220> FEATURE:
<223> OTHER INFORMATION: Forward primer

<400> SEQUENCE: 176
taaccattgt acgctttgga                                                  20

<210> SEQ ID NO 177
<211> LENGTH: 14
<212> TYPE: DNA
<213> ORGANISM: Artificial sequence
<220> FEATURE:
<223> OTHER INFORMATION: Probe
```

```
<400> SEQUENCE: 177
ctggaggact tgag                                                        14

<210> SEQ ID NO 178
<211> LENGTH: 22
<212> TYPE: DNA
<213> ORGANISM: Artificial sequence
<220> FEATURE:
<223> OTHER INFORMATION: Reverse primer

<400> SEQUENCE: 178
carragrgga ragtggaatt cc                                               22

<210> SEQ ID NO 179
<211> LENGTH: 20
<212> TYPE: DNA
<213> ORGANISM: Artificial sequence
<220> FEATURE:
<223> OTHER INFORMATION: Forward primer

<400> SEQUENCE: 179
caaccaatgt acgctttgga                                                  20

<210> SEQ ID NO 180
<211> LENGTH: 14
<212> TYPE: DNA
<213> ORGANISM: Artificial sequence
<220> FEATURE:
<223> OTHER INFORMATION: Probe

<400> SEQUENCE: 180
ctggagaact tgag                                                        14

<210> SEQ ID NO 181
<211> LENGTH: 22
<212> TYPE: DNA
<213> ORGANISM: Artificial sequence
<220> FEATURE:
<223> OTHER INFORMATION: Reverse primer

<400> SEQUENCE: 181
carragrgga ragtggaatt cc                                               22

<210> SEQ ID NO 182
<211> LENGTH: 20
<212> TYPE: DNA
<213> ORGANISM: Artificial sequence
<220> FEATURE:
<223> OTHER INFORMATION: Forward primer

<400> SEQUENCE: 182
taaccatagt aggctttgga                                                  20

<210> SEQ ID NO 183
<211> LENGTH: 14
<212> TYPE: DNA
<213> ORGANISM: Artificial sequence
<220> FEATURE:
<223> OTHER INFORMATION: Probe

<400> SEQUENCE: 183
ctgtttaact tgag                                                        14

<210> SEQ ID NO 184
<211> LENGTH: 22
```

```
<212> TYPE: DNA
<213> ORGANISM: Artificial sequence
<220> FEATURE:
<223> OTHER INFORMATION: Reverse primer

<400> SEQUENCE: 184
carragrgga ragtggaatt cc                                              22

<210> SEQ ID NO 185
<211> LENGTH: 21
<212> TYPE: DNA
<213> ORGANISM: Artificial sequence
<220> FEATURE:
<223> OTHER INFORMATION: Forward primer

<400> SEQUENCE: 185
taaccccggg tctgcattcg a                                               21

<210> SEQ ID NO 186
<211> LENGTH: 14
<212> TYPE: DNA
<213> ORGANISM: Artificial sequence
<220> FEATURE:
<223> OTHER INFORMATION: Probe

<400> SEQUENCE: 186
cgggctagct agag                                                       14

<210> SEQ ID NO 187
<211> LENGTH: 22
<212> TYPE: DNA
<213> ORGANISM: Artificial sequence
<220> FEATURE:
<223> OTHER INFORMATION: Reverse primer

<400> SEQUENCE: 187
yggtagggga gatcggaatt cc                                              22

<210> SEQ ID NO 188
<211> LENGTH: 21
<212> TYPE: DNA
<213> ORGANISM: Artificial sequence
<220> FEATURE:
<223> OTHER INFORMATION: Forward primer

<400> SEQUENCE: 188
taactgtgag cgtgcgggcg a                                               21

<210> SEQ ID NO 189
<211> LENGTH: 14
<212> TYPE: DNA
<213> ORGANISM: Artificial sequence
<220> FEATURE:
<223> OTHER INFORMATION: Probe

<400> SEQUENCE: 189
cgggcagact agag                                                       14

<210> SEQ ID NO 190
<211> LENGTH: 22
<212> TYPE: DNA
<213> ORGANISM: Artificial sequence
<220> FEATURE:
<223> OTHER INFORMATION: Reverse primer

<400> SEQUENCE: 190
```

```
ctgcagggga gactggaatt cc                                              22

<210> SEQ ID NO 191
<211> LENGTH: 21
<212> TYPE: DNA
<213> ORGANISM: Artificial sequence
<220> FEATURE:
<223> OTHER INFORMATION: Forward primer

<400> SEQUENCE: 191
caacttgggt gctgcattcc a                                               21

<210> SEQ ID NO 192
<211> LENGTH: 14
<212> TYPE: DNA
<213> ORGANISM: Artificial sequence
<220> FEATURE:
<223> OTHER INFORMATION: Probe

<400> SEQUENCE: 192
ctggttatct agag                                                       14

<210> SEQ ID NO 193
<211> LENGTH: 22
<212> TYPE: DNA
<213> ORGANISM: Artificial sequence
<220> FEATURE:
<223> OTHER INFORMATION: Reverse primer

<400> SEQUENCE: 193
caggagagga gagtggaatt cc                                              22

<210> SEQ ID NO 194
<211> LENGTH: 28
<212> TYPE: DNA
<213> ORGANISM: Artificial sequence
<220> FEATURE:
<223> OTHER INFORMATION: Forward primer

<400> SEQUENCE: 194
tatgcagtct gagttgatta tcgtaatc                                        28

<210> SEQ ID NO 195
<211> LENGTH: 19
<212> TYPE: DNA
<213> ORGANISM: Artificial sequence
<220> FEATURE:
<223> OTHER INFORMATION: Probe

<400> SEQUENCE: 195
ctcttggttc cggcatcga                                                  19

<210> SEQ ID NO 196
<211> LENGTH: 19
<212> TYPE: DNA
<213> ORGANISM: Artificial sequence
<220> FEATURE:
<223> OTHER INFORMATION: Reverse primer

<400> SEQUENCE: 196
gcatttcgct gcgttcttc                                                  19

<210> SEQ ID NO 197
<211> LENGTH: 29
<212> TYPE: DNA
<213> ORGANISM: Artificial sequence
```

```
<220> FEATURE:
<223> OTHER INFORMATION: Forward primer

<400> SEQUENCE: 197
cagaggtcta aacttacaac caatttttt                                29

<210> SEQ ID NO 198
<211> LENGTH: 19
<212> TYPE: DNA
<213> ORGANISM: Artificial sequence
<220> FEATURE:
<223> OTHER INFORMATION: Probe

<400> SEQUENCE: 198
ctcttggttc tcgcatcga                                           19

<210> SEQ ID NO 199
<211> LENGTH: 19
<212> TYPE: DNA
<213> ORGANISM: Artificial sequence
<220> FEATURE:
<223> OTHER INFORMATION: Reverse primer

<400> SEQUENCE: 199
gcatttcgct gcgttcttc                                           19

<210> SEQ ID NO 200
<211> LENGTH: 23
<212> TYPE: DNA
<213> ORGANISM: Artificial sequence
<220> FEATURE:
<223> OTHER INFORMATION: Forward primer

<400> SEQUENCE: 200
ggcaaacgca aataaatca aaa                                       23

<210> SEQ ID NO 201
<211> LENGTH: 19
<212> TYPE: DNA
<213> ORGANISM: Artificial sequence
<220> FEATURE:
<223> OTHER INFORMATION: Probe

<400> SEQUENCE: 201
ctcttggctc tggcatcga                                           19

<210> SEQ ID NO 202
<211> LENGTH: 19
<212> TYPE: DNA
<213> ORGANISM: Artificial sequence
<220> FEATURE:
<223> OTHER INFORMATION: Reverse primer

<400> SEQUENCE: 202
gcatttcgct gcgttcttc                                           19

<210> SEQ ID NO 203
<211> LENGTH: 19
<212> TYPE: DNA
<213> ORGANISM: Artificial sequence
<220> FEATURE:
<223> OTHER INFORMATION: Forward primer

<400> SEQUENCE: 203
aattaaaact ttcaacaac                                           19
```

```
<210> SEQ ID NO 204
<211> LENGTH: 19
<212> TYPE: DNA
<213> ORGANISM: Artificial sequence
<220> FEATURE:
<223> OTHER INFORMATION: Probe

<400> SEQUENCE: 204
ctcttggctc tggcatcga                                                  19

<210> SEQ ID NO 205
<211> LENGTH: 15
<212> TYPE: DNA
<213> ORGANISM: Artificial sequence
<220> FEATURE:
<223> OTHER INFORMATION: Reverse primer

<400> SEQUENCE: 205
acttatcgca tttcg                                                      15

<210> SEQ ID NO 206
<211> LENGTH: 25
<212> TYPE: DNA
<213> ORGANISM: Artificial sequence
<220> FEATURE:
<223> OTHER INFORMATION: Forward primer

<400> SEQUENCE: 206
gaaaacaaaa aaacaagtt aaaac                                            25

<210> SEQ ID NO 207
<211> LENGTH: 19
<212> TYPE: DNA
<213> ORGANISM: Artificial sequence
<220> FEATURE:
<223> OTHER INFORMATION: Probe

<400> SEQUENCE: 207
ctcttggttc tggcatcga                                                  19

<210> SEQ ID NO 208
<211> LENGTH: 21
<212> TYPE: DNA
<213> ORGANISM: Artificial sequence
<220> FEATURE:
<223> OTHER INFORMATION: Reverse primer

<400> SEQUENCE: 208
cacattactt atcgcatttc g                                               21

<210> SEQ ID NO 209
<211> LENGTH: 22
<212> TYPE: DNA
<213> ORGANISM: Artificial sequence
<220> FEATURE:
<223> OTHER INFORMATION: Forward primer

<400> SEQUENCE: 209
tccagtcaaa actttcaaca ac                                              22

<210> SEQ ID NO 210
<211> LENGTH: 19
<212> TYPE: DNA
<213> ORGANISM: Artificial sequence
<220> FEATURE:
<223> OTHER INFORMATION: Probe
```

```
<400> SEQUENCE: 210
ctcttggttc cgacatcga                                                  19

<210> SEQ ID NO 211
<211> LENGTH: 17
<212> TYPE: DNA
<213> ORGANISM: Artificial sequence
<220> FEATURE:
<223> OTHER INFORMATION: Reverse primer

<400> SEQUENCE: 211
gcatttcgct gcgttct                                                    17

<210> SEQ ID NO 212
<211> LENGTH: 22
<212> TYPE: DNA
<213> ORGANISM: Artificial sequence
<220> FEATURE:
<223> OTHER INFORMATION: Forward primer

<400> SEQUENCE: 212
caataataaa actttcaaca ac                                              22

<210> SEQ ID NO 213
<211> LENGTH: 19
<212> TYPE: DNA
<213> ORGANISM: Artificial sequence
<220> FEATURE:
<223> OTHER INFORMATION: Probe

<400> SEQUENCE: 213
ctcttggctt ccacatcga                                                  19

<210> SEQ ID NO 214
<211> LENGTH: 14
<212> TYPE: DNA
<213> ORGANISM: Artificial sequence
<220> FEATURE:
<223> OTHER INFORMATION: Reverse primer

<400> SEQUENCE: 214
cgctgcgttc ttca                                                       14

<210> SEQ ID NO 215
<211> LENGTH: 14
<212> TYPE: DNA
<213> ORGANISM: Artificial sequence
<220> FEATURE:
<223> OTHER INFORMATION: Forward primer

<400> SEQUENCE: 215
ggttccggca tcga                                                       14

<210> SEQ ID NO 216
<211> LENGTH: 14
<212> TYPE: DNA
<213> ORGANISM: Artificial sequence
<220> FEATURE:
<223> OTHER INFORMATION: Probe

<400> SEQUENCE: 216
cgataagtaa tgtg                                                       14

<210> SEQ ID NO 217
```

```
<211> LENGTH: 20
<212> TYPE: DNA
<213> ORGANISM: Artificial sequence
<220> FEATURE:
<223> OTHER INFORMATION: Reverse primer

<400> SEQUENCE: 217
gattcactga attctgcaat                                              20

<210> SEQ ID NO 218
<211> LENGTH: 15
<212> TYPE: DNA
<213> ORGANISM: Artificial sequence
<220> FEATURE:
<223> OTHER INFORMATION: Forward primer

<400> SEQUENCE: 218
tggttctcgc atcga                                                   15

<210> SEQ ID NO 219
<211> LENGTH: 14
<212> TYPE: DNA
<213> ORGANISM: Artificial sequence
<220> FEATURE:
<223> OTHER INFORMATION: Probe

<400> SEQUENCE: 219
cgatacgtaa tatg                                                    14

<210> SEQ ID NO 220
<211> LENGTH: 19
<212> TYPE: DNA
<213> ORGANISM: Artificial sequence
<220> FEATURE:
<223> OTHER INFORMATION: Reverse primer

<400> SEQUENCE: 220
cacgaatatc tgcacaatt                                               19

<210> SEQ ID NO 221
<211> LENGTH: 14
<212> TYPE: DNA
<213> ORGANISM: Artificial sequence
<220> FEATURE:
<223> OTHER INFORMATION: Forward primer

<400> SEQUENCE: 221
ggctctggca tcga                                                    14

<210> SEQ ID NO 222
<211> LENGTH: 14
<212> TYPE: DNA
<213> ORGANISM: Artificial sequence
<220> FEATURE:
<223> OTHER INFORMATION: Probe

<400> SEQUENCE: 222
cgataagtaa tgtg                                                    14

<210> SEQ ID NO 223
<211> LENGTH: 18
<212> TYPE: DNA
<213> ORGANISM: Artificial sequence
<220> FEATURE:
<223> OTHER INFORMATION: Reverse primer

<400> SEQUENCE: 223
```
ttcactgaat tctgcaat                                              18

<210> SEQ ID NO 224
<211> LENGTH: 13
<212> TYPE: DNA
<213> ORGANISM: Artificial sequence
<220> FEATURE:
<223> OTHER INFORMATION: Forward primer

<400> SEQUENCE: 224
aacgcagcga aat                                                   13

<210> SEQ ID NO 225
<211> LENGTH: 14
<212> TYPE: DNA
<213> ORGANISM: Artificial sequence
<220> FEATURE:
<223> OTHER INFORMATION: Probe

<400> SEQUENCE: 225
cgataagtaa tgtg                                                  14

<210> SEQ ID NO 226
<211> LENGTH: 18
<212> TYPE: DNA
<213> ORGANISM: Artificial sequence
<220> FEATURE:
<223> OTHER INFORMATION: Reverse primer

<400> SEQUENCE: 226
atgattcact gaattctg                                              18

<210> SEQ ID NO 227
<211> LENGTH: 15
<212> TYPE: DNA
<213> ORGANISM: Artificial sequence
<220> FEATURE:
<223> OTHER INFORMATION: Forward primer

<400> SEQUENCE: 227
tggttctggc atcga                                                 15

<210> SEQ ID NO 228
<211> LENGTH: 14
<212> TYPE: DNA
<213> ORGANISM: Artificial sequence
<220> FEATURE:
<223> OTHER INFORMATION: Probe

<400> SEQUENCE: 228
cgataagtaa tgtg                                                  14

<210> SEQ ID NO 229
<211> LENGTH: 19
<212> TYPE: DNA
<213> ORGANISM: Artificial sequence
<220> FEATURE:
<223> OTHER INFORMATION: Reverse primer

<400> SEQUENCE: 229
attcactgaa ttctgcaat                                             19

<210> SEQ ID NO 230
<211> LENGTH: 15
<212> TYPE: DNA

```
<213> ORGANISM: Artificial sequence
<220> FEATURE:
<223> OTHER INFORMATION: Forward primer

<400> SEQUENCE: 230
tggttccgac atcga                                                    15

<210> SEQ ID NO 231
<211> LENGTH: 14
<212> TYPE: DNA
<213> ORGANISM: Artificial sequence
<220> FEATURE:
<223> OTHER INFORMATION: Probe

<400> SEQUENCE: 231
cgataagtaa tgtg                                                     14

<210> SEQ ID NO 232
<211> LENGTH: 16
<212> TYPE: DNA
<213> ORGANISM: Artificial sequence
<220> FEATURE:
<223> OTHER INFORMATION: Reverse primer

<400> SEQUENCE: 232
cacggaattc tgcaat                                                   16

<210> SEQ ID NO 233
<211> LENGTH: 16
<212> TYPE: DNA
<213> ORGANISM: Artificial sequence
<220> FEATURE:
<223> OTHER INFORMATION: Forward primer

<400> SEQUENCE: 233
aagaacgcag cgaaat                                                   16

<210> SEQ ID NO 234
<211> LENGTH: 14
<212> TYPE: DNA
<213> ORGANISM: Artificial sequence
<220> FEATURE:
<223> OTHER INFORMATION: Probe

<400> SEQUENCE: 234
cgataagtaa tgtg                                                     14

<210> SEQ ID NO 235
<211> LENGTH: 19
<212> TYPE: DNA
<213> ORGANISM: Artificial sequence
<220> FEATURE:
<223> OTHER INFORMATION: Reverse primer

<400> SEQUENCE: 235
attcactgaa ttctgcaat                                                19

<210> SEQ ID NO 236
<211> LENGTH: 20
<212> TYPE: DNA
<213> ORGANISM: Artificial sequence
<220> FEATURE:
<223> OTHER INFORMATION: Forward primer

<400> SEQUENCE: 236
aagtaatgtg aattgcagaa                                               20
```

<210> SEQ ID NO 237
<211> LENGTH: 13
<212> TYPE: DNA
<213> ORGANISM: Artificial sequence
<220> FEATURE:
<223> OTHER INFORMATION: Probe

<400> SEQUENCE: 237
gtgaatcatc gag                                                          13

<210> SEQ ID NO 238
<211> LENGTH: 14
<212> TYPE: DNA
<213> ORGANISM: Artificial sequence
<220> FEATURE:
<223> OTHER INFORMATION: Reverse primer

<400> SEQUENCE: 238
cccccggaat acca                                                         14

<210> SEQ ID NO 239
<211> LENGTH: 23
<212> TYPE: DNA
<213> ORGANISM: Artificial sequence
<220> FEATURE:
<223> OTHER INFORMATION: Forward primer

<400> SEQUENCE: 239
cgtaatatga attgcagata ttc                                               23

<210> SEQ ID NO 240
<211> LENGTH: 13
<212> TYPE: DNA
<213> ORGANISM: Artificial sequence
<220> FEATURE:
<223> OTHER INFORMATION: Probe

<400> SEQUENCE: 240
gtgaatcatc gaa                                                          13

<210> SEQ ID NO 241
<211> LENGTH: 14
<212> TYPE: DNA
<213> ORGANISM: Artificial sequence
<220> FEATURE:
<223> OTHER INFORMATION: Reverse primer

<400> SEQUENCE: 241
gagggcgcaa tgtg                                                         14

<210> SEQ ID NO 242
<211> LENGTH: 18
<212> TYPE: DNA
<213> ORGANISM: Artificial sequence
<220> FEATURE:
<223> OTHER INFORMATION: Forward primer

<400> SEQUENCE: 242
gcgaaatgcg ataagtaa                                                     18

<210> SEQ ID NO 243
<211> LENGTH: 13
<212> TYPE: DNA
<213> ORGANISM: Artificial sequence
<220> FEATURE:

<223> OTHER INFORMATION: Probe

<400> SEQUENCE: 243
gtgaattgca gaa                                                          13

<210> SEQ ID NO 244
<211> LENGTH: 19
<212> TYPE: DNA
<213> ORGANISM: Artificial sequence
<220> FEATURE:
<223> OTHER INFORMATION: Reverse primer

<400> SEQUENCE: 244
gattcgatga ttcactgaa                                                    19

<210> SEQ ID NO 245
<211> LENGTH: 16
<212> TYPE: DNA
<213> ORGANISM: Artificial sequence
<220> FEATURE:
<223> OTHER INFORMATION: Forward primer

<400> SEQUENCE: 245
aatgtgaatt gcagaa                                                       16

<210> SEQ ID NO 246
<211> LENGTH: 13
<212> TYPE: DNA
<213> ORGANISM: Artificial sequence
<220> FEATURE:
<223> OTHER INFORMATION: Probe

<400> SEQUENCE: 246
gtgaatcatc gaa                                                          13

<210> SEQ ID NO 247
<211> LENGTH: 12
<212> TYPE: DNA
<213> ORGANISM: Artificial sequence
<220> FEATURE:
<223> OTHER INFORMATION: Reverse primer

<400> SEQUENCE: 247
gggcgcaatg tg                                                           12

<210> SEQ ID NO 248
<211> LENGTH: 20
<212> TYPE: DNA
<213> ORGANISM: Artificial sequence
<220> FEATURE:
<223> OTHER INFORMATION: Forward primer

<400> SEQUENCE: 248
aagtaatgtg aattgcagaa                                                   20

<210> SEQ ID NO 249
<211> LENGTH: 13
<212> TYPE: DNA
<213> ORGANISM: Artificial sequence
<220> FEATURE:
<223> OTHER INFORMATION: Probe

<400> SEQUENCE: 249
gtgaatcatc gaa                                                          13

```
<210> SEQ ID NO 250
<211> LENGTH: 12
<212> TYPE: DNA
<213> ORGANISM: Artificial sequence
<220> FEATURE:
<223> OTHER INFORMATION: Reverse primer

<400> SEQUENCE: 250
cgggcgcaat gt                                                          12

<210> SEQ ID NO 251
<211> LENGTH: 20
<212> TYPE: DNA
<213> ORGANISM: Artificial sequence
<220> FEATURE:
<223> OTHER INFORMATION: Forward primer

<400> SEQUENCE: 251
aagtaatgtg aattgcagaa                                                  20

<210> SEQ ID NO 252
<211> LENGTH: 13
<212> TYPE: DNA
<213> ORGANISM: Artificial sequence
<220> FEATURE:
<223> OTHER INFORMATION: Probe

<400> SEQUENCE: 252
gtgaatcatc gaa                                                         13

<210> SEQ ID NO 253
<211> LENGTH: 14
<212> TYPE: DNA
<213> ORGANISM: Artificial sequence
<220> FEATURE:
<223> OTHER INFORMATION: Reverse primer

<400> SEQUENCE: 253
gagggcgcaa tgtg                                                        14

<210> SEQ ID NO 254
<211> LENGTH: 20
<212> TYPE: DNA
<213> ORGANISM: Artificial sequence
<220> FEATURE:
<223> OTHER INFORMATION: Forward primer

<400> SEQUENCE: 254
aagtaatgtg aattgcagaa                                                  20

<210> SEQ ID NO 255
<211> LENGTH: 13
<212> TYPE: DNA
<213> ORGANISM: Artificial sequence
<220> FEATURE:
<223> OTHER INFORMATION: Probe

<400> SEQUENCE: 255
gtgaatcatc gag                                                         13

<210> SEQ ID NO 256
<211> LENGTH: 17
<212> TYPE: DNA
<213> ORGANISM: Artificial sequence
<220> FEATURE:
<223> OTHER INFORMATION: Reverse primer
```

<400> SEQUENCE: 256
caagttgcgt tcaaaga                                                  17

<210> SEQ ID NO 257
<211> LENGTH: 25
<212> TYPE: DNA
<213> ORGANISM: Artificial sequence
<220> FEATURE:
<223> OTHER INFORMATION: Forward primer

<400> SEQUENCE: 257
tcagtgaatc atcgagtctt tgaac                                         25

<210> SEQ ID NO 258
<211> LENGTH: 14
<212> TYPE: DNA
<213> ORGANISM: Artificial sequence
<220> FEATURE:
<223> OTHER INFORMATION: Probe

<400> SEQUENCE: 258 cccectggta ttcc                                                     14

<210> SEQ ID NO 259
<211> LENGTH: 18
<212> TYPE: DNA
<213> ORGANISM: Artificial sequence
<220> FEATURE:
<223> OTHER INFORMATION: Reverse primer

<400> SEQUENCE: 259
tgcttgaggg cagcaatg                                                 18

<210> SEQ ID NO 260
<211> LENGTH: 23
<212> TYPE: DNA
<213> ORGANISM: Artificial sequence
<220> FEATURE:
<223> OTHER INFORMATION: Forward primer

<400> SEQUENCE: 260
tcgtgaatca tcgaatcttt gaa                                           23

<210> SEQ ID NO 261
<211> LENGTH: 14
<212> TYPE: DNA
<213> ORGANISM: Artificial sequence
<220> FEATURE:
<223> OTHER INFORMATION: Probe

<400> SEQUENCE: 261
ccctctggta ttcc                                                     14

<210> SEQ ID NO 262
<211> LENGTH: 21
<212> TYPE: DNA
<213> ORGANISM: Artificial sequence
<220> FEATURE:
<223> OTHER INFORMATION: Reverse primer

<400> SEQUENCE: 262
ggagaaacga cgctcaaaca g                                             21

<210> SEQ ID NO 263
<211> LENGTH: 25

```
<212> TYPE: DNA
<213> ORGANISM: Artificial sequence
<220> FEATURE:
<223> OTHER INFORMATION: Forward primer

<400> SEQUENCE: 263
ttcagtgaat catcgaatct ttgaa                                          25

<210> SEQ ID NO 264
<211> LENGTH: 13
<212> TYPE: DNA
<213> ORGANISM: Artificial sequence
<220> FEATURE:
<223> OTHER INFORMATION: Probe

<400> SEQUENCE: 264
cccgccaggc tct                                                       13

<210> SEQ ID NO 265
<211> LENGTH: 19
<212> TYPE: DNA
<213> ORGANISM: Artificial sequence
<220> FEATURE:
<223> OTHER INFORMATION: Reverse primer

<400> SEQUENCE: 265
gcatttcgct gcgttcttc                                                 19

<210> SEQ ID NO 266
<211> LENGTH: 25
<212> TYPE: DNA
<213> ORGANISM: Artificial sequence
<220> FEATURE:
<223> OTHER INFORMATION: Forward primer

<400> SEQUENCE: 266
tcagtgaatc atcgaatctt tgaac                                          25

<210> SEQ ID NO 267
<211> LENGTH: 14
<212> TYPE: DNA
<213> ORGANISM: Artificial sequence
<220> FEATURE:
<223> OTHER INFORMATION: Probe

<400> SEQUENCE: 267
cccgccagta ttct                                                      14

<210> SEQ ID NO 268
<211> LENGTH: 22
<212> TYPE: DNA
<213> ORGANISM: Artificial sequence
<220> FEATURE:
<223> OTHER INFORMATION: Reverse primer

<400> SEQUENCE: 268
ggttgtaatg acgctcgaac ag                                             22

<210> SEQ ID NO 269
<211> LENGTH: 24
<212> TYPE: DNA
<213> ORGANISM: Artificial sequence
<220> FEATURE:
<223> OTHER INFORMATION: Forward primer

<400> SEQUENCE: 269
```

```
gcagaattca gtgaatcatc gaat                                              24

<210> SEQ ID NO 270
<211> LENGTH: 14
<212> TYPE: DNA
<213> ORGANISM: Artificial sequence
<220> FEATURE:
<223> OTHER INFORMATION: Probe

<400> SEQUENCE: 270
cccggcagta atct                                                         14

<210> SEQ ID NO 271
<211> LENGTH: 22
<212> TYPE: DNA
<213> ORGANISM: Artificial sequence
<220> FEATURE:
<223> OTHER INFORMATION: Reverse primer

<400> SEQUENCE: 271
gaggttcgag ggttgaaatg ac                                                22

<210> SEQ ID NO 272
<211> LENGTH: 22
<212> TYPE: DNA
<213> ORGANISM: Artificial sequence
<220> FEATURE:
<223> OTHER INFORMATION: Forward primer

<400> SEQUENCE: 272
ccgtgaatca tcgaatcttt ga                                                22

<210> SEQ ID NO 273
<211> LENGTH: 14
<212> TYPE: DNA
<213> ORGANISM: Artificial sequence
<220> FEATURE:
<223> OTHER INFORMATION: Probe

<400> SEQUENCE: 273
ccctctggta ttcc                                                         14

<210> SEQ ID NO 274
<211> LENGTH: 18
<212> TYPE: DNA
<213> ORGANISM: Artificial sequence
<220> FEATURE:
<223> OTHER INFORMATION: Reverse primer

<400> SEQUENCE: 274
gcgcttgagg gttgcaat                                                     18

<210> SEQ ID NO 275
<211> LENGTH: 22
<212> TYPE: DNA
<213> ORGANISM: Artificial sequence
<220> FEATURE:
<223> OTHER INFORMATION: Forward primer

<400> SEQUENCE: 275
tcgagtcttt gaacgcaact tg                                                22

<210> SEQ ID NO 276
<211> LENGTH: 14
<212> TYPE: DNA
<213> ORGANISM: Artificial sequence
```

```
<220> FEATURE:
<223> OTHER INFORMATION: Probe

<400> SEQUENCE: 276
ccctttggta ttcc                                                         14

<210> SEQ ID NO 277
<211> LENGTH: 23
<212> TYPE: DNA
<213> ORGANISM: Artificial sequence
<220> FEATURE:
<223> OTHER INFORMATION: Reverse primer

<400> SEQUENCE: 277
cgagggattg agattttcat gac                                               23

<210> SEQ ID NO 278
<211> LENGTH: 22
<212> TYPE: DNA
<213> ORGANISM: Artificial sequence
<220> FEATURE:
<223> OTHER INFORMATION: Gram-negative and Gram-positive reverse primer

<400> SEQUENCE: 278
gtattaccgc ggctgctggc ac                                                22

<210> SEQ ID NO 279
<211> LENGTH: 21
<212> TYPE: DNA
<213> ORGANISM: Artificial sequence
<220> FEATURE:
<223> OTHER INFORMATION: Chlamydia and Chlamydophila forward primer

<400> SEQUENCE: 279
actcctacgg gaggctgcag t                                                 21

<210> SEQ ID NO 280
<211> LENGTH: 22
<212> TYPE: DNA
<213> ORGANISM: Artificial sequence
<220> FEATURE:
<223> OTHER INFORMATION: Chlamydia and Chlamydophila reverse primer

<400> SEQUENCE: 280
gtattaccgc ggcagctggc ac                                                22

<210> SEQ ID NO 281
<211> LENGTH: 13
<212> TYPE: DNA
<213> ORGANISM: Artificial sequence
<220> FEATURE:
<223> OTHER INFORMATION: Gram-positive probe Group 1

<400> SEQUENCE: 281
agcaacgccg cgt                                                          13

<210> SEQ ID NO 282
<211> LENGTH: 13
<212> TYPE: DNA
<213> ORGANISM: Artificial sequence
<220> FEATURE:
<223> OTHER INFORMATION: Gram-positive probe Group 2

<400> SEQUENCE: 282
agcgacgccg cgt                                                          13
```

```
<210> SEQ ID NO 283
<211> LENGTH: 13
<212> TYPE: DNA
<213> ORGANISM: Artificial sequence
<220> FEATURE:
<223> OTHER INFORMATION: Gram-negative probe Group 3

<400> SEQUENCE: 283
agccatgccg cgt                                                          13

<210> SEQ ID NO 284
<211> LENGTH: 13
<212> TYPE: DNA
<213> ORGANISM: Artificial sequence
<220> FEATURE:
<223> OTHER INFORMATION: Gram-negative probe Group 4

<400> SEQUENCE: 284
agcaatgccg cgt                                                          13

<210> SEQ ID NO 285
<211> LENGTH: 13
<212> TYPE: DNA
<213> ORGANISM: Artificial sequence
<220> FEATURE:
<223> OTHER INFORMATION: Gram-negative probe Group 5

<400> SEQUENCE: 285
agccataccg cgt                                                          13

<210> SEQ ID NO 286
<211> LENGTH: 13
<212> TYPE: DNA
<213> ORGANISM: Artificial sequence
<220> FEATURE:
<223> OTHER INFORMATION: Gram-negative probe Group 6

<400> SEQUENCE: 286
agccaagtag cgt                                                          13

<210> SEQ ID NO 287
<211> LENGTH: 13
<212> TYPE: DNA
<213> ORGANISM: Artificial sequence
<220> FEATURE:
<223> OTHER INFORMATION: Gram-negative probe Group 7

<400> SEQUENCE: 287
agccaagtcg cgt                                                          13

<210> SEQ ID NO 288
<211> LENGTH: 12
<212> TYPE: DNA
<213> ORGANISM: Artificial sequence
<220> FEATURE:
<223> OTHER INFORMATION: Gram-positive probe Group 1a

<400> SEQUENCE: 288
aaccagaaag cc                                                           12

<210> SEQ ID NO 289
<211> LENGTH: 12
<212> TYPE: DNA
<213> ORGANISM: Artificial sequence
<220> FEATURE:
<223> OTHER INFORMATION: Gram-positive probe Group 1b
```

```
<400> SEQUENCE: 289
aaccagaaag gg                                                          12

<210> SEQ ID NO 290
<211> LENGTH: 12
<212> TYPE: DNA
<213> ORGANISM: Artificial sequence
<220> FEATURE:
<223> OTHER INFORMATION: Gram-positive probe Group 1c

<400> SEQUENCE: 290
aaccagaaag tc                                                          12

<210> SEQ ID NO 291
<211> LENGTH: 12
<212> TYPE: DNA
<213> ORGANISM: Artificial sequence
<220> FEATURE:
<223> OTHER INFORMATION: Gram-negative probe Group 1d

<400> SEQUENCE: 291
aacgaataag ca                                                          12

<210> SEQ ID NO 292
<211> LENGTH: 12
<212> TYPE: DNA
<213> ORGANISM: Artificial sequence
<220> FEATURE:
<223> OTHER INFORMATION: Gram-positive probe Group 1e

<400> SEQUENCE: 292
aaggaggaag cc                                                          12

<210> SEQ ID NO 293
<211> LENGTH: 12
<212> TYPE: DNA
<213> ORGANISM: Artificial sequence
<220> FEATURE:
<223> OTHER INFORMATION: Gram-positive probe Group 1f

<400> SEQUENCE: 293
aatcagaaag cc                                                          12

<210> SEQ ID NO 294
<211> LENGTH: 12
<212> TYPE: DNA
<213> ORGANISM: Artificial sequence
<220> FEATURE:
<223> OTHER INFORMATION: Gram-positive probe Group 1g

<400> SEQUENCE: 294
gaagaataag ct                                                          12

<210> SEQ ID NO 295
<211> LENGTH: 12
<212> TYPE: DNA
<213> ORGANISM: Artificial sequence
<220> FEATURE:
<223> OTHER INFORMATION: Gram-negative probe Group 1h

<400> SEQUENCE: 295
gaatagaaag cc                                                          12

<210> SEQ ID NO 296
```

-continued

```
<211> LENGTH: 12
<212> TYPE: DNA
<213> ORGANISM: Artificial sequence
<220> FEATURE:
<223> OTHER INFORMATION: Gram-positive probe Group 1i

<400> SEQUENCE: 296
gaggaggaag cc                                                          12

<210> SEQ ID NO 297
<211> LENGTH: 12
<212> TYPE: DNA
<213> ORGANISM: Artificial sequence
<220> FEATURE:
<223> OTHER INFORMATION: Gram-positive probe Group 1j

<400> SEQUENCE: 297
taccagaaag cc                                                          12

<210> SEQ ID NO 298
<211> LENGTH: 12
<212> TYPE: DNA
<213> ORGANISM: Artificial sequence
<220> FEATURE:
<223> OTHER INFORMATION: Gram-positive probe Group 1k

<400> SEQUENCE: 298
taccagaaag gg                                                          12

<210> SEQ ID NO 299
<211> LENGTH: 12
<212> TYPE: DNA
<213> ORGANISM: Artificial sequence
<220> FEATURE:
<223> OTHER INFORMATION: Gram-positive probe Group 1l

<400> SEQUENCE: 299
tgtgaggaag cc                                                          12

<210> SEQ ID NO 300
<211> LENGTH: 12
<212> TYPE: DNA
<213> ORGANISM: Artificial sequence
<220> FEATURE:
<223> OTHER INFORMATION: Gram-positive probe Group 2a

<400> SEQUENCE: 300
agataagaag ca                                                          12

<210> SEQ ID NO 301
<211> LENGTH: 12
<212> TYPE: DNA
<213> ORGANISM: Artificial sequence
<220> FEATURE:
<223> OTHER INFORMATION: Gram-positive probe Group 2b

<400> SEQUENCE: 301
gcagaagaag ca                                                          12

<210> SEQ ID NO 302
<211> LENGTH: 12
<212> TYPE: DNA
<213> ORGANISM: Artificial sequence
<220> FEATURE:
<223> OTHER INFORMATION: Gram-positive probe Group 2c

<400> SEQUENCE: 302
```
gcagaagaag cg 12

<210> SEQ ID NO 303
<211> LENGTH: 12
<212> TYPE: DNA
<213> ORGANISM: Artificial sequence
<220> FEATURE:
<223> OTHER INFORMATION: Gram-negative probe Group 2d

<400> SEQUENCE: 303
gcctaaagca cc 12

<210> SEQ ID NO 304
<211> LENGTH: 12
<212> TYPE: DNA
<213> ORGANISM: Artificial sequence
<220> FEATURE:
<223> OTHER INFORMATION: Gram-positive probe Group 2e

<400> SEQUENCE: 304
ggagaagaag ca 12

<210> SEQ ID NO 305
<211> LENGTH: 12
<212> TYPE: DNA
<213> ORGANISM: Artificial sequence
<220> FEATURE:
<223> OTHER INFORMATION: Gram-positive probe Group 2f

<400> SEQUENCE: 305
ggataagaag ca 12

<210> SEQ ID NO 306
<211> LENGTH: 12
<212> TYPE: DNA
<213> ORGANISM: Artificial sequence
<220> FEATURE:
<223> OTHER INFORMATION: Gram-positive probe Group 2g

<400> SEQUENCE: 306
ggggaagaag cg 12

<210> SEQ ID NO 307
<211> LENGTH: 12
<212> TYPE: DNA
<213> ORGANISM: Artificial sequence
<220> FEATURE:
<223> OTHER INFORMATION: Gram-negative probe Group 2h

<400> SEQUENCE: 307
ggtaaagaag ca 12

<210> SEQ ID NO 308
<211> LENGTH: 12
<212> TYPE: DNA
<213> ORGANISM: Artificial sequence
<220> FEATURE:
<223> OTHER INFORMATION: Gram-positive probe Group 2i

<400> SEQUENCE: 308
gtagaagaag ca 12

<210> SEQ ID NO 309
<211> LENGTH: 12
<212> TYPE: DNA

```
<213> ORGANISM: Artificial sequence
<220> FEATURE:
<223> OTHER INFORMATION: Gram-positive probe Group 2j

<400> SEQUENCE: 309
gttgaagaag ca                                                           12

<210> SEQ ID NO 310
<211> LENGTH: 12
<212> TYPE: DNA
<213> ORGANISM: Artificial sequence
<220> FEATURE:
<223> OTHER INFORMATION: Gram-negative probe Group 3a

<400> SEQUENCE: 310
acagaagaag ca                                                           12

<210> SEQ ID NO 311
<211> LENGTH: 12
<212> TYPE: DNA
<213> ORGANISM: Artificial sequence
<220> FEATURE:
<223> OTHER INFORMATION: Gram-negative probe Group 3b

<400> SEQUENCE: 311
acagaataag ca                                                           12

<210> SEQ ID NO 312
<211> LENGTH: 12
<212> TYPE: DNA
<213> ORGANISM: Artificial sequence
<220> FEATURE:
<223> OTHER INFORMATION: Gram-negative probe Group 3c

<400> SEQUENCE: 312
gaagaataag ca                                                           12

<210> SEQ ID NO 313
<211> LENGTH: 12
<212> TYPE: DNA
<213> ORGANISM: Artificial sequence
<220> FEATURE:
<223> OTHER INFORMATION: Gram-negative probe Group 3d

<400> SEQUENCE: 313
gcagaagaag ca                                                           12

<210> SEQ ID NO 314
<211> LENGTH: 12
<212> TYPE: DNA
<213> ORGANISM: Artificial sequence
<220> FEATURE:
<223> OTHER INFORMATION: Gram-negative probe Group 3e

<400> SEQUENCE: 314
gcagaataag ca                                                           12

<210> SEQ ID NO 315
<211> LENGTH: 12
<212> TYPE: DNA
<213> ORGANISM: Artificial sequence
<220> FEATURE:
<223> OTHER INFORMATION: Gram-negative probe Group 3f

<400> SEQUENCE: 315
ggagaagaag cc                                                           12
```

```
<210> SEQ ID NO 316
<211> LENGTH: 12
<212> TYPE: DNA
<213> ORGANISM: Artificial sequence
<220> FEATURE:
<223> OTHER INFORMATION: Gram-negative probe Group 3g

<400> SEQUENCE: 316
taagaataag ga                                                        12

<210> SEQ ID NO 317
<211> LENGTH: 12
<212> TYPE: DNA
<213> ORGANISM: Artificial sequence
<220> FEATURE:
<223> OTHER INFORMATION: Gram-negative probe Group 4a

<400> SEQUENCE: 317
acagaagaac ca                                                        12

<210> SEQ ID NO 318
<211> LENGTH: 12
<212> TYPE: DNA
<213> ORGANISM: Artificial sequence
<220> FEATURE:
<223> OTHER INFORMATION: Gram-negative probe Group 4b

<400> SEQUENCE: 318
gaagaataag ca                                                        12

<210> SEQ ID NO 319
<211> LENGTH: 12
<212> TYPE: DNA
<213> ORGANISM: Artificial sequence
<220> FEATURE:
<223> OTHER INFORMATION: Gram-negative probe Group 4c

<400> SEQUENCE: 319
gcagaagaag ca                                                        12

<210> SEQ ID NO 320
<211> LENGTH: 12
<212> TYPE: DNA
<213> ORGANISM: Artificial sequence
<220> FEATURE:
<223> OTHER INFORMATION: Gram-negative probe Group 6a

<400> SEQUENCE: 320
catgaataag ga                                                        12

<210> SEQ ID NO 321
<211> LENGTH: 12
<212> TYPE: DNA
<213> ORGANISM: Artificial sequence
<220> FEATURE:
<223> OTHER INFORMATION: Gram-negative probe Group 6b

<400> SEQUENCE: 321
tacgaataag ga                                                        12

<210> SEQ ID NO 322
<211> LENGTH: 12
<212> TYPE: DNA
<213> ORGANISM: Artificial sequence
<220> FEATURE:
```

<223> OTHER INFORMATION: Gram-negative probe Group 6c

<400> SEQUENCE: 322
tatgaataag ga                                                      12

<210> SEQ ID NO 323
<211> LENGTH: 12
<212> TYPE: DNA
<213> ORGANISM: Artificial sequence
<220> FEATURE:
<223> OTHER INFORMATION: Gram-negative probe Group 6d

<400> SEQUENCE: 323
ttagaataag ga                                                      12

<210> SEQ ID NO 324
<211> LENGTH: 12
<212> TYPE: DNA
<213> ORGANISM: Artificial
<220> FEATURE:
<223> OTHER INFORMATION: TaqMan MGB FAM probe

<400> SEQUENCE: 324
ttccggcatc ga                                                      12

<210> SEQ ID NO 325
<211> LENGTH: 12
<212> TYPE: DNA
<213> ORGANISM: Artificial
<220> FEATURE:
<223> OTHER INFORMATION: TaqMan MGB VIC probe

<400> SEQUENCE: 325
ttctcgcatc ga                                                      12

<210> SEQ ID NO 326
<211> LENGTH: 23
<212> TYPE: DNA
<213> ORGANISM: Artificial
<220> FEATURE:
<223> OTHER INFORMATION: Yeast and fungal species forward primer

<400> SEQUENCE: 326
caaaactttc aacaacggat ctc                                          23

<210> SEQ ID NO 327
<211> LENGTH: 23
<212> TYPE: DNA
<213> ORGANISM: Artificial
<220> FEATURE:
<223> OTHER INFORMATION: Yeast and fungal species forward primer

<400> SEQUENCE: 327
taaaactttc aacaacggat ctc                                          23

<210> SEQ ID NO 328
<211> LENGTH: 18
<212> TYPE: DNA
<213> ORGANISM: Artificial
<220> FEATURE:
<223> OTHER INFORMATION: Yeast and fungal species reverse primer

<400> SEQUENCE: 328
gacgctcgga caggcatg                                                18

```
<210> SEQ ID NO 329
<211> LENGTH: 18
<212> TYPE: DNA
<213> ORGANISM: Artificial
<220> FEATURE:
<223> OTHER INFORMATION: Yeast and fungal species reverse primer

<400> SEQUENCE: 329
gacgctcaaa caggcatg                                                    18

<210> SEQ ID NO 330
<211> LENGTH: 24
<212> TYPE: DNA
<213> ORGANISM: Artificial
<220> FEATURE:
<223> OTHER INFORMATION: Forward primer

<400> SEQUENCE: 330
aactttcaac aacggatctc ttgg                                             24

<210> SEQ ID NO 331
<211> LENGTH: 24
<212> TYPE: DNA
<213> ORGANISM: Artificial
<220> FEATURE:
<223> OTHER INFORMATION: Forward primer

<400> SEQUENCE: 331 aactttaac aacggatctc ttgg                                              24

<210> SEQ ID NO 332
<211> LENGTH: 24
<212> TYPE: DNA
<213> ORGANISM: Artificial
<220> FEATURE:
<223> OTHER INFORMATION: Reverse primer

<400> SEQUENCE: 332
gcgttcaaag attcgatgat tcac                                             24

<210> SEQ ID NO 333
<211> LENGTH: 24
<212> TYPE: DNA
<213> ORGANISM: Artificial
<220> FEATURE:
<223> OTHER INFORMATION: Reverse primer

<400> SEQUENCE: 333
gcgttcaaag actcgatgat tcac                                             24

<210> SEQ ID NO 334
<211> LENGTH: 15
<212> TYPE: DNA
<213> ORGANISM: Artificial
<220> FEATURE:
<223> OTHER INFORMATION: Probe

<400> SEQUENCE: 334
aaatgcgata cgtaa                                                       15

<210> SEQ ID NO 335
<211> LENGTH: 13
<212> TYPE: DNA
<213> ORGANISM: Artificial
<220> FEATURE:
<223> OTHER INFORMATION: Probe
```

```
<400> SEQUENCE: 335
atgcgataag taa                                                              13
```

MICROBIAL MARKERS AND USES THEREFOR

RELATED APPLICATIONS

This application is a U.S. national phase of International Application No. PCT/AU2014/050053, filed May 29, 2014, entitled "Microbial Markers and Uses Therefor," which application claims priority to Australian Provisional Application No. 2013901907, entitled "Microbial Markers and Uses Therefor," filed on May 29, 2013, and to Australian Provisional Application No. 2013903914, entitled "Microbial Markers and Uses Therefor," filed on Oct. 11, 2013, the subject matter of each of which is incorporated herein by reference in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is DAVI_038_00US_ST25.txt. The text file is 65 KB, was created on Nov. 25, 2015, and is being submitted electronically via EFS-Web.

FIELD OF THE INVENTION

This invention relates generally to methods for identifying and/or classifying microbes using one or more single nucleotide polymorphisms (SNPs) in 16S ribosomal RNA (16S rRNA) of prokaryotes and/or one or more SNPs in 5.8S ribosomal RNA (5.8S rRNA) of eukaryotes. The invention also relates to probes, primers and kits that are useful in the methods of the invention.

BACKGROUND OF THE INVENTION

Prokaryotes are organisms that lack a nucleus or any membrane-bound organelles and are generally unicellular. Most prokaryotes can be broadly categorized into Gram-positive or Gram-negative, based on the peptidoglycan of Gram-positive microbes' outer cell wall staining with crystal violet and safranin (or carbol fuchsin), although some prokaryotes have a variable Gram stain. Prokaryotes contain 16S (Svedberg unit) rRNA, which is a component of the 30S small subunit of prokaryotic ribosomes. 16S rRNA is approximately 1500 nucleotides in length, encoded by the 16S rRNA gene (sometimes referred to as 16S rDNA), which is generally part of a co-transcribed operon also containing the 23S and 5S rRNA genes. The DNA sequence of the 16S rRNA genes (and thus the RNA sequence of the 16S rRNA molecules) is highly conserved between prokaryotes, although there are regions of variation (Weisburg W G, et al., (1991) *J Bacterial.* 173 (2): 697-703).

In contrast, eukaryotes are organisms containing membranes within cells, in particular a nuclear membrane containing DNA, and can be unicellular (e.g. most yeasts) or multicellular. All eukaryotes contain 5.8S rRNA, which is a component of the large 60S small subunit of eukaryotic ribosomes. Its length varies between species but it is usually around 160 nucleotides. The 5.8S rRNA gene (often referred to as 5.8S rDNA) is part of the 45S rDNA, which also contains the 18S and 28S rRNA genes separated by 2 internally transcribed spacers. In humans, the 45S rDNA is present in 5 clusters on 5 different chromosomes, each cluster having 30-40 repeats. The 45S rDNA is transcribed by RNA polymerase I as a single transcription unit (45S), which is then processed to produce the 5.8S, 18S and 28S rRNA molecules. The sequence of 5.8S rRNA gene (and thus the sequence of the 5.8S rRNA molecule) is highly conserved between eukaryotes, although there are regions of variation that can be used in phylogenetic studies (Field K. G et al., (1988) Science 239(4841): 748-753).

It is often desirable to classify prokaryotic and eukaryotic microbes in a sample. For example, the classification of microbes that contaminate solutions, materials or foodstuffs, and pose a threat to the wellbeing of other organisms or the quality of production of solutions or materials or foodstuffs, assists in the identification of pathogens, and management, control, eradication, elimination, limitation or removal of such microbes. It may also be desirable to determine the natural microbial population (the "microbiome") of a sample, such as for ecological studies of microbial diversity, phylum spectrum, relative phylum abundance (Gehron, M. J. et al. (1984) J. Microbiol. Methods 2, 165-176; Claesson, M. J. et al. (2010) Nucl Acids Res 38(22), e200), or for determining or monitoring deviation of the microbiome balance from a normal state in pathological conditions, such as enteric (e.g. gastroenteritis, rumenitis, colitis, typhlitis; Bailey, S. R., et al. (2003). Appl. Environ. Microbiol. 69, 2087-2093), respiratory (e.g. pneumonia, bronchitis, mucositis), urinary (e.g. cystitis, nephritis, urethritis) and skin (e.g. wounds, pruritis, dermatitis, psoriasis) disorders including viral, fungal, parasitic and bacterial infections. It may also be useful to determine the microbiome of a sample in response to therapies or treatments or modulations such as the use of antibiotics, steroids, immune modulators, pre and probiotics, soil or water treatments, filtration, sterilization procedures, antiseptics.

Current microorganism classification schemes include, but are not limited to, phenotypic, chemotypic and genotypic. Within phenotypic classification are the sub-classification methods of Gram staining, growth requirements, biochemical reactions, antibiotic sensitivity, serological systems, environmental reservoirs (or where such microbes preferentially live and grow). Within chemotypic classification are the sub-classification methods using various technologies that can include analysis of microbial components consisting of sugars, fats, proteins or minerals. Within genotypic classification are the sub-classification methods of restriction fragment length analysis and ribosomal RNA sequence analysis, both reliant on different levels of interpretation of genetic material.

Phenotypic classification methods can suffer from a lack of sensitivity and specificity, are not rapid or easy, and have limited ability to be automated. Chemotypic methods also lack sensitivity and specificity and currently are not cost effective. Genotypic methods are often more sensitive, rapid, easy to perform, cost effective, and are able to be automated and multiplexed.

Various attempts have been made to differentiate Gram-positive and Gram-negative prokaryotes using nucleic acid molecular techniques (see e.g. Bispo, P. J. M., et al., (2011) Ophthalmol. Vis. Sci. 52, 873-881; Klaschik, S. et al. (2002) Journal of Clinical Microbiology 40, 4304-4307; Shigemura, K. et al. (2005) Clin Exp Med 4, 196-201 (2005); Carroll, N. M. et al. (2005) Journal of Clinical Microbiology 38, 1753-1757). These attempts are mostly limited in scope by the number of pathogens they detect and differentiate because of the focus on a limited number of particular pathological specimens (blood, urine, ophthalmic) and pathogen types. The implications of this deficiency could have serious downstream ramifications in, for example, a patient with a prokaryotic infection not able to be detected.

Such reported methods are generally not quantitative, which can be important. Samples rarely consist of a single type of organism and, for pathology samples, are often contaminated with potentially irrelevant and non-pathogenic prokaryotes. In addition, very few solutions or materials or foodstuffs are free of microbes and it is the number of microbes present that determines the level of contamination, lack of quality, or threat to the wellbeing of other organisms. Various methods of quantitation of microbes exist, including but not limited to, plating onto growth media and counting microbial colonies, the use of spectrophotometry to determine turbidity and the use of nanoparticles (Zhao X et al., A rapid bioassay for single bacterial cell quantitation using bioconjugated nanoparticles. PNAS, 101(42): 15027-15032. 2004.)

Few existing methods combine genotypic classification with quantification. One such example is Spiro et al., 2000 (A bead-based method for multiplexed identification and quantitation of DNA sequences using flow cytometry. App Env Micro 66(10): 4258-4265). However, this method does not describe the genotypic classification of microbes. Rather, it demonstrates the ability of bead technology to identify particular DNA sequences in an heterogenous mixture. More recent developments such as Next Generation Sequencing (NGS) hold promise for generating large quantities of data on the microbiome of samples (Claesson, M. J. et al. Comparison of two next-generation sequencing technologies for resolving highly complex microbiota composition using tandem variable 16S rRNA gene regions. Nucl Acids Res 38(22), e200 (2010)). However, these technologies currently suffer from a number of limitations especially with respect to determining the simple Gram status of a sample including: lack of sensitivity (samples require PCR amplification prior and in some instances library manufacture prior to sequencing), cost, PCR bias, sequencing inaccuracies, and complex software and algorithms required to interpret the large amount of data generated.

Thus, in the field of microbiology, there is a need for a method of broad microbial classification and quantitation, which is suitably in the form of a single test, that is discriminatory, sensitive, specific, rapid, easy to perform and interpret, inexpensive, lends itself to automation and with the minimum amount of multiplexing, and preferentially performed in the field, remotely, or beside a patient or at least inexpensively in a laboratory. Such a test would allow for rapid and informed management, monitoring, enumeration, quantitation, differentiation, control, eradication, elimination, limitation or removal of such microbes.

In particular, there is a need for a method of broad microbial classification and quantitation of microbes of health significance, such as those that cause sepsis in humans.

Systemic inflammatory response syndrome (SIRS) is an overwhelming whole body reaction that may have an infectious aetiology or non-infectious aetiology (i.e. infection-negative SIRS, or inSIRS). Sepsis is SIRS that occurs during infection. Sepsis in this instance is diagnosed by a clinician (when there is suspected infection) or through culture of an organism. Both SIRS and sepsis are defined by a number of non-specific host response parameters including changes in heart and respiratory rate, body temperature and white cell counts (Levy et al., (2003) Critical Care Medicine 31: 1250-1256; Reinhart et al., (2012) Clinical Microbiology Reviews 25(4): 609-634)

Sepsis and SIRS have had an increasing impact on health care systems worldwide. In the United States from 1993 to 2009, the number of sepsis-related hospital stays more than doubled, increasing by 153% overall, with an average annual increase of 6%. In 2009, 4,600 new patients per day were treated in hospital for sepsis, and nearly one in 23 patients in hospital had sepsis. The in-hospital sepsis mortality rate was approximately 16 percent, which has not changed since 2000, and is more than eight times higher than the mortality rate for other hospital stays. Sepsis was also the most expensive reason for hospitalization in 2009 in the United States, totaling an estimated $15.4 billion in aggregate hospital costs.

SIRS can be triggered by a number of insults including local or systemic infection, trauma, burns, surgery and sterile inflammation and consists of aberrations in at least two of four nominated clinical criteria (temperature, heart rate, respiratory rate and white blood cells). In a comprehensive survey conducted by Rangel-Fausto et al., 68% of admitted patients over a 9-month period met at least two criteria for SIRS and the incidence density of SIRS in the surveyed hospital across different wards was determined to be between 320 and 857 episodes per 1000 patient days (Rangel-Frausto et al. (1995) JAMA 273(2): 117-123. Thus, SIRS has a high incidence in hospitals.

Confirmation of a diagnosis of sepsis usually requires isolation and identification of live pathogens from blood samples using culture, but this technique has its limitations. Microbial culture usually takes a number of days to obtain a positive result and over five days to confirm a negative result. Further, culture has problems with reliability with respect to sensitivity, specificity and predictive value (Jean-Louis Vincent et al., (2006) Critical Care Medicine 34: 344-353; Lamy et al., (2002) Clinical Infectious Diseases 35: 842-850. A large percentage of blood cultures drawn from patients with suspected sepsis are either negative or contaminated (Coburn et al. (2012) JAMA 308, 502-511). Over 90% of all blood cultures drawn from patients are negative. Of the small percentage of blood cultures that are positive (4-7%) up to half are due to contaminants (false positives) as a result of poor sampling technique. False-positive blood cultures can result in an increase in total hospital charges, an increase in median length of hospital stay, and an increase in laboratory charges. Therefore, poor diagnostic procedures for determining the presence of sepsis, including sampling and testing, places a significant financial burden on the healthcare system. Other potential consequences of the diagnostic limitations of blood culture in patients suspected of having sepsis include the use and misuse of broad-spectrum antibiotics, the development of antimicrobial resistance and *Clostridium difficile* infection, adverse reactions, and increased treatment costs.

Alternative diagnostic approaches to SIRS and sepsis have been extensively investigated and generally fall into one of two categories: pathogen detection, or determination of host response using biomarkers. Promising rapid and sensitive pathogen detection technology includes the use of Polymerase Chain Reaction (PCR), for example, Roche's Lightcycler® SeptiFast, especially when used in conjunction with blood culture (Bauer and Reinhart (2010) International Journal of Medical Microbiology 300: 411-413; Uwe Lodes et al. (2012) Langenbeck's Archives of Surgery 397: 447-455; and Pasqualini et al., (2012) Journal of Clinical Microbiology 50: 1285-1288). A current quandary when using this technology is how best to interpret early positive PCR results in the absence of blood culture results or relevant clinical signs. Such tests are complex and involve multiple multiplexed reactions. Further, accurate quantitation of microorganisms is important in determining the relevance of pathogen detection when using sensitive assay methods. A further technical difficulty associated with PCR-based pathogen detection, especially in peripheral blood samples, is the lack of ability to detect small quantities of pathogen nucleic acid in a background of host nucleic acid.

Given that the majority of patients (>80%) admitted to the tertiary care ICU setting have SIRS, of varying aetiologies including following major surgery, it is of enormous clinical importance that those patients who have a suspected infection or are at high risk of infection can be identified early and be graded and monitored, in order to initiate evidence-based and goal-orientated medical therapy (Kumar, A. et al. (2006) Critical Care Medicine 34, 1589-1596). This is critical, as the acute management plans for SIRS with and without infection are very different. Dependence on empiric treatment means that some patients may be receiving excessive antibiotics while others are receiving treatment (e.g. corticosteroids) that is immunosuppressive because a clear site of infection has not been identified. Thus, there is a continued need for a test that is able to differentiate infection-negative SIRS (inSIRS) from infection-positive-SIRS (e.g. sepsis), quantitate microbial DNA, differentiate prokaryotic and eukaryotic DNA and differentiate Gram-positive from Gram-negative DNA across a broad range of potential pathogens, so as to assist clinicians in making appropriate patient management and treatment decisions in such patients.

There is also a need for rapid assays and tests that further classify bacteria beyond Gram-positive and Gram-negative, so as to assist the clinician to determine an appropriate course of treatment. Traditional methods typically require culturing the bacteria, typically for 2 to 10 days, depending on the species of bacteria (e.g. slow-growing and fastidious organisms such as mycobacteria can take 10 days). This culturing of bacteria, in particular anaerobic bacteria, can be labour intensive, burdensome and require special equipment and reagents. Once cultured, the first procedure the laboratory generally performs is a Gram stain and morphology assessment, the results of which are reported to clinicians promptly. A Gram stain allows for classification of the bacteria grown, if grown, into the following groups: Gram-positive cocci, Gram-positive bacilli, Gram-negative bacilli, Gram-negative cocci, anaerobes, and *Candida* spp. Such information, in combination with other data, may be sufficient to make an appropriate antibiotic choice. Further tests can then help determine antibiotic sensitivity and species identification, although these tests are not always performed due to cost and logistics.

Because of the high mortality associated with bacteraemia, the dangers of under treating some infections, or concern about using inappropriate antibiotics, clinicians tend to order blood cultures liberally and put patients on empirical antibiotics soon after blood cultures are taken. Thus, patients with suspected sepsis are generally put on empirical antibiotics shortly after blood cultures are taken and prior to receiving any culture or further test results. The choice of empirical antibiotic used depends on factors such as: site of infection (e.g. respiratory, skin, urinary, gastro-intestinal etc), whether the infection is hospital acquired or community acquired, epidemiology of pathogens, hospital microbial resistance patterns, whether the patient has been or is on antibiotics, patient allergies, and patient co-morbidities and known antibiotic toxicities. Guidance to clinicians on choice of empirical antibiotics is often available through hospital publications, health maintenance organisations (HMOs), specialist organisations and the scientific literature (by example see http://www.clevelandclinicmeded.com/medicalpubs/antimicrobial-guidelines/; http://www.uphs.upenn.edu/bugdrug/; Huttner B, Jones M, Huttner A, Rubin M, Samore M H (2013) Antibiotic prescription practices for pneumonia, skin and soft tissue infections and urinary tract infections throughout the US Veterans Affairs system. J Antimicrob Chemother 68: 2393-2399. doi:10.1093/jac/dkt171; Snydman D R (2012) Empiric antibiotic selection strategies for healthcare-associated pneumonia, intra-abdominal infections, and catheter-associated bacteremia. J Hosp Med 7 Suppl 1: S2S12. doi:10.1002/jhm.980; Maxwell D J, Easton K L, Brien J-A E, Kaye K I (2005) Antibiotic guidelines in NSW hospitals. Aust Health Rev 29: 416-421.). However, because of the development of microbial antibiotic resistance, the aim and purpose of microbiology testing is to provide evidence and guidance on the appropriate use of narrow spectrum antibiotics and subsequently the reduction in the use of empirical broad-spectrum antibiotics. Therefore, a test that can provide timely guidance on the appropriate use of narrow spectrum antibiotics is needed, preferably without having to grow the organism.

SUMMARY OF THE INVENTION

The present invention is based on the determination that one or more single nucleotide polymorphisms within rRNA genes of bacteria and fungi are unique to Gram-positive bacteria, Gram-negative bacteria or fungi, and in some instances are unique to particular species or groups of species. Based on this determination, the inventors have developed various methods and kits that take advantage of these differentiating SNPs to identify the presence or absence of a bacterium and/or a fungus in a sample, differentiate the bacterium from the fungus, classify the bacterium as Gram-positive or Gram-negative, classify the bacterium as a member of a particular group of pathogens, identify the species of bacterium or identify the bacterium as one of several possible species, and/or identify the species of fungus. In particular instances, the methods and kits also facilitate quantitation of the microorganism in the sample.

While some of the methods and kits of the invention can be used to determine the presence of, differentiate and/or identify bacteria or fungi in any sample, in some embodiments the methods and kits of the present invention are particularly useful for determining the presence of, differentiating and/or identifying bacteria or fungi in a biological sample, such as a biological sample from a mammalian (e.g., human) subject. Even more particularly, the methods and kits are suitable for analysing blood from a subject with SIRS, to determine whether the SIRS has an infectious origin, i.e. whether the subject has sepsis, or whether the SIRS is infection-negative, or analysing blood from a subject suspected of having sepsis to determine whether the subject does indeed have sepsis. In instances where the subject has sepsis resulting from a bacterial or fungal infection, the methods and kits of the present invention can be used to determine whether the bacterium is Gram-positive or Gram-negative; classify or categorize the bacterium, for example as aerobic or anaerobic or as a member of a major antibiotic treatment group; identify the species of bacterium or identify the bacterium as one of several possible species; and/or identify the species of fungus present in the blood of the subject. Furthermore, the severity of the infection, as measured by the number of bacteria or fungi in the blood, can also be determined. As a result, the methods and kits of the present invention can be used to guide a clinician as to whether or not to hospitalize the subject, and what course of treatment, if any, is required. The methods and kits of the present invention also can be used to guide a clinician on what further tests should be performed to determine antibiotic resistance, microbial virulence and, if necessary, pinpoint the bacterial species. Because of the speed at which the methods of the invention can be performed, these decisions can be made within hours, rather than days, of the subject first being assessed by the clinician. Thus, the methods and kits of the present invention can reduce the unnecessary hospitalization, unnecessary administration of antibiotics and/or administration of ineffective or unsuitable antibiotics that may be associated with methods of the prior art, and facilitate the rapid implementation of a suitable and effective treatment regimen.

In one aspect, the present invention provides a method for determining the Gram status of a bacterium in a sample, comprising analyzing nucleic acid from the sample for single nucleotide polymorphisms (SNPs) in a 16S rRNA gene, wherein the SNPs are at positions corresponding to positions 396 and 398 of the 16S rRNA gene set forth in SEQ ID NO:1, wherein: the bacterium is determined to be a Gram-negative bacterium when there is a C at position 396 and a T, A or C at position 398; and the bacterium is determined to be a Gram-positive bacterium when there is an A, T or G at position 396 and a C at position 398.

In some embodiments, the bacterium is selected from among *Acinetobacter* spp.; *Actinobaccillus* spp.; *Actinomadura* spp.; *Actinomyces* spp.; *Actinoplanes* spp.; *Aeromonas* spp.; *Agrobacterium* spp.; *Alistipes* spp.; *Anaerococcus* spp.; *Arthrobacter* spp.; *Bacillus* spp.; *Brucella* spp.; *Bulleidia* spp.; *Burkholderia* spp.; *Cardiobacterium* spp.; *Citrobacter* spp.; *Clostridium* spp.; *Corynebacterium* spp.; *Dermatophilus* spp.; *Dorea* spp.; *Edwardsiella* spp.; *Enterobacter* spp.; *Enterococcus* spp.; *Erysipelothrix* spp.; *Escherichia* spp.; *Eubacterium* spp.; *Faecalibacterium* spp.; *Filifactor* spp.; *Finegoldia* spp.; *Flavobacterium* spp.; *Gallicola* spp.; *Haemophilus* spp.; *Helcococcus* spp.; *Holdemania* spp.; *Hyphomicrobium* spp.; *Klebsiella* spp.; *Lactobacillus* spp.; *Legionella* spp.; *Listeria* spp.; *Methylobacterium* spp.; *Micrococcus* spp.; *Micromonospora* spp.; *Mobiluncus* spp.; *Moraxella* spp.; *Morganella* spp.; *Mycobacterium* spp.; *Neisseria* spp.; *Nocardia* spp.; *Paenibacillus* spp.; *Parabacteroides* spp.; *Pasteurella* spp.; *Peptoniphilus* spp.; *Peptostreptococcus* spp.; *Planococcus* spp.; *Planomicrobium* spp.; *Plesiomonas* spp.; *Porphyromonas* spp.; *Prevotella* spp.; *Propionibacterium* spp.; *Proteus* spp.; *Providentia* spp.; *Pseudomonas* spp.; *Ralstonia* spp.; *Rhodococcus* spp.; *Roseburia* spp.; *Ruminococcus* spp.; *Salmonella* spp.; *Sedimentibacter* spp.; *Serratia* spp.; *Shigella* spp.; *Solobacterium* spp.; *Sphingomonas* spp.; *Sporanaerobacter* spp.; *Staphylococcus* spp.; *Stenotrophomonas* spp.; *Streptococcus* spp.; *Streptomyces* spp.; *Tissierella* spp.; *Vibrio* spp.; and *Yersinia* spp. In other embodiments, the bacterium is selected from among Bacterial ID Nos. 1-1430. In particular examples, the bacterium is a mammalian (e.g., human) sepsis-associated bacterium, such as one selected from among *Staphylococcus aureus, Staphylococcus epidermidis, Staphylococcus haemolyticus, Staphylococcus hominis, Staphylococcus saprophyticus, Enterococcus faecalis, Enterococcus faecium, Clostridium perfringens, Streptococcus anginosus, Streptococcus constellatus, Streptococcus intermedius, Streptococcus mitis, Streptococcus mutans, Streptococcus sanguinis, Streptococcus sobrinus, Streptococcus oralis, Streptococcus pneumoniae, Streptococcus agalactiae, Streptococcus bovis, Streptococcus sanguinis, Streptococcus dysgalactiae, Streptococcus mutans* and *Streptococcus pyogenes, Escherichia coli, Acinetobacter baumannii, Bacteroides fragilis, Burkholderia cepacia, Klebsiella pneumonia, Klebsiella oxytoca, Pseudomonas aeruginosa, Enterobacter aerogenes, Enterobacter cloacae, Serratia marcescens, Proteus mirabilis, Citrobacter freundii, Morganella morganii, Haemophilus influenzae, Neisseria meningitidis, Stenotrophomonas maltophila, Prevotella buccae, Prevotella intermedia* and *Prevotella melaninogenica.*

A further aspect of the invention is directed to a method for determining the Gram status of a mammalian (e.g., human) sepsis-associated bacterium in a sample, comprising analyzing nucleic acid from the sample for a single nucleotide polymorphism (SNP) in a 16S rRNA gene, wherein the SNP is at a position corresponding to position 396 of the 16S rRNA gene set forth in SEQ ID NO:1, wherein the bacterium is determined to be a Gram-negative bacterium when there is a C at position 396; and the bacterium is determined to be a Gram-positive bacterium when there is a G at position 396. In some embodiments the mammalian (e.g., human) sepsis-associated bacterium is selected from *Staphylococcus aureus, Staphylococcus epidermidis, Staphylococcus haemolyticus, Staphylococcus hominis, Staphylococcus saprophyticus, Enterococcus faecalis, Enterococcus faecium, Clostridium perfringens, Streptococcus anginosus, Streptococcus constellatus, Streptococcus intermedius, Streptococcus mitis, Streptococcus mutans, Streptococcus sanguinis, Streptococcus sobrinus* and *Streptococcus oralis, Streptococcus pneumoniae, Streptococcus agalactiae, Streptococcus bovis, Streptococcus sanguinis, Streptococcus dysgalactiae, Streptococcus mutans* and *Streptococcus pyogenes, Escherichia coli, Acinetobacter baumannii, Bacteroides fragilis, Burkholderia cepacia, Klebsiella pneumonia, Klebsiella oxytoca, Pseudomonas aeruginosa, Enterobacter aerogenes, Enterobacter cloacae, Serratia marcescens, Proteus mirabilis, Citrobacter freundii, Morganella morganii, Haemophilus influenzae, Neisseria meningitidis, Stenotrophomonas maltophila, Prevotella buccae, Prevotella intermedia* and *Prevotella melaninogenica.*

In another aspect, the invention provides a method for determining the Gram status of a mammalian (e.g., human) sepsis-associated bacterium in a sample, comprising analyzing nucleic acid from the sample for single nucleotide polymorphisms (SNPs) in a 16S rRNA gene, wherein the SNPs are at positions corresponding to positions 278, 286, 396, 398, and 648 of the 16S rRNA gene set forth in SEQ ID NO:1, wherein the bacterium is determined to be a Gram-negative bacterium when there is a C at position 396; an A at position 396, a C at position 398 and a T at position 278; an A at position 396, a C at position 398, an A at position 278, a G at position 286 and a G at position 648; or an A at position 396, a C at position 398, an G at position 278, a G at position 286 and a G at position 648; and the bacterium is determined to be a Gram-positive bacterium when there is a G at position 396; an A at position 396, a C at position 398 and a C at position 278; an A at position 396, a C at position 398, a G at position 278, and an A at position 286; an A at position 396, a C at position 398, an A at position 278 and an A at position 286; an A at position 396, a C at position 398, an A at position 278, a G at position 286 and an A at position 648; or an A at position 396, a C at position 398, a G at position 278, a G at position 286 and a T or A at position 648. In some embodiments, bacterium is selected from *Staphylococcus aureus, Staphylococcus epidermidis, Staphylococcus haemolyticus, Staphylococcus hominis, Staphylococcus saprophyticus, Enterococcus faecalis, Enterococcus faecium, Clostridium perfringens, Strep-* tococcus anginosus, Streptococcus constellatus, Streptococcus intermedius, Streptococcus mitis, Streptococcus mutans, Streptococcus sanguinis, Streptococcus sobrinus and Streptococcus oralis, Streptococcus pneumoniae, Streptococcus agalactiae, Streptococcus bovis, Streptococcus sanguinis, Streptococcus dysgalactiae, Streptococcus mutans, Streptococcus pyogenes, Escherichia coli, Acinetobacter baumannii, Bacteroides fragilis, Burkholderia cepacia, Klebsiella pneumonia, Klebsiella oxytoca, Pseudomonas aeruginosa, Enterobacter aerogenes, Enterobacter cloacae, Serratia marcescens, Proteus mirabilis, Citrobacter freundii, Morganella morganii, Haemophilus influenzae, Neisseria meningitidis, Stenotrophomonas maltophila, Prevotella buccae, Prevotella intermedia, Prevotella melaninogenica, Salmonella enterica, Serratia marcescens, Haemophilus influenzae, Campylobacter coli, Campylobacter jejuni, Campylobacter lari, Campylobacter fetus, Helicobacter cinaedi, Helicobacter pylori, Chlamydophila abortus, Veillonella atypica, Veillonella parvula, Veillonella denticariosi, Veillonella rogosae, Streptomyces anulatus, Streptomyces somaliensis and Mycobacterium tuberculosis.

The method may also comprise identifying the bacterium or identifying the bacterium as being one of a group of bacteria, wherein: a C at position 396 indicates that the bacterium is a Gram-negative bacterium selected from Prevotella melaninogenica, Prevotella intermedia, Prevotella buccae, Bacteroides fragilis, Citrobacter freundii, Enterobacter aerogenes, Klebsiella oxytoca, Serratia marcescens, Morganella morganii, Stenotrophomonas maltophila, Acinetobacter baumannii, Enterobacter cloacae, Klebsiella pneumoniae, Salmonella enterica, Escherichia coli, Proteus mirabilis, Neisseria meningitidis, Pseudomonas aeruginosa, Haemophilus influenzae and Burkholderia cepacia; an A at position 396, a C at position 398 and a T at position 278 indicates that the bacterium is a Gram-negative bacteria selected from Campylobacter coli, Campylobact jejuni, Campylobacter lari, Campylobacter fetus, Helicobacter cinaedi, Helicobacter pylori and Chlamydophila abortus; an A at position 396, a C at position 398, an A at position 278, a G at position 286 and a G at position 648 indicates that the bacterium is the Gram-negative bacterium Veillonella rogosae; an A at position 396, a C at position 398, an G at position 278, a G at position 286 and a G at position 648 indicates that the bacterium is the Gram-negative bacterium Veillonella atypica, Veillonella parvula and Veillonella denticariosi; a G at position 396 indicates that the bacteria is a Gram-positive bacterium selected from among Streptomyces anulatus, Streptomyces somaliensis and Mycobacterium tuberculosis; an A at position 396, a C at position 398 and a C at position 278 indicates that the bacterium is the Gram-positive bacteria Enterococcus faecalis or Enterococcus faecium; an A at position 396, a C at position 398, a G at position 278, a T at position 286 and a T at position 648 indicates that the bacterium is the Gram-positive bacterium Clostridium perfringens; an A at position 396, a C at position 398, a G at position 278, and an A at position 286 indicates that the bacterium is the Gram-positive bacterium Streptococcus bovis, Streptococcus agalactiae, Streptococcus agalactiae, Streptococcus agalactiae, Streptococcus dysgalactiae, Streptococcus pyogenes, Streptococcus anginosus, Streptococcus intermedius, Streptococcus mitis, Streptococcus mutans, Streptococcus pneumoniae and Streptococcus sanguinis; or an A at position 396, a C at position 398, a A at position 278 and an A at position 286 indicates that the bacterium is a Gram-positive bacterium selected from among Staphylococcus aureus, Streptococcus sobrinus, Streptococcus constellatus and Streptococcus oralis; an A at position 396, a C at position 398, an A at position 278, a G at position 286 and an A at position 648 indicates that the bacterium is the Gram-positive bacterium Staphylococcus epidermidis or Staphylococcus hominus; and an A at position 396, a C at position 398, a G at position 278, a G at position 286 and a T or A at position 648 indicates that the bacterium is the Gram-positive bacterium Staphylococcus haemolyticus.

In one aspect, the invention provides a method for categorizing a mammalian (e.g., human) sepsis-associated bacterium in a sample as one of seven groups of mammalian (e.g., human) sepsis-associated bacteria, comprising analyzing nucleic acid from the sample for single nucleotide polymorphisms (SNPs) in a 16S rRNA gene, wherein the SNPs are at positions corresponding to positions 396, 398, 399, 400 and 401 of the 16S rRNA gene set forth in SEQ ID NO:1, wherein: the bacterium is determined to be a Group 1 pathogen selected from among the Gram-positive species Bacillus anthracis, Enterococcus faecalis, Enterococcus faecium, Listeria monocytogenes, Streptococcus agalactiae, Streptococcus anginosus, Streptococcus constellatus, Streptococcus dysgalactiae, Streptococcus intermedius, Streptococcus pyogenes, Lactobacillus intestinalis, Clostridium perfringens, Staphylococcus aureus, Staphylococcus epidermidis, Staphylococcus haemolyticus, Staphylococcus hominis, Staphylococcus saprophyticus, Eubacterium desmolans, Clostridium difficile, Erysipelothrix rhusiopathiae, Streptococcus bovis, Streptococcus mitis, Streptococcus mutans, Streptococcus oralis, Streptococcus pneumonia, Streptococcus sanguinis, Streptococcus sobrinus and Peptostreptococcus stomatis or Gram-negative species Helicobacter pylori, Campylobacter coli and Veillonella dispar when there is an A, C, G, C and C at positions 396, 398, 399, 400 and 401, respectively; the bacterium is determined to be a Group 2 pathogen selected from among the Gram-positive species Corynebacterium diphtheria, Dermatophilus congolensis, Micrococcus luteus, Rhodococcus equi, Streptomyces anulatus, Streptomyces somaliensis, Mycobacterium tuberculosis, Corynebacterium jeikeium, Corynebacterium urealyticum, Mobiluncus curtisii, Nocardia asteroids, Nocardia brasiliensis and Actinomyces massiliensis or the Gram-negative species Leptospira interrogans, Chlamydia trachomatis and Chlamydophila pneumoniae when there is a G, C, G, C and C at positions 396, 398, 399, 400 and 401, respectively; the bacterium is determined to be a Group 3 pathogen selected from among Gram-negative aerobic bacterium selected from among Actinobacillus hominis, Edwardsiella tarda, Haemophilus ducreyi, Haemophilus influenzae, Haemophilus parahaemolyticus, Haemophilus parainfluenzae, Morganella morganii, Pasteurella multocida, Providencia alcalifaciens, Vibrio cholerae, Moraxella catarrhalis, Pseudomonas aeruginosa, Neisseria gonorrhoeae, Neisseria meningitides, Aeromonas hydrophila, Citrobacter freundii, Enterobacter aerogenes, Enterobacter cloacae, Escherichia coli, Klebsiella oxytoca, Klebsiella pneumonia, Proteus mirabilis, Salmonella enterica, Serratia marcescens, Shigella dysenteriae, Shigella sonnei, Yersinia enterocolitica, Yersinia pestis, Acinetobacter baumannii, Brucella abortus and Flavobacterium ceti when there is a C, T, G, C and C at positions 396, 398, 399, 400 and 401 respectively; the bacterium is determined to be a Group 4 pathogen selected from among the Gram-negative aerobic species Legionella pneumophila, Burkholderia cepacia and Cardiobacterium valvarum when there is an A, T, G, C and C at positions 396, 398, 399, 400 and 401, respectively; the bacterium is determined to be the Group 5 pathogen Stenotrophomonas maltophila when there is a C, T, A, C and C at positions 396, 398, 399, 400 and 401, respectively; the bacterium is determined to be a Group 6 pathogen selected from among the Gram-negative anaerobic species *Prevotella buccae, Prevotella melaninogenica, Bacteroides fragilis, Prevotella intermedia* when there is a C, A, G, T and A at positions 396, 398, 399, 400 and 401, respectively; or the bacterium is determined to be the Group 7 pathogen *Porphyromonas gingivalis* when there is a C, A, G, T and C at positions 396, 398, 399, 400 and 401, respectively.

The invention also provides a method for categorizing a mammalian (e.g., human) sepsis-associated bacterium in a sample, comprising analyzing nucleic acid from the sample for single nucleotide polymorphisms (SNPs) at positions corresponding to positions 396 and 398 of the 16S rRNA gene set forth in SEQ ID NO:1, and positions corresponding to positions 399, 400 and 401 or positions 278, 286 and 648 of the 16S rRNA gene set forth in SEQ ID NO:1; wherein if positions 396, 398, 399, 400 and 401 are assessed the bacterium is categorized into one of seven groups of mammalian (e.g., human) sepsis-associated bacteria; wherein the bacterium is determined to be a Group 1 pathogen selected from among the Gram-positive species *Bacillus anthracis, Enterococcus faecalis, Enterococcus faecium, Listeria monocytogenes, Streptococcus agalactiae, Streptococcus anginosus, Streptococcus constellatus, Streptococcus dysgalactiae, Streptococcus intermedius, Streptococcus pyogenes, Lactobacillus intestinalis, Clostridium perfringens, Staphylococcus aureus, Staphylococcus epidermidis, Staphylococcus haemolyticus, Staphylococcus hominis, Staphylococcus saprophyticus, Eubacterium desmolans, Clostridium difficile, Erysipelothrix rhusiopathiae, Streptococcus bovis, Streptococcus mitis, Streptococcus mutans, Streptococcus oralis, Streptococcus pneumonia, Streptococcus sanguinis, Streptococcus sobrinus* and *Peptostreptococcus stomatis* or Gram-negative species *Helicobacter pylori, Campylobacter coli* and *Veillonella dispar* when there is an A, C, G, C and C at positions 396, 398, 399, 400 and 401, respectively; the bacterium is determined to be a Group 2 pathogen selected from among the Gram-positive species *Corynebacterium diphtheria, Dermatophilus congolensis, Micrococcus luteus, Rhodococcus equi, Streptomyces anulatus, Streptomyces somaliensis, Mycobacterium tuberculosis, Corynebacterium jeikeium, Corynebacterium urealyticum, Mobiluncus curtisii, Nocardia asteroids, Nocardia brasiliensis* and *Actinomyces massiliensis* or the Gram-negative species *Leptospira interrogans, Chlamydia trachomatis* and *Chlamydophila pneumoniae* when there is a G, C, G, C and C at positions 396, 398, 399, 400 and 401, respectively; the bacterium is determined to be a Group 3 pathogen selected from among Gram-negative aerobic bacterium selected from among *Actinobacillus hominis, Edwardsiella tarda, Haemophilus ducreyi, Haemophilus influenzae, Haemophilus parahaemolyticus, Haemophilus parainfluenzae, Morganella morganii, Pasteurella multocida, Providencia alcalifaciens, Vibrio cholerae, Moraxella catarrhalis, Pseudomonas aeruginosa, Neisseria gonorrhoeae, Neisseria meningitides, Aeromonas hydrophila, Citrobacter freundii, Enterobacter aerogenes, Enterobacter cloacae, Escherichia coli, Klebsiella oxytoca, Klebsiella pneumonia, Proteus mirabilis, Salmonella enterica, Serratia marcescens, Shigella dysenteriae, Shigella sonnei, Yersinia enterocolitica, Yersinia pestis, Acinetobacter baumannii, Brucella abortus* and *Flavobacterium ceti* when there is a C, T, G, C and C at positions 396, 398, 399, 400 and 401 respectively; the bacterium is determined to be a Group 4 pathogen selected from among the Gram-negative aerobic species *Legionella pneumophila, Burkholderia cepacia* and *Cardiobacterium valvarum* when there is an A, T, G, C and C at positions 396, 398, 399, 400 and 401, respectively; the bacterium is determined to be the Group 5 pathogen *Stenotrophomonas maltophila* when there is a C, T, A, C and C at positions 396, 398, 399, 400 and 401, respectively; the bacterium is determined to be a Group 6 pathogen selected from among the Gram-negative anaerobic species *Prevotella buccae, Prevotella melaninogenica, Bacteroides fragilis, Prevotella intermedia* when there is a C, A, G, T and A at positions 396, 398, 399, 400 and 401, respectively; or the bacterium is determined to be the Group 7 pathogen *Porphyromonas gingivalis* when there is a C, A, G, T and C at positions 396, 398, 399, 400 and 401, respectively; and if positions 278, 286 396, 398 and 648 are assessed the bacterium is categorized as Gram-positive or Gram-negative; wherein the bacterium is determined to be a Gram-negative bacterium when there is a C at position 396; an A at position 396, a C at position 398 and a T at position 278; an A at position 396, a C at position 398, an A at position 278, a G at position 286 and a G at position 648; or an A at position 396, a C at position 398, an G at position 278, a G at position 286 and a G at position 648; and the bacterium is determined to be a Gram-positive bacterium when there is a G at position 396; an A at position 396, a C at position 398 and a C at position 278; an A at position 396, a C at position 398, a G at position 278, and an A at position 286; an A at position 396, a C at position 398, an A at position 278 and an A at position 286; an A at position 396, a C at position 398, an A at position 278, a G at position 286 and an A at position 648; or an A at position 396, a C at position 398, a G at position 278, a G at position 286 and a T or A at position 648.

In some embodiments, if the bacterium is determined to be a Group 1 bacterium, the methods of the invention may further comprise analyzing the nucleic acid for SNPs at positions corresponding to positions 490, 491, 492, 493, 495, 496, 500 and 501 of the 16S rRNA gene set forth in SEQ ID NO:1, wherein the bacterium is determined to be a Group 1a bacterium selected from among *Bacillus anthracis, Enterococcus faecalis, Enterococcus faecium* and *Listeria monocytogenes* when there is an A, A, C, C, G, A, C, and C at positions 490, 491, 492, 493, 495, 496, 500 and 501, respectively; the bacterium is determined to be a Group 1b bacterium selected from among *Streptococcus agalactiae, Streptococcus anginosus, Streptococcus constellatus, Streptococcus dysgalactiae, Streptococcus intermedius* and *Streptococcus pyogenes* when there is an A, A, C, C, G, A, G and G at positions 490, 491, 492, 493, 495, 496, 500 and 501, respectively; the bacterium is determined to be the Group 1c bacterium *Lactobacillus intestinali*, when there is an A, A, C, C, G, A, T and C at positions 490, 491, 492, 493, 495, 496, 500 and 501, respectively; the bacterium is determined to be a Group 1d bacterium selected from among *Helicobacter pylori* and *Campylobacter coli* when there is an A, A, C, G, A, T, C and A at positions 490, 491, 492, 493, 495, 496, 500 and 501, respectively; the bacterium is determined to be the Group 1e bacterium *Clostridium perfringens* when there is an A, A, G, G, G, G, C and C at positions 490, 491, 492, 493, 495, 496, 500 and 501, respectively; the bacterium is determined to be a Group 1f bacterium selected from among *Staphylococcus aureus, Staphylococcus epidermidis, Staphylococcus haemolyticus, Staphylococcus hominis* and *Staphylococcus saprophyticus* when there is an A, A, T, C, G, A, C and C at positions 490, 491, 492, 493, 495, 496, 500 and 501, respectively; the bacterium is determined to be the Group 1g bacterium *Eubacterium desmolans* when there is a G, A, A, G, A, T, C and T at positions 490, 491, 492, 493, 495, 496, 500 and 501, respectively; the bacterium is determined to be the Group 1h bacterium *Veillonella dispar* when there is a G, A, A, T, G, A, C, and C at positions 490, 491, 492, 493, 495, 496, 500 and 501, respectively; the bacterium is determined to be the Group 1i bacterium *Clostridium difficile* when there is a G, A, G, G, G, G, C and C at positions 490, 491, 492, 493, 495, 496, 500 and 501, respectively; wherein the bacterium is determined to be the Group 1j bacterium *Erysipelothrix rhusiopathiae* when there is a T, A, C, C, G, A, C and C at positions 490, 491, 492, 493, 495, 496, 500 and 501, respectively; the bacterium is determined to be a Group 1k bacterium selected from among *Streptococcus bovis, Streptococcus mitis, Streptococcus mutans, Streptococcus oralis, Streptococcus pneumonia, Streptococcus sanguinis, Streptococcus sobrinus*, when there is a T, A, C, C, G, A, G and G at positions 490, 491, 492, 493, 495, 496, 500 and 501, respectively; and the bacterium is determined to be the Group 1l bacterium *Peptostreptococcus stomatis* when there is a T, G, T, G, G, G, C and C at positions 490, 491, 492, 493, 495, 496, 500 and 501, respectively.

If the bacterium is determined to be a Group 2 bacterium, the method may further comprise analyzing the nucleic acid for SNPs at positions corresponding to positions 490, 491, 492, 493, 496, 499 and 501 of the 16S rRNA gene set forth in SEQ ID NO:1, wherein the bacterium is determined to be the Group 2a bacterium *Corynebacterium diptheriae* when there is an A, G, A, T, G, G and A at positions 490, 491, 492, 493, 496, 499 and 501, respectively; the bacterium is determined to be a Group 2b bacterium selected from among *Dermatophilus congolensis, Micrococcus luteus* and *Rhodococcus equi* when there is a G, C, A, G, G, G and A at positions 490, 491, 492, 493, 496, 499 and 501, respectively; the bacterium is determined to be a Group 2c bacterium selected from among *Streptomyces anulatus* and *Streptomyces somaliensis* when there is a G, C, A, G, G, G and A at positions 490, 491, 492, 493, 496, 499 and 501, respectively; the bacterium is determined to be the Group 2d bacterium *Leptospira interogans* when there is a G, C, C, T, A, A and C at positions 490, 491, 492, 493, 496, 499 and 501, respectively; the bacterium is determined to be the Group 2e bacterium *Mycobacterium tuberculosis* when there is a G, G, A, G, G, G and A at positions 490, 491, 492, 493, 496, 499 and 501, respectively; the bacterium is determined to be a Group 2f bacterium selected from among *Corynebacterium jeikeium* and *Corynebacterium urealyticum* when there is a G, G, A, T, G, G and A at positions 490, 491, 492, 493, 496, 499 and 501, respectively; the bacterium is determined to be the Group 2g bacterium *Mobiluncus curtisii* when there is a G, G, G, G, G, G and G at positions 490, 491, 492, 493, 496, 499 and 501, respectively; the bacterium is determined to be a Group 2h bacterium selected from among *Chlamydia trachomatis* and *Chlamydophila pneumoniae* when there is a G, G, T, A, G, G and A at positions 490, 491, 492, 493, 496, 499 and 501, respectively; the bacterium is determined to be a Group 2i bacterium selected from among *Nocardia asteroids* and *Nocardia brasiliensis* when there is a G, T, A, G, G, G and A at positions 490, 491, 492, 493, 496, 499 and 501, respectively, and the bacterium is determined to be a Group 2j bacterium *Actinomyces massiliensis* when there is a G, T, T, G, G, G and A at positions 490, 491, 492, 493, 496, 499 and 501, respectively.

In instances where the bacterium is determined to be a Group 3 bacterium, the method can further comprise analyzing the nucleic acid for SNPs at positions corresponding to positions 490, 491, 496, and 501 of the 16S rRNA gene set forth in SEQ ID NO:1, wherein the bacterium is determined to be a Group 3a bacterium selected from among *Actinobacillus hominis, Edwardsiella tarda, Haemophilus ducreyi, Haemophilus influenzae, Haemophilus parahaemolyticus, Haemophilus parainfluenzae, Morganella morganii, Pasteurella multocida, Providencia alcalifaciens* and *Vibrio cholerae* when there is an A, C, G and A at positions 490, 491, 496, and 501, respectively; the bacterium is determined to be a Group 3b bacterium selected from among *Moraxella catharrallis* and *Pseudomonas aeruginosa*, when there is an A, C, T and A at positions 490, 491, 496, and 501, respectively; the bacterium is determined to be a Group 3c bacterium selected from among *Neisseria gonorrhoeae* and *Neisseria meningitides* when there is a G, A T and A at positions 490, 491, 496, and 501, respectively; the bacterium is determined to be a Group 3d bacterium selected from among *Aeromonas hydrophila, Citrobacter freundii, Enterobacter aerogenes, Enterobacter cloacae, Escherichia coli, Klebsiella oxytoca, Klebsiella pneumonia, Proteus mirabilis, Salmonella enterica, Serratia marcescens, Shigella dysenteriae, Shigella sonnei, Yersinia enterocolitica* and *Yersinia pestis* when there is an G, C, G and A at positions 490, 491, 496, and 501, respectively; the bacterium is determined to be the Group 3e bacterium *Acinetobacter baumannii* when there is a G, C, T and A at positions 490, 491, 496, and 501, respectively; the bacterium is determined to be the Group 3f bacterium *Brucella abortus* when there is a G, G, G and C at positions 490, 491, 496, and 501, respectively; and the bacterium is determined to be the Group 3g bacterium *Flavobacterium ceti* when there is a T, A, T and A at positions 490, 491, 496, and 501, respectively.

If the bacterium is determined to be a Group 4 bacterium, the method can further comprise analyzing the nucleic acid for SNPs at positions corresponding to positions 490, 491, 496, and 499 of the 16S rRNA gene set forth in SEQ ID NO:1, wherein the bacterium is determined to be the Group 4a bacterium *Legionella pneumophila* when there is an A, C, G and C at positions 490, 491, 496, and 499, respectively; the bacterium is determined to be the Group 4b bacterium *Burkholderia cepacia* when there is a G, A, T and G at positions 490, 491, 496, and 499, respectively; and the bacterium is determined to be the Group 4c bacterium *Cardiobacterium valvarum* when there is a G, C, G and G at positions 490, 491, 496, and 499, respectively.

If the bacterium is determined to be a Group 6 bacterium, the method may further comprise analyzing the nucleic acid for SNPs at positions corresponding to positions 490, 491 and 496 of the 16S rRNA gene set forth in SEQ ID NO:1, wherein the bacterium is determined to be the Group 6a bacterium *Prevotella buccae* when there is a C, A and T at positions 490, 491 and 496, respectively; the bacterium is determined to be the Group 6b bacterium *Prevotella melaninogenica* when there is a T, A and C at positions 490, 491 and 496, respectively; the bacterium is determined to be the Group 6c bacterium *Bacteroides fragilis*, when there is an T, A and T at positions 490, 491 and 496, respectively; and the bacterium is determined to be the Group 6b bacterium *Prevotella intermedia* when there is a T, T and C at positions 490, 491 and 496, respectively.

In some embodiments, the methods of the invention further comprise determining whether the bacterium is resistant to one or more antibiotics.

In one embodiment, the methods described above and herein further comprise analyzing the sample to determine the presence or absence of a w452w3aq34t5yghus in the sample, which further analysis comprises analyzing the nucleic acid for a single nucleotide polymorphism (SNP) within a 5.8S rRNA gene at a position corresponding to position 142, 144, 146, 147, 148, 154, 157, 164, 167, 185, 187, 188, 194, 197, 213, 215, 216, 219, 223, 231, 232, 236, 245, 251, or 256 of the 5.8S rRNA gene set forth in SEQ ID NO:2, which SNP is indicative of the presence of a fungus in the sample, wherein the SNP is selected from among a C at position 142; an A at position 144; an A at position 146; an A at position 147; a C at position 148; a T at position 154; a T at position 157; a C or G at position 164; an A at position 167; a G at position 185; an A at position 187; an A at position 188; a T at position 194; a G at position 197; an A at position 213; a T at position 215; a T at position 216; a G at position 219; an A at position 223; a G or A at position 231; a T at position 232; a T at position 236; a C or A at position 245; a C at position 251; and a T at position 256.

The method may further comprise analyzing the sample to determine the presence and identity of a mammalian (e.g., human) fungal pathogen in the sample, which further analysis comprises analyzing the nucleic acid for at least four SNPs within a 5.8S rRNA gene, wherein: the at least four SNPs include those at a position corresponding to position 254 of SEQ ID NO:2; a position corresponding to position 160 or 255 of SEQ ID NO:2; and any two of positions corresponding to positions 163, 164, 165, 196, 202, 223, 224 or 259 of SEQ ID NO:2; the mammalian (e.g., human) fungal pathogen is selected from *Candida albicans, Candida tropicalis, Candida parapsilosis, Candida krusei, Candida glabrata, Ajellomyces capsulatus, Stachybotrys* sp., *Scedosporium apiospermum, Fusarium* sp., *Aspergillus fumigatus* and *Cryptococcus neoformans*; and the presence and identity of the pathogen is determined based on the presence of SNPs set forth in following table:

from the sample prior to analysis. In further embodiments, the analysis comprises amplification of the nucleic acid. In some examples, the analysis is performed using sequencing, 5' nuclease digestion, molecular beacons, oligonucleotide ligation, microarray, or any combination thereof.

A further aspect of the invention is directed to a method for determining the presence or absence of fungi in a sample, comprising analyzing nucleic acid from the sample for a single nucleotide polymorphism (SNP) in a 5.8S rRNA gene, which SNP is indicative of the presence of fungi in the sample, wherein the SNP is selected from among a C at position 142; an A at position 144; an A at position 146; an A at position 147; a C at position 148; a T at position 154; a T at position 157; a C or G at position 164; an A at position 167; a G at position 185; an A at position 187; an A at position 188; a T at position 194; a G at position 197; an A at position 213; a T at position 215; a T at position 216; a G at position 219; an A at position 223; a G or A at position 231; a T at position 232; a T at position 236; a C or A at position 245; a C at position 251; and a T at position 256. In some embodiments, the sample is selected from soil, food, water, surface swab and biological sample from a subject. In a particular embodiment, the biological sample is selected from among blood, tissue, sputum, lavage fluid, feces, urine and saliva.

The method may further comprise determining the number of fungal cells in the sample. In particular examples, nucleic acid is extracted from the sample prior to analysis. In some embodiments, the analysis comprises amplification of the nucleic acid. In further embodiments, the analysis is

|  | SNP position | | | | | | | | | | |
|---|---|---|---|---|---|---|---|---|---|---|---|
|  | 160 | 163 | 164 | 165 | 196 | 202 | 223 | 224 | 254 | 255 | 259 |
| *Candida albicans* | T | T | C | G | C | A | A | T | T | C | T |
| *Candida tropicalis* | T | T | C | G | C | A | A | T | T | T | T |
| *Candida parapsilosis* | T | T | C | G | A | A | A | T | T | T | T |
| *Candida krusei* | T | T | C | G | C | G | A | T | C | T | C |
| *Candida glabrata* | T | T | C | G | C | G | A | T | T | C | T |
| *Ajellomyces capsulatus* | T | C | G | A | A | G | A | T | T | C | T |
| *Stachybotrys* sp. | C | T | G | G | A | G | A | T | G | C | C |
| *Scedosporium apiospermum* | T | T | G | G | A | G | A | T | G | C | T |
| *Fusarium* sp. | C | T | G | G | A | G | A | T | G | C | T |
| *Aspergillus fumigatus* | T | C | G | G | A | G | A | T | C | C | T |
| *Cryptococcus neoformans* | C | C | C | A | A | G | A | T | T | T | T |

In some embodiments, the at least four SNPs are at a position corresponding to position 254 of SEQ ID NO:2; a position corresponding to position 160 or 255 of SEQ ID NO:2; a position corresponding to position 164 of SEQ ID NO:2; and a position corresponding to position 163, 165, 196, 202, 223, 224 or 259 of SEQ ID NO:2. In other embodiments, the at least four SNPs are at a position corresponding to position 254 of SEQ ID NO:2; a position corresponding to position 160 or 255 of SEQ ID NO:2; a position corresponding to position 223 of SEQ ID NO:2; and a position corresponding to position 163, 164, 165, 196, 202, 224 or 259 of SEQ ID NO:2.

In some embodiments, the methods of the invention further comprise determining the number of bacteria and/or the number of fungal cells in the sample. In particular examples, the sample is a biological sample from a mammalian (e.g., human) subject presenting with systemic inflammatory response syndrome (SIRS) or suspected of having sepsis, such as a blood sample. In some embodiments of the methods of the invention, the nucleic acid is extracted performed using sequencing, 5' nuclease digestion, molecular beacons, oligonucleotide ligation, microarray, or any combination thereof.

The present invention also provides a method for determining the identity of a mammalian (e.g., human) fungal pathogen in a sample, comprising analyzing nucleic acid from the sample for at least 4 SNPs in a 5.8S rRNA gene, wherein: the at least four SNPs are at a position corresponding to position 254 of SEQ ID NO:2; a position corresponding to position 160 or 255 of SEQ ID NO:2; and any two of positions corresponding to positions 163, 164, 165, 196, 202, 223, 224 or 259 of SEQ ID NO:2; the mammalian (e.g., human) fungal pathogen is selected from *Candida albicans, Candida tropicalis, Candida parapsilosis, Candida krusei, Candida glabrata, Ajellomyces capsulatus, Stachybotrys* sp., *Scedosporium apiospermum, Fusarium* sp., *Aspergillus fumigatus* and *Cryptococcus neoformans*; and the identity of the pathogen is determined based on the presence of SNPs set forth in following table:

|  | SNP position | | | | | | | | | | |
| --- | --- | --- | --- | --- | --- | --- | --- | --- | --- | --- | --- |
|  | 160 | 163 | 164 | 165 | 196 | 202 | 223 | 224 | 254 | 255 | 259 |
| Candida albicans | T | T | C | G | C | A | A | T | T | C | T |
| Candida tropicalis | T | T | C | G | C | A | A | T | T | T | T |
| Candida parapsilosis | T | T | C | G | A | A | A | T | T | T | T |
| Candida krusei | T | T | C | G | C | G | A | T | C | T | C |
| Candida glabrata | T | T | C | G | C | G | A | T | T | C | T |
| Ajellomyces capsulatus | T | C | G | A | A | G | A | T | T | C | T |
| Stachybotrys sp. | C | T | G | G | A | G | A | T | G | C | C |
| Scedosporium apiospermum | T | T | G | G | A | G | A | T | G | C | T |
| Fusarium sp. | C | T | G | G | A | G | A | T | G | C | T |
| Aspergillus fumigatus | T | C | G | G | A | G | A | T | C | C | T |
| Cryptococcus neoformans | C | C | C | A | A | G | A | T | T | T | T |

In particular examples, the at least four SNPs are at a position corresponding to position 254 of SEQ ID NO:2; a position corresponding to position 160 or 255 of SEQ ID NO:2; a position corresponding to position 164 of SEQ ID NO:2; and a position corresponding to position 163, 165, 196, 202, 223, 224 or 259 of SEQ ID NO:2. In other examples, the at least four SNPs are at a position corresponding to position 254 of SEQ ID NO:2; a position corresponding to position 160 or 255 of SEQ ID NO:2; a position corresponding to position 223 of SEQ ID NO:2; and a position corresponding to position 163, 164, 165, 196, 202, 224 or 259 of SEQ ID NO:2.

The present invention also provides a method for determining the identity of a mammalian (e.g., human) fungal pathogen in a sample, comprising analyzing nucleic acid from the sample for at least two SNPs in a 5.8S rRNA gene, wherein: the at least two SNPs are at a position corresponding to position 163 of SEQ ID NO:2, and a position corresponding to position 164 of SEQ ID NO:2, wherein the presence of T at position 163 and C at position 164 indicates that the fungal pathogen in the sample is a *Candida* species. Suitably, the *Candida* species is selected from *Candida albicans, Candida tropicalis, Candida parapsilosis, Candida krusei* and *Candida glabrata*.

The present invention also provides a method for determining the presence or absence of a *Candida* species in a sample, comprising analyzing nucleic acid from the sample for at least two SNPs in a 5.8S rRNA gene, wherein: the at least two SNPs are at a position corresponding to position 163 of SEQ ID NO:2, and a position corresponding to position 164 of SEQ ID NO:2, wherein the presence of T at position 163 and C at position 164 indicates the presence of a *Candida* species in the sample, and wherein the absence of T at position 163 and C at position 164 indicates the absence of a *Candida* species in the sample. Suitably, the *Candida* species is selected from *Candida albicans, Candida tropicalis, Candida parapsilosis, Candida krusei* and *Candida glabrata*.

In some embodiments, the method for determining the identity of a mammalian (e.g., human) fungal pathogen in a sample further comprises determining the Gram status of a mammalian (e.g., human) sepsis-associated bacterium in the sample, comprising analyzing nucleic acid from the sample for a single nucleotide polymorphism (SNP) in a 16S rRNA gene, wherein the SNP is at a position corresponding to position 396 of the 16S rRNA gene set forth in SEQ ID NO:1, wherein: the bacterium is determined to be a Gram-negative bacterium when there is a C at position 396; and the bacterium is determined to be a Gram-positive bacterium when there is a G at position 396. In some examples the bacterium is selected from among *Staphylococcus aureus, Staphylococcus epidermidis, Staphylococcus haemolyticus, Staphylococcus hominis, Staphylococcus saprophyticus, Enterococcus faecalis, Enterococcus faecium, Clostridium perfringens, Streptococcus anginosus, Streptococcus constellatus, Streptococcus intermedius, Streptococcus mitis, Streptococcus mutans, Streptococcus sanguinis, Streptococcus sobrinus* and *Streptococcus oralis, Streptococcus pneumoniae, Streptococcus agalactiae, Streptococcus bovis, Streptococcus sanguinis, Streptococcus dysgalactiae, Streptococcus mutans* and *Streptococcus pyogenes, Escherichia coli, Acinetobacter baumannii, Bacteroides fragilis, Burkholderia cepacia, Klebsiella pneumonia, Klebsiella oxytoca, Pseudomonas aeruginosa, Enterobacter aerogenes, Enterobacter cloacae, Serratia marcescens, Proteus mirabilis, Citrobacter freundii, Morganella morganii, Haemophilus influenzae, Neisseria meningitidis, Stenotrophomonas maltophila, Prevotella buccae, Prevotella intermedia* and *Prevotella melaninogenica*.

In further embodiments, the method for determining the identity of a mammalian (e.g., human) fungal pathogen in a sample further comprises determining the Gram status of a mammalian (e.g., human) sepsis-associated bacterium in the sample, comprising analyzing nucleic acid from the sample for SNPs in a 16S rRNA gene, wherein the SNPs are at positions corresponding to positions 278, 286, 396, 398, and 648 of the 16S rRNA gene set forth in SEQ ID NO:1, wherein: the bacterium is determined to be a Gram-negative bacterium when there is: a C at position 396; an A at position 396, a C at position 398 and a T at position 278; an A at position 396, a C at position 398, an A at position 278, a G at position 286 and a G at position 648; or an A at position 396, a C at position 398, an G at position 278, a G at position 286 and a G at position 648; and the bacterium is determined to be a Gram-positive bacterium when there is: a G at position 396; an A at position 396, a C at position 398 and a C at position 278; an A at position 396, a C at position 398, a G at position 278, and an A at position 286; an A at position 396, a C at position 398, an A at position 278 and an A at position 286; an A at position 396, a C at position 398, an A at position 278, a G at position 286 and an A at position 648; or an A at position 396, a C at position 398, a G at position 278, a G at position 286 and a T or A at position 648. In some examples, the bacterium is selected from *Staphylococcus aureus, Staphylococcus epidermidis, Staphylococcus haemolyticus, Staphylococcus hominis, Staphylococcus saprophyticus, Enterococcus faecalis, Enterococcus faecium, Clostridium perfringens, Streptococcus anginosus, Streptococcus constellatus, Streptococcus intermedius, Streptococcus mitis, Streptococcus mutans, Streptococcus sanguinis, Streptococcus sobrinus* and *Streptococcus oralis, Streptococcus pneumoniae, Streptococcus agalactiae, Streptococcus bovis, Streptococcus sanguinis, Streptococcus dysgalactiae, Streptococcus mutans, Streptococcus pyogenes, Escherichia coli, Acinetobacter baumannii, Bacteroides fragilis, Burkholderia cepacia, Klebsiella pneumonia, Klebsiella oxytoca, Pseudomonas aeruginosa, Enterobacter aerogenes, Enterobacter cloacae, Serratia marcescens, Proteus mirabilis, Citrobacter freundii, Morganella morganii, Haemophilus influenzae, Neisseria meningitidis, Stenotrophomonas maltophila, Prevotella buccae, Prevotella intermedia, Prevotella melaninogenica, Salmonella enterica, Serratia marcescens, Haemophilus influenzae, Campylobacter coli, Campylobacter jejuni, Campylobacter lari, Campylobacter fetus, Helicobacter cinaedi, Helicobacter pylori, Chlamydophila abortus, Veillonella atypica, Veillonella parvula, Veillonella denticariosi, Veillonella rogosae, Streptomyces anulatus, Streptomyces somaliensis and Mycobacterium tuberculosis.

The methods may further comprising identifying the bacterium or identifying the bacterium as being one of a group of bacteria, wherein: a C at position 396 indicates that the bacterium is a Gram-negative bacterium selected from Prevotella melaninogenica, Prevotella intermedia, Prevotella buccae, Bacteroides fragilis, Citrobacter freundii, Enterobacter aerogenes, Klebsiella oxytoca, Serratia marcescens, Morganella morganii, Stenotrophomonas maltophila, Acinetobacter baumannii, Enterobacter cloacae, Klebsiella pneumoniae, Salmonella enterica, Escherichia coli, Proteus mirabilis, Neisseria meningitidis, Pseudomonas aeruginosa, Haemophilus influenzae and Burkholderia cepacia; an A at position 396, a C at position 398 and a T at position 278 indicates that the bacterium is a Gram-negative bacteria selected from Campylobacter coli, Campylobacter jejuni, Campylobacter lari, Campylobacter fetus, Helicobacter cinaedi, Helicobacter pylori and Chlamydophila abortus; an A at position 396, a C at position 398, an A at position 278, a G at position 286 and a G at position 648 indicates that the bacterium is the Gram-negative bacterium Veillonella rogosae; an A at position 396, a C at position 398, an G at position 278, a G at position 286 and a G at position 648 indicates that the bacterium is the Gram-negative bacterium Veillonella atypica, Veillonella parvula and Veillonella denticariosi; a G at position 396 indicates that the bacteria is a Gram-positive bacterium selected from among Streptomyces anulatus, Streptomyces somaliensis and Mycobacterium tuberculosis; an A at position 396, a C at position 398 and a C at position 278 indicates that the bacterium is the Gram-positive bacteria Enterococcus faecalis or Enterococcus faecium; an A at position 396, a C at position 398, a G at position 278, a T at position 286 and a T at position 648 indicates that the bacterium is the Gram-positive bacterium Clostridium perfringens; an A at position 396, a C at position 398, a G at position 278, and an A at position 286 indicates that the bacterium is the Gram-positive bacterium Streptococcus bovis, Streptococcus agalactiae, Streptococcus agalactiae, Streptococcus agalactiae, Streptococcus dysgalactiae, Streptococcus pyogenes, Streptococcus anginosus, Streptococcus intermedius, Streptococcus mitis, Streptococcus mutans, Streptococcus pneumoniae and Streptococcus sanguinis; or an A at position 396, a C at position 398, an A at position 278 and an A at position 286 indicates that the bacterium is a Gram-positive bacterium selected from among Staphylococcus aureus, Streptococcus sobrinus, Streptococcus constellatus and Streptococcus oralis; an A at position 396, a C at position 398, an A at position 278, a G at position 286 and an A at position 648 indicates that the bacterium is the Gram-positive bacterium Staphylococcus epidermidis or Staphylococcus hominus; and an A at position 396, a C at position 398, a G at position 278, a G at position 286 and a T or A at position 648 indicates that the bacterium is the Gram-positive bacterium Staphylococcus haemolyticus.

The methods also may further include categorizing a mammalian (e.g., human) sepsis-associated bacterium in the sample as one of seven groups of mammalian (e.g., human) sepsis-associated bacteria, comprising analyzing nucleic acid from the sample for single nucleotide polymorphisms (SNPs) in a 16S rRNA gene, wherein the SNPs are at positions corresponding to positions 396, 398, 399, 400 and 401 of the 16S rRNA gene set forth in SEQ ID NO:1, as described above and herein. In addition, further grouping of the bacteria into Groups 1a-l, 2a-j, 3a-g, 4a-c and 6a-d, can be performed as described above and herein.

In some examples, the number of fungal cells and/or bacteria in the sample is also determined. The sample may be, for example, a biological sample from a mammalian (e.g., human) subject, such as for example blood, tissue, sputum, lavage fluid, feces, urine or saliva. In particular embodiments, the biological sample is blood. In some embodiments, the nucleic acid is extracted from the sample prior to analysis. In further embodiments, the analysis comprises amplification of the nucleic acid. In some instances, the analysis is performed using sequencing, 5' nuclease digestion, molecular beacons, oligonucleotide ligation, microarray, or any combination thereof.

The present invention also provides a method for diagnosing sepsis in a mammalian (e.g., human) subject, comprising analysing nucleic acid from the blood of the subject for a SNP in a 16S rRNA gene and a SNP in a 5.8s rRNA gene, wherein the presence of the SNP is indicative of sepsis, wherein: the SNP in the 16S rRNA gene is at a position corresponding to position 396 of the 16S rRNA gene set forth in SEQ ID NO:1 and wherein sepsis resulting from a Gram-negative bacterial infection is diagnosed when there is a C at position 396, and sepsis resulting from a Gram-positive bacterial infection is diagnosed when there is a G at position 396; and the SNP in the 5.8S rRNA gene is at a position corresponding to position 142, 144, 146, 147, 148, 154, 157, 164, 167, 185, 187, 188, 194, 197, 213, 215, 216, 219, 223, 231, 232, 236, 245, 251, or 256 of the 5.8S rRNA gene set forth in SEQ ID NO:2, and sepsis resulting from a fungal infection is diagnosed when there is a C at position 142; an A at position 144; an A at position 146; an A at position 147; a C at position 148; a T at position 154; a T at position 157; a C or G at position 164; an A at position 167; a G at position 185; an A at position 187; an A at position 188; a T at position 194; a G at position 197; an A at position 213; a T at position 215; a T at position 216; a G at position 219; an A at position 223; a G or A at position 231; a T at position 232; a T at position 236; a C or A at position 245; a C at position 251; or a T at position 256. In some embodiments of the method, the bacterial infection is an infection by a bacterium selected from among Staphylococcus aureus, Staphylococcus epidermidis, Staphylococcus haemolyticus, Staphylococcus hominis, Staphylococcus saprophyticus, Enterococcus faecalis, Enterococcus faecium, Clostridium perfringens, Streptococcus anginosus, Streptococcus constellatus, Streptococcus intermedius, Streptococcus mitis, Streptococcus mutans, Streptococcus sanguinis, Streptococcus sobrinus and Streptococcus oralis, Streptococcus pneumoniae, Streptococcus agalactiae, Streptococcus bovis, Streptococcus sanguinis, Streptococcus dysgalactiae, Streptococcus mutans and Streptococcus pyogenes, Escherichia coli, Acinetobacter baumannii, Bacteroides fragilis, Burkholderia cepacia, Klebsiella pneumoniae, Klebsiella oxytoca, Pseudomonas aeruginosa, Enterobacter aerogenes, Enterobacter cloacae, Serratia marcescens, Proteus mirabilis, Citrobacter freundii, Morganella morganii, Haemophilus influenzae, Neisseria meningitidis, Stenotrophomonas maltophila, Prevotella buccae, Prevotella intermedia and Prevotella melaninogenica.

In another aspect, the invention provides a method for diagnosing sepsis in a mammalian (e.g., human) subject, comprising analysing nucleic acid from the blood of the subject for SNPs in a 16S rRNA gene and a SNP in a 5.8s rRNA gene, wherein the presence of the SNP(s) is indicative of sepsis, wherein: the SNPs in the 16S rRNA gene are at positions corresponding to positions 278, 286, 396, 398, and 648 of the 16S rRNA gene set forth in SEQ ID NO:1, and wherein: sepsis resulting from a Gram-negative bacterial infection is diagnosed when there is: a C at position 396; an A at position 396, a C at position 398 and a T at position 278; an A at position 396, a C at position 398, an A at position 278, a G at position 286 and a G at position 648; or an A at position 396, a C at position 398, an G at position 278, a G at position 286 and a G at position 648; and sepsis resulting from a Gram-positive bacterial infection is diagnosed when there is: a G at position 396; an A at position 396, a C at position 398 and a C at position 278; an A at position 396, a C at position 398, a G at position 278, and an A at position 286; an A at position 396, a C at position 398, an A at position 278 and an A at position 286; an A at position 396, a C at position 398, an A at position 278, a G at position 286 and an A at position 648; or an A at position 396, a C at position 398, a G at position 278, a G at position 286 and a T or A at position 648; and the SNP in the 5.8S rRNA gene is at a position corresponding to position 142, 144, 146, 147, 148, 154, 157, 164, 167, 185, 187, 188, 194, 197, 213, 215, 216, 219, 223, 231, 232, 236, 245, 251, or 256 of the 5.8S rRNA gene set forth in SEQ ID NO:2, and sepsis resulting from a fungal infection is diagnosed when there is a C at position 142; an A at position 144; an A at position 146; an A at position 147; a C at position 148; a T at position 154; a T at position 157; a C or G at position 164; an A at position 167; a G at position 185; an A at position 187; an A at position 188; a T at position 194; a G at position 197; an A at position 213; a T at position 215; a T at position 216; a G at position 219; an A at position 223; a G or A at position 231; a T at position 232; a T at position 236; a C or A at position 245; a C at position 251; or a T at position 256.

In one example, the bacterial infection is an infection by a bacterium selected from among *Staphylococcus aureus*, *Staphylococcus epidermidis*, *Staphylococcus haemolyticus*, *Staphylococcus hominis*, *Staphylococcus saprophyticus*, *Enterococcus faecalis*, *Enterococcus faecium*, *Clostridium perfringens*, *Streptococcus anginosus*, *Streptococcus constellatus*, *Streptococcus intermedius*, *Streptococcus mitis*, *Streptococcus mutans*, *Streptococcus sanguinis*, *Streptococcus sobrinus* and *Streptococcus oralis*, *Streptococcus pneumoniae*, *Streptococcus agalactiae*, *Streptococcus bovis*, *Streptococcus sanguinis*, *Streptococcus dysgalactiae*, *Streptococcus mutans*, *Streptococcus pyogenes*, *Escherichia coli*, *Acinetobacter baumannii*, *Bacteroides fragilis*, *Burkholderia cepacia*, *Klebsiella pneumonia*, *Klebsiella oxytoca*, *Pseudomonas aeruginosa*, *Enterobacter aerogenes*, *Enterobacter cloacae*, *Serratia marcescens*, *Proteus mirabilis*, *Citrobacter freundii*, *Morganella morganii*, *Haemophilus influenzae*, *Neisseria meningitidis*, *Stenotrophomonas maltophila*, *Prevotella buccae*, *Prevotella intermedia*, *Prevotella melaninogenica*, *Salmonella enterica*, *Serratia marcescens*, *Haemophilus influenzae*, *Campylobacter coli*, *Campylobacter jejuni*, *Campylobacter lari*, *Campylobacter fetus*, *Helicobacter cinaedi*, *Helicobacter pylori*, *Chlamydophila abortus*, *Veillonella atypica*, *Veillonella parvula*, *Veillonella denticariosi*, *Veillonella rogosae*, *Streptomyces anulatus*, *Streptomyces somaliensis* and *Mycobacterium tuberculosis*.

In some embodiments, the methods further comprise identifying the bacterium or identifying the bacterium as being one of a group of bacteria when the sepsis is determined to be caused by a Gram-positive bacterium or a Gram-negative bacterium, wherein a C at position 396 indicates that the bacterium is a Gram-negative bacterium selected from *Prevotella melaninogenica*, *Prevotella intermedia*, *Prevotella buccae*, *Bacteroides fragilis*, *Citrobacter freundii*, *Enterobacter aerogenes*, *Klebsiella oxytoca*, *Serratia marcescens*, *Morganella morganii*, *Stenotrophomonas maltophila*, *Acinetobacter baumannii*, *Enterobacter cloacae*, *Klebsiella pneumoniae*, *Salmonella enterica*, *Escherichia coli*, *Proteus mirabilis*, *Neisseria meningitidis*, *Pseudomonas aeruginosa*, *Haemophilus influenzae* and *Burkholderia cepacia*; an A at position 396, a C at position 398 and a T at position 278 indicates that the bacterium is a Gram-negative bacteria selected from *Campylobacter coli*, *Campylobacter jejuni*, *Campylobacter lari*, *Campylobacter fetus*, *Helicobacter cinaedi*, *Helicobacter pylori* and *Chlamydophila abortus*; an A at position 396, a C at position 398, an A at position 278, a G at position 286 and a G at position 648 indicates that the bacterium is the Gram-negative bacterium *Veillonella rogosae*; an A at position 396, a C at position 398, an G at position 278, a G at position 286 and a G at position 648 indicates that the bacterium is the Gram-negative bacterium *Veillonella atypica*, *Veillonella parvula* and *Veillonella denticariosi*; a G at position 396 indicates that the bacteria is a Gram-positive bacterium selected from among *Streptomyces anulatus*, *Streptomyces somaliensis* and *Mycobacterium tuberculosis*; an A at position 396, a C at position 398 and a C at position 278 indicates that the bacterium is the Gram-positive bacteria *Enterococcus faecalis* or *Enterococcus faecium*; an A at position 396, a C at position 398, a G at position 278, a T at position 286 and a T at position 648 indicates that the bacterium is the Gram-positive bacterium *Clostridium perfringens*; an A at position 396, a C at position 398, a G at position 278, and an A at position 286 indicates that the bacterium is the Gram-positive bacterium *Streptococcus bovis*, *Streptococcus agalactiae*, *Streptococcus agalactiae*, *Streptococcus agalactiae*, *Streptococcus dysgalactiae*, *Streptococcus pyogenes*, *Streptococcus anginosus*, *Streptococcus intermedius*, *Streptococcus mitis*, *Streptococcus mutans*, *Streptococcus pneumoniae* and *Streptococcus sanguinis*; or an A at position 396, a C at position 398, an A at position 278 and an A at position 286 indicates that the bacterium is a Gram-positive bacterium selected from among *Staphylococcus aureus*, *Streptococcus sobrinus*, *Streptococcus constellatus* and *Streptococcus oralis*; an A at position 396, a C at position 398, an A at position 278, a G at position 286 and an A at position 648 indicates that the bacterium is the Gram-positive bacterium *Staphylococcus epidermidis* or *Staphylococcus hominis*; and an A at position 396, a C at position 398, a G at position 278, a G at position 286 and a T or A at position 648 indicates that the bacterium is the Gram-positive bacterium *Staphylococcus haemolyticus*.

In another aspect, the invention provides a method for diagnosing sepsis in a mammalian (e.g., human) subject, comprising analysing nucleic acid from the blood of the subject for a SNP in a 16S rRNA gene and a SNP in a 5.8s rRNA gene, wherein the presence of the SNP is indicative of sepsis, wherein: the SNP in the 16S rRNA gene is at a position corresponding to position 396 of the 16S rRNA gene set forth in SEQ ID NO:1 and wherein sepsis resulting from a Gram-negative bacterial infection is diagnosed when there is a C at position 396 or and sepsis resulting from a Gram-positive bacterial infection is diagnosed when there is a G at position 396; and the SNPs in the 5.8S rRNA gene are at a position corresponding to position 254 of SEQ ID NO:2; a position corresponding to position 160 or 255 of SEQ ID NO:2; and any two of positions corresponding to positions 163, 164, 165, 196, 202, 223, 224 or 259 of SEQ ID NO:2, and wherein sepsis resulting from an infection by a fungus selected from among *Candida albicans, Candida tropicalis, Candida parapsilosis, Candida krusei, Candida glabrata, Ajellomyces capsulatus, Stachybotrys* sp., *Scedosporium apiospermum, Fusarium* sp., *Aspergillus fumigatus* and *Cryptococcus neoformans* is diagnosed based on the presence of SNPs set forth in following table:

Also provided is a method for diagnosing sepsis in a mammalian (e.g., human) subject, comprising analysing nucleic acid from the blood of the subject for SNPs in a 16S rRNA gene and a SNP in a 5.8s rRNA gene, wherein the presence of the SNP(s) is indicative of sepsis, wherein: the SNPs in the 16S rRNA gene are at positions corresponding to positions 278, 286, 396, 398, and 648 of the 16S rRNA gene set forth in SEQ ID NO:1, and wherein sepsis resulting from a Gram-negative bacterial infection is diagnosed when there is: a C at position 396; an A at position 396, a C at position 398 and a T at position 278; an A at position 396, a C at position 398, an A at position 278, a G at position 286 and a G at position 648; or an A at position 396, a C at position 398, an G at position 278, a G at position 286 and a G at position 648; and sepsis resulting from a Gram-positive bacterial infection is diagnosed when there is a G at position 396; an A at position 396, a C at position 398 and a C at position 278; an A at position 396, a C at position 398,

| | SNP position | | | | | | | | | | |
|---|---|---|---|---|---|---|---|---|---|---|---|
| | 160 | 163 | 164 | 165 | 196 | 202 | 223 | 224 | 254 | 255 | 259 |
| *Candida albicans* | T | T | C | G | C | A | A | T | T | C | T |
| *Candida tropicalis* | T | T | C | G | C | A | A | T | T | T | T |
| *Candida parapsilosis* | T | T | C | G | A | A | A | T | T | T | T |
| *Candida krusei* | T | T | C | G | C | G | A | T | C | T | C |
| *Candida glabrata* | T | T | C | G | C | G | A | T | T | C | T |
| *Ajellomyces capsulatus* | T | C | G | A | A | G | A | T | T | C | T |
| *Stachybotrys* sp. | C | T | G | G | A | G | A | T | G | C | C |
| *Scedosporium apiospermum* | T | T | G | G | A | G | A | T | G | C | T |
| *Fusarium* sp. | C | T | G | G | A | G | A | T | G | C | T |
| *Aspergillus fumigatus* | T | C | G | G | A | G | A | T | C | C | T |
| *Cryptococcus neoformans* | C | C | C | A | A | G | A | T | T | T | T |

In some embodiments, the bacterial infection is an infection by a bacterium selected from among *Staphylococcus aureus, Staphylococcus epidermidis, Staphylococcus haemolyticus, Staphylococcus hominis, Staphylococcus saprophyticus, Enterococcus faecalis, Enterococcus faecium, Clostridium perfringens, Streptococcus anginosus, Streptococcus constellatus, Streptococcus intermedius, Streptococcus mitis, Streptococcus mutans, Streptococcus sanguinis, Streptococcus sobrinus* and *Streptococcus oralis, Streptococcus pneumoniae, Streptococcus agalactiae, Streptococcus bovis, Streptococcus sanguinis, Streptococcus dysgalactiae, Streptococcus mutans* and *Streptococcus pyogenes, Escherichia coli, Acinetobacter baumannii, Bacteroides fragilis, Burkholderia cepacia, Klebsiella pneumonia, Klebsiella oxytoca, Pseudomonas aeruginosa, Enterobacter aerogenes, Enterobacter cloacae, Serratia marcescens, Proteus mirabilis, Citrobacter freundii, Morganella morganii, Haemophilus influenzae, Neisseria meningitidis, Stenotrophomonas maltophila, Prevotella buccae, Prevotella intermedia* and *Prevotella melaninogenica*.

a G at position 278, and an A at position 286; an A at position 396, a C at position 398, an A at position 278 and an A at position 286; an A at position 396, a C at position 398, an A at position 278, a G at position 286 and an A at position 648; or an A at position 396, a C at position 398, a G at position 278, a G at position 286 and a T or A at position 648; and the SNPs in the 5.8S rRNA gene are at a position corresponding to position 254 of SEQ ID NO:2; a position corresponding to position 160 or 255 of SEQ ID NO:2; and any two of positions corresponding to positions 163, 164, 165, 196, 202, 223, 224 or 259 of SEQ ID NO:2, and wherein sepsis resulting from an infection by a fungus selected from among *Candida albicans, Candida tropicalis, Candida parapsilosis, Candida krusei, Candida glabrata, Ajellomyces capsulatus, Stachybotrys* sp., *Scedosporium apiospermum, Fusarium* sp., *Aspergillus fumigatus* and *Cryptococcus neoformans* is diagnosed based on the presence of SNPs set forth in following table:

| | SNP position | | | | | | | | | | |
|---|---|---|---|---|---|---|---|---|---|---|---|
| | 160 | 163 | 164 | 165 | 196 | 202 | 223 | 224 | 254 | 255 | 259 |
| *Candida albicans* | T | T | C | G | C | A | A | T | T | C | T |
| *Candida tropicalis* | T | T | C | G | C | A | A | T | T | T | T |
| *Candida parapsilosis* | T | T | C | G | A | A | A | T | T | T | T |
| *Candida krusei* | T | T | C | G | C | G | A | T | C | T | C |
| *Candida glabrata* | T | T | C | G | C | G | A | T | T | C | T |
| *Ajellomyces capsulatus* | T | C | G | A | A | G | A | T | T | C | T |
| *Stachybotrys* sp. | C | T | G | G | A | G | A | T | G | C | C |
| *Scedosporium apiospermum* | T | T | G | G | A | G | A | T | G | C | T |
| *Fusarium* sp. | C | T | G | G | A | G | A | T | G | C | T |

-continued

| | \multicolumn{11}{c}{SNP position} |
| | 160 | 163 | 164 | 165 | 196 | 202 | 223 | 224 | 254 | 255 | 259 |
|---|---|---|---|---|---|---|---|---|---|---|---|
| Aspergillus fumigatus | T | C | G | G | A | G | A | T | C | C | T |
| Cryptococcus neoformans | C | C | C | A | A | G | A | T | T | T | T |

In particular embodiments, the bacterial infection is an infection by a bacterium selected from among *Staphylococcus aureus, Staphylococcus epidermidis, Staphylococcus haemolyticus, Staphylococcus hominis, Staphylococcus saprophyticus, Enterococcus faecalis, Enterococcus faecium, Clostridium perfringens, Streptococcus anginosus, Streptococcus constellatus, Streptococcus intermedius, Streptococcus mitis, Streptococcus mutans, Streptococcus sanguinis, Streptococcus sobrinus* and *Streptococcus oralis, Streptococcus pneumoniae, Streptococcus agalactiae, Streptococcus bovis, Streptococcus sanguinis, Streptococcus dysgalactiae, Streptococcus mutans, Streptococcus pyogenes, Escherichia coli, Acinetobacter baumannii, Bacteroides fragilis, Burkholderia cepacia, Klebsiella pneumonia, Klebsiella oxytoca, Pseudomonas aeruginosa, Enterobacter aerogenes, Enterobacter cloacae, Serratia marcescens, Proteus mirabilis, Citrobacter freundii, Morganella morganii, Haemophilus influenzae, Neisseria meningitidis, Stenotrophomonas maltophila, Prevotella buccae, Prevotella intermedia, Prevotella melaninogenica, Salmonella enterica, Serratia marcescens, Haemophilus influenzae, Campylobacter coli, Campylobacter jejuni, Campylobacter lari, Campylobacter fetus, Helicobacter cinaedi, Helicobacter pylori, Chlamydophila abortus, Veillonella atypica, Veillonella parvula, Veillonella denticariosi, Veillonella rogosae, Streptomyces anulatus, Streptomyces somaliensis* and *Mycobacterium tuberculosis*.

In some example, the method further comprises identifying the bacterium or identifying the bacterium as being one of a group of bacteria when the sepsis is determined to be caused by a Gram-positive bacterium or a Gram-negative bacterium, wherein: a C at position 396 indicates that the bacterium is a Gram-negative bacterium selected from *Prevotella melaninogenica, Prevotella intermedia, Prevotella buccae, Bacteroides fragilis, Citrobacter freundii, Enterobacter aerogenes, Klebsiella oxytoca, Serratia marcescens, Morganella morganii, Stenotrophomonas maltophila, Acinetobacter baumannii, Enterobacter cloacae, Klebsiella pneumoniae, Salmonella enterica, Escherichia coli, Proteus mirabilis, Neisseria meningitidis, Pseudomonas aeruginosa, Haemophilus influenzae* and *Burkholderia cepacia*; an A at position 396, a C at position 398 and a T at position 278 indicates that the bacterium is a Gram-negative bacteria selected from *Campylobacter coli, Campylobacter jejuni, Campylobacter lari, Campylobacter fetus, Helicobacter cinaedi, Helicobacter pylori* and *Chlamydophila abortus*; an A at position 396, a C at position 398, an A at position 278, a G at position 286 and a G at position 648 indicates that the bacterium is the Gram-negative bacterium *Veillonella rogosae*; an A at position 396, a C at position 398, an G at position 278, a G at position 286 and a G at position 648 indicates that the bacterium is the Gram-negative bacterium *Veillonella atypica, Veillonella parvula* and *Veillonella denticariosi*; a G at position 396 indicates that the bacteria is a Gram-positive bacterium selected from among *Streptomyces anulatus, Streptomyces somaliensis* and *Mycobacterium tuberculosis*; an A at position 396, a C at position 398 and a C at position 278 indicates that the bacterium is the Gram-positive bacteria *Enterococcus faecalis* or *Enterococcus faecium*; an A at position 396, a C at position 398, a G at position 278, a T at position 286 and a T at position 648 indicates that the bacterium is the Gram-positive bacterium *Clostridium perfringens*; an A at position 396, a C at position 398, a G at position 278, and an A at position 286 indicates that the bacterium is the Gram-positive bacterium *Streptococcus bovis, Streptococcus agalactiae, Streptococcus agalactiae, Streptococcus agalactiae, Streptococcus dysgalactiae, Streptococcus pyogenes, Streptococcus anginosus, Streptococcus intermedius, Streptococcus mitis, Streptococcus mutans, Streptococcus pneumoniae* and *Streptococcus sanguinis*; or an A at position 396, a C at position 398, an A at position 278 and an A at position 286 indicates that the bacterium is a Gram-positive bacterium selected from among *Staphylococcus aureus, Streptococcus sobrinus, Streptococcus constellatus* and *Streptococcus oralis*; an A at position 396, a C at position 398, a A at position 278, a G at position 286 and an A at position 648 indicates that the bacterium is the Gram-positive bacterium *Staphylococcus epidermidis* or *Staphylococcus hominis*; and an A at position 396, a C at position 398, a G at position 278, a G at position 286 and a T or A at position 648 indicates that the bacterium is the Gram-positive bacterium *Staphylococcus haemolyticus*.

The invention also provides a method for diagnosing sepsis in a mammalian (e.g., human) subject, comprising analysing nucleic acid from the blood of the subject for SNPs in a 16S rRNA gene and a SNP in a 5.8s rRNA gene, wherein the presence of the SNP(s) is indicative of sepsis, wherein the SNPs in the 16S rRNA gene are at positions corresponding to positions 396, 398, 399, 400 and 401 of the 16S rRNA gene set forth in SEQ ID NO:1, and wherein sepsis resulting from a Group 1 bacterium selected from among the Gram-positive species *Bacillus anthracis, Enterococcus faecalis, Enterococcus faecium, Listeria monocytogenes, Streptococcus agalactiae, Streptococcus anginosus, Streptococcus constellatus, Streptococcus dysgalactiae, Streptococcus intermedius, Streptococcus pyogenes, Lactobacillus intestinalis, Clostridium perfringens, Staphylococcus aureus, Staphylococcus epidermidis, Staphylococcus haemolyticus, Staphylococcus hominis, Staphylococcus saprophyticus, Eubacterium desmolans, Clostridium difficile, Erysipelothrix rhusiopathiae, Streptococcus bovis, Streptococcus mitis, Streptococcus mutans, Streptococcus oralis, Streptococcus pneumonia, Streptococcus sanguinis, Streptococcus sobrinus* and *Peptostreptococcus stomatis* or Gram-negative species *Helicobacter pylori, Campylobacter coli* and *Veillonella dispar* is diagnosed when there is an A, C, G, C and C at positions 396, 398, 399, 400 and 401, respectively; sepsis resulting from a Group 2 bacterium selected from among the Gram-positive species *Corynebacterium diphtheria, Dermatophilus congolensis, Micrococcus luteus, Rhodococcus equi, Streptomyces anulatus, Streptomyces somaliensis, Mycobacterium tuberculosis, Corynebacterium jeikeium, Corynebacterium urealyticum, Mobi-

*luncus curtisii, Nocardia asteroids, Nocardia brasiliensis* and *Actinomyces massiliensis* or the Gram-negative species *Leptospira interrogans, Chlamydia trachomatis* and *Chlamydophila pneumoniae* is diagnosed when there is a G, C, G, C and C at positions 396, 398, 399, 400 and 401, respectively; sepsis resulting from a Group 3 bacterium selected from among Gram-negative aerobic bacterium selected from among *Actinobacillus hominis, Edwardsiella tarda, Haemophilus ducreyi, Haemophilus influenzae, Haemophilus parahaemolyticus, Haemophilus parainfluenzae, Morganella morganii, Pasteurella multocida, Providencia alcalifaciens, Vibrio cholerae, Moraxella catarrhalis, Pseudomonas aeruginosa, Neisseria gonorrhoeae, Neisseria meningitides, Aeromonas hydrophila, Citrobacter freundii, Enterobacter aerogenes, Enterobacter cloacae, Escherichia coli, Klebsiella oxytoca, Klebsiella pneumonia, Proteus mirabilis, Salmonella enterica, Serratia marcescens, Shigella dysenteriae, Shigella sonnei, Yersinia enterocolitica, Yersinia pestis, Acinetobacter baumannii, Brucella abortus* and *Flavobacterium ceti* is diagnosed when there is a C, T, G, C and C at positions 396, 398, 399, 400 and 401 respectively; sepsis resulting from a Group 4 bacterium selected from among the Gram-negative aerobic species *Legionella pneumophila, Burkholderia cepacia* and *Cardiobacterium valvarum* is determined when there is an A, T, G, C and C at positions 396, 398, 399, 400 and 401, respectively; sepsis resulting from the Group 5 bacterium *Stenotrophomonas maltophila* is diagnosed when there is a C, T, A, C and C at positions 396, 398, 399, 400 and 401, respectively; sepsis resulting from a Group 6 bacterium selected from among the Gram-negative anaerobic species *Prevotella buccae, Prevotella melaninogenica, Bacteroides fragilis, Prevotella intermedia* is diagnosed when there is a C, A, G, T and A at positions 396, 398, 399, 400 and 401, respectively; sepsis resulting from the Group 7 bacterium *Porphyromonas gingivalis* is diagnosed when there is a C, A, G, T and C at positions 396, 398, 399, 400 and 401, respectively; and the SNP in the 5.8S rRNA gene is at a position corresponding to position 142, 144, 146, 147, 148, 154, 157, 164, 167, 185, 187, 188, 194, 197, 213, 215, 216, 219, 223, 231, 232, 236, 245, 251, or 256 of the 5.8S rRNA gene set forth in SEQ ID NO:2, and sepsis resulting from a fungal infection is diagnosed when there is a C at position 142; an A at position 144; an A at position 146; an A at position 147; a C at position 148; a T at position 154; a T at position 157; a C or G at position 164; an A at position 167; a G at position 185; an A at position 187; an A at position 188; a T at position 194; a G at position 197; an A at position 213; a T at position 215; a T at position 216; a G at position 219; an A at position 223; a G or A at position 231; a T at position 232; a T at position 236; a C or A at position 245; a C at position 251; or a T at position 256.

In another aspect, the invention provides a method for diagnosing sepsis in a mammalian (e.g., human) subject, comprising analysing nucleic acid from the blood of the subject for SNPs in a 16S rRNA gene and a SNP in a 5.8s rRNA gene, wherein the presence of the SNP(s) is indicative of sepsis, wherein the SNPs in the 16S rRNA gene are at positions corresponding to positions 396, 398, 399, 400 and 401 of the 16S rRNA gene set forth in SEQ ID NO:1, and wherein sepsis resulting from a Group 1 bacterium selected from among the Gram-positive species *Bacillus anthracis, Enterococcus faecalis, Enterococcus faecium, Listeria monocytogenes, Streptococcus agalactiae, Streptococcus anginosus, Streptococcus constellatus, Streptococcus dysgalactiae, Streptococcus intermedius, Streptococcus pyogenes, Lactobacillus intestinalis, Clostridium perfringens, Staphylococcus aureus, Staphylococcus epidermidis, Staphylococcus haemolyticus, Staphylococcus hominis, Staphylococcus saprophyticus, Eubacterium desmolans, Clostridium difficile, Erysipelothrix rhusiopathiae, Streptococcus bovis, Streptococcus mitis, Streptococcus mutans, Streptococcus oralis, Streptococcus pneumonia, Streptococcus sanguinis, Streptococcus sobrinus* and *Peptostreptococcus stomatis* or Gram-negative species *Helicobacter pylori, Campylobacter coli* and *Veillonella dispar* is diagnosed when there is an A, C, G, C and C at positions 396, 398, 399, 400 and 401, respectively; sepsis resulting from a Group 2 bacterium selected from among the Gram-positive species *Corynebacterium diphtheria, Dermatophilus congolensis, Micrococcus luteus, Rhodococcus equi, Streptomyces anulatus, Streptomyces somaliensis, Mycobacterium tuberculosis, Corynebacterium jeikeium, Corynebacterium urealyticum, Mobiluncus curtisii, Nocardia asteroids, Nocardia brasiliensis* and *Actinomyces massiliensis* or the Gram-negative species *Leptospira interrogans, Chlamydia trachomatis* and *Chlamydophila pneumoniae* is diagnosed when there is a G, C, G, C and C at positions 396, 398, 399, 400 and 401, respectively; sepsis resulting from a Group 3 bacterium selected from among Gram-negative aerobic bacterium selected from among *Actinobacillus hominis, Edwardsiella tarda, Haemophilus ducreyi, Haemophilus influenzae, Haemophilus parahaemolyticus, Haemophilus parainfluenzae, Morganella morganii, Pasteurella multocida, Providencia alcalifaciens, Vibrio cholerae, Moraxella catarrhalis, Pseudomonas aeruginosa, Neisseria gonorrhoeae, Neisseria meningitides, Aeromonas hydrophila, Citrobacter freundii, Enterobacter aerogenes, Enterobacter cloacae, Escherichia coli, Klebsiella oxytoca, Klebsiella pneumonia, Proteus mirabilis, Salmonella enterica, Serratia marcescens, Shigella dysenteriae, Shigella sonnei, Yersinia enterocolitica, Yersinia pestis, Acinetobacter baumannii, Brucella abortus* and *Flavobacterium ceti* is diagnosed when there is a C, T, G, C and C at positions 396, 398, 399, 400 and 401 respectively; sepsis resulting from a Group 4 bacterium selected from among the Gram-negative aerobic species *Legionella pneumophila, Burkholderia cepacia* and *Cardiobacterium valvarum* is determined when there is an A, T, G, C and C at positions 396, 398, 399, 400 and 401, respectively; sepsis resulting from the Group 5 bacterium *Stenotrophomonas maltophila* is diagnosed when there is a C, T, A, C and C at positions 396, 398, 399, 400 and 401, respectively; sepsis resulting from a Group 6 bacterium selected from among the Gram-negative anaerobic species *Prevotella* buccae, *Prevotella melaninogenica, Bacteroides fragilis, Prevotella intermedia* is diagnosed when there is a C, A, G, T and A at positions 396, 398, 399, 400 and 401, respectively; sepsis resulting from the Group 7 bacterium *Porphyromonas gingivalis* is diagnosed when there is a C, A, G, T and C at positions 396, 398, 399, 400 and 401, respectively; and the SNPs in the 5.8S rRNA gene are at a position corresponding to position 254 of SEQ ID NO:2; a position corresponding to position 160 or 255 of SEQ ID NO:2; and any two of positions corresponding to positions 163, 164, 165, 196, 202, 223, 224 or 259 of SEQ ID NO:2, and wherein sepsis resulting from an infection by a fungus selected from among *Candida albicans, Candida tropicalis, Candida parapsilosis, Candida krusei, Candida glabrata, Ajellomyces capsulatus, Stachybotrys* sp., *Scedosporium apiospermum, Fusarium* sp., *Aspergillus fumigatus* and *Cryptococcus neoformans* is diagnosed based on the presence of SNPs set forth in following table:

| | SNP position | | | | | | | | | | |
|---|---|---|---|---|---|---|---|---|---|---|---|
| | 160 | 163 | 164 | 165 | 196 | 202 | 223 | 224 | 254 | 255 | 259 |
| Candida albicans | T | T | C | G | C | A | A | T | T | C | T |
| Candida tropicalis | T | T | C | G | C | A | A | T | T | T | T |
| Candida parapsilosis | T | T | C | G | A | A | A | T | T | T | T |
| Candida krusei | T | T | C | G | C | G | A | T | C | T | C |
| Candida glabrata | T | T | C | G | C | G | A | T | T | C | T |
| Ajellomyces capsulatus | T | C | G | A | A | G | A | T | T | C | T |
| Stachybotrys sp. | C | T | G | G | A | G | A | T | G | C | C |
| Scedosporium apiospermum | T | T | G | G | A | G | A | T | G | C | T |
| Fusarium sp. | C | T | G | G | A | G | A | T | G | C | T |
| Aspergillus fumigatus | T | C | G | G | A | G | A | T | C | C | T |
| Cryptococcus neoformans | C | C | C | A | A | G | A | T | T | T | T |

In some embodiments of the present methods, if sepsis is determined to result from a bacterium from Group 1, 2, 3, 4, or 6, further grouping of the bacteria into Groups 1a-l, 2a-j, 3a-g, 4a-c and 6a-d, can be performed as described above and herein.

In some embodiments, the number of bacteria and/or fungi in the sample is also determined. In one example, the nucleic acid is extracted from the sample prior to analysis. In further examples, the analysis comprises amplification of the nucleic acid. In one embodiment, the analysis is performed using sequencing, 5' nuclease digestion, molecular beacons, oligonucleotide ligation, microarray, or any combination thereof. In further embodiments, the methods of diagnosis further comprise administering a therapeutic agent to the subject, such as an anti-fungal agent or an antibiotic.

BRIEF DESCRIPTION OF THE DRAWINGS

FIG. 1 shows the results of a quantitative RT-PCR assay (TaqMan® assay) of whole blood spiked with Gram-negative, Gram-positive or fungal organisms.

TABLE A

BRIEF DESCRIPTION OF THE SEQUENCES

| Sequence ID Number | Sequence |
|---|---|
| SEQ ID NO: 1 | Escherichia coli 16S rRNA gene (Genbank accession NR_074891) |
| SEQ ID NO: 2 | Candida albicans 5.8S rRNA gene (Genbank accession JQ070104.1) |
| SEQ ID NO: 3 | Homo sapiens 5.8S rRNA gene (Genbank accession NR_003285.2) |
| SEQ ID NO: 4 | Gram-positive 396/398 probe GCAACGCCGCGT |
| SEQ ID NO: 5 | Gram-positive 396/398 probe GCGACGCCGCGT |
| SEQ ID NO: 6 | Gram-negative 396/398 probe GCCAAGTAGCGT |
| SEQ ID NO: 7 | Gram-negative 396/398 probe GCCATGCCGCGT |
| SEQ ID NO: 8 | Gram-negative and Gram-positive 396/398 fwd primer ACTCCTACGGGAGGCAGCAGT |
| SEQ ID NO: 9 | Gram-negative 396/398 rev primer GCCAGCAGCYGCGGTAATACG |
| SEQ ID NO: 10 | Gram-positive 396/398 rev primer GCCAGCAGCCGCGGTAATACG |
| SEQ ID NO: 11 | Gram-negative 278/286 probe GCGATGATCAGTAG |
| SEQ ID NO: 12 | Gram-negative 278/286 probe GCTATGACGCTTAA |
| SEQ ID NO: 13 | Gram-negative 278/286 probe GCTTTGACGCATAA |
| SEQ ID NO: 14 | Gram-negative 278/286 probe GCTATGACGGGTAT |
| SEQ ID NO: 15 | Gram-negative 278/286 probe GCAATGATCAGTAG |
| SEQ ID NO: 16 | Gram-negative 278/286 probe GTTTTGACGTCTAG |
| SEQ ID NO: 17 | Gram-positive 278/286 probe GCAACGATGCATAG |
| SEQ ID NO: 18 | Gram-positive 278/286 probe GCAACGATGCGTAG |
| SEQ ID NO: 19 | Gram-positive 278/286 probe GCCACGATACATAG |
| SEQ ID NO: 20 | Gram-negative 278/286 fwd primer TGWAGGAGGGGATTGCGTC |

TABLE A -continued

BRIEF DESCRIPTION OF THE SEQUENCES

| Sequence ID Number | Sequence |
|---|---|
| SEQ ID NO: 21 | Gram-negative 278/286 fwd primer TGTAGGATGAGACTATATW |
| SEQ ID NO: 22 | Gram-negative 278/286 fwd primer TAARRGATCAGCCTATGTC |
| SEQ ID NO: 23 | Gram-positive 278/286 fwd primer TTATAGATGGATCCGCGCY |
| SEQ ID NO: 24 | Gram-positive 278/286 fwd primer TGATGGATGGACCCGCGGT |
| SEQ ID NO: 25 | Gram-negative 278/286 rev primer ATGAACGGCCACATTGG |
| SEQ ID NO: 26 | Gram-negative 278/286 rev primer ATGATCAGTCACACTGG |
| SEQ ID NO: 27 | Gram-negative 278/286 rev primer GTGAWCGGACACACTGG |
| SEQ ID NO: 28 | Gram-positive 278/286 rev primer GTGATCGGCCACACTGGRACT |
| SEQ ID NO: 29 | Gram-negative 648 probe CTGCTGATCTAGAG |
| SEQ ID NO: 30 | Gram-positive 648 probe CTGGAAAACTTGAG |
| SEQ ID NO: 31 | Gram-positive 648 probe CTGGGAGACTTGAG |
| SEQ ID NO: 32 | Gram-negative 648 fwd primer TAACCCCGTGAKGGGATGGA |
| SEQ ID NO: 33 | Gram-positive 648 fwd primer CAACCGKGGAGGGTCATTGGA |
| SEQ ID NO: 34 | Gram-negative 648 rev primer TCGGAGAGGAAAGTGGAATTCC |
| SEQ ID NO: 35 | Gram-positive 648 rev primer CARRAGRGGARAGTGGAATTCC |
| SEQ ID NO: 36 | Fungi 164/165 probe CTCTTGGTTCCGGCATCGA |
| SEQ ID NO: 37 | Fungi 164/165 probe CTCTTGGTTCTCGCATCGA |
| SEQ ID NO: 38 | Fungi 164/165 fwd primer TATGCAGTCTGAGTTGATTATCGTAATC |
| SEQ ID NO: 39 | Fungi 164/165 fwd primer CAGAGGTCTAAACTTACAACCAATTTTTT |
| SEQ ID NO: 40 | Fungi 164/165 rev primer GCATTTCGCTGCGTTCTTC |
| SEQ ID NO: 41 | Forward primer TGTAGGATGAGACTATATW |
| SEQ ID NO: 42 | Probe GCTATGACGCTTAA |
| SEQ ID NO: 43 | Reverse primer ATGATCAGTCACACTGG |
| SEQ ID NO: 44 | Forward primer TGTAGGATGAGACTATATW |
| SEQ ID NO: 45 | Probe GCTTTGACGCATAA |
| SEQ ID NO: 46 | Reverse primer ATGATCAGTCACACTGG |
| SEQ ID NO: 47 | Forward primer TAARRGATCAGCCTATGTC |
| SEQ ID NO: 48 | Probe GCTATGACGGGTAT |
| SEQ ID NO: 49 | Reverse primer GTGAWCGGACACACTGG |
| SEQ ID NO: 50 | Forward primer CATCAGATGTGCCCAGATG |
| SEQ ID NO: 51 | Probe GCGACGATCCCTAG |
| SEQ ID NO: 52 | Reverse primer ATGACCAGCCACACTGG |
| SEQ ID NO: 53 | Forward primer TATCGGATGAACCCATATG |
| SEQ ID NO: 54 | Probe GCGACGATCTCTAG |
| SEQ ID NO: 55 | Reverse primer ATGACCAGCCACACTGG |
| SEQ ID NO: 56 | Forward primer TATTCGAGCGGCCGATATC |
| SEQ ID NO: 57 | Probe CCTGCGATCTCTAG |
| SEQ ID NO: 58 | Reverse primer ATGACCAGCCACACTGG |

TABLE A -continued

BRIEF DESCRIPTION OF THE SEQUENCES

| Sequence ID Number | Sequence |
|---|---|
| SEQ ID NO: 59 | Forward primer TATCAGATGAGCCTAGGTC |
| SEQ ID NO: 60 | Probe GCGACGATCCGTAA |
| SEQ ID NO: 61 | Reverse primer ATGATCAGTCACACTGG |
| SEQ ID NO: 62 | Forward primer TATTCGAGCGGCCGATATC |
| SEQ ID NO: 63 | Probe GCGACGATCAGTAG |
| SEQ ID NO: 64 | Reverse primer ATGACCAGCCACACTGG |
| SEQ ID NO: 65 | Forward primer TGWAGGAGGGGATTGCGTC |
| SEQ ID NO: 66 | Probe GCGATGATCAGTAG |
| SEQ ID NO: 67 | Reverse primer ATGAACGGCCACATTGG |
| SEQ ID NO: 68 | Forward primer TGWAGGAGGGGATTGCGTC |
| SEQ ID NO: 69 | Probe GCAATGATCAGTAG |
| SEQ ID NO: 70 | Reverse primer ATGAACGGCCACATTGG |
| SEQ ID NO: 71 | Forward primer TTAAGGGAGAGTCTATGGG |
| SEQ ID NO: 72 | Probe GTTTTGACGTCTAG |
| SEQ ID NO: 73 | Reverse primer TTGACCGCCAACACTGG |
| SEQ ID NO: 74 | Forward primer TAAAGGATGGGGATGCGTT |
| SEQ ID NO: 75 | Probe CCTTCGATGGATAG |
| SEQ ID NO: 76 | Reverse primer AAGGTCCCCCACATTGG |
| SEQ ID NO: 77 | Forward primer ACTCCTACGGGAGGCAGCAGT |
| SEQ ID NO: 78 | Probe GCAACGCCGCGT |
| SEQ ID NO: 79 | Reverse primer GCCAGCAGCYGCGGTAATACG |
| SEQ ID NO: 80 | Forward primer ACTCCTACGGGAGGCAGCAGT |
| SEQ ID NO: 81 | Probe GCCAAGTAGCGT |
| SEQ ID NO: 82 | Reverse primer GCCAGCAGCYGCGGTAATACG |
| SEQ ID NO: 83 | Forward primer ACTCCTACGGGAGGCAGCAGT |
| SEQ ID NO: 84 | Probe GCCATGCCGCGT |
| SEQ ID NO: 85 | Reverse primer GCCAGCAGCYGCGGTAATACG |
| SEQ ID NO: 86 | Forward primer TAACCATTAAACTGCTTGAGA |
| SEQ ID NO: 87 | Probe CTGATAATCTAGAG |
| SEQ ID NO: 88 | Reverse primer DGGGAGAGGYAGRTGGAATTSG |
| SEQ ID NO: 89 | Forward primer TAACCGTTGAACTGCTTGGGA |
| SEQ ID NO: 90 | Probe CTGGTAATCTAGAG |
| SEQ ID NO: 91 | Reverse primer DGGGAGAGGYAGRTGGAATTSG |
| SEQ ID NO: 92 | Forward primer TAACTACAGAACTGCATTTGA |
| SEQ ID NO: 93 | Probe CTGACTATCTAGAG |
| SEQ ID NO: 94 | Reverse primer DGGGAGAGGYAGRTGGAATTSG |
| SEQ ID NO: 95 | Forward primer TAACCATAGAACTGCATTTGA |

TABLE A -continued

BRIEF DESCRIPTION OF THE SEQUENCES

| Sequence ID Number | Sequence | |
|---|---|---|
| SEQ ID NO: 96 | Probe | CTACTATTCTAGAG |
| SEQ ID NO: 97 | Reverse primer | DGGGAGAGGYAGRTGGAATTSG |
| SEQ ID NO: 98 | Forward primer | TAACTACAGAACTGCATTTGA |
| SEQ ID NO: 99 | Probe | CTGACTATCTAGAG |
| SEQ ID NO: 100 | Reverse primer | DGGGAGAGGYAGRTGGAATTSG |
| SEQ ID NO: 101 | Forward primer | TAACTACAGAACTGCATTTGA |
| SEQ ID NO: 102 | Probe | CTACTATTCTAGAG |
| SEQ ID NO: 103 | Reverse primer | DGGGAGAGGYAGRTGGAATTSG |
| SEQ ID NO: 104 | Forward primer | CAACCTGGGAACTGCATTTGA |
| SEQ ID NO: 105 | Probe | CTGGCAGGCTGGAG |
| SEQ ID NO: 106 | Reverse primer | TYGTAGAGGGGGTAGAATTCC |
| SEQ ID NO: 107 | Forward primer | CAACCTGGGAACTGCATTCGA |
| SEQ ID NO: 108 | Probe | CTGGCAGGCTTGAG |
| SEQ ID NO: 109 | Reverse primer | TYGTAGAGGGGGTAGAATTCC |
| SEQ ID NO: 110 | Forward primer | CAACCTGGGAACTGCATTTGA |
| SEQ ID NO: 111 | Probe | CTGGCAAGCTAGAG |
| SEQ ID NO: 112 | Reverse primer | TYGTAGAGGGGGTAGAATTCC |
| SEQ ID NO: 113 | Forward primer | CAACCTGGGAACTGCATCTGA |
| SEQ ID NO: 114 | Probe | CTGGCAAGCTTGAG |
| SEQ ID NO: 115 | Reverse primer | TYGTAGAGGGGGTAGAATTCC |
| SEQ ID NO: 116 | Forward primer | CAACCTGGGAACTGCATCCAA |
| SEQ ID NO: 117 | Probe | CTACTGAGCTAGAG |
| SEQ ID NO: 118 | Reverse primer | CGGTAGAGGGTGGTGGAATTTC |
| SEQ ID NO: 119 | Forward primer | TAACTTGGGAATTGCATCTGA |
| SEQ ID NO: 120 | Probe | CTGGTTGGCTAGAG |
| SEQ ID NO: 121 | Reverse primer | TYGTAGAGGGGGTAGAATTCC |
| SEQ ID NO: 122 | Forward primer | TAACCTAGGAATTGCATTTCA |
| SEQ ID NO: 123 | Probe | CTGGGTAACTAGAG |
| SEQ ID NO: 124 | Reverse primer | CTTTAGGGAGGGGTAGAATTCC |
| SEQ ID NO: 125 | Forward primer | CAACCCGGGAACTGCGTTCTG |
| SEQ ID NO: 126 | Probe | CTGGGTGACTCGAG |
| SEQ ID NO: 127 | Reverse primer | TGTCAGAGGGAGGTAGAATTCC |
| SEQ ID NO: 128 | Forward primer | TAACCCCGTGAKGGGATGGA |
| SEQ ID NO: 129 | Probe | CTGCTGATCTAGAG |
| SEQ ID NO: 130 | Reverse primer | TCGGAGAGGAAAGTGGAATTCC |
| SEQ ID NO: 131 | Forward primer | TAACCCCGTGAKGGGATGGA |
| SEQ ID NO: 132 | Probe | CTGCCAATCTAGAG |
| SEQ ID NO: 133 | Reverse primer | TCGGAGAGGAAAGTGGAATTCC |

TABLE A -continued

BRIEF DESCRIPTION OF THE SEQUENCES

| Sequence ID Number | Sequence |
|---|---|
| SEQ ID NO: 134 Forward primer | CAACCCCAAGCCAGCATCTAA |
| SEQ ID NO: 135 Probe | CTATCTTTCTAGAG |
| SEQ ID NO: 136 Reverse primer | TAGATGGAGAAAAGGGAATTCC |
| SEQ ID NO: 137 Forward primer | CAACCGTAAAATTGCAGTTGA |
| SEQ ID NO: 138 Probe | CTGTCAGTCTTGAG |
| SEQ ID NO: 139 Reverse primer | CAGTAGAGGTGGGCGGAATTCG |
| SEQ ID NO: 140 Forward primer | TTATAGATGGATCCGCGCY |
| SEQ ID NO: 141 Probe | GCAACGATGCATAG |
| SEQ ID NO: 142 Reverse primer | GTGATCGGCCACACTGGRACT |
| SEQ ID NO: 143 Forward primer | TTATAGATGGATCCGCGCY |
| SEQ ID NO: 144 Probe | GCAACGATGCGTAG |
| SEQ ID NO: 145 Reverse primer | GTGATCGGCCACACTGGRACT |
| SEQ ID NO: 146 Forward primer | TRTGAGATGGACCTGCGTT |
| SEQ ID NO: 147 Probe | GCGACGATACATAG |
| SEQ ID NO: 148 Reverse primer | GTGATCGGCCACACTGGRACT |
| SEQ ID NO: 149 Forward primer | TACCAGATGGACCTGCGTT |
| SEQ ID NO: 150 Probe | GCGACGATACATAG |
| SEQ ID NO: 151 Reverse primer | GTGATCGGCCACACTGGRACT |
| SEQ ID NO: 152 Forward primer | TGATGGATGGACCCGCGGT |
| SEQ ID NO: 153 Probe | GCCACGATGCATAG |
| SEQ ID NO: 154 Reverse primer | GTGATCGGCCACACTGGRACT |
| SEQ ID NO: 155 Forward primer | TGMAGGATGRGCCCGCGGC |
| SEQ ID NO: 156 Probe | GCGACGACGGGTAG |
| SEQ ID NO: 157 Reverse primer | GCGACCGGCCACACTGGGACT |
| SEQ ID NO: 158 Forward primer | TGTGGGATGAGCCCGCGGC |
| SEQ ID NO: 159 Probe | GCGACGACGGGTAG |
| SEQ ID NO: 160 Reverse primer | GTGTCCGGCCACACTGGGACT |
| SEQ ID NO: 161 Forward primer | TATGAGATGGACCCGCGGC |
| SEQ ID NO: 162 Probe | GCGACGATGCTGTAG |
| SEQ ID NO: 163 Reverse primer | GTGATCGGCCACATTGGGACT |
| SEQ ID NO: 164 Forward primer | ACTCCTACGGGAGGCAGCAGT |
| SEQ ID NO: 165 Probe | GCAACGCCGCGT |
| SEQ ID NO: 166 Reverse primer | GCCAGCAGCCGCGGTAATACG |
| SEQ ID NO: 167 Forward primer | ACTCCTACGGGAGGCAGCAGT |
| SEQ ID NO: 168 Probe | GCGACGCCGCGT |
| SEQ ID NO: 169 Reverse primer | GCCAGCAGCCGCGGTAATACG |
| SEQ ID NO: 170 Forward primer | CAACCGKGGAGGGTCATTGGA |

TABLE A -continued

BRIEF DESCRIPTION OF THE SEQUENCES

| Sequence ID Number | Sequence |
|---|---|
| SEQ ID NO: 171 Probe | CTGGAAAACTTGAG |
| SEQ ID NO: 172 Reverse primer | CARRAGRGGARAGTGGAATTCC |
| SEQ ID NO: 173 Forward primer | CAACCGKGGAGGGTCATTGGA |
| SEQ ID NO: 174 Probe | CTGGGAGACTTGAG |
| SEQ ID NO: 175 Reverse primer | CARRAGRGGARAGTGGAATTCC |
| SEQ ID NO: 176 Forward primer | TAACCATTGTACGCTTTGGA |
| SEQ ID NO: 177 Probe | CTGGAGGACTTGAG |
| SEQ ID NO: 178 Reverse primer | CARRAGRGGARAGTGGAATTCC |
| SEQ ID NO: 179 Forward primer | CAACCAATGTACGCTTTGGA |
| SEQ ID NO: 180 Probe | CTGGAGAACTTGAG |
| SEQ ID NO: 181 Reverse primer | CARRAGRGGARAGTGGAATTCC |
| SEQ ID NO: 182 Forward primer | TAACCATAGTAGGCTTTGGA |
| SEQ ID NO: 183 Probe | CTGTTTAACTTGAG |
| SEQ ID NO: 184 Reverse primer | CARRAGRGGARAGTGGAATTCC |
| SEQ ID NO: 185 Forward primer | TAACCCCGGGTCTGCATTCGA |
| SEQ ID NO: 186 Probe | CGGGCTAGCTAGAG |
| SEQ ID NO: 187 Reverse primer | YGGTAGGGGAGATCGGAATTCC |
| SEQ ID NO: 188 Forward primer | TAACTGTGAGCGTGCGGGCGA |
| SEQ ID NO: 189 Probe | CGGGCAGACTAGAG |
| SEQ ID NO: 190 Reverse primer | CTGCAGGGGAGACTGGAATTCC |
| SEQ ID NO: 191 Forward primer | CAACTTGGGTGCTGCATTCCA |
| SEQ ID NO: 192 Probe | CTGGTTATCTAGAG |
| SEQ ID NO: 193 Reverse primer | CAGGAGAGGAGAGTGGAATTCC |
| SEQ ID NO: 194 Forward primer | TATGCAGTCTGAGTTGATTATCGTAATC |
| SEQ ID NO: 195 Probe | CTCTTGGTTCCGGCATCGA |
| SEQ ID NO: 196 Reverse primer | GCATTTCGCTGCGTTCTTC |
| SEQ ID NO: 197 Forward primer | CAGAGGTCTAAACTTACAACCAATTTTTT |
| SEQ ID NO: 198 Probe | CTCTTGGTTCTCGCATCGA |
| SEQ ID NO: 199 Reverse primer | GCATTTCGCTGCGTTCTTC |
| SEQ ID NO: 200 Forward primer | GGCAAACGCAAAATAAATCAAAA |
| SEQ ID NO: 201 Probe | CTCTTGGCTCTGGCATCGA |
| SEQ ID NO: 202 Reverse primer | GCATTTCGCTGCGTTCTTC |
| SEQ ID NO: 203 Forward primer | AATTAAAACTTTCAACAAC |
| SEQ ID NO: 204 Probe | CTCTTGGCTCTGGCATCGA |
| SEQ ID NO: 205 Reverse primer | ACTTATCGCATTTCG |
| SEQ ID NO: 206 Forward primer | GAAAACAAAAAAAACAAGTTAAAAC |
| SEQ ID NO: 207 Probe | CTCTTGGTTCTGGCATCGA |
| SEQ ID NO: 208 Reverse primer | CACATTACTTATCGCATTTCG |

TABLE A -continued

BRIEF DESCRIPTION OF THE SEQUENCES

Sequence ID
Number        Sequence

SEQ ID NO: 209 Forward primer TCCAGTCAAAACTTTCAACAAC

SEQ ID NO: 210 Probe CTCTTGGTTCCGACATCGA

SEQ ID NO: 211 Reverse primer GCATTTCGCTGCGTTCT

SEQ ID NO: 212 Forward primer CAATAATAAAACTTTCAACAAC

SEQ ID NO: 213 Probe CTCTTGGCTTCCACATCGA

SEQ ID NO: 214 Reverse primer CGCTGCGTTCTTCA

SEQ ID NO: 215 Forward primer GGTTCCGGCATCGA

SEQ ID NO: 216 Probe CGATAAGTAATGTG

SEQ ID NO: 217 Reverse primer GATTCACTGAATTCTGCAAT

SEQ ID NO: 218 Forward primer TGGTTCTCGCATCGA

SEQ ID NO: 219 Probe CGATACGTAATATG

SEQ ID NO: 220 Reverse primer CACGAATATCTGCACAATT

SEQ ID NO: 221 Forward primer GGCTCTGGCATCGA

SEQ ID NO: 222 Probe CGATAAGTAATGTG

SEQ ID NO: 223 Reverse primer TTCACTGAATTCTGCAAT

SEQ ID NO: 224 Forward primer AACGCAGCGAAAT

SEQ ID NO: 225 Probe CGATAAGTAATGTG

SEQ ID NO: 226 Reverse primer ATGATTCACTGAATTCTG

SEQ ID NO: 227 Forward primer TGGTTCTGGCATCGA

SEQ ID NO: 228 Probe CGATAAGTAATGTG

SEQ ID NO: 229 Reverse primer ATTCACTGAATTCTGCAAT

SEQ ID NO: 230 Forward primer TGGTTCCGACATCGA

SEQ ID NO: 231 Probe CGATAAGTAATGTG

SEQ ID NO: 232 Reverse primer CACGGAATTCTGCAAT

SEQ ID NO: 233 Forward primer AAGAACGCAGCGAAAT

SEQ ID NO: 234 Probe CGATAAGTAATGTG

SEQ ID NO: 235 Reverse primer ATTCACTGAATTCTGCAAT

SEQ ID NO: 236 Forward primer AAGTAATGTGAATTGCAGAA

SEQ ID NO: 237 Probe GTGAATCATCGAG

SEQ ID NO: 238 Reverse primer CCCCCGGAATACCA

SEQ ID NO: 239 Forward primer CGTAATATGAATTGCAGATATTC

SEQ ID NO: 240 Probe GTGAATCATCGAA

SEQ ID NO: 241 Reverse primer GAGGGCGCAATGTG

SEQ ID NO: 242 Forward primer GCGAAATGCGATAAGTAA

SEQ ID NO: 243 Probe GTGAATTGCAGAA

SEQ ID NO: 244 Reverse primer GATTCGATGATTCACTGAA

SEQ ID NO: 245 Forward primer AATGTGAATTGCAGAA

TABLE A -continued

BRIEF DESCRIPTION OF THE SEQUENCES

| Sequence ID Number | Sequence |
|---|---|
| SEQ ID NO: 246 | Probe GTGAATCATCGAA |
| SEQ ID NO: 247 | Reverse primer GGGCGCAATGTG |
| SEQ ID NO: 248 | Forward primer AAGTAATGTGAATTGCAGAA |
| SEQ ID NO: 249 | Probe GTGAATCATCGAA |
| SEQ ID NO: 250 | Reverse primer CGGGCGCAATGT |
| SEQ ID NO: 251 | Forward primer AAGTAATGTGAATTGCAGAA |
| SEQ ID NO: 252 | Probe GTGAATCATCGAA |
| SEQ ID NO: 253 | Reverse primer GAGGGCGCAATGTG |
| SEQ ID NO: 254 | Forward primer AAGTAATGTGAATTGCAGAA |
| SEQ ID NO: 255 | Probe GTGAATCATCGAG |
| SEQ ID NO: 256 | Reverse primer CAAGTTGCGTTCAAAGA |
| SEQ ID NO: 257 | Forward primer TCAGTGAATCATCGAGTCTTTGAAC |
| SEQ ID NO: 258 | Probe CCCCCTGGTATTCC |
| SEQ ID NO: 259 | Reverse primer TGCTTGAGGGCAGCAATG |
| SEQ ID NO: 260 | Forward primer TCGTGAATCATCGAATCTTTGAA |
| SEQ ID NO: 261 | Probe CCCTCTGGTATTCC |
| SEQ ID NO: 262 | Reverse primer GGAGAAACGACGCTCAAACAG |
| SEQ ID NO: 263 | Forward primer TTCAGTGAATCATCGAATCTTTGAA |
| SEQ ID NO: 264 | Probe CCCGCCAGGCTCT |
| SEQ ID NO: 265 | Reverse primer GCATTTCGCTGCGTTCTTC |
| SEQ ID NO: 266 | Forward primer TCAGTGAATCATCGAATCTTTGAAC |
| SEQ ID NO: 267 | Probe CCCGCCAGTATTCT |
| SEQ ID NO: 268 | Reverse primer GGTTGTAATGACGCTCGAACAG |
| SEQ ID NO: 269 | Forward primer GCAGAATTCAGTGAATCATCGAAT |
| SEQ ID NO: 270 | Probe CCCGGCAGTAATCT |
| SEQ ID NO: 271 | Reverse primer GAGGTTCGAGGGTTGAAATGAC |
| SEQ ID NO: 272 | Forward primer CCGTGAATCATCGAATCTTTGA |
| SEQ ID NO: 273 | Probe CCCTCTGGTATTCC |
| SEQ ID NO: 274 | Reverse primer GCGCTTGAGGGTTGCAAT |
| SEQ ID NO: 275 | Forward primer TCGAGTCTTTGAACGCAACTTG |
| SEQ ID NO: 276 | Probe CCCTTTGGTATTCC |
| SEQ ID NO: 277 | Reverse primer CGAGGGATTGAGATTTTCATGAC |
| SEQ ID NO: 278 | Gram-negative and Gram-positive reverse primer GTATTACCGCGGCTGCTGGCAC |
| SEQ ID NO: 279 | *Chlamydia* and *Chlamydophila* forward primer ACTCCTACGGGAGGCTGCAGT |
| SEQ ID NO: 280 | *Chlamydia* and *Chlamydophila* reverse primer GTATTACCGCGGCAGCTGGCAC |
| SEQ ID NO: 281 | Gram-positive probe Group 1 AGCAACGCCGCGT |

TABLE A -continued

BRIEF DESCRIPTION OF THE SEQUENCES

| Sequence ID Number | Sequence |
|---|---|
| SEQ ID NO: 282 | Gram-positive probe Group 2 AGCGACGCCGCGT |
| SEQ ID NO: 283 | Gram-negative probe Group 3 AGCCATGCCGCGT |
| SEQ ID NO: 284 | Gram-negative probe Group 4 AGCAATGCCGCGT |
| SEQ ID NO: 285 | Gram-negative probe Group 5 AGCCATACCGCGT |
| SEQ ID NO: 286 | Gram-negative probe Group 6 AGCCAAGTAGCGT |
| SEQ ID NO: 287 | Gram-negative probe Group 7 AGCCAAGTCGCGT |
| SEQ ID NO: 288 | Gram-positive probe Group 1a AACCAGAAAGCC |
| SEQ ID NO: 289 | Gram-positive probe Group 1b AACCAGAAAGGG |
| SEQ ID NO: 290 | Gram-positive probe Group 1c AACCAGAAAGTC |
| SEQ ID NO: 291 | Gram-negative probe Group 1d AACGAATAAGCA |
| SEQ ID NO: 292 | Gram-positive probe Group 1e AAGGAGGAAGCC |
| SEQ ID NO: 293 | Gram-positive probe Group 1f AATCAGAAAGCC |
| SEQ ID NO: 294 | Gram-positive probe Group 1g GAAGAATAAGCT |
| SEQ ID NO: 295 | Gram-negative probe Group 1h GAATAGAAAGCC |
| SEQ ID NO: 296 | Gram-positive probe Group 1i GAGGAGGAAGCC |
| SEQ ID NO: 297 | Gram-positive probe Group 1j TACCAGAAAGCC |
| SEQ ID NO: 298 | Gram-positive probe Group 1k TACCAGAAAGGG |
| SEQ ID NO: 299 | Gram-positive probe Group 1l TGTGAGGAAGCC |
| SEQ ID NO: 300 | Gram-positive probe Group 2a AGATAAGAAGCA |
| SEQ ID NO: 301 | Gram-positive probe Group 2b GCAGAAGAAGCA |
| SEQ ID NO: 302 | Gram-positive probe Group 2c GCAGAAGAAGCG |
| SEQ ID NO: 303 | Gram-negative probe Group 2d GCCTAAAGCACC |
| SEQ ID NO: 304 | Gram-positive probe Group 2e GGAGAAGAAGCA |
| SEQ ID NO: 305 | Gram-positive probe Group 2f GGATAAGAAGCA |
| SEQ ID NO: 306 | Gram-positive probe Group 2g GGGGAAGAAGCG |
| SEQ ID NO: 307 | Gram-negative probe Group 2h GGTAAAGAAGCA |
| SEQ ID NO: 308 | Gram-positive probe Group 2i GTAGAAGAAGCA |
| SEQ ID NO: 309 | Gram-positive probe Group 2j GTTGAAGAAGCA |
| SEQ ID NO: 310 | Gram-negative probe Group 3a ACAGAAGAAGCA |
| SEQ ID NO: 311 | Gram-negative probe Group 3b ACAGAATAAGCA |
| SEQ ID NO: 312 | Gram-negative probe Group 3c GAAGAATAAGCA |
| SEQ ID NO: 313 | Gram-negative probe Group 3d GCAGAAGAAGCA |
| SEQ ID NO: 314 | Gram-negative probe Group 3e GCAGAATAAGCA |
| SEQ ID NO: 315 | Gram-negative probe Group 3f GGAGAAGAAGCC |
| SEQ ID NO: 316 | Gram-negative probe Group 3g TAAGAATAAGGA |
| SEQ ID NO: 317 | Gram-negative probe Group 4a ACAGAAGAACCA |
| SEQ ID NO: 318 | Gram-negative probe Group 4b GAAGAATAAGCA |
| SEQ ID NO: 319 | Gram-negative probe Group 4c GCAGAAGAAGCA |

TABLE A -continued

BRIEF DESCRIPTION OF THE SEQUENCES

| Sequence ID Number | | Sequence |
|---|---|---|
| SEQ ID NO: 320 | Gram-negative probe Group 6a | CATGAATAAGGA |
| SEQ ID NO: 321 | Gram-negative probe Group 6b | TACGAATAAGGA |
| SEQ ID NO: 322 | Gram-negative probe Group 6c | TATGAATAAGGA |
| SEQ ID NO: 323 | Gram-negative probe Group 6d | TTAGAATAAGGA |
| SEQ ID NO: 324 | Probe | TTCCGGCATCGA |
| SEQ ID NO: 325 | Probe | TTCTCGCATCGA |
| SEQ ID NO: 326 | Forward primer | CAAAACTTTCAACAACGGATCTC |
| SEQ ID NO: 327 | Forward primer | TAAAACTTTCAACAACGGATCTC |
| SEQ ID NO: 328 | Reverse primer | GACGCTCGGACAGGCATG |
| SEQ ID NO: 329 | Reverse primer | GACGCTCAAACAGGCATG |
| SEQ ID NO: 330 | Forward primer | AACTTTCAACAACGGATCTCTTGG |
| SEQ ID NO: 331 | Forward primer | AACTTTTAACAACGGATCTCTTGG |
| SEQ ID NO: 332 | Reverse primer | GCGTTCAAAGATTCGATGATTCAC |
| SEQ ID NO: 333 | Reverse primer | GCGTTCAAAGACTCGATGATTCAC |
| SEQ ID NO: 334 | Probe | AAATGCGATACGTAA |
| SEQ ID NO: 335 | Probe | ATGCGATAAGTAA |

TABLE B

NUCLEOTIDE SYMBOLS

| Symbol | Description |
|---|---|
| A | Adenosine |
| C | Cytidine |
| G | Guanosine |
| T | Thymidine |
| U | Uridine |
| M | Amino (adenosine, cytosine) |
| K | Keto (guanosine, thymidine) |
| R | Purine (adenosine, guanosine) |
| Y | Pyrimidine (cytosine, thymidine) |
| N | Any nucleotide |

DETAILED DESCRIPTION OF THE INVENTION

1. Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e. to at least one) of the grammatical object of the article. By way of example, "an element" means one element or more than one element.

"Amplification product" refers to a nucleic acid product generated by nucleic acid amplification techniques.

The term "biological sample" as used herein refers to a sample that may be extracted, untreated, treated, diluted or concentrated from a patient. Suitably, the biological sample is selected from any part of a patient's body, including, but lot limited to hair, skin, nails, tissues or bodily fluids such as saliva and blood.

Throughout this specification, unless the context requires otherwise, the words "comprise," "comprises" and "comprising" will be understood to imply the inclusion of a stated step or element or group of steps or elements but not the exclusion of any other step or element or group of steps or elements.

As used herein, "corresponding" nucleic acid positions or nucleotides refer to positions or nucleotides that occur at aligned loci of two or more nucleic acid molecules. Related or variant polynucleotides can be aligned by any method known to those of skill in the art. Such methods typically maximize matches, and include methods such as using manual alignments and by using the numerous alignment programs available (for example, BLASTN) and others known to those of skill in the art. By aligning the sequences of polynucleotides, one skilled in the art can identify corresponding nucleotides or positions using identical nucleotides as guides. For example, by aligning the sequences of the gene encoding the *E. coli* 16S rRNA (set forth in SEQ ID NO:1) with a gene encoding a 16S rRNA from another species, one of skill in the art can identify corresponding positions and nucleotides using conserved nucleotides as guides.

By "gene" is meant a unit of inheritance that occupies a specific locus on a genome and consists of transcriptional and/or translational regulatory sequences and/or a coding region and/or non-translated sequences (i.e., introns, 5' and 3' untranslated sequences).

"Homology" refers to the percentage number of nucleic or amino acids that are identical or constitute conservative substitutions. Homology may be determined using sequence comparison programs such as GAP (Deveraux et al., 1984, Nucleic Acids Research 12, 387-395) which is incorporated herein by reference. In this way sequences of a similar or substantially different length to those cited herein could be compared by insertion of gaps into the alignment, such gaps being determined, for example, by the comparison algorithm used by GAP.

"Hybridization" is used herein to denote the pairing of complementary nucleotide sequences to produce a DNA-DNA hybrid or a DNA-RNA hybrid. Complementary base sequences are those sequences that are related by the base-pairing rules. In DNA, A pairs with T and C pairs with G. In RNA U pairs with A and C pairs with G. In this regard, the terms "match" and "mismatch" as used herein refer to the hybridization potential of paired nucleotides in complementary nucleic acid strands. Matched nucleotides hybridise efficiently, such as the classical A-T and G-C base pair mentioned above. Mismatches are other combinations of nucleotides that do not hybridise efficiently.

By "isolated" is meant material that is substantially or essentially free from components that normally accompany it in its native state.

The term "oligonucleotide" as used herein refers to a polymer composed of a multiplicity of nucleotide residues (deoxyribonucleotides or ribonucleotides, or related structural variants or synthetic analogues thereof) linked via phosphodiester bonds (or related structural variants or synthetic analogues thereof). Thus, while the term "oligonucleotide" typically refers to a nucleotide polymer in which the nucleotide residues and linkages between them are naturally occurring, it will be understood that the term also includes within its scope various analogues including, but not restricted to, peptide nucleic acids (PNAs), phosphoramidates, phosphorothioates, methyl phosphonates, 2-O-methyl ribonucleic acids, and the like. The exact size of the molecule can vary depending on the particular application. An oligonucleotide is typically rather short in length, generally from about 10 to 30 nucleotide residues, but the term can refer to molecules of any length, although the term "polynucleotide" or "nucleic acid" is typically used for large oligonucleotides.

The terms "patient" and "subject" are used interchangeably and refer to patients and subjects of human or other mammal and includes any individual it is desired to examine or treat using the methods of the invention. However, it will be understood that "patient" does not imply that symptoms are present. Suitable mammals that fall within the scope of the invention include, but are not restricted to, primates, livestock animals (e.g., sheep, cows, horses, donkeys, pigs), laboratory test animals (e.g., rabbits, mice, rats, guinea pigs, hamsters), companion animals (e.g., cats, dogs) and captive wild animals (e.g., foxes, deer, dingoes).

The term "polymorphism", as used herein, refers to a difference in the nucleotide or amino acid sequence of a given region as compared to a nucleotide or amino acid sequence in a homologous-region of another individual, in particular, a difference in the nucleotide of amino acid sequence of a given region which differs between individuals of the same species. A polymorphism is generally defined in relation to a reference sequence. Polymorphisms include single nucleotide differences, differences in sequence of more than one nucleotide, and single or multiple nucleotide insertions, inversions and deletions; as well as single amino acid differences, differences in sequence of more than one amino acid, and single or multiple amino acid insertions, inversions, and deletions. A "polymorphic site" is the locus at which the variation occurs. It shall be understood that where a polymorphism is present in a nucleic acid sequence, and reference is made to the presence of a particular base or bases at a polymorphic site, the present invention encompasses the complementary base or bases on the complementary strand at that site.

The term "polynucleotide" or "nucleic acid" as used herein designates mRNA, RNA, rRNA, cRNA, cDNA or DNA. The term typically refers to oligonucleotides greater than 30 nucleotide residues in length.

By "primer" is meant an oligonucleotide which, when paired with a strand of DNA, is capable of initiating the synthesis of a primer extension product in the presence of a suitable polymerizing agent. The primer is preferably single-stranded for maximum efficiency in amplification but can alternatively be double-stranded. A primer must be sufficiently long to prime the synthesis of extension products in the presence of the polymerization agent. The length of the primer depends on many factors, including application, temperature to be employed, template reaction conditions, other reagents, and source of primers. For example, depending on the complexity of the target sequence, the oligonucleotide primer typically contains 15 to 35 or more nucleotide residues, although it can contain fewer nucleotide residues. Primers can be large polynucleotides, such as from about 200 nucleotide residues to several kilobases or more. Primers can be selected to be "substantially complementary" to the sequence on the template to which it is designed to hybridize and serve as a site for the initiation of synthesis. By "substantially complementary", it is meant that the primer is sufficiently complementary to hybridize with a target polynucleotide. In some embodiments, the primer contains no mismatches with the template to which it is designed to hybridize but this is not essential. For example, non-complementary nucleotide residues can be attached to the 5' end of the primer, with the remainder of the primer sequence being complementary to the template. Alternatively, non-complementary nucleotide residues or a stretch of non-complementary nucleotide residues can be interspersed into a primer, provided that the primer sequence has sufficient complementarity with the sequence of the template to hybridize therewith and thereby form a template for synthesis of the extension product of the primer.

"Probe" refers to a molecule that binds to a specific sequence or sub-sequence or other moiety of another molecule. Unless otherwise indicated, the term "probe" typically refers to a polynucleotide probe that binds to another polynucleotide, often called the "target polynucleotide", through complementary base pairing. Probes can bind target polynucleotides lacking complete sequence complementarity with the probe, depending on the stringency of the hybridization conditions. Probes can be labeled directly or indirectly.

The term "sepsis" is used herein in accordance with its normal meaning in clinical medicine, and includes, for example systemic and/or blood-borne infections, such as bacterial or fungal infections.

The term "sepsis-associated bacteria" refers to bacteria that have been identified as being able to cause sepsis in a subject, or have been identified in the blood of a subject with sepsis. "Mammalian (e.g., human) sepsis-associated bacteria" therefore refers to bacteria that have been identified as being able to cause sepsis in a mammalian (e.g., human) subject, or have been identified in the blood of a mammalian (e.g., human) subject with sepsis. Examples of mammalian (e.g., human) sepsis-associated bacteria include *Acinetobacter baumannii, Actinobacillus hominis, Actinomyces massiliensis, Aeromonas hydrophila, Bacillus anthracis, Bacteroides fragilis, Brucella abortus, Burkholderia cepacia, Campylobacter coli, Campylobacter fetus, Campylobacter jejuni, Campylobacter lari, Cardiobacterium valvarum, Chlamydia trachomatis, Chlamydophila abortus, Chlamydophila pneumoniae, Citrobacter freundii, Clostridium difficile, Clostridium perfringens, Corynebacterium diphtheriae, Corynebacterium jeikeium, Corynebacterium urealyticum, Dermatophilus congolensis, Edwardsiella tarda, Enterobacter aerogenes, Enterobacter cloacae, Enterococcus faecalis, Enterococcus faecium, Erysipelothrix rhusiopathiae, Escherichia coli, Eubacterium desmolans, Flavobacterium ceti, Haemophilus ducreyi, Haemophilus influenzae, Haemophilus parahaemolyticus, Haemophilus parainfluenzae, Helicobacter cinaedi, Helicobacter pylori, Klebsiella oxytoca, Klebsiella pneumonia, Lactobacillus intestinalis, Legionella pneumophila, Leptospira interrogans, Listeria monocytogenes, Micrococcus luteus, Mobiluncus curtisii, Moraxella catarrhalis, Morganella morganii, Mycobacterium tuberculosis, Neisseria gonorrhoeae, Neisseria meningitidis, Nocardia asteroids, Nocardia brasiliensis, Pasteurella multocida, Peptostreptococcus stomatis, Porphyromonas gingivalis, Prevotella buccae, Prevotella intermedia, Prevotella melaninogenica, Proteus mirabilis, Providencia alcalifaciens, Pseudomonas aeruginosa, Rhodococcus equi, Salmonella enterica, Serratia marcescens, Shigella dysenteriae, Shigella sonnei, Staphylococcus aureus, Staphylococcus epidermidis, Staphylococcus haemolyticus, Staphylococcus hominis, Staphylococcus saprophyticus, Stenotrophomonas maltophila, Streptococcus agalactiae, Streptococcus anginosus, Streptococcus bovis, Streptococcus constellatus, Streptococcus dysgalactiae, Streptococcus intermedius, Streptococcus mitis, Streptococcus mutans, Streptococcus oralis, Streptococcus pneumoniae, Streptococcus pyogenes, Streptococcus sanguinis, Streptococcus sobrinus, Streptomyces anulatus, Streptomyces somaliensis, Veillonella atypica, Veillonella denticariosi, Veillonella dispar, Veillonella parvula, Veillonella rogosae, Vibrio cholerae, Yersinia enterocolitica* and *Yersinia pestis.*

The term "sepsis-associated fungi" refers to fungi (including yeast) that have been identified as being able to cause sepsis in a subject, or have been identified in the blood of a subject with sepsis. "Mammalian (e.g., human) sepsis-associated fungi" therefore refers to fungi that have been identified as being able to cause sepsis in a mammalian (e.g., human) subject, or have been identified in the blood of a mammalian (e.g., human) subject with sepsis. Examples of mammalian (e.g., human) sepsis associated fungi include *Candida albicans, Ajellomyces capsulatus, Stachybotrys* species, *Scedosporium apiospermum, Fusarium* species, *Aspergillus fumigatus,* and *Cryptococcus neoformans.*

As used herein, "sepsis" is defined as SIRS with a presumed or confirmed infectious process. Confirmation of infectious process can be determined using microbiological culture or isolation of the infectious agent. From an immunological perspective, sepsis may be seen as a systemic response to microorganisms or systemic infection.

The term "sequence identity" as used herein refers to the extent that sequences are identical on a nucleotide-by-nucleotide basis or an amino acid-by-amino acid basis over a window of comparison. Thus, a "percentage of sequence identity" is calculated by comparing two optimally aligned sequences over the window of comparison, determining the number of positions at which the identical nucleic acid base (e.g., A, T, C, G, I) occurs in both sequences to yield the number of matched positions, dividing the number of matched positions by the total number of positions in the window of comparison (i.e., the window size), and multiplying the result by 100 to yield the percentage of sequence identity.

As used herein, the term single nucleotide polymorphism (SNP) refers to nucleotide sequence variations that occur when a single nucleotide (A, T, C or G) in the genome sequence is altered (such as via substitutions, addition or deletion). SNPs can occur in both coding (gene) and non-coding regions of the genome such as the genome of a prokaryotic or eukaryotic microorganism.

"Systemic Inflammatory Response Syndrome (SIRS)," as used herein, refers to a clinical response arising from a non-specific insult with two or more of the following measurable clinical characteristics; a body temperature greater than 38° C. or less than 36° C., a heart rate greater than 90 beats per minute, a respiratory rate greater than 20 per minute, a white blood cell count (total leukocytes) greater than 12,000 per mm$^3$ or less than 4,000 per mm$^3$, or a band neutrophil percentage greater than 10%. From an immunological perspective, it may be seen as representing a systemic response to insult (e.g., major surgery) or systemic inflammation. As used herein, therefore, "infection-negative SIRS (inSIRS)" includes the clinical response noted above but in the absence of an identifiable infectious process.

As used herein, the terms "treatment," "treating," and the like, refer to obtaining a desired pharmacologic and/or physiologic effect. The effect may be prophylactic in terms of completely or partially preventing an infection, condition or symptom thereof and/or may be therapeutic in terms of a partial or complete cure for an infection, condition and/or adverse affect attributable to the infection or condition. "Treatment," as used herein, covers any treatment of an infection or condition in a mammal (e.g., a human), and includes: (a) preventing the infection or condition from occurring in a subject which may be predisposed to the infection or condition but has not yet been diagnosed as having it; (b) inhibiting the infection or condition, i.e., arresting its development; and (c) relieving the infection or condition, i.e., causing regression of the infection or condition.

2. Polymorphisms of the Invention

The present invention is based in part on the determination that SNPs within the 16S rRNA gene (and thus within the 16S rRNA molecule) of bacteria can be used to classify the bacteria as Gram-positive or Gram-negative. Particular combinations of SNPs can be used to classify bacteria further, and in particular further classify or identify mammalian (e.g., human) sepsis-associated bacterial pathogens. The present invention is also based in part on the determination that a single SNP within the 5.8S rRNA gene (and thus within the 5.8S rRNA molecule) of eukaryotes can be used to differentiate fungal cells (including yeast cells) from mammalian cells. It has further been determined that a combination of SNPs within the 5.8S rRNA of eukaryotes can be used to differentiate and identify the most common mammalian (e.g., human) fungal pathogens.

2.1 Classification of Bacteria Using SNPs in 16S rRNA

The present invention provides methods for determining the Gram status of bacteria in a sample, i.e. determining whether the bacteria are Gram-positive or Gram-negative. As demonstrated herein, polymorphisms at nucleotide positions of the gene encoding 16S rRNA (and thus of the 16S rRNA molecule itself) that correspond to positions 396 and 398 of the *E. coli* 16S rRNA gene set forth in SEQ ID NO:1 can be used to determine the Gram status of the vast majority of bacteria, including most mammalian (e.g., human) pathogens (including common bacteria found contaminating red blood cell and platelet preparations, the most common bacteria found in mammalian (e.g., human) faecal samples and many pathogens causing sepsis), the most common soil bacteria, and common bacteria found in work environments. Positions corresponding to positions 396 and 398 of SEQ ID NO:1 in any prokaryotic 16S rRNA gene (or 16S rRNA molecule or DNA copy thereof) are readily identifiable by alignment with the *Escherichia coli* 16S rRNA gene set forth in SEQ ID NO:1. In some examples, a highly conserved sequence that corresponds to nucleotides 518-537 of SEQ ID NO:1 and that is common to nearly 7000 bacterial species across its entire length, can be used to assist alignment. The general rules for differentiating most Gram-positive and Gram-negative prokaryotes using these two SNPs are depicted in Table 1.

TABLE 1

| Gram Status | SNP 396 | SNP 398 |
|---|---|---|
| Negative | C | T/A/C |
| Positive | A/T/G | C |

Thus, the present invention provides methods for determining the Gram status of a bacterium in a sample, by analyzing nucleic acid from the sample for SNPs in the 16S rRNA gene (or 16S rRNA or DNA copy thereof) at positions corresponding to positions 396 and 398 of the 16S rRNA gene set forth in SEQ ID NO:1, wherein a C at position 396 and a T, A or C at position 398 indicates that the bacterium in the sample is a Gram-negative bacterium; and an A, T or G at position 396 and a C at position 398 indicates that the bacterium is a Gram-positive bacterium. Bacteria that can be classified as Gram-positive or Gram-negative using SNPs at positions corresponding to 396 and 398 of the *E. coli* 16S rRNA gene set forth in SEQ ID NO:1 include, for example, *Acinetobacter* spp.; *Actinobaccillus* spp.; *Actinomadura* spp.; *Actinomyces* spp.; *Actinoplanes* spp.; *Aeromonas* spp.; *Agrobacterium* spp.; *Alistipes* spp.; *Anaerococcus* spp.; *Arthrobacter* spp.; *Bacillus* spp.; *Brucella* spp.; *Bulleidia* spp.; *Burkholderia* spp.; *Cardiobacterium* spp.; *Citrobacter* spp.; *Clostridium* spp.; *Corynebacterium* spp.; *Dermatophilus* spp.; *Dorea* spp.; *Edwardsiella* spp.; *Enterobacter* spp.; *Enterococcus* spp.; *Erysipelothrix* spp.; *Escherichia* spp.; *Eubacterium* spp.; *Faecalibacterium* spp.; *Filifactor* spp.; *Finegoldia* spp.; *Flavobacterium* spp.; *Gallicola* spp.; *Haemophilus* spp.; *Helcococcus* spp.; *Holdemania* spp.; *Hyphomicrobium* spp.; *Klebsiella* spp.; *Lactobacillus* spp.; *Legionella* spp.; *Listeria* spp.; *Methylobacterium* spp.; *Micrococcus* spp.; *Micromonospora* spp.; *Mobiluncus* spp.; *Moraxella* spp.; *Morganella* spp.; *Mycobacterium* spp.; *Neisseria* spp.; *Nocardia* spp.; *Paenibacillus* spp.; *Parabacteroides* spp.; *Pasteurella* spp.; *Peptoniphilus* spp.; *Peptostreptococcus* spp.; *Planococcus* spp.; *Planomicrobium* spp.; *Plesiomonas* spp.; *Porphyromonas* spp.; *Prevotella* spp.; *Propionibacterium* spp.; *Proteus* spp.; *Providentia* spp.; *Pseudomonas* spp.; *Ralstonia* spp.; *Rhodococcus* spp.; *Roseburia* spp.; *Ruminococcus* spp.; *Salmonella* spp.; *Sedimentibacter* spp.; *Serratia* spp.; *Shigella* spp.; *Solobacterium* spp.; *Sphingomonas* spp.; *Sporanaerobacter* spp.; *Staphylococcus* spp.; *Stenotrophomonas* spp.; *Streptococcus* spp.; *Streptomyces* spp.; *Tissierella* spp.; *Vibrio* spp.; and *Yersinia* spp.

Particular examples of pathogens that can be classified as Gram-positive or Gram-negative using SNPs at positions 396 and 398 include, but are not limited to, those set forth in Table 2.

TABLE 2

| Bacterial ID No. | Species | 16S rRNA Genbank Acc. No. |
|---|---|---|
| 1 | *Acinetobacter baumannii* ATCC 17978 strain ATCC 17978 | NR_074737.1 |
| 2 | *Acinetobacter calcoaceticus* NCCB 22016 strain: NCCB 22016 | NR_042387.1 |
| 3 | *Actinobacillus arthritidis* strain ACCUG 24862 | NR_044613.1 |
| 4 | *Actinobacillus capsulatus* strain CCUG 12396 | NR_042864.1 |
| 5 | *Actinobacillus delphinicola* strain NCTC 12870 | NR_042865.1 |
| 6 | *Actinobacillus equuli* subsp. *equuli* strain ATCC 19392 | NR_041837.1 |
| 7 | *Actinobacillus equuli* subsp. *haemolyticus* strain F 154 | NR_036871.1 |
| 8 | *Actinobacillus hominis* strain NCTC 11529 | NR_042866.1 |
| 9 | *Actinobacillus indolicus* strain 46KC2 | NR_042867.1 |
| 10 | *Actinobacillus lignieresii* strain NCTC 4189 | NR_042868.1 |
| 11 | *Actinobacillus minor* NM305 strain NM305 | NR_042869.1 |
| 12 | *Actinobacillus muris* strain NCTC 12432 | NR_042870.1 |
| 13 | *Actinobacillus pleuropneumoniae* | NR_044752.1 |
| 14 | *Actinobacillus pleuropneumoniae* serovar 5b str. L20 strain L20 | NR_074857.1 |
| 15 | *Actinobacillus porcinus* strain NM319 | NR_026030.1 |
| 16 | *Actinobacillus rossii* strain ATCC 27072 | NR_042871.1 |
| 17 | *Actinobacillus scotiae* strain M2000/95/1 | NR_027207.1 |
| 18 | *Actinobacillus seminis* strain CCUG 27187 | NR_042872.1 |
| 19 | *Actinobacillus succinogenes* 130Z strain 130Z | NR_074818.1 |
| 20 | *Actinobacillus succinogenes* strain 130Z | NR_024860.1 |
| 21 | *Actinobacillus suis* ATCC 33415 strain ATCC 33415 | NR_042873.1 |
| 22 | *Actinobacillus suis* H91-0380 strain H91-0380 | NR_074909.1 |
| 23 | *Actinobacillus ureae* ATCC 25976 strain CCUG 2139 | NR_042874.1 |
| 24 | *Actinomyces bovis* strain NCTC 11535 | NR_044862.1 |
| 25 | *Actinomyces bowdenii* strain M1956/95/1 | NR_041982.1 |
| 26 | *Actinomyces canis* strain CCUG 41706 | NR_025366.1 |
| 27 | *Actinomyces cardiffensis* strain CCUG 44997 | NR_025521.1 |
| 28 | *Actinomyces catuli* strain CCUG 41709 | NR_025397.1 |
| 29 | *Actinomyces coleocanis* strain M343/98/2 | NR_028905.1 |

TABLE 2-continued

| Bacterial ID No. | Species | 16S rRNA Genbank Acc. No. |
|---|---|---|
| 30 | *Actinomyces dentalis* strain R18165 | NR_025633.1 |
| 31 | *Actinomyces denticolens* strain NCTC 11490 | NR_026181.1 |
| 32 | *Actinomyces europaeus* strain CCUG 32789A | NR_026363.1 |
| 33 | *Actinomyces funkei* strain CCUG 42773 | NR_028960.1 |
| 34 | *Actinomyces georgiae* strain 6843 DSM | NR_026182.1 |
| 35 | *Actinomyces graevenitzii* strain: CCUG 27294 | NR_042167.1 |
| 36 | *Actinomyces hongkongensis* strain HKU8 | NR_025200.1 |
| 37 | *Actinomyces hordeovulneris* strain CIP 103149 | NR_026225.1 |
| 38 | *Actinomyces howellii* strain NCTC 11636 | NR_026180.1 |
| 39 | *Actinomyces hyovaginalis* strain BM 1192/5 | NR_026097.1 |
| 40 | *Actinomyces marimammalium* strain CCUG 41710 | NR_025395.1 |
| 41 | *Actinomyces massiliensis* strain 4401292 | NR_044288.1 |
| 42 | *Actinomyces meyeri* strain Prevot 2477B | NR_029286.1 |
| 43 | *Actinomyces naeslundii* strain CDC W826 | NR_037033.1 |
| 44 | *Actinomyces nasicola* strain R2014 | NR_025568.1 |
| 45 | *Actinomyces odontolyticus* strain CCUG 20536 | NR_041983.1 |
| 46 | *Actinomyces radicidentis* strain CCUG 36733 | NR_025379.1 |
| 47 | *Actinomyces radingae* strain ATCC 51856 | NR_026169.1 |
| 48 | *Actinomyces ruminicola* strain B71 | NR_043523.1 |
| 49 | *Actinomyces slackii* strain CCUG 32792 | NR_041984.1 |
| 50 | *Actinomyces suimastitidis* strain CCUG 39276 | NR_025401.1 |
| 51 | *Actinomyces turicensis* strain APL10 | NR_037020.1 |
| 52 | *Actinomyces urogenitalis* strain CCUG 38702 | NR_025364.1 |
| 53 | *Actinomyces vaccimaxillae* strain R10176 | NR_025523.1 |
| 54 | *Actinomyces viscosus* strain NCTC 10951 | NR_026228.1 |
| 55 | *Aeromonas hydrophila* strain CCM 7232; ATCC 7966 | NR_043638.1 |
| 56 | *Aeromonas hydrophila* subsp. *dhakensis* strain: LMG 19562 | NR_042155.1 |
| 57 | *Aeromonas hydrophila* subsp. *hydrophila* ATCC 7966 strain ATCC 7966 | NR_074841.1 |
| 58 | *Aeromonas hydrophila* subsp. *ranae* strain: CIP 107985 | NR_042518.1 |
| 59 | *Aeromonas veronii* | NR_044845.1 |
| 60 | *Bacillus acidiceler* strain CBD 119 | NR_043774.1 |
| 61 | *Bacillus acidicola* strain 105-2 | NR_041942.1 |
| 62 | *Bacillus aeolius* strain 4-1 | NR_025557.1 |
| 63 | *Bacillus aerius* strain: 24K | NR_042338.1 |
| 64 | *Bacillus aerophiles* strain: 28K | NR_042339.1 |
| 65 | *Bacillus agaradhaerens* strain DSM 8721 | NR_026142.1 |
| 66 | *Bacillus akibai* strain 1139 | NR_028620.1 |
| 67 | *Bacillus alcalophilus* strain 1 | NR_036889.1 |
| 68 | *Bacillus algicola* strain F12 | NR_029077.1 |
| 69 | *Bacillus alkalidiazotrophicus* strain MS 6 | NR_044420.1 |
| 70 | *Bacillus alkalinitrilicus* strain ANL-iso4 | NR_044204.1 |
| 71 | *Bacillus alkalitelluris* strain BA288 | NR_043210.1 |
| 72 | *Bacillus altitudinis* strain: 41KF2b | NR_042337.1 |
| 73 | *Bacillus alveayuensis* strain TM 1 | NR_043013.1 |
| 74 | *Bacillus amyloliquefaciens* FZB42 strain FZB42 | NR_075005.1 |
| 75 | *Bacillus amyloliquefaciens* strain NBRC 15535 | NR_041455.1 |
| 76 | *Bacillus anthracis* str. Ames strain Ames | NR_074453.1 |
| 77 | *Bacillus anthracis* strain ATCC 14578 | NR_041248.1 |
| 78 | *Bacillus aquimaris* strain TF-12 | NR_025241.1 |
| 79 | *Bacillus arseniciselenatis* strain E1H | NR_036852.1 |
| 80 | *Bacillus asahii* strain MA001 | NR_024817.1 |
| 81 | *Bacillus atrophaeus* 1942 strain 1942 | NR_075016.1 |
| 82 | *Bacillus atrophaeus* strain JCM9070 | NR_024689.1 |
| 83 | *Bacillus aurantiacus* strain: K1-5 | NR_042213.1 |
| 84 | *Bacillus azotoformans* strain NBRC 15712 | NR_041641.1 |
| 85 | *Bacillus badius* strain 110 | NR_036893.1 |
| 86 | *Bacillus barbaricus* strain V2-BIII-A2 | NR_028967.1 |
| 87 | *Bacillus bataviensis* strain IDA1115 | NR_036766.1 |
| 88 | *Bacillus benzoevorans* strain NCIMB 12555 | NR_044828.1 |
| 89 | *Bacillus bogoriensis* strain LBB3 | NR_042894.1 |
| 90 | *Bacillus boroniphilus* strain T-15Z | NR_041275.1 |
| 91 | *Bacillus butanolivorans* strain K9 | NR_044170.1 |
| 92 | *Bacillus carboniphilus* strain JCM9731 | NR_024690.1 |
| 93 | *Bacillus cecembensis* | NR_042648.1 |
| 94 | *Bacillus cellulosilyticus* DSM 2522 strain DSM 2522 | NR_074904.1 |
| 95 | *Bacillus cellulosilyticus* DSM 2522 strain N-4 | NR_040850.1 |
| 96 | *Bacillus cereus* ATCC 14579 strain ATCC 14579 | NR_074540.1 |
| 97 | *Bacillus cibi* strain JG-30 | NR_042974.1 |
| 98 | *Bacillus circulans* | NR_042726.1 |
| 99 | *Bacillus clarkii* strain DSM 8720 | NR_026141.1 |
| 100 | *Bacillus clausii* KSM-K16 strain KSM-K16 | NR_074988.1 |
| 101 | *Bacillus coagulans* strain NBRC 12583 | NR_041523.1 |
| 102 | *Bacillus coahuilensis* m4-4 strain m4-4 | NR_044037.1 |
| 103 | *Bacillus cohnii* strain DSM 6307 | NR_026138.1 |
| 104 | *Bacillus cytotoxicus* NVH 391-98 strain NVH 391-98 | NR_074914.1 |
| 105 | *Bacillus decolorationis* strain LMG 19507 | NR_025473.1 |
| 106 | *Bacillus drentensis* strain IDA1967 | NR_029002.1 |

TABLE 2-continued

| Bacterial ID No. | Species | 16S rRNA Genbank Acc. No. |
|---|---|---|
| 107 | *Bacillus edaphicus* strain T7 | NR_028674.1 |
| 108 | *Bacillus endophyticus* strain 2DT | NR_025122.1 |
| 109 | *Bacillus farraginis* strain R-6540 | NR_025785.1 |
| 110 | *Bacillus fastidiosus* strain DSM 91 | NR_044829.1 |
| 111 | *Bacillus firmus* strain IAM 12464 | NR_025842.1 |
| 112 | *Bacillus firmus* strain KSC_SF8b | NR_043991.1 |
| 113 | *Bacillus flexus* strain IFO15715 | NR_024691.1 |
| 114 | *Bacillus foraminis* strain: CV53 | NR_042274.1 |
| 115 | *Bacillus fordii* strain R-7190 | NR_025786.1 |
| 116 | *Bacillus fortis* strain R-6514 | NR_042905.1 |
| 117 | *Bacillus fumarioli* strain LMG 17489 | NR_025370.1 |
| 118 | *Bacillus funiculus* strain NAF001 | NR_028624.1 |
| 119 | *Bacillus galactosidilyticus* strain LMG 17892 | NR_025580.1 |
| 120 | *Bacillus gelatini* strain LMG 21880 | NR_025595.1 |
| 121 | *Bacillus ginsengi* strain ge14 | NR_044193.1 |
| 122 | *Bacillus ginsengihumi* strain Gsoil 114 | NR_041378.1 |
| 123 | *Bacillus halmapalus* strain DSM 8723 | NR_026144.1 |
| 124 | *Bacillus halodurans* C-125 strain C-125 | NR_074984.1 |
| 125 | *Bacillus halodurans* strain DSM 497 | NR_025446.1 |
| 126 | *Bacillus hemicellulosilyticus* strain C-11 | NR_040848.1 |
| 127 | *Bacillus herbersteinensis* strain: D-1,5a | NR_042286.1 |
| 128 | *Bacillus horikoshii* strain DSM8719 | NR_040852.1 |
| 129 | *Bacillus horti* strain K13 | NR_036860.1 |
| 130 | *Bacillus humi* strain LMG 22167 | NR_025626.1 |
| 131 | *Bacillus hwajinpoensis* strain SW-72 | NR_025264.1 |
| 132 | *Bacillus idriensis* strain SMC 4352-2 | NR_043268.1 |
| 133 | *Bacillus indicus* strain Sd/3 | NR_029022.1 |
| 134 | *Bacillus infantis* strain SMC 4352-1 | NR_043267.1 |
| 135 | *Bacillus infernus* strain TH-23 | NR_027227.1 |
| 136 | *Bacillus isabeliae* strain: CVS-8 | NR_042619.1 |
| 137 | *Bacillus jeotgali* strain YKJ-10 | NR_025060.1 |
| 138 | *Bacillus koreensis* strain BR030 | NR_043084.1 |
| 139 | *Bacillus korlensis* strain ZLC-26 | NR_044538.1 |
| 140 | *Bacillus kribbensis* strain BT080 | NR_043682.1 |
| 141 | *Bacillus krulwichiae* strain AM31D | NR_024798.1 |
| 142 | *Bacillus lehensis* strain MLB2 | NR_036940.1 |
| 143 | *Bacillus lentus* strain NCIMB8773 | NR_040792.1 |
| 144 | *Bacillus licheniformis* DSM 13 = ATCC 14580 strain ATCC 14580; DSM 13 | NR_074923.1 |
| 145 | *Bacillus litoralis* strain SW-211 | NR_043015.1 |
| 146 | *Bacillus luciferensis* strain LMG 18422 | NR_025511.1 |
| 147 | *Bacillus macauensis* strain ZFHKF-1 | NR_042892.1 |
| 148 | *Bacillus macyae* strain JMM-4 | NR_025650.1 |
| 149 | *Bacillus mannanilyticus* strain AM-001 | NR_040851.1 |
| 150 | *Bacillus marisflavi* strain TF-11 | NR_025240.1 |
| 151 | *Bacillus massiliensis* strain 4400831 | NR_043092.1 |
| 152 | *Bacillus megaterium* QM B1551 strain QM B1551 | NR_074290.1 |
| 153 | *Bacillus megaterium* strain IAM 13418 | NR_043401.1 |
| 154 | *Bacillus methanolicus* strain NCIMB 13113 | NR_040985.1 |
| 155 | *Bacillus mojavensis* strain IFO15718 | NR_024693.1 |
| 156 | *Bacillus mucilaginosus* strain 1480D | NR_028675.1 |
| 157 | *Bacillus murimartini* strain LMG 21005 | NR_042084.1 |
| 158 | *Bacillus mycoides* strain 273 | NR_036880.1 |
| 159 | *Bacillus nealsonii* strain DSM 15077 | NR_044546.1 |
| 160 | *Bacillus niabensis* strain 4T19 | NR_043334.1 |
| 161 | *Bacillus niacini* strain IFO15566 | NR_024695.1 |
| 162 | *Bacillus novalis* strain: LMG 21837 | NR_042168.1 |
| 163 | *Bacillus odysseyi* strain 34hs1 | NR_025258.1 |
| 164 | *Bacillus okhensis* strain Kh10-101 | NR_043484.1 |
| 165 | *Bacillus okuhidensis* strain GTC 854 | NR_024766.1 |
| 166 | *Bacillus oleronius* strain ATCC 700005 | NR_043325.1 |
| 167 | *Bacillus oshimensis* strain K11 | NR_041241.1 |
| 168 | *Bacillus panaciterrae* strain Gsoil 1517 | NR_041379.1 |
| 169 | *Bacillus plakortidis* strain: P203 | NR_042383.1 |
| 170 | *Bacillus pocheonensis* strain Gsoil 420 | NR_041377.1 |
| 171 | *Bacillus polygoni* strain YN-1 | NR_041571.1 |
| 172 | *Bacillus pseudalcaliphilus* DSM 8725 | NR_026145.1 |
| 173 | *Bacillus pseudofirmus* strain DSM 8715 | NR_026139.1 |
| 174 | *Bacillus psychrosaccharolyticus* strain ATCC23296 | NR_040793.1 |
| 175 | *Bacillus pumilus* SAFR-032 strain SAFR-032 | NR_074977.1 |
| 176 | *Bacillus pumilus* strain ATCC 7061 | NR_043242.1 |
| 177 | *Bacillus ruris* strain: R-6760 = LMG 22866 | NR_042161.1 |
| 178 | *Bacillus safensis* strain FO-036b | NR_041794.1 |
| 179 | *Bacillus schlegelii* strain ATCC 43741 | NR_040845.1 |
| 180 | *Bacillus selenatarsenatis* strain SF-1 | NR_041465.1 |
| 181 | *Bacillus seohaeanensis* strain BH724 | NR_043083.1 |
| 182 | *Bacillus shackletonii* strain LMG 18435 | NR_025373.1 |

TABLE 2-continued

| Bacterial ID No. | Species | 16S rRNA Genbank Acc. No. |
|---|---|---|
| 183 | *Bacillus simplex* strain DSM 1321 | NR_042136.1 |
| 184 | *Bacillus siralis* strain 171544 | NR_028709.1 |
| 185 | *Bacillus smithii* strain NRS-173 | NR_036987.1 |
| 186 | *Bacillus soli* strain R-16300 | NR_025591.1 |
| 187 | *Bacillus solisalsi* strain YC1 | NR_044387.1 |
| 188 | *Bacillus sonorensis* strain NRRL B-23154 | NR_025130.1 |
| 189 | *Bacillus* sp. LMG 20238 strain LMG 20238 | NR_042083.1 |
| 190 | *Bacillus sporothermodurans* strain M215 | NR_026010.1 |
| 191 | *Bacillus stratosphericus* strain: 41KF2a | NR_042336.1 |
| 192 | *Bacillus subtilis* subsp. *spizizenii* strain NRRL B-23049 | NR_024931.1 |
| 193 | *Bacillus subtilis* subsp. *subtilis* strain DSM 10 | NR_027552.1 |
| 194 | *Bacillus taeanensis* strain BH030017 | NR_043012.1 |
| 195 | *Bacillus thermoamylovorans* strain DKP | NR_029151.1 |
| 196 | *Bacillus thermocloaceae* strain S 6025 | NR_036986.1 |
| 197 | *Bacillus thioparans* strain BMP-1 | NR_043762.1 |
| 198 | *Bacillus thuringiensis* strain IAM 12077 | NR_043403.1 |
| 199 | *Bacillus vallismortis* strain DSM11031 | NR_024696.1 |
| 200 | *Bacillus vedderi* strain JaH | NR_026526.1 |
| 201 | *Bacillus vietnamensis* strain 15-1 | NR_024808.1 |
| 202 | *Bacillus vireti* strain R-15447 | NR_025590.1 |
| 203 | *Bacillus wakoensis* strain N-1 | NR_040849.1 |
| 204 | *Bacillus weihenstephanensis* KBAB4 strain KBAB4 | NR_074926.1 |
| 205 | *Bacillus weihenstephanensis* strain DSM11821 | NR_024697.1 |
| 206 | *Bacteroides acidifaciens* strain A40 | NR_028607.1 |
| 207 | *Bacteroides barnesiae* strain JCM 13652 | NR_041446.1 |
| 208 | *Bacteroides caccae* strain ATCC 43185 | NR_026242.1 |
| 209 | *Bacteroides cellulosilyticus* DSM 14838 strain: CRE21 | NR_042203.1 |
| 210 | *Bacteroides cellulosolvens* strain ATCC 35603 | NR_025918.1 |
| 211 | *Bacteroides coprocola* DSM 17136 strain M16 | NR_041278.1 |
| 212 | *Bacteroides coprophilus* DSM 18228 strain CB42 (=JCM 13818, =DSM 18228) | NR_041461.1 |
| 213 | *Bacteroides coprosuis* DSM 18011 strain PC139 | NR_041818.1 |
| 214 | *Bacteroides dorei* DSM 17855 strain JCM 13471 | NR_041351.1 |
| 215 | *Bacteroides eggerthii* DSM 20697 strain DSM 20697 | NR_040864.1 |
| 216 | *Bacteroides finegoldii* DSM 17565 strain JCM 13345 | NR_041313.1 |
| 217 | *Bacteroides fragilis* NCTC 9343 strain ATCC 25285 = NCTC 9343 | NR_074784.1 |
| 218 | *Bacteroides fragilis* YCH46 strain YCH46 | NR_074839.1 |
| 219 | *Bacteroides gallinarum* strain JCM 13658 | NR_041448.1 |
| 220 | *Bacteroides graminisolvens* strain XDT-1 | NR_041642.1 |
| 221 | *Bacteroides helcogenes* P 36-108 strain P 36-108 | NR_074546.1 |
| 222 | *Bacteroides helcogenes* strain JCM 6297 | NR_041279.1 |
| 223 | *Bacteroides heparinolyticus* | NR_044633.1 |
| 224 | *Bacteroides intestinalis* DSM 17393 strain JCM 13265 | NR_041307.1 |
| 225 | *Bacteroides massiliensis* strain B84634 | NR_042745.1 |
| 226 | *Bacteroides nordii* strain WAL 11050 | NR_043017.1 |
| 227 | *Bacteroides ovatus* strain JCM 5824 | NR_040865.1 |
| 228 | *Bacteroides plebeius* DSM 17135 strain M12 | NR_041277.1 |
| 229 | *Bacteroides propionicifaciens* strain SV434 | NR_041485.1 |
| 230 | *Bacteroides pyogenes* strain JCM 10003 | NR_041280.1 |
| 231 | *Bacteroides pyogenes* strain JCM 6294 | NR_041281.1 |
| 232 | *Bacteroides salanitronis* DSM 18170 strain DSM 18170 | NR_074616.1 |
| 233 | *Bacteroides salanitronis* DSM 18170 strain JCM 13657 | NR_041447.1 |
| 234 | *Bacteroides salyersiae* strain WAL 10018 | NR_043016.1 |
| 235 | *Bacteroides stercoris* ATCC 43183 | NR_027196.1 |
| 236 | *Bacteroides thetaiotaomicron* VPI-5482 strain VPI-5482 | NR_074277.1 |
| 237 | *Bacteroides uniformis* strain JCM 5828 | NR_040866.1 |
| 238 | *Bacteroides vulgatus* ATCC 8482 strain ATCC 8482 | NR_074515.1 |
| 239 | *Bacteroides xylanisolvens* strain: XB1A | NR_042499.1 |
| 240 | *Brucella abortus* strain: NCTC 10093 | NR_042460.1 |
| 241 | *Brucella canis* | NR_044652.1 |
| 242 | *Brucella canis* ATCC 23365 | NR_074286.1 |
| 243 | *Brucella ceti* strain NCTC 12891 | NR_042463.1 |
| 244 | *Brucella melitensis* biovar *Melitensis* strain 2000031283; ATCC 23456 | NR_043003.1 |
| 245 | *Brucella microti* CCM 4915 strain CCM 4915 | NR_074336.1 |
| 246 | *Brucella microti* CCM 4915 strain CCM 4915 | NR_042549.1 |
| 247 | *Brucella neotomae* 5K33 strain 2002721533; ATCC 23459 | NR_043004.1 |
| 248 | *Brucella ovis* strain 63/290 | NR_036772.1 |
| 249 | *Brucella pinnipedialis* B2/94 strain B2/94 | NR_074332.1 |
| 250 | *Brucella pinnipedialis* strain NCTC 12890 | NR_042462.1 |
| 251 | *Brucella suis* 1330 strain: NCTC 10316 | NR_042461.1 |
| 252 | *Burkholderia cepacia* strain 717 | NR_029209.1 |
| 253 | *Burkholderia cepacia* strain LMG 14294 | NR_041719.1 |
| 254 | *Burkholderia pseudomallei* K96243 strain K96243 | NR_074340.1 |
| 255 | *Burkholderia pseudomallei* strain ATCC 23343 | NR_043553.1 |
| 256 | *Cardiobacterium valvarum* strain MDA3079 | NR_028847.1 |
| 257 | *Citrobacter braakii* strain 167 | NR_028687.1 |
| 258 | *Citrobacter farmeri* strain CDC 2991-81 | NR_024861.1 |

TABLE 2-continued

| Bacterial ID No. | Species | 16S rRNA Genbank Acc. No. |
|---|---|---|
| 259 | *Citrobacter freundii* strain DSM 30039 | NR_028894.1 |
| 260 | *Citrobacter gillenii* strain CDC 4693-86 | NR_041697.1 |
| 261 | *Citrobacter murliniae* strain CDC 2970-59 | NR_028688.1 |
| 262 | *Citrobacter rodentium* ICC168 strain ICC168 | NR_074903.1 |
| 263 | *Citrobacter rodentium* strain DO 14784 | NR_028685.1 |
| 264 | *Citrobacter sedlakii* strain I-75 | NR_028686.1 |
| 265 | *Citrobacter werkmanii* strain CDC 0876-58 | NR_024862.1 |
| 266 | *Citrobacter youngae* strain GTC 1314 | NR_041527.1 |
| 267 | *Clostridium botulinum* A strain ELTDK 103 | NR_029157.1 |
| 268 | *Clostridium botulinum* strain 2318 | NR_036786.1 |
| 269 | *Clostridium difficile* 630 strain 630 | NR_074454.1 |
| 270 | *Clostridium perfringens* strain 13 | NR_074482.1 |
| 271 | *Corynebacterium accolens* strain CIP104783T, (ATCC49724T) | NR_042139.1 |
| 272 | *Corynebacterium afermentans* strain CIP 103500 | NR_044865.1 |
| 273 | *Corynebacterium afermentans* subsp. *afermentans* strain CIP 103499 | NR_026214.1 |
| 274 | *Corynebacterium ammoniagenes* strain Cooke J.V 9.6 | NR_037039.1 |
| 275 | *Corynebacterium amycolatum* strain CIP 103452 | NR_026215.1 |
| 276 | *Corynebacterium appendicis* strain IMMIB R-3491 | NR_028951.1 |
| 277 | *Corynebacterium aquilae* strain S-613 | NR_028989.1 |
| 278 | *Corynebacterium atypicum* strain R2070 | NR_025540.1 |
| 279 | *Corynebacterium aurimucosum* strain IMMIB D-1488 | NR_028941.1 |
| 280 | *Corynebacterium auris* strain DZZM 328 | NR_026211.1 |
| 281 | *Corynebacterium auriscanis* strain CCUG 39784 | NR_025365.1 |
| 282 | *Corynebacterium bovis* strain ATCC13722 | NR_041812.1 |
| 283 | *Corynebacterium bovis* strain Evans | NR_037042.1 |
| 284 | *Corynebacterium callunae* strain NCIMB 10338 | NR_037036.1 |
| 285 | *Corynebacterium camporealensis* strain CRS-51 | NR_029326.1 |
| 286 | *Corynebacterium capitovis* strain CCUG 39779 | NR_025436.1 |
| 287 | *Corynebacterium casei* strain LMG S-19264 | NR_025101.1 |
| 288 | *Corynebacterium caspium* strain M/106/00/5 | NR_029017.1 |
| 289 | *Corynebacterium ciconiae* strain BS13 | NR_029007.1 |
| 290 | *Corynebacterium confusum* strain DMMZ 2439 | NR_026449.1 |
| 291 | *Corynebacterium coyleae* strain: DSM 44184 = CCUG 35014 = DMMZ 214 | NR_044905.1 |
| 292 | *Corynebacterium cystitidis* strain 42 Fukuya | NR_037037.1 |
| 293 | *Corynebacterium diphtheriae* strain C7 s (—) tox | NR_037079.1 |
| 294 | *Corynebacterium durum* strain IBS G15036 | NR_026539.1 |
| 295 | *Corynebacterium efficiens* YS-314 | NR_024772.1 |
| 296 | *Corynebacterium falsenii* CCUG 33651 | NR_026415.1 |
| 297 | *Corynebacterium felinum* strain CCUG 39943 | NR_025496.1 |
| 298 | *Corynebacterium flavescens* strain NCDO 1320 | NR_037040.1 |
| 299 | *Corynebacterium freiburgense* strain 1045 | NR_044584.1 |
| 300 | *Corynebacterium freneyi* strain 20695110 | NR_042025.1 |
| 301 | *Corynebacterium glaucum* strain IMMIB R-5091 | NR_028971.1 |
| 302 | *Corynebacterium glutamicum* strain ATCC 13032 | NR_074663.1 |
| 303 | *Corynebacterium glutamicum* strain ATCC13032 | NR_041817.1 |
| 304 | *Corynebacterium halotolerans* strain YIM70093 | NR_029074.1 |
| 305 | *Corynebacterium hansenii* strain: DSM 45109 | NR_042703.1 |
| 306 | *Corynebacterium imitans* strain 2023 | NR_026369.1 |
| 307 | *Corynebacterium jeikeium* K411 strain K411 = NCTC 11915 | NR_074706.1 |
| 308 | *Corynebacterium jeikeium* strain A376/84 | NR_037035.1 |
| 309 | *Corynebacterium kroppenstedtii* strain DSM 44385 | NR_074408.1 |
| 310 | *Corynebacterium kroppenstedtii* strain CCUG 35717 | NR_026380.1 |
| 311 | *Corynebacterium kutscheri* strain CIP 103423 | NR_037034.1 |
| 312 | *Corynebacterium lipophiloflavum* strain DSM 44291 | NR_026370.1 |
| 313 | *Corynebacterium lubricantis* strain: KSS-3Se | NR_044603.1 |
| 314 | *Corynebacterium macginleyi* strain CIP104099T, (ATCC51787T) | NR_042138.1 |
| 315 | *Corynebacterium massiliense* strain 5402485 | NR_044182.1 |
| 316 | *Corynebacterium mastitidis* strain S-8 | NR_026376.1 |
| 317 | *Corynebacterium matruchotii* strain CIP 81.82 | NR_026216.1 |
| 318 | *Corynebacterium minutissimum* strain NCTC 10288 | NR_037124.1 |
| 319 | *Corynebacterium mucifaciens* strain DMMZ 2278 | NR_026396.1 |
| 320 | *Corynebacterium mycetoides* strain NCTC 9864 | NR_037078.1 |
| 321 | *Corynebacterium phocae* strain M408/89/1 | NR_026379.1 |
| 322 | *Corynebacterium pilosum* strain ATCC 29592 | NR_026212.1 |
| 323 | *Corynebacterium propinquum* strain B 77159 | NR_037038.1 |
| 324 | *Corynebacterium pseudodiphtheriticum* strain CIP103420T, (ATCC10700) | NR_042137.1 |
| 325 | *Corynebacterium pseudotuberculosis* strain E 23 | NR_037070.1 |
| 326 | *Corynebacterium renale* strain Charita a | NR_037069.1 |
| 327 | *Corynebacterium resistens* strain DSM 45100 | NR_074826.1 |
| 328 | *Corynebacterium resistens* strain GTC 2026 | NR_040999.1 |
| 329 | *Corynebacterium riegelii* strain DMMZ 2415 | NR_026434.1 |
| 330 | *Corynebacterium simulans* strain UCL553 | NR_025309.1 |
| 331 | *Corynebacterium singulare* strain IBS B52218 | NR_026394.1 |
| 332 | *Corynebacterium sphenisci* strain CECT 5990 | NR_028015.1 |
| 333 | *Corynebacterium spheniscorum* strain PG 39 | NR_027201.1 |

TABLE 2-continued

| Bacterial ID No. | Species | 16S rRNA Genbank Acc. No. |
|---|---|---|
| 334 | *Corynebacterium sputi* strain: IMMIB L-999 | NR_042686.1 |
| 335 | *Corynebacterium striatum* strain Minnett | NR_037041.1 |
| 336 | *Corynebacterium suicordis* strain S-81/02 | NR_042151.1 |
| 337 | *Corynebacterium sundsvallense* strain CCUG 36622 | NR_026375.1 |
| 338 | *Corynebacterium terpenotabidum* strain IFO 14764 | NR_040775.1 |
| 339 | *Corynebacterium testudinoris* strain CCUG 41823 | NR_025434.1 |
| 340 | *Corynebacterium thomssenii* strain DSM 44276 | NR_024849.1 |
| 341 | *Corynebacterium timonense* strain 5401744 | NR_044181.1 |
| 342 | *Corynebacterium tuberculostearicum* strain Medalle X | NR_028975.1 |
| 343 | *Corynebacterium tuscaniense* strain ISS-5309; ATCC BAA-1141; CCUG 51321 | NR_043093.1 |
| 344 | *Corynebacterium ulcerans* BR-AD22 strain BR-AD22 | NR_074467.1 |
| 345 | *Corynebacterium ulcerans* strain NCTC 7910 | NR_029292.1 |
| 346 | *Corynebacterium ulceribovis* strain: IMMIB L-1395 | NR_042681.1 |
| 347 | *Corynebacterium urealyticum* | NR_027597.1 |
| 348 | *Corynebacterium urealyticum* strain DSM 7109 | NR_074344.1 |
| 349 | *Corynebacterium ureicelerivorans* strain: IMMIB RIV-2301 | NR_042558.1 |
| 350 | *Corynebacterium variabile* strain DSM 20132 | NR_025314.1 |
| 351 | *Corynebacterium xerosis* strain ATCC 373 | NR_026213.1 |
| 352 | *Dermatophilus congolensis* strain DSM 44180 | NR_041990.1 |
| 353 | *Edwardsiella tarda* strain ATCC15947 | NR_024770.1 |
| 354 | *Enterobacter aerogenes* strain JCM1235 | NR_024643.1 |
| 355 | *Enterobacter cloacae* strain 279-56 | NR_028912.1 |
| 356 | *Enterobacter cloacae* subsp. *dissolvens* strain LMG 2683 | NR_044978.1 |
| 357 | *Enterococcus faecalis* strain JCM 5803 | NR_040789.1 |
| 358 | *Enterococcus faecalis* V583 strain V583 | NR_074637.1 |
| 359 | *Enterococcus faecium* strain LMG 11423 | NR_042054.1 |
| 360 | *Erysipelothrix rhusiopathiae* str. Fujisawa strain Fujisawa | NR_074878.1 |
| 361 | *Erysipelothrix rhusiopathiae* strain ATCC 19414 | NR_040837.1 |
| 362 | *Eubacterium acidaminophilum* strain DSM 3953 | NR_024922.1 |
| 363 | *Eubacterium angustum* | NR_044642.1 |
| 364 | *Eubacterium brachy* strain BR-179 | NR_036993.1 |
| 365 | *Eubacterium budayi* strain JCM 9989 | NR_024682.1 |
| 366 | *Eubacterium cellulosolvens* 6 | NR_026106.1 |
| 367 | *Eubacterium combesii* strain ATCC 25545 | NR_042951.1 |
| 368 | *Eubacterium desmolans* | NR_044644.1 |
| 369 | *Eubacterium eligens* strain ATCC 27750 | NR_074613.1 |
| 370 | *Eubacterium infirmum* strain W 1471 | NR_029178.1 |
| 371 | *Eubacterium minutum* strain SC 87K | NR_036949.1 |
| 372 | *Eubacterium multiforme* strain JCM 6484 | NR_024683.1 |
| 373 | *Eubacterium nitritogenes* strain JCM 6485 | NR_024684.1 |
| 374 | *Eubacterium nodatum* strain AK-5 | NR_036994.1 |
| 375 | *Eubacterium pyruvativorans* | NR_042074.1 |
| 376 | *Eubacterium rectale* strain ATCC 33656 | NR_074634.1 |
| 377 | *Eubacterium ruminantium* strain GA195 | NR_024661.1 |
| 378 | *Eubacterium saphenum* ATCC 49989 strain 164-47 | NR_026031.1 |
| 379 | *Eubacterium sulci* strain ATCC 35585 | NR_025289.1 |
| 380 | *Flavobacterium anhuiense* strain D3 | NR_044388.1 |
| 381 | *Flavobacterium antarcticum* strain AT1026 | NR_042998.2 |
| 382 | *Flavobacterium aquatile* strain: DSM 1132 | NR_042495.1 |
| 383 | *Flavobacterium aquidurense* strain: WB 1.1-56 | NR_042470.1 |
| 384 | *Flavobacterium ceti* strain: 454-2 | NR_042540.1 |
| 385 | *Flavobacterium cheniae* strain NJ-26 | NR_044198.1 |
| 386 | *Flavobacterium chungangense* strain CJ7 | NR_044581.1 |
| 387 | *Flavobacterium columnare* strain ATCC 49512 | NR_074580.1 |
| 388 | *Flavobacterium columnare* strain IFO 15943 | NR_040907.1 |
| 389 | *Flavobacterium croceum* strain EMB47 | NR_043768.1 |
| 390 | *Flavobacterium cucumis* strain R2A45-3 | NR_044107.1 |
| 391 | *Flavobacterium daejeonense* strain GH1-10 | NR_043654.1 |
| 392 | *Flavobacterium defluvii* strain EMB117 | NR_043772.1 |
| 393 | *Flavobacterium degerlachei* strain R-9106 | NR_029009.1 |
| 394 | *Flavobacterium denitrificans* strain: ED5 | NR_042088.1 |
| 395 | *Flavobacterium filum* strain EMB34 | NR_043767.1 |
| 396 | *Flavobacterium frigidarium* strain A2i | NR_025020.1 |
| 397 | *Flavobacterium frigidimaris* strain KUC-1 | NR_041057.1 |
| 398 | *Flavobacterium frigoris* strain R-9014 | NR_025597.1 |
| 399 | *Flavobacterium fryxellicola* strain: LMG 22022 | NR_042332.1 |
| 400 | *Flavobacterium gelidilacus* strain R-8899 | NR_025538.1 |
| 401 | *Flavobacterium glaciei* strain 0499 | NR_043891.1 |
| 402 | *Flavobacterium granuli* strain Kw05 | NR_041052.1 |
| 403 | *Flavobacterium hercynium* strain: WB 4.2-33 | NR_042520.1 |
| 404 | *Flavobacterium hibernum* strain ATCC 51468 | NR_025923.1 |
| 405 | *Flavobacterium hydatis* | NR_044695.1 |
| 406 | *Flavobacterium indicum* strain GPTSA100-9 | NR_074422.1 |
| 407 | *Flavobacterium indicum* strain GPTSA100-9 | NR_043269.1 |
| 408 | *Flavobacterium johnsoniae* | NR_044738.1 |
| 409 | *Flavobacterium johnsoniae* strain: DSM 2064 | NR_042496.1 |

TABLE 2-continued

| Bacterial ID No. | Species | 16S rRNA Genbank Acc. No. |
|---|---|---|
| 410 | *Flavobacterium johnsoniae* strain UW101; ATCC 17061 | NR_074455.1 |
| 411 | *Flavobacterium limicola* strain ST-82 | NR_024787.1 |
| 412 | *Flavobacterium lindanitolerans* strain IP10 | NR_044208.1 |
| 413 | *Flavobacterium micromati* strain R-9192 | NR_029010.1 |
| 414 | *Flavobacterium omnivorum* strain AS 1.2747 | NR_025202.1 |
| 415 | *Flavobacterium psychrolimnae* strain: LMG 22018 | NR_042207.1 |
| 416 | *Flavobacterium psychrophilum* JIP02/86 strain JIP02/86 | NR_074630.1 |
| 417 | *Flavobacterium psychrophilum* strain IFO 15942 | NR_040914.1 |
| 418 | *Flavobacterium resistens* strain BD-b365 | NR_044292.1 |
| 419 | *Flavobacterium saccharophilum* strain: DSM 1811 | NR_042497.1 |
| 420 | *Flavobacterium saliperosum* strain AS 1.3801 | NR_043481.1 |
| 421 | *Flavobacterium sasangense* strain YC6274 | NR_044492.1 |
| 422 | *Flavobacterium segetis* strain AT1048; IMSNU 14050; KCTC 12224 | NR_043000.1 |
| 423 | *Flavobacterium soli* strain DS-6 | NR_043613.1 |
| 424 | *Flavobacterium* sp. strain A103 | NR_044804.1 |
| 425 | *Flavobacterium* sp. strain IC001 | NR_044805.1 |
| 426 | *Flavobacterium succinicans* strain: DSM 4002 | NR_042498.1 |
| 427 | *Flavobacterium suncheonense* strain GH29-5 | NR_043655.1 |
| 428 | *Flavobacterium terrae* strain R2A1-13 | NR_044096.1 |
| 429 | *Flavobacterium terrigena* strain DS-20 | NR_044006.1 |
| 430 | *Flavobacterium weaverense* strain AT1042; IMSNU 14048; KCTC 12223 | NR_042999.1 |
| 431 | *Flavobacterium xanthum* strain ACAM 81 | NR_024865.1 |
| 432 | *Flavobacterium xinjiangense* strain AS 1.2749 | NR_025201.1 |
| 433 | *Haemophilus aegyptius* strain CCUG 25716 | NR_042875.1 |
| 434 | *Haemophilus ducreyi* 35000HP strain 35000HP | NR_074837.1 |
| 435 | *Haemophilus ducreyi* strain CIP 542 | NR_044741.1 |
| 436 | *Haemophilus felis* strain ATCC49733 | NR_025073.1 |
| 437 | *Haemophilus haemoglobinophilus* strain CCUG 3714 | NR_042877.1 |
| 438 | *Haemophilus influenzae* | NR_044682.1 |
| 439 | *Haemophilus influenzae* Rd KW20 | NR_074863.1 |
| 440 | *Haemophilus paracuniculus* | NR_044751.1 |
| 441 | *Haemophilus parahaemolyticus* strain 536 | NR_025938.1 |
| 442 | *Haemophilus parainfluenzae* strain CCUG 12836 | NR_042878.1 |
| 443 | *Haemophilus paraphrohaemolyticus* | NR_044753.1 |
| 444 | *Haemophilus parasuis* strain CCUG 3712 | NR_042879.1 |
| 445 | *Haemophilus pittmaniae* strain HK85 | NR_025423.1 |
| 446 | *Haemophilus somnus* strain 129P | NR_074278.1 |
| 447 | *Klebsiella oxytoca* strain ATCC 13182 | NR_041749.1 |
| 448 | *Klebsiella pneumoniae* strain DSM 30104 | NR_036794.1 |
| 449 | *Klebsiella pneumoniae* subsp. *ozaenae* strain ATCC11296 | NR_041750.1 |
| 450 | *Klebsiella pneumoniae* subsp. *pneumoniae* strain ATCC 700721; MGH 78578 | NR_074913.1 |
| 451 | *Klebsiella pneumoniae* subsp. *rhinoscleromatis* strain R-70 | NR_037084.1 |
| 452 | *Lactobacillus acetotolerans* strain DSM 20749 | NR_044699.1 |
| 453 | *Lactobacillus acidipiscis* strain FS60-1 | NR_024718.1 |
| 454 | *Lactobacillus acidophilus* 30SC strain 30SC | NR_075049.1 |
| 455 | *Lactobacillus acidophilus* strain NCFM | NR_075045.1 |
| 456 | *Lactobacillus acidophilus* strain BCRC10695 | NR_043182.1 |
| 457 | *Lactobacillus algidus* strain M 6 A9 | NR_028617.1 |
| 458 | *Lactobacillus amylolyticus* strain LA 5 | NR_029352.1 |
| 459 | *Lactobacillus amylophilus* | NR_044702.1 |
| 460 | *Lactobacillus amylotrophicus* strain: LMG 11400 | NR_042511.1 |
| 461 | *Lactobacillus amylovorus* strain GRL 1112 | NR_075048.1 |
| 462 | *Lactobacillus amylovorus* strain DSM 20531 | NR_043287.1 |
| 463 | *Lactobacillus animalis* strain NBRC 15882 | NR_041610.1 |
| 464 | *Lactobacillus apodemi* strain: ASB1 | NR_042367.1 |
| 465 | *Lactobacillus aviarius* | NR_044703.1 |
| 466 | *Lactobacillus bobalius* strain 203 | NR_043096.1 |
| 467 | *Lactobacillus brevis* | NR_044704.1 |
| 468 | *Lactobacillus brevis* strain ATCC 367 | NR_075024.1 |
| 469 | *Lactobacillus buchneri* strain JCM1115 | NR_041293.1 |
| 470 | *Lactobacillus cacaonum* strain: LMG 24285 | NR_042677.1 |
| 471 | *Lactobacillus camelliae* strain MCH3-1 | NR_041457.1 |
| 472 | *Lactobacillus capillatus* strain YIT 11306 (=JCM 15044, =DSM 19910 =BCRC 17811) | NR_041655.1 |
| 473 | *Lactobacillus casei* strain ATCC 334 | NR_075032.1 |
| 474 | *Lactobacillus casei* strain JCM 1136 | NR_043408.1 |
| 475 | *Lactobacillus casei* subsp. *casei* strain ATCC 393 | NR_041893.1 |
| 476 | *Lactobacillus catenaformis* strain: DSM 20559 | NR_042228.1 |
| 477 | *Lactobacillus ceti* strain: 142-2 | NR_042539.1 |
| 478 | *Lactobacillus collinoides* strain JCM1123 | NR_024645.1 |
| 479 | *Lactobacillus composti* strain NRIC 0689 | NR_041509.1 |
| 480 | *Lactobacillus concavus* strain AS 1.5017 | NR_043105.1 |
| 481 | *Lactobacillus coryniformis* | NR_044705.1 |
| 482 | *Lactobacillus coryniformis* subsp. *torquens* strain 30 | NR_029018.1 |
| 483 | *Lactobacillus crispatus* ST1 strain ST1 | NR_074986.1 |

TABLE 2-continued

| Bacterial ID No. | Species | 16S rRNA Genbank Acc. No. |
|---|---|---|
| 484 | *Lactobacillus crispatus* strain ATCC33820 | NR_041800.1 |
| 485 | *Lactobacillus crustorum* strain: LMG 23699 | NR_042533.1 |
| 486 | *Lactobacillus curvatus* strain: DSM 20019 | NR_042437.1 |
| 487 | *Lactobacillus delbrueckii* subsp. *bulgaricus* ATCC 11842 strain ATCC 11842 | NR_075019.1 |
| 488 | *Lactobacillus delbrueckii* subsp. *delbrueckii* strain BCRC12195 | NR_043183.1 |
| 489 | *Lactobacillus delbrueckii* subsp. *indicus* strain NCC725 | NR_029106.1 |
| 490 | *Lactobacillus delbrueckii* subsp. *lactis* DSM 20072 strain ATCC 12315 | NR_042728.1 |
| 491 | *Lactobacillus dextrinicus* strain JCM 5887 | NR_036861.1 |
| 492 | *Lactobacillus diolivorans* strain JKD6 | NR_037004.1 |
| 493 | *Lactobacillus equi* strain YIT 0455 | NR_028623.1 |
| 494 | *Lactobacillus fabifermentans* strain: LMG 24284 | NR_042676.1 |
| 495 | *Lactobacillus farraginis* strain NRIC 0676 | NR_041467.1 |
| 496 | *Lactobacillus fornicalis* strain TV1018 | NR_026509.1 |
| 497 | *Lactobacillus gallinarum* strain ATCC 33199 | NR_042111.1 |
| 498 | *Lactobacillus gasseri* | NR_041920.1 |
| 499 | *Lactobacillus gasseri* strain ATCC 33323 | NR_075051.1 |
| 500 | *Lactobacillus ghanensis* strain L489 | NR_043896.1 |
| 501 | *Lactobacillus graminis* strain: DSM 20719 | NR_042438.1 |
| 502 | *Lactobacillus hammesii* strain: TMW 1.1236 | NR_042243.1 |
| 503 | *Lactobacillus hamsteri* strain DSM 5661 | NR_025448.1 |
| 504 | *Lactobacillus harbinensis* strain SBT10908 | NR_041263.1 |
| 505 | *Lactobacillus hayakitensis* | NR_041498.1 |
| 506 | *Lactobacillus helveticus* strain DPC 4571 | NR_075047.1 |
| 507 | *Lactobacillus helveticus* DSM 20075 | NR_042439.1 |
| 508 | *Lactobacillus hilgardii* | NR_044708.1 |
| 509 | *Lactobacillus hordei* strain UCC128; DSM19519; LMG24241 | NR_044394.1 |
| 510 | *Lactobacillus iners* strain DSM 13335 | NR_036982.1 |
| 511 | *Lactobacillus intestinalis* strain DSM 6629 | NR_025449.1 |
| 512 | *Lactobacillus jensenii* strain ATCC 25258 | NR_025087.1 |
| 513 | *Lactobacillus johnsonii* NCC 533 strain NCC 533 | NR_075064.1 |
| 514 | *Lactobacillus johnsonii* strain ATCC 33200 | NR_025273.1 |
| 515 | *Lactobacillus kalixensis* strain Kx127A2 | NR_029083.1 |
| 516 | *Lactobacillus kefiranofaciens* subsp. *kefiranofaciens* strain: DSM 5016 | NR_042440.1 |
| 517 | *Lactobacillus kefiranofaciens* subsp. *kefirgranum* strain: DSM 10550 | NR_042441.1 |
| 518 | *Lactobacillus kefiri* strain: LMG 9480 | NR_042230.1 |
| 519 | *Lactobacillus kimchii* strain MT-1077 | NR_025045.1 |
| 520 | *Lactobacillus kisonensis* strain YIT 11168 (=NRIC 0741, =JCM 15041, =DSM 19906) | NR_041658.1 |
| 521 | *Lactobacillus kitasatonis* strain JCM 1039 | NR_024813.1 |
| 522 | *Lactobacillus kunkeei* strain YH-15 | NR_026404.1 |
| 523 | *Lactobacillus lindneri* strain KPA | NR_029308.1 |
| 524 | *Lactobacillus malefermentans* strain DSM 5705 | NR_042442.1 |
| 525 | *Lactobacillus manihotivorans* strain OND 32 | NR_024835.1 |
| 526 | *Lactobacillus mindensis* strain TMW 1.80 | NR_028949.1 |
| 527 | *Lactobacillus nagelii* strain NRIC 0559 | NR_041007.1 |
| 528 | *Lactobacillus nantensis* strain LP33 | NR_043114.1 |
| 529 | *Lactobacillus nodensis* strain iz4b-1 | NR_041629.1 |
| 530 | *Lactobacillus oeni* strain 59b | NR_043095.1 |
| 531 | *Lactobacillus oligofermentans* strain AMKR18 | NR_043148.1 |
| 532 | *Lactobacillus otakiensis* strain YIT 11163 (=NRIC 0742, =JCM 15040, =DSM 19908) | NR_041657.1 |
| 533 | *Lactobacillus pantheris* strain LMG 21017 | NR_025189.1 |
| 534 | *Lactobacillus parabrevis* strain: LMG 11984 | NR_042456.1 |
| 535 | *Lactobacillus parabuchneri* strain JCM 12493 | NR_041294.1 |
| 536 | *Lactobacillus paracasei* subsp. *paracasei* strain R094 | NR_025880.1 |
| 537 | *Lactobacillus paracasei* subsp. *tolerans* strain NBRC 15906 | NR_041054.1 |
| 538 | *Lactobacillus paracollinoides* strain: DSM 15502 | NR_042322.1 |
| 539 | *Lactobacillus parafarraginis* strain NRIC 0677 | NR_041468.1 |
| 540 | *Lactobacillus parakefiri* strain GCL 1731 | NR_029039.1 |
| 541 | *Lactobacillus paralimentarius* strain TB 1 | NR_036879.1 |
| 542 | *Lactobacillus paraplantarum* strain DSM 10667 | NR_025447.1 |
| 543 | *Lactobacillus pentosus* strain 124-2 | NR_029133.1 |
| 544 | *Lactobacillus perolens* strain L532 | NR_029360.1 |
| 545 | *Lactobacillus plantarum* strain NRRL B-14768 | NR_042394.1 |
| 546 | *Lactobacillus plantarum* subsp. *argentoratensis* strain: DK0 22 | NR_042254.1 |
| 547 | *Lactobacillus plantarum* WCFS1 strain WCFS1 | NR_075041.1 |
| 548 | *Lactobacillus rapi* strain YIT 11204 (=NRIC 0743, =JCM 15042, =DSM 19907) | NR_041659.1 |
| 549 | *Lactobacillus rennini* strain CECT 5922 | NR_042195.1 |
| 550 | *Lactobacillus rossiae* strain CS1 | NR_029014.1 |
| 551 | *Lactobacillus ruminis* strain NBRC 102161 | NR_041611.1 |
| 552 | *Lactobacillus saerimneri* strain GDA154 | NR_029085.1 |
| 553 | *Lactobacillus sakei* strain: DSM 20017 | NR_042443.1 |
| 554 | *Lactobacillus sakei* subsp. *carnosus* strain CCUG 34545 | NR_025719.1 |
| 555 | *Lactobacillus sakei* subsp. *sakei* 23K strain 23K | NR_075042.1 |
| 556 | *Lactobacillus salivarius* strain HO 66 | NR_028725.1 |

TABLE 2-continued

| Bacterial ID No. | Species | 16S rRNA Genbank Acc. No. |
|---|---|---|
| 557 | *Lactobacillus salivarius* strain UCC118 | NR_074589.1 |
| 558 | *Lactobacillus sanfranciscensis* strain L-12 | NR_029261.1 |
| 559 | *Lactobacillus sanfranciscensis* strain TMW 1.1304 | NR_075038.1 |
| 560 | *Lactobacillus satsumensis* strain NRIC 0604 | NR_028658.1 |
| 561 | *Lactobacillus senmaizukei* strain L13 | NR_041584.1 |
| 562 | *Lactobacillus sharpeae* | NR_044711.1 |
| 563 | *Lactobacillus spicheri* strain LTH 5753 | NR_025579.1 |
| 564 | *Lactobacillus suebicus* strain CECT 5917 | NR_042190.1 |
| 565 | *Lactobacillus sunkii* strain YIT 11161 (=NRIC 0744, =JCM 15039, =DSM 19904) | NR_041656.1 |
| 566 | *Lactobacillus taiwanensis* strain BCRC 17755 | NR_044507.1 |
| 567 | *Lactobacillus thailandensis* strain MCH5-2 | NR_041456.1 |
| 568 | *Lactobacillus tucceti* strain CECT 5920 | NR_042194.1 |
| 569 | *Lactobacillus ultunensis* strain Kx146C1; LMG 22117T; DSM 16047T; CCUG 48460 | NR_042802.1 |
| 570 | *Lactobacillus vaginalis* strain ATCC49540 | NR_041796.1 |
| 571 | *Lactobacillus versmoldensis* strain KU-3 | NR_028990.1 |
| 572 | *Lactobacillus vini* strain: CECT 5924 | NR_042196.1 |
| 573 | *Lactobacillus vitulinus* strain JCM 1143 | NR_041305.1 |
| 574 | *Lactobacillus zeae* strain RIA 482 | NR_037122.1 |
| 575 | *Legionella pneumophila* subsp. *pneumophila* str. Philadelphia 1 strain Philadelphia 1 | NR_074231.1 |
| 576 | *Listeria monocytogenes* strain NCTC10357 | NR_044823.1 |
| 577 | *Micrococcus antarcticus* strain T2 | NR_025285.1 |
| 578 | *Micrococcus endophyticus* strain YIM 56238 | NR_044365.1 |
| 579 | *Micrococcus flavus* strain LW4 | NR_043881.1 |
| 580 | *Micrococcus luteus* NCTC 2665 strain NCTC 2665 | NR_075062.1 |
| 581 | *Micrococcus luteus* strain DSM 20030 | NR_037113.1 |
| 582 | *Micrococcus lylae* strain DSM 20315 | NR_026200.1 |
| 583 | *Mobiluncus curtisii* ATCC 43063 strain ATCC 43063 | NR_074732.1 |
| 584 | *Mobiluncus curtisii* subsp. *curtisii* ATCC 35241 strain CCUG 21018 | NR_042085.1 |
| 585 | *Mobiluncus curtisii* subsp. *holmesii* ATCC 35242 strain: CCUG 17762 | NR_042124.1 |
| 586 | *Mobiluncus mulieris* strain CCUG 20071 | NR_042086.1 |
| 587 | *Moraxella boevrei* strain ATCC 700022 | NR_043585.1 |
| 588 | *Moraxella bovis* strain L-3 | NR_028668.1 |
| 589 | *Moraxella bovoculi* 237 strain 237 | NR_043583.1 |
| 590 | *Moraxella canis* strain N7 | NR_028914.1 |
| 591 | *Moraxella caprae* strain ATCC 700019 | NR_043586.1 |
| 592 | *Moraxella catarrhalis* strain Ne 11 | NR_028669.1 |
| 593 | *Moraxella caviae* strain GP11 | NR_028671.1 |
| 594 | *Moraxella cuniculi* strain CCUG 2154 | NR_041695.1 |
| 595 | *Moraxella equi* strain 327/72 | NR_041694.1 |
| 596 | *Moraxella lacunata* strain Morax 260 | NR_036825.1 |
| 597 | *Moraxella ovis* strain 199/55 | NR_028670.1 |
| 598 | *Moraxella pluranimalium* strain: 248-01 | NR_042666.1 |
| 599 | *Morganella morganii* strain DSM 14850 | NR_043751.1 |
| 600 | *Morganella morganii* strain M11 | NR_028938.1 |
| 601 | *Morganella psychrotolerans* strain U2/3 | NR_043750.1 |
| 602 | *Mycobacterium massiliense* str. strain GO 06 | NR_074421.1 |
| 603 | *Mycobacterium tuberculosis* strain NCTC 7416 H37Rv | NR_044826.1 |
| 604 | *Neisseria animalis* strain NA 1 | NR_028900.1 |
| 605 | *Neisseria animaloris* strain LMG 23011 | NR_043458.1 |
| 606 | *Neisseria bacilliformis* ATCC BAA-1200 strain MDA2833 | NR_042978.1 |
| 607 | *Neisseria canis* | NR_044614.1 |
| 608 | *Neisseria dentiae* strain V33 | NR_028843.1 |
| 609 | *Neisseria elongata* subsp. *elongata* strain ATCC 25295 | NR_025893.1 |
| 610 | *Neisseria flavescens* strain N 155 | NR_025892.1 |
| 611 | *Neisseria gonorrhoeae* strain NCTC 83785 | NR_026079.1 |
| 612 | *Neisseria lactamica* strain NCTC 10617 | NR_028899.1 |
| 613 | *Neisseria meningitidis* strain N.934/01 | AY238932.1 |
| 614 | *Neisseria polysaccharea* strain NCTC11858 | NR_041988.1 |
| 615 | *Neisseria subflava* strain U37 | NR_041989.1 |
| 616 | *Neisseria weaveri* strain CDC 8142 | NR_025902.1 |
| 617 | *Neisseria zoodegmatis* strain LMG 23012 | NR_043459.1 |
| 618 | *Nocardia abscessus* strain IMMIB D-1592 | NR_025059.1 |
| 619 | *Nocardia acidivorans* strain: GW4-1778 | NR_042566.1 |
| 620 | *Nocardia africana* strain DSM 44491 | NR_041872.1 |
| 621 | *Nocardia alba* strain YIM 30243 | NR_025726.1 |
| 622 | *Nocardia altamirensis* strain DSM 44997 | NR_044366.1 |
| 623 | *Nocardia amamiensis* strain TT 00-78 | NR_041531.1 |
| 624 | *Nocardia anaemiae* strain IFM 0323 | NR_041010.1 |
| 625 | *Nocardia aobensis* strain IFM 0372 | NR_040995.1 |
| 626 | *Nocardia araoensis* strain IFM 0575 | NR_028652.1 |
| 627 | *Nocardia arthritidis* strain IFM 10035 | NR_028654.1 |
| 628 | *Nocardia asiatica* strain IFM 0245 | NR_028644.1 |
| 629 | *Nocardia asteroides* strain DSM 43757 | NR_041856.1 |
| 630 | *Nocardia beijingensis* strain AS4.1521 | NR_025017.1 |

TABLE 2-continued

| Bacterial ID No. | Species | 16S rRNA Genbank Acc. No. |
|---|---|---|
| 631 | *Nocardia blacklockiae* strain ATCC 700035 | NR_044402.1 |
| 632 | *Nocardia brasiliensis* ATCC 700358 strain HUJEG-1 | NR_074743.1 |
| 633 | *Nocardia brasiliensis* strain DSM 43758 | NR_041860.1 |
| 634 | *Nocardia brevicatena* strain DSM 43024 | NR_041862.1 |
| 635 | *Nocardia caishijiensis* strain F829 | NR_025216.1 |
| 636 | *Nocardia carnea* strain DSM 43397 | NR_041859.1 |
| 637 | *Nocardia cerradoensis* strain Y9 | NR_028704.1 |
| 638 | *Nocardia concava* strain IFM 0354 | NR_040996.1 |
| 639 | *Nocardia coubleae* strain OFN N11 | NR_043669.1 |
| 640 | *Nocardia crassostreae* strain JCM 10500 | NR_041868.1 |
| 641 | *Nocardia cummidelens* strain DSM 44490 | NR_041871.1 |
| 642 | *Nocardia cyriacigeorgica* strain GUH-2 | NR_074699.1 |
| 643 | *Nocardia cyriacigeorgica* strain DSM 44484 | NR_041857.1 |
| 644 | *Nocardia elegans* strain: IMMIB N-402 | NR_042353.1 |
| 645 | *Nocardia exalbida* strain IFM 0803 | NR_041237.1 |
| 646 | *Nocardia farcinica* IFM 10152 strain IFM 10152 | NR_074702.1 |
| 647 | *Nocardia farcinica* strain Goodfellow N898 | NR_036996.1 |
| 648 | *Nocardia flavorosea* strain 10.268-1 | NR_026525.1 |
| 649 | *Nocardia fluminea* strain S1 | NR_028791.1 |
| 650 | *Nocardia gamkensis* strain CZH20 | NR_043667.1 |
| 651 | *Nocardia harenae* strain WS-26 | NR_043686.1 |
| 652 | *Nocardia higoensis* strain IFM 10084 | NR_028651.1 |
| 653 | *Nocardia ignorata* strain IMMIB R-1434 | NR_028006.1 |
| 654 | *Nocardia inohanensis* strain IFM 0092 | NR_037051.1 |
| 655 | *Nocardia jejuensis* strain N3-2 | NR_043305.1 |
| 656 | *Nocardia jiangxiensis* strain 43401 | NR_043060.1 |
| 657 | *Nocardia jinanensis* strain 04-5195 | NR_043870.1 |
| 658 | *Nocardia kruczakiae* strain MB2876; ATCC BAA-948 | NR_042902.1 |
| 659 | *Nocardia lijiangensis* strain YIM 33378 | NR_043185.1 |
| 660 | *Nocardia miyunensis* strain 117 | NR_043059.1 |
| 661 | *Nocardia neocaledoniensis* strain SBHR OA6 | NR_029094.1 |
| 662 | *Nocardia niigatensis* strain DSM 44670 | NR_043916.1 |
| 663 | *Nocardia ninae* strain OFN 02.72 | NR_043668.1 |
| 664 | *Nocardia nova* strain JCM 6044 | NR_041858.1 |
| 665 | *Nocardia otitidiscaviarum* strain DSM 43242 | NR_041874.1 |
| 666 | *Nocardia paucivorans* strain DSM 44386 | NR_041863.1 |
| 667 | *Nocardia pneumoniae* strain IFM 0784 | NR_028653.1 |
| 668 | *Nocardia pseudobrasiliensis* strain DSM 44290 | NR_041864.1 |
| 669 | *Nocardia pseudovaccinii* strain DSM 43406 | NR_025199.1 |
| 670 | *Nocardia puris* strain IMMIB R-145 | NR_028994.1 |
| 671 | *Nocardia salmonicida* strain DSM 40472 | NR_041869.1 |
| 672 | *Nocardia seriolae* strain DSM 44129 | NR_041861.1 |
| 673 | *Nocardia shimofusensis* strain YZ-96 | NR_028650.1 |
| 674 | *Nocardia sienata* strain IFM 10088 | NR_024825.1 |
| 675 | *Nocardia soli* strain DSM 44488 | NR_041870.1 |
| 676 | *Nocardia speluncae* strain: N2-11 | NR_042591.1 |
| 677 | *Nocardia takedensis* strain MS1-3 | NR_024832.1 |
| 678 | *Nocardia tenerifensis* | NR_042176.1 |
| 679 | *Nocardia terpenica* strain IFM 0706 | NR_041289.1 |
| 680 | *Nocardia testacea* strain JCM 12235 | NR_041251.1 |
| 681 | *Nocardia thailandica* strain IFM 10145 | NR_040994.1 |
| 682 | *Nocardia transvalensis* strain DSM 43405 | NR_041867.1 |
| 683 | *Nocardia uniformis* strain DSM 43136 | NR_041865.1 |
| 684 | *Nocardia vaccinii* strain DSM 43285 | NR_041866.1 |
| 685 | *Nocardia vermiculata* strain IFM 0391 | NR_040993.1 |
| 686 | *Nocardia veterana* strain M157222 | NR_037097.1 |
| 687 | *Nocardia vinacea* strain MK703-102F1 | NR_024722.1 |
| 688 | *Nocardia wallacei* strain ATCC 49873 | NR_044401.1 |
| 689 | *Nocardia xishanensis* strain AS 4.1860 | NR_025759.1 |
| 690 | *Nocardia yamanashiensis* strain IFM 0265 | NR_024803.1 |
| 691 | *Pasteurella multocida* subsp. *gallicida* strain CCUG 17978 | NR_041811.1 |
| 692 | *Pasteurella multocida* subsp. *multocida* strain CCUG 17976 | NR_041809.1 |
| 693 | *Peptostreptococcus anaerobius* strain NCTC 11460 | NR_042847.1 |
| 694 | *Peptostreptococcus stomatis* strain W2278 | NR_043589.1 |
| 695 | *Plesiomonas shigelloides* strain: NCIMB9242 | NR_044827.1 |
| 696 | *Porphyromonas asaccharolytica* | NR_044635.1 |
| 697 | *Porphyromonas asaccharolytica* strain DSM 20707 | NR_074588.1 |
| 698 | *Porphyromonas bennonis* strain WAL 1926C | NR_044491.1 |
| 699 | *Porphyromonas cangingivalis* strain VPB 4874 | NR_026136.1 |
| 700 | *Porphyromonas cansulci* strain VPB 4875 | NR_026137.1 |
| 701 | *Porphyromonas catoniae* strain ATCC 51270 | NR_026230.1 |
| 702 | *Porphyromonas circumdentaria* | NR_044639.1 |
| 703 | *Porphyromonas endodontalis* strain ATCC 35406 | NR_042803.1 |
| 704 | *Porphyromonas gingivalis* strain ATCC 33277 | NR_074234.1 |
| 705 | *Porphyromonas gingivalis* strain ATCC33277 | NR_040838.1 |
| 706 | *Porphyromonas gingivalis* W83 strain W83 | NR_074230.1 |
| 707 | *Porphyromonas gulae* strain Loup-1 | NR_025052.1 |

TABLE 2-continued

| Bacterial ID No. | Species | 16S rRNA Genbank Acc. No. |
|---|---|---|
| 708 | *Porphyromonas levii* strain ATCC 29147 | NR_025907.1 |
| 709 | *Porphyromonas somerae* strain WAL 6690 | NR_043312.1 |
| 710 | *Porphyromonas uenonis* strain WAL 9902; ATCC BAA-906; CCUG 48615 | NR_042986.1 |
| 711 | *Prevotella albensis* strain M384 | NR_025300.1 |
| 712 | *Prevotella amnii* strain: CCUG 53648 | NR_042587.1 |
| 713 | *Prevotella baroniae* | NR_043224.1 |
| 714 | *Prevotella bergensis* strain 94067913 | NR_042857.1 |
| 715 | *Prevotella bivia* | NR_044629.1 |
| 716 | *Prevotella brevis* strain GA33 | NR_041954.1 |
| 717 | *Prevotella bryantii* B14 | NR_028866.1 |
| 718 | *Prevotella buccae* | NR_044631.1 |
| 719 | *Prevotella buccalis* | NR_044630.1 |
| 720 | *Prevotella copri* strain CB7 | NR_040877.1 |
| 721 | *Prevotella corporis* | NR_044627.1 |
| 722 | *Prevotella dentalis* strain ES2772 | NR_029284.1 |
| 723 | *Prevotella denticola* strain ATCC 35308 | NR_042842.1 |
| 724 | *Prevotella disiens* strain EUH N 1304-72B | NR_029149.1 |
| 725 | *Prevotella enoeca* strain ATCC 51261 | NR_025281.1 |
| 726 | *Prevotella falsenii* strain 04052 (= JCM 15124) | NR_041684.1 |
| 727 | *Prevotella histicola* strain T05-04 | NR_044407.1 |
| 728 | *Prevotella intermedia* strain B422 | NR_026119.1 |
| 729 | *Prevotella loescheii* strain NCTC 11321 | NR_043216.1 |
| 730 | *Prevotella maculosa* strain W1609 | NR_044270.1 |
| 731 | *Prevotella marshii* strain E9.34 | NR_041907.1 |
| 732 | *Prevotella melaninogenica* strain ATCC 25845 | NR_042843.1 |
| 733 | *Prevotella micans* strain E7.56 | NR_041908.1 |
| 734 | *Prevotella multiformis* strain PPPA21 | NR_041056.1 |
| 735 | *Prevotella multisaccharivorax* strain JCM 12954 | NR_041285.1 |
| 736 | *Prevotella nanceiensis* strain AIP 261.03 | NR_043292.1 |
| 737 | *Prevotella nigrescens* strain NCTC 9336 | NR_044850.1 |
| 738 | *Prevotella oralis* strain ATCC 33269 | NR_042841.1 |
| 739 | *Prevotella oris* | NR_044628.1 |
| 740 | *Prevotella oulorum* strain WPH 179 | NR_029147.1 |
| 741 | *Prevotella pollens* strain 10371 | NR_026417.1 |
| 742 | *Prevotella paludivivens* strain KB7 | NR_040924.1 |
| 743 | *Prevotella pleuritidis* strain JCM 14110 | NR_041541.1 |
| 744 | *Prevotella ruminicola* | NR_044632.1 |
| 745 | *Prevotella salivae* strain EPSA11 | NR_024816.1 |
| 746 | *Prevotella shahii* strain EHS11 | NR_024815.1 |
| 747 | *Prevotella stercorea* strain CB35 | NR_041364.1 |
| 748 | *Prevotella tannerae* strain VPI N14B-15 | NR_037088.1 |
| 749 | *Prevotella timonensis* strain 4401737 | NR_043894.1 |
| 750 | *Prevotella veroralis* strain ATCC 33779 | NR_029148.1 |
| 751 | *Propionibacterium acidipropionici* strain NCFB 570 | NR_042268.1 |
| 752 | *Propionibacterium acnes* | NR_040847.1 |
| 753 | *Propionibacterium acnes* KPA171202 strain KPA171202 | NR_074675.1 |
| 754 | *Propionibacterium australiense* strain LCDC-98A072 | NR_025076.1 |
| 755 | *Propionibacterium avidum* strain DSM 4901 | NR_025274.1 |
| 756 | *Propionibacterium cyclohexanicum* strain TA-12 | NR_036827.1 |
| 757 | *Propionibacterium freudenreichii* strain DSM 20271 | NR_044816.1 |
| 758 | *Propionibacterium freudenreichil* subsp. *shermanii* strain E11 | NR_036972.1 |
| 759 | *Propionibacterium granulosum* strain DSM 20700 | NR_025276.1 |
| 760 | *Propionibacterium jensenii* strain: DSM 20535 | NR_042269.1 |
| 761 | *Propionibacterium microaerophilum* strain M 5 | NR_028778.1 |
| 762 | *Propionibacterium propionicum* strain DSM 43307 | NR_025277.1 |
| 763 | *Propionibacterium thoenii* strain: NCFB 568 | NR_042270.1 |
| 764 | *Proteus mirabilis* HI4320 strain HI4320 | NR_074898.1 |
| 765 | *Proteus mirabilis* strain NCTC 11938 | NR_043997.1 |
| 766 | *Proteus vulgaris* strain DSM 30118 | NR_025336.1 |
| 767 | *Providencia alcalifaciens* strain CIP8290T (ATCC9886T) | NR_042053.1 |
| 768 | *Providencia heimbachae* strain: DSM 3591 | NR_042412.1 |
| 769 | *Providencia rettgeri* strain: DSM 4542 | NR_042413.1 |
| 770 | *Providencia rustigianii* strain: DSM 4541 | NR_042411.1 |
| 771 | *Providencia stuartii* strain ATCC 29914 | NR_024848.1 |
| 772 | *Providencia vermicola* strain: OP1 | NR_042415.1 |
| 773 | *Pseudomonas aeruginosa* PAO1 strain PAO1 | NR_074828.1 |
| 774 | *Pseudomonas aeruginosa* strain DSM 50071 | NR_026078.1 |
| 775 | *Rhodococcus aetherivorans* strain 10bc312 | NR_025208.1 |
| 776 | *Rhodococcus baikonurensis* strain A1-22 | NR_024784.1 |
| 777 | *Rhodococcus coprophilus* strain CUB 687 | NR_029206.1 |
| 778 | *Rhodococcus corynebacterioides* strain DSM 20151 | NR_041873.1 |
| 779 | *Rhodococcus equi* strain DSM 20307 | NR_041910.1 |
| 780 | *Rhodococcus erythropolis* PR4 strain PR4 (=NBRC 100887) | NR_074622.1 |
| 781 | *Rhodococcus erythropolis* strain N11 | NR_037024.1 |
| 782 | *Rhodococcus fascians* strain CF17 | NR_037021.1 |
| 783 | *Rhodococcus globerulus* strain DSM 4954 | NR_026184.1 |

TABLE 2-continued

| Bacterial ID No. | Species | 16S rRNA Genbank Acc. No. |
|---|---|---|
| 784 | *Rhodococcus gordoniae* strain W4937 | NR_025730.1 |
| 785 | *Rhodococcus intechensis* strain RKJ300 | NR_042946.1 |
| 786 | *Rhodococcus jostii* RHA1 strain RHA1 | NR_074610.1 |
| 787 | *Rhodococcus jostii* strain IFO 16295 | NR_024765.1 |
| 788 | *Rhodococcus koreensis* strain DNP505 | NR_024973.1 |
| 789 | *Rhodococcus kroppenstedtii* strain K07-23 | NR_043144.1 |
| 790 | *Rhodococcus kunmingensis* strain YIM 45607 | NR_044034.1 |
| 791 | *Rhodococcus kyotonensis* strain DS472 | NR_041512.1 |
| 792 | *Rhodococcus maanshanensis* strain M712 | NR_025190.1 |
| 793 | *Rhodococcus marinonascens* strain DSM 43752 | NR_026183.1 |
| 794 | *Rhodococcus opacus* B4 strain B4 | NR_074632.1 |
| 795 | *Rhodococcus opacus* strain DSM 43205 | NR_026186.1 |
| 796 | *Rhodococcus percolatus* strain MBS1 | NR_044878.1 |
| 797 | *Rhodococcus phenolicus* strain G2P | NR_042950.1 |
| 798 | *Rhodococcus pyridinivorans* strain PDB9 | NR_025033.1 |
| 799 | *Rhodococcus qingshengii* strain djl-6 | NR_043535.1 |
| 800 | *Rhodococcus rhodnii* strain B/O | NR_037029.1 |
| 801 | *Rhodococcus rhodochrous* strain 372 | NR_037023.1 |
| 802 | *Rhodococcus ruber* strain: DSM43338 | NR_026185.1 |
| 803 | *Rhodococcus triatomae* strain: IMMIB RIV-085 | NR_042352.1 |
| 804 | *Rhodococcus tukisamuensis* strain Mb8 | NR_028629.1 |
| 805 | *Rhodococcus wratislaviensis* strain NCIMB 13082 | NR_026524.1 |
| 806 | *Rhodococcus yunnanensis* strain YIM 70056 | NR_043009.1 |
| 807 | *Rhodococcus zopfii* strain DSM 44108 | NR_041775.1 |
| 808 | *Salmonella bongori* strain NCTC 12419 | NR_074888.1 |
| 809 | *Salmonella bongori* strain BR 1859 | NR_041699.1 |
| 810 | *Salmonella enterica* subsp. *arizonae* strain ATCC 13314 | NR_041696.1 |
| 811 | *Salmonella enterica* subsp. *diarizonae* strain DSM 14847 | NR_044373.1 |
| 812 | *Salmonella enterica* subsp. *enterica* serovar Choleraesuis str. SC-B67 strain SC-B67 | NR_074800.1 |
| 813 | *Salmonella enterica* subsp. *enterica* serovar Enteritidis str. P125109 strain P125109 | NR_074985.1 |
| 814 | *Salmonella enterica* subsp. *enterica* serovar Paratyphi A str. AKU_12601 strain AKU12601 | NR_074935.1 |
| 815 | *Salmonella enterica* subsp. *enterica* serovar Paratyphi A str. ATCC 9150 strain ATCC 9150 | NR_074934.1 |
| 816 | *Salmonella enterica* subsp. *enterica* serovar Paratyphi C strain RKS4594 strain RKS4594 | NR_074899.1 |
| 817 | *Salmonella enterica* subsp. *enterica* serovar Typhi str. Ty2 strain Ty2 | NR_074799.1 |
| 818 | *Salmonella enterica* subsp. *enterica* serovar Typhimurium str. LT2 strain LT2; SGSC 1412; ATCC 700720 | NR_074910.1 |
| 819 | *Salmonella enterica* subsp. *houtenae* strain DSM 9221 | NR_044371.1 |
| 820 | *Salmonella enterica* subsp. *indica* strain DSM 14848 | NR_044370.1 |
| 821 | *Salmonella enterica* subsp. *salamae* strain DSM 9220 | NR_044372.1 |
| 822 | *Serratia liquefaciens* strain CIP 103238 | NR_042062.1 |
| 823 | *Serratia marcescens* subsp. *marcescens* ATCC 13880 strain DSM 30121 | NR_041980.1 |
| 824 | *Serratia marcescens* subsp. *sakuensis* strain KRED | NR_036886.1 |
| 825 | *Shigella boydii* Sb227 strain Sb227 | NR_074893.1 |
| 826 | *Shigella dysenteriae* Sd197 strain Sd197 | NR_074892.1 |
| 827 | *Shigella dysenteriae* strain ATCC 13313 | NR_026332.1 |
| 828 | *Shigella flexneri* 2a str. 301 strain 301 | NR_074882.1 |
| 829 | *Shigella flexneri* strain ATCC 29903 | NR_026331.1 |
| 830 | *Shigella sonnei* Ss046 strain Ss046 | NR_074894.1 |
| 831 | *Staphylococcus aureus* subsp. *anaerobius* strain MVF-7 | NR_036828.1 |
| 832 | *Staphylococcus aureus* subsp. *aureus* JH1 strain JH1 | NR_074925.1 |
| 833 | *Staphylococcus aureus* subsp. *aureus* N315 strain N315 | NR_075000.1 |
| 834 | *Staphylococcus aureus* subsp. *aureus* strain S33 R | NR_037007.1 |
| 835 | *Staphylococcus epidermidis* RP62A strain RP62A | NR_074995.1 |
| 836 | *Staphylococcus epidermidis* strain Fussel | NR_036904.1 |
| 837 | *Staphylococcus saprophyticus* subsp. *bovis* strain GTC 843 | NR_041324.1 |
| 838 | *Staphylococcus saprophyticus* subsp. *saprophyticus* ATCC 15305 strain ATCC 15305 | NR_074999.1 |
| 839 | *Streptococcus agalactiae* strain JCM 5671 | NR_040821.1 |
| 840 | *Streptococcus alactolyticus* strain ATCC 43077; DSM 20728 | NR_041781.1 |
| 841 | *Streptococcus anginosus* strain ATCC33397 | NR_041722.1 |
| 842 | *Streptococcus australis* strain AI-1 | NR_036936.1 |
| 843 | *Streptococcus bovis* strain ATCC 33317, NCDO 597 | AB002482.1 |
| 844 | *Streptococcus caballi* strain 151 | NR_044190.1 |
| 845 | *Streptococcus canis* strain STR T1 | NR_024633.1 |
| 846 | *Streptococcus castoreus* strain: M605815/03/2 | NR_042215.1 |
| 847 | *Streptococcus constellatus* strain ATCC27823 | NR_041721.1 |
| 848 | *Streptococcus constellatus* subsp. *pharyngis* strain MM9889a | NR_042833.1 |
| 849 | *Streptococcus criceti* strain ATCC19642 | NR_042119.1 |
| 850 | *Streptococcus cristatus* strain ATCC 51100 | NR_042771.1 |
| 851 | *Streptococcus dentirousetti* strain NUM 1303 | NR_041460.1 |
| 852 | *Streptococcus devriesei* strain CCUG 47156 | NR_029015.1 |
| 853 | *Streptococcus didelphis* strain W94-11374-1 | NR_025036.1 |

TABLE 2-continued

| Bacterial ID No. | Species | 16S rRNA Genbank Acc. No. |
|---|---|---|
| 854 | Streptococcus downei strain ATCC 33748 | NR_042774.1 |
| 855 | Streptococcus dysgalactiae subsp. dysgalactiae strain ATCC 43078 | NR_027517.1 |
| 856 | Streptococcus dysgalactiae subsp. equisimilis strain CIP 105120 | NR_043661.1 |
| 857 | Streptococcus entericus strain CECT 5353 | NR_025500.1 |
| 858 | Streptococcus equi subsp. equi strain ATCC 33398 | NR_043703.1 |
| 859 | Streptococcus equi subsp. ruminatorum strain CECT 5772 | NR_025609.1 |
| 860 | Streptococcus equi subsp. zooepidemicus strain ATCC 43079 | NR_036758.1 |
| 861 | Streptococcus equinus strain ATCC 9812 | NR_042052.1 |
| 862 | Streptococcus ferus strain 8S1 | NR_036845.1 |
| 863 | Streptococcus gallinaceus strain CCUG 42692 | NR_025453.1 |
| 864 | Streptococcus gallolyticus subsp. gallolyticus strain ACM 3611 | NR_044904.1 |
| 865 | Streptococcus gallolyticus UCN34 strain UCN34 | NR_074849.1 |
| 866 | Streptococcus gordonii str. Challis substr. CH1 strain Challis | NR_074516.1 |
| 867 | Streptococcus gordonii strain SK3 | NR_028666.1 |
| 868 | Streptococcus halichoeri strain M512/02/1 | NR_029025.1 |
| 869 | Streptococcus henryi strain 126 | NR_044189.1 |
| 870 | Streptococcus hyointestinalis strain ATCC 49169; DSM 20770 | NR_041780.1 |
| 871 | Streptococcus infantarius strain HDP90104; SLB | NR_028761.1 |
| 872 | Streptococcus infantis strain ATCC 700779 | NR_042928.1 |
| 873 | Streptococcus iniae strain ATCC 29178 | NR_025148.1 |
| 874 | Streptococcus intermedius strain 1877 | NR_028736.1 |
| 875 | Streptococcus luteciae strain NEM 782 | NR_042051.1 |
| 876 | Streptococcus lutetiensis strain HDP90246 | NR_037096.1 |
| 877 | Streptococcus macacae strain ATCC 35911 | NR_042775.1 |
| 878 | Streptococcus macedonicus strain ACA-DC 198 | NR_074404.1 |
| 879 | Streptococcus macedonicus strain LAB617 | NR_037002.1 |
| 880 | Streptococcus marimammalium strain M54/01/1 | NR_025630.1 |
| 881 | Streptococcus massiliensis strain 4401825 | NR_043173.1 |
| 882 | Streptococcus merionis strain: WUE3771 = DSM 19192 | NR_042553.1 |
| 883 | Streptococcus minor strain ON59 | NR_025729.1 |
| 884 | Streptococcus mitis strain NS51 | NR_028664.1 |
| 885 | Streptococcus mutans strain ATCC 25175 | NR_042772.1 |
| 886 | Streptococcus mutans UA159 strain UA159 | NR_074983.1 |
| 887 | Streptococcus oligofermentans strain 2-4 | NR_029052.1 |
| 888 | Streptococcus oralis strain ATCC 35037 | NR_042927.1 |
| 889 | Streptococcus orisratti strain ATCC 700640 | NR_024974.1 |
| 890 | Streptococcus orisuis strain NUM 1001 | NR_041055.1 |
| 891 | Streptococcus ovis strain S369-98-1 | NR_026471.1 |
| 892 | Streptococcus parasanguinis strain ATCC 15912 | NR_024842.1 |
| 893 | Streptococcus parauberis strain DSM 6631 | NR_043001.1 |
| 894 | Streptococcus pasteurianus strain CIP 107122 | NR_043660.1 |
| 895 | Streptococcus peroris strain GTC848 | NR_024659.1 |
| 896 | Streptococcus phocae strain CCUG 35103 | NR_042227.1 |
| 897 | Streptococcus plurextorum strain: 1956-02 | NR_042649.1 |
| 898 | Streptococcus pneumoniae R6 strain R6 | NR_074564.1 |
| 899 | Streptococcus pneumoniae strain ATCC 33400 | NR_028665.1 |
| 900 | Streptococcus porcinus strain 176 | NR_024634.1 |
| 901 | Streptococcus pseudopneumoniae strain IS7493 | NR_074987.1 |
| 902 | Streptococcus pseudopneumoniae strain 108 | NR_027214.1 |
| 903 | Streptococcus pseudoporcinus strain LQ 940-04 | NR_043704.1 |
| 904 | Streptococcus pyogenes strain SF370 | NR_074091.1 |
| 905 | Streptococcus pyogenes strain I-273 | NR_028598.1 |
| 906 | Streptococcus ratti strain ATCC 19645 | NR_025516.1 |
| 907 | Streptococcus salivarius strain ATCC 7073 | NR_042776.1 |
| 908 | Streptococcus sanguinis SK36 strain SK36 | NR_074974.1 |
| 909 | Streptococcus sanguinis strain ATCC 10556 | NR_024841.1 |
| 910 | Streptococcus sinensis strain HKU4 | NR_028833.1 |
| 911 | Streptococcus sobrinus strain ATCC 33478 | NR_042773.1 |
| 912 | Streptococcus sp. strain SHV515 | NR_044912.1 |
| 913 | Streptococcus suis strain BM407 | NR_074918.1 |
| 914 | Streptococcus suis strain S735 | NR_036918.1 |
| 915 | Streptococcus thermophilus strain MN-ZLW-002 | NR_074827.1 |
| 916 | Streptococcus thermophilus strain ATCC 19258 | NR_042778.1 |
| 917 | Streptococcus thoraltensis strain S69 | NR_026368.1 |
| 918 | Streptococcus uberis strain 0140J | NR_074912.1 |
| 919 | Streptococcus uberis strain JCM 5709 | NR_040820.1 |
| 920 | Streptococcus urinalis strain 2285-97 | NR_037101.1 |
| 921 | Streptococcus vestibularis strain ATCC 49124 | NR_042777.1 |
| 922 | Streptococcus viridans | AF076036.1 |
| 923 | Streptomyces aburaviensis strain AS 4.1869 | NR_043375.1 |
| 924 | Streptomyces achromogenes subsp. rubradiris strain KCTC 9742 | NR_043365.1 |
| 925 | Streptomyces acidiscabies strain RL-110 | NR_025866.1 |
| 926 | Streptomyces aculeolatus strain NBRC 14824 | NR_041166.1 |
| 927 | Streptomyces africanus strain CPJVR-H | NR_025722.1 |
| 928 | Streptomyces alanosinicus strain NBRC 13493 | NR_041148.1 |
| 929 | Streptomyces albaduncus strain JCM 4715 | NR_043343.1 |
| 930 | Streptomyces albiaxialis strain NRRL B-24327 | NR_043378.1 |

TABLE 2-continued

| Bacterial ID No. | Species | 16S rRNA Genbank Acc. No. |
|---|---|---|
| 931 | *Streptomyces albidochromogenes* strain NBRC 101003 | NR_041422.1 |
| 932 | *Streptomyces albidoflavus* strain NBRC 13010 | NR_041095.1 |
| 933 | *Streptomyces albiflaviniger* strain: NRRL B-1356 | NR_042094.1 |
| 934 | *Streptomyces albofaciens* strain JCM 4342 | NR_024760.1 |
| 935 | *Streptomyces alboflavus* strain NRRL B-2373 | NR_044151.1 |
| 936 | *Streptomyces albolongus* strain NBRC 13465 | NR_041144.1 |
| 937 | *Streptomyces alboniger* strain DSM 40043; ATCC 12461; KCTC 9014 | NR_043228.1 |
| 938 | *Streptomyces albospinus* strain JCM 3399 | NR_043342.1 |
| 939 | *Streptomyces albosporeus* subsp. *labilomyceticus* strain NBRC 15387 | NR_041170.1 |
| 940 | *Streptomyces albovinaceus* strain NBRC 12739 | NR_041425.1 |
| 941 | *Streptomyces albulus* strain IMC S-0802 | NR_024723.1 |
| 942 | *Streptomyces albus* subsp. *albus* strain DSM 40313 | NR_025615.1 |
| 943 | *Streptomyces albus* subsp. *albus* strain NBRC 3418 | NR_041208.1 |
| 944 | *Streptomyces albus* subsp. *pathocidicus* strain NBRC 13812 | NR_041152.1 |
| 945 | *Streptomyces alni* strain D65 | NR_043866.1 |
| 946 | *Streptomyces althioticus* strain KCTC 9752 | NR_043359.1 |
| 947 | *Streptomyces amakusaensis* strain NRRL B-3351 | NR_043349.1 |
| 948 | *Streptomyces ambofaciens* strain NBRC 12836 | NR_041079.1 |
| 949 | *Streptomyces anandii* strain NBRC 13438 | NR_041135.1 |
| 950 | *Streptomyces anthocyanicus* strain NBRC 14892 | NR_041168.1 |
| 951 | *Streptomyces antibioticus* strain NRRL B-1701 | NR_043348.1 |
| 952 | *Streptomyces antimycoticus* strain NBRC 12839 | NR_041080.1 |
| 953 | *Streptomyces anulatus* strain NBRC 12755 | NR_041062.1 |
| 954 | *Streptomyces anulatus* strain NRRL B-2000 | NR_043489.1 |
| 955 | *Streptomyces ardus* strain NBRC 13430 | NR_041227.1 |
| 956 | *Streptomyces arenae* strain ISP 5293 | NR_025494.1 |
| 957 | *Streptomyces armeniacus* strain 26A-32 | NR_036815.1 |
| 958 | *Streptomyces asiaticus* strain NBRC 100774 | NR_041418.1 |
| 959 | *Streptomyces asterosporus* strain NBRC 15872 | NR_041193.1 |
| 960 | *Streptomyces atratus* strain NRRL B-16927 | NR_043490.1 |
| 961 | *Streptomyces atroaurantiacus* strain NRRL B-24282 | NR_043493.1 |
| 962 | *Streptomyces atroolivaceus* strain: LMG 19306 | NR_042289.1 |
| 963 | *Streptomyces atrovirens* strain NRRL B-16357 | NR_043508.1 |
| 964 | *Streptomyces aurantiacus* strain: LMG 19358 | NR_042310.1 |
| 965 | *Streptomyces aurantiogriseus* strain NBRC 12842 | NR_041081.1 |
| 966 | *Streptomyces auratus* strain: NRRL 8097 | NR_042098.1 |
| 967 | *Streptomyces aureocirculatus* strain IFO 13018 | NR_043371.1 |
| 968 | *Streptomyces aureofaciens* strain KACC 20180 | NR_042792.1 |
| 969 | *Streptomyces aureorectus* strain NBRC 15896 | NR_041195.1 |
| 970 | *Streptomyces aureoverticillatus* strain NRRL B-3326 | NR_043346.1 |
| 971 | *Streptomyces aureus* strain B7319 | NR_025663.1 |
| 972 | *Streptomyces avellaneus* strain NBRC 13451 | NR_041138.1 |
| 973 | *Streptomyces avermitilis* strain MA-4680 | NR_074747.1 |
| 974 | *Streptomyces avidinii* strain NBRC 13429 | NR_041132.1 |
| 975 | *Streptomyces axinellae* strain Pol001 | NR_044553.1 |
| 976 | *Streptomyces azureus* strain NRRL B-2655 | NR_044136.1 |
| 977 | *Streptomyces bacillaris* strain NBRC 13487 | NR_041146.1 |
| 978 | *Streptomyces badius* strain NRRL B-2567 | NR_043350.1 |
| 979 | *Streptomyces bambergiensis* strain NBRC 13479 | NR_041230.1 |
| 980 | *Streptomyces bangladeshensis* strain AAB-4 | NR_043164.1 |
| 981 | *Streptomyces beijiangensis* strain YIM6 | NR_028825.1 |
| 982 | *Streptomyces bikiniensis* strain DSM 40581 | NR_026177.1 |
| 983 | *Streptomyces bingchenggensis* strain BCW-1 | NR_074824.1 |
| 984 | *Streptomyces blastmyceticus* strain NRRL B-5480 | NR_043357.1 |
| 985 | *Streptomyces bluensis* strain NBRC 13460 | NR_041142.1 |
| 986 | *Streptomyces bobili* strain NBRC 13199 | NR_041121.1 |
| 987 | *Streptomyces bottropensis* strain NBRC 13023 | NR_041096.1 |
| 988 | *Streptomyces brasiliensis* strain NBRC 101283 | NR_041435.1 |
| 989 | *Streptomyces bungoensis* strain NBRC 15711 | NR_041191.1 |
| 990 | *Streptomyces cacaoi* subsp. *asoensis* strain NRRL B-16592 | NR_043492.1 |
| 991 | *Streptomyces cacaoi* subsp. *cacaoi* strain NBRC 12748 | NR_041061.1 |
| 992 | *Streptomyces caelestis* strain NRRL 2418 | NR_026202.1 |
| 993 | *Streptomyces caeruleus* strain NRRL B-2194 | NR_044137.1 |
| 994 | *Streptomyces calvus* strain NBRC 13200 | NR_041122.1 |
| 995 | *Streptomyces canarius* strain NBRC 13431 | NR_041133.1 |
| 996 | *Streptomyces candidus* strain NRRL ISP-5141 | NR_043504.1 |
| 997 | *Streptomyces cangkringensis* strain D13P3 | NR_028957.1 |
| 998 | *Streptomyces caniferus* strain NBRC 15389 | NR_041171.1 |
| 999 | *Streptomyces canus* strain NRRL B-1989 | NR_043347.1 |
| 1000 | *Streptomyces capillispiralis* strain NBRC 14222 | NR_041158.1 |
| 1001 | *Streptomyces capoamus* strain JCM 4734 | NR_040856.1 |
| 1002 | *Streptomyces carpaticus* strain NRRL B-16359 | NR_043814.1 |
| 1003 | *Streptomyces carpinensis* strain NBRC 14214 | NR_041157.1 |
| 1004 | *Streptomyces castelarensis* strain BJ-608 | NR_029114.1 |
| 1005 | *Streptomyces catenulae* strain DSM 40258 | NR_025624.1 |
| 1006 | *Streptomyces cavourensis* subsp. *cavourensis* strain NRRL 2740 | NR_043851.1 |
| 1007 | *Streptomyces cellostaticus* strain ISP 5189 | NR_043339.1 |

TABLE 2-continued

| Bacterial ID No. | Species | 16S rRNA Genbank Acc. No. |
|---|---|---|
| 1008 | *Streptomyces celluloflavus* strain NBRC 13780 | NR_041150.1 |
| 1009 | *Streptomyces cellulosae* strain NRRL B-2889 | NR_043815.1 |
| 1010 | *Streptomyces chartreusis* strain NBRC 12753 | NR_041216.1 |
| 1011 | *Streptomyces cheonanensis* strain VC-A46 | NR_043208.1 |
| 1012 | *Streptomyces chrestomyceticus* strain DSM 40545 | NR_025621.1 |
| 1013 | *Streptomyces chromofuscus* strain NBRC 12851 | NR_041082.1 |
| 1014 | *Streptomyces chryseus* strain NRRL B-12347 | NR_043353.1 |
| 1015 | *Streptomyces chrysomallus* subsp. *fumigatus* strain NBRC 15394 | NR_041172.1 |
| 1016 | *Streptomyces cinereorectus* strain M-5 | NR_037062.1 |
| 1017 | *Streptomyces cinereorectus* strain NBRC 15395 | NR_041173.1 |
| 1018 | *Streptomyces cinereoruber* subsp. *cinereoruber* strain JCM 4205 | NR_043345.1 |
| 1019 | *Streptomyces cinereoruber* subsp. *fructofermentans* strain JCM 4956 | NR_043344.1 |
| 1020 | *Streptomyces cinereospinus* strain NBRC 15397 | NR_041174.1 |
| 1021 | *Streptomyces cinereus* strain NBRC 12247 | NR_041058.1 |
| 1022 | *Streptomyces cinerochromogenes* strain NBRC 13822 | NR_041153.1 |
| 1023 | *Streptomyces cinnabarinus* strain NBRC 13028 | NR_041097.1 |
| 1024 | *Streptomyces cinnamonensis* strain NBRC 15873 | NR_041194.1 |
| 1025 | *Streptomyces cinnamoneus* strain NBRC 12852 | NR_041223.1 |
| 1026 | *Streptomyces cirratus* strain NRRL B-3250 | NR_043356.1 |
| 1027 | *Streptomyces ciscaucasicus* strain NBRC 12872 | NR_041085.1 |
| 1028 | *Streptomyces clavifer* strain NRRL B-2557 | NR_043507.1 |
| 1029 | *Streptomyces clavuligerus* strain NRRL 3585 | NR_043335.1 |
| 1030 | *Streptomyces coelescens* strain AS 4.1594 | NR_027222.1 |
| 1031 | *Streptomyces coelicoflavus* strain NBRC 15399 | NR_041175.1 |
| 1032 | *Streptomyces coeruleofuscus* strain NRRL B-5417 | NR_043506.1 |
| 1033 | *Streptomyces coeruleoprunus* strain NBRC 15400 | NR_041176.1 |
| 1034 | *Streptomyces coeruleorubidus* strain ISP 5145 | NR_043336.1 |
| 1035 | *Streptomyces coeruleorubidus* strain NBRC 12761 | NR_041217.1 |
| 1036 | *Streptomyces coeruleorubidus* strain NBRC 12844 | NR_041222.1 |
| 1037 | *Streptomyces coerulescens* strain ISP 5146 | NR_043337.1 |
| 1038 | *Streptomyces collinus* strain NBRC 12759 | NR_041063.1 |
| 1039 | *Streptomyces colombiensis* strain NRRL B-1990 | NR_043494.1 |
| 1040 | *Streptomyces corchorusii* strain NBRC 13032 | NR_041098.1 |
| 1041 | *Streptomyces costaricanus* strain NBRC 100773 | NR_041414.1 |
| 1042 | *Streptomyces cremeus* strain JCM 4362 | NR_043340.1 |
| 1043 | *Streptomyces crystallinus* strain NBRC 15401 | NR_041177.1 |
| 1044 | *Streptomyces cuspidosporus* strain NBRC 12378 | NR_041059.1 |
| 1045 | *Streptomyces cyaneofuscatus* strain NBRC 13190 | NR_041226.1 |
| 1046 | *Streptomyces cyaneus* strain H-112 | NR_037094.1 |
| 1047 | *Streptomyces cyanoalbus* strain NBRC 12857 | NR_041232.1 |
| 1048 | *Streptomyces daghestanicus* strain NRRL B-5418 | NR_043816.1 |
| 1049 | *Streptomyces deccanensis* | NR_044183.1 |
| 1050 | *Streptomyces demainii* strain NRRL B-1478 | NR_043723.1 |
| 1051 | *Streptomyces diastaticus* subsp. *ardesiacus* strain NRRL B-1773 | NR_043486.1 |
| 1052 | *Streptomyces diastaticus* subsp. *diastaticus* strain NBRC 3714 | NR_041209.1 |
| 1053 | *Streptomyces diastatochromogenes* strain ATCC 12309 | NR_025867.1 |
| 1054 | *Streptomyces djakartensis* strain NBRC 15409 | NR_041178.1 |
| 1055 | *Streptomyces drozdowiczii* strain NBRC 101007 | NR_041424.1 |
| 1056 | *Streptomyces durhamensis* strain NRRL B-3309 | NR_043352.1 |
| 1057 | *Streptomyces durmitorensis* strain MS405 | NR_043520.1 |
| 1058 | *Streptomyces ederensis* strain KCTC 9726 | NR_043362.1 |
| 1059 | *Streptomyces ehimensis* strain KCTC 9727 | NR_043363.1 |
| 1060 | *Streptomyces emeiensis* strain 4776 | NR_043869.1 |
| 1061 | *Streptomyces endus* strain NRRL 2339 | NR_043379.1 |
| 1062 | *Streptomyces enissocaesilis* strain NBRC 100763 | NR_041411.1 |
| 1063 | *Streptomyces erythrogriseus* strain: LMG 19406 | NR_042294.1 |
| 1064 | *Streptomyces eurocidicus* strain NRRL B-1676 | NR_043355.1 |
| 1065 | *Streptomyces europaeiscabiei* strain KACC 20186 | NR_042790.1 |
| 1066 | *Streptomyces eurythermus* strain ATCC 14975 | NR_025869.1 |
| 1067 | *Streptomyces exfoliatus* strain NBRC 13191 | NR_041117.1 |
| 1068 | *Streptomyces exfoliatus* strain NBRC 13475 | NR_041229.1 |
| 1069 | *Streptomyces ferralitis* strain SFOp68 | NR_029087.1 |
| 1070 | *Streptomyces filamentosus* strain NBRC 12767 | NR_041064.1 |
| 1071 | *Streptomyces filipinensis* strain NBRC 12860 | NR_041083.1 |
| 1072 | *Streptomyces fimbriatus* strain DSM 40942 | NR_043364.1 |
| 1073 | *Streptomyces fimicarius* strain ISP 5322 | NR_043351.1 |
| 1074 | *Streptomyces finlayi* strain NRRL B-12114 | NR_043354.1 |
| 1075 | *Streptomyces flaveolus* strain NBRC 3408 | NR_041206.1 |
| 1076 | *Streptomyces flaveus* strain NRRL B-16074 | NR_043491.1 |
| 1077 | *Streptomyces flavidovirens* strain NBRC 13039 | NR_041099.1 |
| 1078 | *Streptomyces flavofungini* strain NBRC 13371 | NR_041125.1 |
| 1079 | *Streptomyces flavogriseus* strain ATCC 33331 | NR_074559.1 |
| 1080 | *Streptomyces flavogriseus* strain CBS 101.34 | NR_028988.1 |
| 1081 | *Streptomyces flavotricini* strain NRRL B-5419 | NR_043380.1 |
| 1082 | *Streptomyces flavovariabilis* strain NRRL B-16367 | NR_044146.1 |
| 1083 | *Streptomyces flavovirens* strain NRRL B-2685 | NR_043487.1 |
| 1084 | *Streptomyces flavoviridis* strain NBRC 12772 | NR_041218.1 |

TABLE 2-continued

| Bacterial ID No. | Species | 16S rRNA Genbank Acc. No. |
|---|---|---|
| 1085 | *Streptomyces flocculus* strain NBRC 13041 | NR_041100.1 |
| 1086 | *Streptomyces fradiae* strain NRRL B-1195 | NR_043485.1 |
| 1087 | *Streptomyces fragilis* strain NRRL 2424 | NR_043381.1 |
| 1088 | *Streptomyces fulvissimus* strain NBRC 3717 | NR_041210.1 |
| 1089 | *Streptomyces fulvorobeus* strain NBRC 15897 | NR_041196.1 |
| 1090 | *Streptomyces fumanus* strain NBRC 13042 | NR_041101.1 |
| 1091 | *Streptomyces fumigatiscleroticus* strain NRRL B-3856 | NR_043817.1 |
| 1092 | *Streptomyces galbus* strain DSM 40089 | NR_026178.1 |
| 1093 | *Streptomyces galilaeus* strain JCM 4757 | NR_040857.1 |
| 1094 | *Streptomyces gancidicus* strain NBRC 15412 | NR_041179.1 |
| 1095 | *Streptomyces gardneri* strain NBRC 3385 | NR_041204.1 |
| 1096 | *Streptomyces gelaticus* strain NRRL B-2928 | NR_043488.1 |
| 1097 | *Streptomyces geldanamycininus* strain NRRL 3602 | NR_043722.1 |
| 1098 | *Streptomyces geysiriensis* strain NRRL B-12102 | NR_043818.1 |
| 1099 | *Streptomyces ghanaensis* strain KCTC 9882 | NR_043366.1 |
| 1100 | *Streptomyces gibsonii* strain NBRC 15415 | NR_041180.1 |
| 1101 | *Streptomyces glaucescens* strain NBRC 12774 | NR_041219.1 |
| 1102 | *Streptomyces glauciniger* strain NBRC 100913 | NR_041428.1 |
| 1103 | *Streptomyces glaucosporus* strain NBRC 15416 | NR_041181.1 |
| 1104 | *Streptomyces glaucus* strain NBRC 15417 | NR_041182.1 |
| 1105 | *Streptomyces globisporus* subsp. *globisporus* strain NRRL B-2872 | NR_044145.1 |
| 1106 | *Streptomyces globosus* strain: LMG 19896 | NR_042295.1 |
| 1107 | *Streptomyces glomeratus* strain NBRC 15898 | NR_041409.1 |
| 1108 | *Streptomyces glomeroaurantiacus* strain NBRC 15418 | NR_041436.1 |
| 1109 | *Streptomyces gobitricini* strain NBRC 15419 | NR_041183.1 |
| 1110 | *Streptomyces goshikiensis* strain NRRL B-5428 | NR_044147.1 |
| 1111 | *Streptomyces gougerotii* strain NBRC 3198 | NR_041201.1 |
| 1112 | *Streptomyces graminearus* strain: LMG 19904 | NR_042296.1 |
| 1113 | *Streptomyces griseiniger* strain: NRRL B-1865 | NR_042099.1 |
| 1114 | *Streptomyces griseoaurantiacus* strain NBRC 15440 | NR_041186.1 |
| 1115 | *Streptomyces griseoflavus* strain: LMG 19344 | NR_042291.1 |
| 1116 | *Streptomyces griseofuscus* strain NBRC 12870 | NR_041084.1 |
| 1117 | *Streptomyces griseoincarnatus* strain: LMG 19316 | NR_042290.1 |
| 1118 | *Streptomyces griseoloalbus* strain NBRC 13046 | NR_041102.1 |
| 1119 | *Streptomyces griseolus* strain NBRC 3415 | NR_041207.1 |
| 1120 | *Streptomyces griseoluteus* strain JCM 4765 | NR_043341.1 |
| 1121 | *Streptomyces griseomycini* strain NBRC 12778 | NR_041065.1 |
| 1122 | *Streptomyces griseoplanus* strain AS 4.1868 | NR_043377.1 |
| 1123 | *Streptomyces griseorubens* strain NBRC 12780 | NR_041066.1 |
| 1124 | *Streptomyces griseoruber* strain NBRC 12873 | NR_041086.1 |
| 1125 | *Streptomyces griseorubiginosus* strain: LMG 19941 | NR_042298.1 |
| 1126 | *Streptomyces griseosporeus* strain NBRC 13458 | NR_041140.1 |
| 1127 | *Streptomyces griseostramineus* strain NBRC 12781 | NR_041067.1 |
| 1128 | *Streptomyces griseoviridis* strain KCTC 9780 | NR_043358.1 |
| 1129 | *Streptomyces griseus* strain KACC 20084 | NR_042791.1 |
| 1130 | *Streptomyces griseus* subsp. *griseus* strain NBRC 13350 | NR_074787.1 |
| 1131 | *Streptomyces guanduensis* strain 701 | NR_043246.1 |
| 1132 | *Streptomyces gulbargensis* strain DAS131 | NR_043714.1 |
| 1133 | *Streptomyces hainanensis* strain: YIM 47672 | NR_042561.1 |
| 1134 | *Streptomyces halstedii* strain NRRL B-1238 | NR_044148.1 |
| 1135 | *Streptomyces hawaiiensis* strain NBRC 12784 | NR_041068.1 |
| 1136 | *Streptomyces hebeiensis* strain YIM 001 | NR_029091.1 |
| 1137 | *Streptomyces heliomycini* strain NBRC 15899 | NR_041197.1 |
| 1138 | *Streptomyces helvaticus* strain NBRC 13382 | NR_041127.1 |
| 1139 | *Streptomyces herbaricolor* strain NBRC 3838 | NR_041212.1 |
| 1140 | *Streptomyces himastatinicus* strain ATCC 53653 | NR_044201.1 |
| 1141 | *Streptomyces hiroshimensis* strain NBRC 3720 | NR_041211.1 |
| 1142 | *Streptomyces hirsutus* strain NRRL B-2713 | NR_043819.1 |
| 1143 | *Streptomyces humidus* strain NRRL B-3172 | NR_043820.1 |
| 1144 | *Streptomyces humiferus* strain DSM 43030 | NR_025250.1 |
| 1145 | *Streptomyces hygroscopicus* strain NRRL 1346 | NR_044200.1 |
| 1146 | *Streptomyces hygroscopicus* strain NRRL B-5491 | NR_044199.1 |
| 1147 | *Streptomyces hygroscopicus* subsp. *angustmyceticus* strain NRRL B-2347 | NR_043821.1 |
| 1148 | *Streptomyces hygroscopicus* subsp. *decoyicus* strain AS 4.1861 | NR_043374.1 |
| 1149 | *Streptomyces hygroscopicus* subsp. *glebosus* strain NBRC 13786 | NR_041151.1 |
| 1150 | *Streptomyces hygroscopicus* subsp. *hygroscopicus* strain NBRC 13472 | NR_041145.1 |
| 1151 | *Streptomyces hygroscopicus* subsp. *jinggangensis* strain 5008 | NR_074563.1 |
| 1152 | *Streptomyces hygroscopicus* subsp. *ossamyceticus* strain NBRC 13983 | NR_041156.1 |
| 1153 | *Streptomyces hypolithicus* strain HSM#10 | NR_044431.1 |
| 1154 | *Streptomyces iakyrus* strain NBRC 13401 | NR_041231.1 |
| 1155 | *Streptomyces indiaensis* strain NBRC 13964 | NR_041155.1 |
| 1156 | *Streptomyces indigoferus* strain NBRC 12878 | NR_041087.1 |
| 1157 | *Streptomyces indonesiensis* strain DSM 41759; A4R2 | NR_043724.1 |
| 1158 | *Streptomyces intermedius* strain NBRC 13049 | NR_041103.1 |
| 1159 | *Streptomyces inusitatus* strain NBRC 13601 | NR_041149.1 |
| 1160 | *Streptomyces ipomoeae* strain NBRC 13050 | NR_041225.1 |

TABLE 2-continued

| Bacterial ID No. | Species | 16S rRNA Genbank Acc. No. |
|---|---|---|
| 1161 | *Streptomyces javensis* strain B22P3 | NR_028958.1 |
| 1162 | *Streptomyces jietaisiensis* strain FXJ46 | NR_042836.1 |
| 1163 | *Streptomyces kanamyceticus* strain NRRL B-2535 | NR_043822.1 |
| 1164 | *Streptomyces kasugaensis* strain M338-M1 | NR_024724.1 |
| 1165 | *Streptomyces katrae* strain NBRC 13447 | NR_041136.1 |
| 1166 | *Streptomyces koyangensis* strain VK-A60 | NR_025662.1 |
| 1167 | *Streptomyces kunmingensis* strain NRRL B-16240 | NR_043823.1 |
| 1168 | *Streptomyces kurssanovii* strain NBRC 13192 | NR_041118.1 |
| 1169 | *Streptomyces labedae* strain NBRC 15864 | NR_041192.1 |
| 1170 | *Streptomyces lanatus* strain NBRC 12787 | NR_041220.1 |
| 1171 | *Streptomyces lateritius* strain: LMG 19372 | NR_042293.1 |
| 1172 | *Streptomyces laurentii* strain: LMG 19959 | NR_042299.1 |
| 1173 | *Streptomyces lavendofoliae* strain: LMG 19935 | NR_042297.1 |
| 1174 | *Streptomyces lavenduligriseus* strain NRRL B-3173 | NR_043824.1 |
| 1175 | *Streptomyces lavendulocolor* strain NRRL B-3367 | NR_043825.1 |
| 1176 | *Streptomyces levis* strain NBRC 15423 | NR_041184.1 |
| 1177 | *Streptomyces libani* subsp. *libani* strain NBRC 13452 | NR_041139.1 |
| 1178 | *Streptomyces libani* subsp. *rufus* strain: LMG 20087 | NR_042301.1 |
| 1179 | *Streptomyces lienomycini* strain: LMG 20091 | NR_042302.1 |
| 1180 | *Streptomyces lilacinus* strain NBRC 3944 | NR_041215.1 |
| 1181 | *Streptomyces lincolnensis* strain NBRC 13054 | NR_041104.1 |
| 1182 | *Streptomyces litmocidini* strain NBRC 12792 | NR_041069.1 |
| 1183 | *Streptomyces lomondensis* strain NBRC 15426 | NR_041185.1 |
| 1184 | *Streptomyces longispororuber* strain NBRC 13488 | NR_041147.1 |
| 1185 | *Streptomyces longisporus* strain ISP 5166 | NR_025492.1 |
| 1186 | *Streptomyces longwoodensis* strain NBRC 14251 | NR_041161.1 |
| 1187 | *Streptomyces lucensis* strain NRRL B-5626 | NR_043827.1 |
| 1188 | *Streptomyces lunalinharesii* strain RCQ1071 | NR_043541.1 |
| 1189 | *Streptomyces luridiscabiei* strain S63 | NR_025155.1 |
| 1190 | *Streptomyces luridus* strain NRRL B-5409 | NR_043828.1 |
| 1191 | *Streptomyces lusitanus* strain NBRC 13464 | NR_041143.1 |
| 1192 | *Streptomyces luteireticuli* strain NBRC 13422 | NR_041431.1 |
| 1193 | *Streptomyces luteogriseus* strain NBRC 13402 | NR_041128.1 |
| 1194 | *Streptomyces luteosporeus* strain NRRL 2401 | NR_043829.1 |
| 1195 | *Streptomyces lydicus* strain ATCC 25470 | NR_026444.1 |
| 1196 | *Streptomyces macrosporus* strain A1201 | NR_026530.1 |
| 1197 | *Streptomyces malachitofuscus* strain NBRC 13059 | NR_041105.1 |
| 1198 | *Streptomyces malachitospinus* strain NBRC 101004 | NR_041423.1 |
| 1199 | *Streptomyces malaysiensis* strain NBRC 16446 | NR_041410.1 |
| 1200 | *Streptomyces mashuensis* strain DSM40221 | NR_026174.1 |
| 1201 | *Streptomyces massasporeus* strain NBRC 12796 | NR_041070.1 |
| 1202 | *Streptomyces matensis* strain NBRC 12889 | NR_041088.1 |
| 1203 | *Streptomyces mauvecolor* strain NBRC 13854 | NR_041154.1 |
| 1204 | *Streptomyces mayteni* strain YIM 60475 | NR_044434.1 |
| 1205 | *Streptomyces megasporus* strain NBRC 14749 | NR_041165.1 |
| 1206 | *Streptomyces melanogenes* strain NBRC 12890 | NR_041089.1 |
| 1207 | *Streptomyces melanosporofaciens* strain NRRL B-12234 | NR_028917.1 |
| 1208 | *Streptomyces mexicanus* strain NBRC 100915 | NR_041429.1 |
| 1209 | *Streptomyces michiganensis* strain NBRC 12797 | NR_041071.1 |
| 1210 | *Streptomyces microflavus* strain NRRL B-2156 | NR_043854.1 |
| 1211 | *Streptomyces minutiscleroticus* strain NRRL B-12202 | NR_044149.1 |
| 1212 | *Streptomyces mirabilis* strain NBRC 13450 | NR_041137.1 |
| 1213 | *Streptomyces misakiensis* strain IFO 12891 | NR_041308.1 |
| 1214 | *Streptomyces misionensis* strain NRRL B-3230 | NR_044138.1 |
| 1215 | *Streptomyces mobaraensis* strain NRRL B-3729 | NR_043830.1 |
| 1216 | *Streptomyces monomycini* strain NRRL B-24309 | NR_043850.1 |
| 1217 | *Streptomyces morookaensis* strain: LMG 20074 | NR_042300.1 |
| 1218 | *Streptomyces murinus* strain NBRC 12799 | NR_041072.1 |
| 1219 | *Streptomyces mutabilis* strain NRRL ISP-5169 | NR_044139.1 |
| 1220 | *Streptomyces mutomycini* strain NBRC 100999 | NR_041421.1 |
| 1221 | *Streptomyces naganishii* strain NRRL B-1816 | NR_043831.1 |
| 1222 | *Streptomyces nanshensis* strain SCSIO 01066 | NR_044534.1 |
| 1223 | *Streptomyces narbonensis* strain NRRL B-1680 | NR_043853.1 |
| 1224 | *Streptomyces nashvillensis* strain NBRC 13064 | NR_041106.1 |
| 1225 | *Streptomyces neyagawaensis* strain ATCC 27449 | NR_025868.1 |
| 1226 | *Streptomyces niger* strain DSM 43049 | NR_025619.1 |
| 1227 | *Streptomyces nigrescens* strain NRRL B-12176 | NR_043832.1 |
| 1228 | *Streptomyces nitrosporeus* strain NRRL B-1316 | NR_044140.1 |
| 1229 | *Streptomyces niveiscabiei* strain S78 | NR_037095.1 |
| 1230 | *Streptomyces niveoruber* strain NRRL B-2724 | NR_043855.1 |
| 1231 | *Streptomyces noboritoensis* strain NBRC 13065 | NR_041107.1 |
| 1232 | *Streptomyces nodosus* strain ATCC14899 | NR_041730.1 |
| 1233 | *Streptomyces nogalater* strain TT2-9 | NR_041316.1 |
| 1234 | *Streptomyces nojiriensis* strain: LMG 20094 | NR_042303.1 |
| 1235 | *Streptomyces noursei* strain NBRC 15452 | NR_041187.1 |
| 1236 | *Streptomyces novaecaesareae* strain NBRC 13368 | NR_041124.1 |
| 1237 | *Streptomyces ochraceiscleroticus* strain NBRC 12394 | NR_041060.1 |

TABLE 2-continued

| Bacterial ID No. | Species | 16S rRNA Genbank Acc. No. |
|---|---|---|
| 1238 | *Streptomyces odorifer* strain DSM 40347 | NR_026535.1 |
| 1239 | *Streptomyces olivaceiscleroticus* strain DSM 40595 | NR_025618.1 |
| 1240 | *Streptomyces olivaceoviridis* strain NBRC 13066 | NR_041108.1 |
| 1241 | *Streptomyces olivaceus* strain NBRC 3200 | NR_041202.1 |
| 1242 | *Streptomyces olivochromogenes* strain DSM 40451 | NR_025664.1 |
| 1243 | *Streptomyces olivoverticillatus* strain NBRC 15273 | NR_041169.1 |
| 1244 | *Streptomyces omiyaensis* strain NRRL B-1587 | NR_044150.1 |
| 1245 | *Streptomyces orinoci* strain NBRC 13466 | NR_041228.1 |
| 1246 | *Streptomyces pactum* strain NBRC 13433 | NR_041134.1 |
| 1247 | *Streptomyces paradoxus* strain NBRC 14887 | NR_041167.1 |
| 1248 | *Streptomyces parvulus* strain NBRC 13193 | NR_041119.1 |
| 1249 | *Streptomyces parvus* strain NRRL B-1455 | NR_043833.1 |
| 1250 | *Streptomyces paucisporeus* strain 1413 | NR_043247.1 |
| 1251 | *Streptomyces peucetius* strain JCM 9920 | NR_024763.1 |
| 1252 | *Streptomyces phaeochromogenes* strain NBRC 3180 | NR_041200.1 |
| 1253 | *Streptomyces phaeofaciens* strain NBRC 13372 | NR_041126.1 |
| 1254 | *Streptomyces phaeogriseichromatogenes* strain: NRRL 2834 | NR_042095.1 |
| 1255 | *Streptomyces phaeoluteichromatogenes* strain: NRRL B-5799 | NR_042096.1 |
| 1256 | *Streptomyces phaeoluteigriseus* strain: ISP 5182 | NR_042097.1 |
| 1257 | *Streptomyces phaeopurpureus* strain NRRL B-2260 | NR_043505.1 |
| 1258 | *Streptomyces pharetrae* strain CZA14 | NR_043130.1 |
| 1259 | *Streptomyces pilosus* strain NBRC 12807 | NR_041073.1 |
| 1260 | *Streptomyces platensis* strain JCM 4662 | NR_024761.1 |
| 1261 | *Streptomyces plicatus* strain NRRL 2428 | NR_043382.1 |
| 1262 | *Streptomyces plumbiresistens* strain CCNWHX 13-160 | NR_044518.1 |
| 1263 | *Streptomyces pluricolorescens* strain NRRL B-2121 | NR_043834.1 |
| 1264 | *Streptomyces polyantibioticus* strain SPR; DSM 44925 | NR_043573.1 |
| 1265 | *Streptomyces polychromogenes* strain NBRC 13072 | NR_041109.1 |
| 1266 | *Streptomyces poonensis* strain NRRL B-2319 | NR_043852.1 |
| 1267 | *Streptomyces prasinopilosus* strain NBRC 12809 | NR_041430.1 |
| 1268 | *Streptomyces prasinosporus* strain NBRC 13419 | NR_041130.1 |
| 1269 | *Streptomyces prasinus* strain NRRL B-2712 | NR_043500.1 |
| 1270 | *Streptomyces prunicolor* strain NRRL B-12281 | NR_043501.1 |
| 1271 | *Streptomyces psammoticus* strain IFO 13971 | NR_043372.1 |
| 1272 | *Streptomyces pseudogriseolus* strain NRRL B-3288 | NR_043835.1 |
| 1273 | *Streptomyces pseudovenezuelae* strain NBRC 12904 | NR_041090.1 |
| 1274 | *Streptomyces pulveraceus* strain NBRC 3855 | NR_041213.1 |
| 1275 | *Streptomyces puniceus* strain NRRL B-2895 | NR_043836.1 |
| 1276 | *Streptomyces puniciscabiei* strain S77 | NR_025156.1 |
| 1277 | *Streptomyces purpeofuscus* strain: LMG 20283 | NR_042304.1 |
| 1278 | *Streptomyces purpurascens* strain NBRC 12831 | NR_041221.1 |
| 1279 | *Streptomyces purpurascens* strain NBRC 12879 | NR_041224.1 |
| 1280 | *Streptomyces purpureus* strain: LMG 19368 | NR_042292.1 |
| 1281 | *Streptomyces purpurogeneiscleroticus* strain DSM 43156 | NR_025616.1 |
| 1282 | *Streptomyces racemochromogenes* strain NRRL B-5430 | NR_043499.1 |
| 1283 | *Streptomyces radiopugnans* strain R97 | NR_044013.1 |
| 1284 | *Streptomyces rameus* strain KCTC 9767 | NR_043361.1 |
| 1285 | *Streptomyces ramulosus* strain NRRL B-2714 | NR_043503.1 |
| 1286 | *Streptomyces rangoonensis* strain NBRC 13078 | NR_041110.1 |
| 1287 | *Streptomyces recifensis* strain NBRC 12813 | NR_041074.1 |
| 1288 | *Streptomyces rectiviolaceus* strain NRRL B-16374 | NR_043502.1 |
| 1289 | *Streptomyces regensis* strain NRRL B-11479 | NR_043495.1 |
| 1290 | *Streptomyces reticuliscabiei* strain CFBP 4531 | NR_025293.1 |
| 1291 | *Streptomyces rhizosphaericus* strain NBRC 100778 | NR_041415.1 |
| 1292 | *Streptomyces rimosus* subsp. *paromomycinus* strain DSM 41429 | NR_025622.1 |
| 1293 | *Streptomyces rimosus* subsp. *rimosus* strain JCM 4667 | NR_024762.1 |
| 1294 | *Streptomyces rishiriensis* strain NRRL B-3239 | NR_044141.1 |
| 1295 | *Streptomyces rochei* strain NBRC 12908 | NR_041091.1 |
| 1296 | *Streptomyces roseiscleroticus* strain NBRC 13002 | NR_041094.1 |
| 1297 | *Streptomyces roseofulvus* strain NBRC 13194 | NR_041120.1 |
| 1298 | *Streptomyces roseolilacinus* strain NBRC 12815 | NR_041075.1 |
| 1299 | *Streptomyces roseolus* strain NBRC 12816 | NR_041076.1 |
| 1300 | *Streptomyces roseoviolaceus* strain ISP 5277 | NR_025493.1 |
| 1301 | *Streptomyces roseoviridis* strain NBRC 12911 | NR_041092.1 |
| 1302 | *Streptomyces ruber* strain NBRC 14600 | NR_041163.1 |
| 1303 | *Streptomyces rubidus* strain 13C15 | NR_043245.1 |
| 1304 | *Streptomyces rubiginosohelvolus* strain NBRC 12912 | NR_041093.1 |
| 1305 | *Streptomyces rubiginosus* strain KCTC 9042 | NR_043360.1 |
| 1306 | *Streptomyces rubrogriseus* strain NBRC 15455 | NR_041188.1 |
| 1307 | *Streptomyces rutgersensis* strain NBRC 12819 | NR_041077.1 |
| 1308 | *Streptomyces sampsonii* strain ATCC 25495 | NR_025870.1 |
| 1309 | *Streptomyces sanglieri* strain NBRC 100784 | NR_041417.1 |
| 1310 | *Streptomyces sannanensis* strain NBRC 14239 | NR_041160.1 |
| 1311 | *Streptomyces scabiei* 87.22 strain 87.22 | NR_074848.1 |
| 1312 | *Streptomyces scabiei* strain RL-34 | NR_025865.1 |
| 1313 | *Streptomyces scabrisporus* strain KM-4927 | NR_028613.1 |
| 1314 | *Streptomyces sclerotialus* strain DSM 43032 | NR_025620.1 |

TABLE 2-continued

| Bacterial ID No. | Species | 16S rRNA Genbank Acc. No. |
|---|---|---|
| 1315 | *Streptomyces scopiformis* strain A25 | NR_028764.1 |
| 1316 | *Streptomyces sedi* strain YIM 65188 | NR_044582.1 |
| 1317 | *Streptomyces seoulensis* strain NBRC 16668 | NR_041432.1 |
| 1318 | *Streptomyces showdoensis* strain NBRC 13417 | NR_041129.1 |
| 1319 | *Streptomyces sindenensis* strain NBRC 3399 | NR_041205.1 |
| 1320 | *Streptomyces sioyaensis* strain NRRL B-5408 | NR_043498.1 |
| 1321 | *Streptomyces sodiiphilus* strain YIM 80305 | NR_042799.1 |
| 1322 | *Streptomyces somaliensis* strain DSM 40738 | NR_025292.1 |
| 1323 | *Streptomyces* sp. 40003 strain 40003 | NR_042760.1 |
| 1324 | *Streptomyces* sp. SirexAA-E strain SirexAA-E | NR_074561.1 |
| 1325 | *Streptomyces* sp. strain ISP 5133 | NR_042100.1 |
| 1326 | *Streptomyces* sp. strain ISP 5310 | NR_042101.1 |
| 1327 | *Streptomyces* sp. strain ISP 5499 | NR_042102.1 |
| 1328 | *Streptomyces sparsogenes* strain NBRC 13086 | NR_041111.1 |
| 1329 | *Streptomyces specialis* strain: GW41-1564 | NR_042689.1 |
| 1330 | *Streptomyces speibonae* strain PK-Blue | NR_025212.1 |
| 1331 | *Streptomyces spinoverrucosus* strain NBRC 14228 | NR_041159.1 |
| 1332 | *Streptomyces spiralis* strain NRRL B-16922 | NR_044142.1 |
| 1333 | *Streptomyces spiroverticillatus* strain NBRC 3931 | NR_041214.1 |
| 1334 | *Streptomyces sporocinereus* strain NBRC 100766 | NR_041412.1 |
| 1335 | *Streptomyces sporoclivatus* strain NBRC 100767 | NR_041413.1 |
| 1336 | *Streptomyces spororaveus* strain: LMG 20313 | NR_042306.1 |
| 1337 | *Streptomyces sporoverrucosus* strain NRRL B-16379 | NR_043837.1 |
| 1338 | *Streptomyces stelliscabiei* strain CFBP 4521 | NR_025294.1 |
| 1339 | *Streptomyces stramineus* strain NBRC 16131 | NR_041198.1 |
| 1340 | *Streptomyces subrutilus* strain DSM 40445 | NR_026203.1 |
| 1341 | *Streptomyces sulfonofaciens* strain NBRC 14260 | NR_041433.1 |
| 1342 | *Streptomyces sulphureus* strain NRRL B-1627 | NR_043838.1 |
| 1343 | *Streptomyces synnematoformans* strain S155 | NR_044098.1 |
| 1344 | *Streptomyces tanashiensis* strain IFO 12919 | NR_043369.1 |
| 1345 | *Streptomyces tauricus* strain JCM 4837 | NR_028621.1 |
| 1346 | *Streptomyces tendae* strain ATCC 19812 | NR_025871.1 |
| 1347 | *Streptomyces termitum* strain NBRC 13087 | NR_041112.1 |
| 1348 | *Streptomyces thermoalcalitolerans* strain NBRC 16322 | NR_041408.1 |
| 1349 | *Streptomyces thermocarboxydovorans* strain AT52 | NR_026071.1 |
| 1350 | *Streptomyces thermocarboxydus* strain AT37 | NR_026072.1 |
| 1351 | *Streptomyces thermocoprophilus* strain B19 | NR_025291.1 |
| 1352 | *Streptomyces thermodiastaticus* strain JCM 4840 | NR_036816.1 |
| 1353 | *Streptomyces thermogriseus* strain NBRC 100772 | NR_041434.1 |
| 1354 | *Streptomyces thermolineatus* strain A1484 | NR_026529.1 |
| 1355 | *Streptomyces thermospinosisporus* strain AT10 | NR_025147.1 |
| 1356 | *Streptomyces thermoviolaceus* subsp. *thermoviolaceus* strain DSM 40443 | NR_027616.1 |
| 1357 | *Streptomyces thermovulgaris* strain R10 | NR_026528.1 |
| 1358 | *Streptomyces thioluteus* strain NBRC 3364 | NR_041203.1 |
| 1359 | *Streptomyces torulosus* strain: LMG 20305 | NR_042305.1 |
| 1360 | *Streptomyces toxytricini* strain NRRL B-5426 | NR_043839.1 |
| 1361 | *Streptomyces tricolor* strain NBRC 15461 | NR_041189.1 |
| 1362 | *Streptomyces tritolerans* strain DAS 165 | NR_043745.1 |
| 1363 | *Streptomyces tubercidicus* strain DSM 40261 | NR_025623.1 |
| 1364 | *Streptomyces tuirus* strain NBRC 15617 | NR_041190.1 |
| 1365 | *Streptomyces turgidiscabies* strain ATCC 700248 | NR_040828.1 |
| 1366 | *Streptomyces umbrinus* strain NBRC 13091 | NR_041113.1 |
| 1367 | *Streptomyces variabilis* strain NRRL B-3984 | NR_043840.1 |
| 1368 | *Streptomyces variegatus* strain: LMG 20315 | NR_042307.1 |
| 1369 | *Streptomyces varsoviensis* strain NRRL B-3589 | NR_043497.1 |
| 1370 | *Streptomyces vastus* strain NRRL B-12232 | NR_043841.1 |
| 1371 | *Streptomyces venezuelae* strain JCM 4526 | NR_024764.1 |
| 1372 | *Streptomyces vietnamensis* strain GIMV4.0001 | NR_043710.1 |
| 1373 | *Streptomyces vinaceus* strain NBRC 13425 | NR_041131.1 |
| 1374 | *Streptomyces vinaceusdrappus* strain NRRL 2363 | NR_043383.1 |
| 1375 | *Streptomyces violaceochromogenes* strain IFO 13100 | NR_043373.1 |
| 1376 | *Streptomyces violaceolatus* strain DSM 40438 | NR_027223.1 |
| 1377 | *Streptomyces violaceorectus* strain NBRC 13102 | NR_041114.1 |
| 1378 | *Streptomyces violaceoruber* strain DSM 40049 | NR_041914.1 |
| 1379 | *Streptomyces violaceorubidus* strain: LMG 20319 | NR_042309.1 |
| 1380 | *Streptomyces violaceus* strain NBRC 13103 | NR_041115.1 |
| 1381 | *Streptomyces violaceusniger* strain NBRC 13459 | NR_041141.1 |
| 1382 | *Streptomyces violaceusniger* strain Tu 4113 | NR_074570.1 |
| 1383 | *Streptomyces violarus* strain NBRC 13104 | NR_041116.1 |
| 1384 | *Streptomyces violascens* strain ISP 5183 | NR_043338.1 |
| 1385 | *Streptomyces violens* strain DSM 40597 | NR_025617.1 |
| 1386 | *Streptomyces virens* strain NRRL B-24331 | NR_043842.1 |
| 1387 | *Streptomyces virginiae* strain NBRC 12827 | NR_041078.1 |
| 1388 | *Streptomyces viridiviolaceus* strain IFO 13359 | NR_043368.1 |
| 1389 | *Streptomyces viridobrunneus* strain: LMG 20317 | NR_042308.1 |
| 1390 | *Streptomyces viridochromogenes* strain NRRL B-1511 | NR_043843.1 |
| 1391 | *Streptomyces viridodiastaticus* strain IFO 13106 | NR_043367.1 |

TABLE 2-continued

| Bacterial ID No. | Species | 16S rRNA Genbank Acc. No. |
|---|---|---|
| 1392 | *Streptomyces viridosporus* strain NRRL 2414 | NR_043844.1 |
| 1393 | *Streptomyces vitaminophilus* strain NBRC 14294 | NR_041162.1 |
| 1394 | *Streptomyces wedmorensis* strain NRRL 3426 | NR_043845.1 |
| 1395 | *Streptomyces werraensis* strain NRRL B-5317 | NR_043846.1 |
| 1396 | *Streptomyces xanthochromogenes* strain NRRL B-5410 | NR_043847.1 |
| 1397 | *Streptomyces xanthocidicus* strain IFO 13469 | NR_043370.1 |
| 1398 | *Streptomyces xantholiticus* strain NBRC 13354 | NR_041123.1 |
| 1399 | *Streptomyces xanthophaeus* strain NRRL B-5414 | NR_043848.1 |
| 1400 | *Streptomyces xiamenensis* strain MCCC 1A01550 | NR_044035.1 |
| 1401 | *Streptomyces yanglinensis* strain 1307 | NR_043244.1 |
| 1402 | *Streptomyces yanii* strain IFO 14669 | NR_040781.1 |
| 1403 | *Streptomyces yatensis* strain NBRC 101000 | NR_041427.1 |
| 1404 | *Streptomyces yeochonensis* strain CN 732 | NR_024953.1 |
| 1405 | *Streptomyces yerevanensis* strain NRRL B-16943 | NR_044143.1 |
| 1406 | *Streptomyces yogyakartensis* strain NBRC 100779 | NR_041416.1 |
| 1407 | *Streptomyces yokosukanensis* strain NRRL B-3353 | NR_043496.1 |
| 1408 | *Streptomyces yunnanensis* strain YIM 41004 | NR_025149.1 |
| 1409 | *Streptomyces zaomyceticus* strain NRRL B-2038 | NR_044144.1 |
| 1410 | *Vibrio alginolyticus* strain ATCC 17749 | NR_044825.1 |
| 1411 | *Vibrio cholerae* bv. *albensis* strain ATCC 14547; RC782 | NR_044050.1 |
| 1412 | *Vibrio cholerae* O1 biovar El Tor strain N16961 | NR_074810.1 |
| 1413 | *Vibrio cholerae* strain O395 | NR_074816.1 |
| 1414 | *Vibrio cholerae* strain CECT 514 | NR_044853.1 |
| 1415 | *Vibrio fluvialis* strain VL 5125 | NR_036790.1 |
| 1416 | *Vibrio metschnikovii* strain Fowl | NR_029258.1 |
| 1417 | *Vibrio mimicus* strain 1721-77 | NR_029259.1 |
| 1418 | *Vibrio parahaemolyticus* strain ATCC 17802 | NR_041838.1 |
| 1419 | *Vibrio vulnificus* CMCP6 strain CMCP6 | NR_074889.1 |
| 1420 | *Vibrio vulnificus* strain 324 | NR_036888.1 |
| 1421 | *Yersinia enterocolitica* strain ATCC 9610 | NR_041832.1 |
| 1422 | *Yersinia enterocolitica* subsp. *enterocolitica* strain 8081 | NR_074308.1 |
| 1423 | *Yersinia pestis* KIM10+ strain KIM | NR_075053.1 |
| 1424 | *Yersinia pestis* strain NCTC 5923 | NR_025160.1 |
| 1425 | *Yersinia pseudotuberculosis* strain IP 32953 | NR_074202.1 |
| 1426 | *Yersinia pseudotuberculosis* strain ATCC 29833 | NR_025158.1 |
| 1427 | *Escherichia coli* | NR_074891.1 |
| 1428 | *Staphylococcus epidermidis* RP62A strain RP62A | NR_074995.1 |
| 1429 | *Staphylococcus haemolyticus* | NR_074994.1 |
| 1430 | *Stenotrophomonas maltophila* | NR_074875.1 |

2.2 Further Classification of Mammalian (e.g., Human) Sepsis-Causing Bacteria Using SNPs in 16S rRNA Bacterial pathogens that commonly cause sepsis in mammals (e.g., humans) include the Gram-positive bacteria *Actinomyces massiliensis, Bacillus anthracis, Clostridium difficile, Clostridium perfringens, Corynebacterium diphtheriae, Corynebacterium jeikeium, Corynebacterium urealyticum, Dermatophilus congolensis, Enterococcus faecalis, Enterococcus faecium, Erysipelothrix rhusiopathiae, Eubacterium desmolans, Lactobacillus intestinalis, Listeria monocytogenes, Micrococcus luteus, Mobiluncus curtisii, Mycobacterium tuberculosis, Nocardia asteroids, Nocardia brasiliensis, Peptostreptococcus stomatis, Rhodococcus equi, Staphylococcus aureus, Staphylococcus epidermidis, Staphylococcus haemolyticus, Staphylococcus hominis, Staphylococcus saprophyticus, Streptococcus agalactiae, Streptococcus anginosus, Streptococcus bovis, Streptococcus constellatus, Streptococcus dysgalactiae, Streptococcus intermedius, Streptococcus mitis, Streptococcus mutans, Streptococcus oralis, Streptococcus pneumonia, Streptococcus pyogenes, Streptococcus sanguinis, Streptococcus sobrinus, Streptomyces anulatus, Streptomyces somaliensis,* and the Gram-negative bacteria *Acinetobacter baumannii, Actinobacillus hominis, Aeromonas hydrophila, Bacteroides fragilis, Brucella abortus, Burkholderia cepacia, Campylobacter coli, Cardiobacterium valvarum, Chlamydia trachomatis, Chlamydophila pneumoniae, Citrobacter freundii, Edwardsiella tarda, Enterobacter aerogenes, Enterobacter cloacae, Escherichia coli, Flavobacterium ceti, Haemophilus ducreyi, Haemophilus influenzae, Haemophilus parahaemolyticus, Haemophilus parainfluenzae, Helicobacter pylori, Klebsiella oxytoca, Klebsiella pneumonia, Legionella pneumophila, Leptospira interrogans, Moraxella catarrhalis, Morganella morganii, Neisseria gonorrhoeae, Neisseria meningitides, Pasteurella multocida, Porphyromonas gingivalis, Prevotella buccae, Prevotella intermedia, Prevotella melaninogenica, Proteus mirabilis, Providencia alcalifaciens, Pseudomonas aeruginosa, Salmonella enterica, Serratia marcescens, Shigella dysenteriae, Shigella sonnei, Stenotrophomonas maltophilia, Veillonella dispar, Vibrio cholerae, Yersinia enterocolitica* and *Yersinia pestis*. These pathogens can be classified into seven groups by analysing nucleic acid for SNPs in the 16S rRNA gene (or 16S rRNA molecule or DNA copy thereof) at positions corresponding to positions 396, 398, 399, 400 and 401 of the 16S rRNA gene set SEQ ID NO:1, and applying the rules set forth in Table 3.

TABLE 3

| Group | Gram Status | 396 | 398 | 399 | 400 | 401 |
|---|---|---|---|---|---|---|
| 1 | Positive or *Helicobacter pylori, Campylobacter coli* or *Veillonella* dispar | A | C | G | C | C |
| 2 | Positive or *Leptospira interrogans, Chlamydia trachomatis,* or *Chlamydophila pneumoniae* | G | C | G | C | C |
| 3 | Negative, aerobic | C | T | G | C | C |
| 4 | Negative, aerobic | A | T | G | C | C |

TABLE 3-continued

| Group | Gram Status | 396 | 398 | 399 | 400 | 401 |
|---|---|---|---|---|---|---|
| 5 | Negative, aerobic | C | T | A | C | C |
| 6 | Negative, anaerobic | C | A | G | T | A |
| 7 | Negative, anaerobic | C | A | G | T | C |

Thus, an A, C, G, C and C at positions 396, 398, 399, 400 and 401, respectively, indicate that the bacterium is a Group 1 pathogen, typically a Gram-positive bacterium, such as *Bacillus anthracis*, *Enterococcus faecalis*, *Enterococcus faecium*, *Listeria monocytogenes*, *Streptococcus agalactiae*, *Streptococcus anginosus*, *Streptococcus constellatus*, *Streptococcus dysgalactiae*, *Streptococcus intermedius*, *Streptococcus pyogenes*, *Lactobacillus intestinalis*, *Clostridium perfringens*, *Staphylococcus aureus*, *Staphylococcus epidermidis*, *Staphylococcus haemolyticus*, *Staphylococcus hominis*, *Staphylococcus saprophyticus*, *Eubacterium desmolans*, *Clostridium difficile*, *Erysipelothrix rhusiopathiae*, *Streptococcus bovis*, *Streptococcus mitis*, *Streptococcus mutans*, *Streptococcus oralis*, *Streptococcus pneumonia*, *Streptococcus sanguinis*, *Streptococcus sobrinus* or *Peptostreptococcus stomatis*, or a Gram-negative bacterium selected from *Helicobacter pylori*, *Campylobacter coli* and *Veillonella dispar*.

G, C, G, C and C at positions 396, 398, 399, 400 and 401, respectively, indicate that the bacterium is a Group 2 pathogen, such as a Gram-positive bacterium selected from *Corynebacterium diphtheria*, *Dermatophilus congolensis*, *Micrococcus luteus*, *Rhodococcus equi*, *Streptomyces anulatus*, *Streptomyces somaliensis*, *Mycobacterium tuberculosis*, *Corynebacterium jeikeium*, *Corynebacterium urealyticum*, *Mobiluncus curtisii*, *Nocardia asteroids*, *Nocardia brasiliensis* and *Actinomyces massiliensis* or a Gram-negative bacterium selected from *Leptospira interogans*, *Chlamydia trachomatis* and *Chlamydophila pneumonia*.

C, T, G, C and C at positions 396, 398, 399, 400 and 401, respectively, indicate that the bacterium is a Group 3 pathogen, which is an aerobic Gram-negative bacterium, including *Actinobacillus hominis*, *Edwardsiella tarda*, *Haemophilus ducreyi*, *Haemophilus influenzae*, *Haemophilus parahaemolyticus*, *Haemophilus parainfluenzae*, *Morganella morganii*, *Pasteurella multocida*, *Providencia alcalifaciens*, *Vibrio cholerae*, *Moraxella catarrhalis*, *Pseudomonas aeruginosa*, *Neisseria gonorrhoeae*, *Neisseria meningitides*, *Aeromonas hydrophila*, *Citrobacter freundii*, *Enterobacter aerogenes*, *Enterobacter cloacae*, *Escherichia coli*, *Klebsiella oxytoca*, *Klebsiella pneumonia*, *Proteus mirabilis*, *Salmonella enterica*, *Serratia marcescens*, *Shigella dysenteriae*, *Shigella sonnei*, *Yersinia enterocolitica*, *Yersinia pestis*, *Acinetobacter baumannii*, *Brucella abortus* and *Flavobacterium ceti*.

A, T, G, C and C at positions 396, 398, 399, 400 and 401, respectively, indicate that the bacterium is a Group 4 pathogen, which is an aerobic Gram-negative bacterium, including *Legionella pneumophila*, *Burkholderia cepacia* and *Cardiobacterium valvarum*

C, T, A, C and C at positions 396, 398, 399, 400 and 401, respectively, indicate that the bacterium is a Group 5 pathogen, which is an aerobic Gram-negative bacterium such as *Stenotrophomonas maltophila*.

C, A, G, T and A at positions 396, 398, 399, 400 and 401, respectively, indicate that the bacteria is a Group 6 pathogen, which is an anerobic Gram-negative bacterium, such as *Prevotella buccae*, *Prevotella melaninogenica*, *Bacteroides fragilis* or *Prevotella intermedia*.

C, A, G, T and C at positions 396, 398, 399, 400 and 401, respectively, indicate that the bacterium is a Group 7 pathogen, which is an anaerobic Gram-negative bacterium such as *Porphyromonas gingivalis*.

Pathogens classified into Group 1 can be further classified into 12 subgroups by analysing nucleic acid for SNPs in the 16S rRNA gene (or 16S rRNA molecule or DNA copy thereof) at positions corresponding to positions 490, 491, 492, 493, 495, 496, 500 and 501 of the 16S rRNA gene set SEQ ID NO:1, and applying the rules set forth in Table 4, wherein A, A, C, C, G, A, C and A at positions 490, 491, 492, 493, 495, 496, 500 and 501, respectively, indicate that the bacterium is a Gram-positive bacterium, aerobic, and potentially vancomycin resistant, and includes the pathogens *Bacillus anthracis*, *Enterococcus faecalis*, *Enterococcus faecium* and *Listeria monocytogenes*; A, A, C, C, G, A, G and G at positions 490, 491, 492, 493, 495, 496, 500 and 501, respectively, indicate that the bacterium is a Gram-positive, aerobic, beta-hemolytic Streptococcal species including *Streptococcus agalactiae*, *Streptococcus anginosus*, *Streptococcus constellatus*, *Streptococcus dysgalactiae*, *Streptococcus intermedius*, *Streptoococcus pyogenes*; A, A, C, C, G, A, T, C at positions 490, 491, 492, 493, 495, 496, 500 and 501, respectively, indicate that the bacterium is the Gram-positive aerobe, *Lactobacillus intestinalis*; A, A, C, G, A, T, C and A at positions 490, 491, 492, 493, 495, 496, 500 and 501, respectively, indicate that the bacterium is a Gram-negative spiral aerobe, either *Helicobacter pylori* or *Campylobacter coli*; A, A, G, G, G, G, C and C at positions 490, 491, 492, 493, 495, 496, 500 and 501, respectively, indicate that the bacterium is the Gram-positive, anaerobic *bacillus*, *Clostridium perfringens*; A, A, T, C, G, A, C and C at positions 490, 491, 492, 493, 495, 496, 500 and 501, respectively, indicate that the bacterium is a Gram-positive *Staphylococcus* with potential oxacillin resistance, including *Staphylococcus aureus*, *Staphylococcus epidermidis*, *Staphylococcus haemolyticus*, *Staphylococcus hominis*, *Staphylococcus saprophyticus*; G, A, A, G, A, T, C and T at positions 490, 491, 492, 493, 495, 496, 500 and 501, respectively, indicate that the bacterium is the Gram-positive anaerobic *bacillus*, *Eubacterium desmolans*; G, A, A, T, G, A, C and C at positions 490, 491, 492, 493, 495, 496, 500 and 501, respectively, indicate that the bacterium is the Gram-negative anaerobic coccus, *Veillonella dispar*; G, A, G, G, G, G, C and C at positions 490, 491, 492, 493, 495, 496, 500 and 501, respectively, indicate that the bacterium is the Gram-positive anaerobic *bacillus*, *Clostridium difficile*; T, A, C, C, G, A, C and C at positions 490, 491, 492, 493, 495, 496, 500 and 501, respectively, indicate that the bacterium is the Gram-positive *bacillus*, *Erysipelothrix rhusiopathiae*; T, A, C, C, G, A, G and G at positions 490, 491, 492, 493, 495, 496, 500 and 501, respectively, indicate that the bacterium is a Gram-positive alpha-hemolytic coccus selected from *Streptococcus Bovis*, *Streptococcus mitis*, *Streptococcus mutans*, *Streptococcus oralis*, *Streptococcus pneumoniae*, *Streptococcus sanguinis*, *Streptococcus sobrinus*; and T, G, T, G, G, G, C and C at positions 490, 491, 492, 493, 495, 496, 500 and 501, respectively, indicate that the bacterium is the Gram-positive, anaerobic coccus, *Peptostreptococcus stomatis*.

TABLE 4

| Group | Status | 490 | 491 | 492 | 493 | 495 | 496 | 500 | 501 |
|---|---|---|---|---|---|---|---|---|---|
| 1a | Gram-positive, aerobic, potential vancomycin | A | A | C | C | G | A | C | C |

TABLE 4-continued

| Group | Status | 490 | 491 | 492 | 493 | 495 | 496 | 500 | 501 |
|---|---|---|---|---|---|---|---|---|---|
| | resistance, *Bacillus anthracis*, *Enterococcus faecalis*, *Enterococcus faecium* and *Listeria monocytogenes* | | | | | | | | |
| 1b | Gram-positive, aerobic, beta-hemolytic *Streptococcal* species including *Streptococcus agalactiae*, *Streptococcus anginosus*, *Streptococcus constellatus*, *Streptococcus dysgalactiae*, *Streptococcus intermedius*, and *Streptoococcus pyogenes* | A | A | C | C | G | A | G | G |
| 1c | Gram-positive, aerobic, *Lactobacillus intestinalis* | A | A | C | C | G | A | T | C |
| 1d | Gram-negative, spiral, aerobic, *Helicobacter pylori*, *Campylobacter coli* | A | A | C | G | A | T | C | A |
| 1e | Gram-positive, anaerobic, bacillus, *Clostridium perfringens* | A | A | G | G | G | G | C | C |
| 1f | Gram-positive *Staphylococcus*, potential oxacillin resistance, *Staphylococcus aureus*, *Staphylococcus epidermidis*, *Staphylococcus haemolyticus*, *Staphylococcus hominis*, and *Staphylococcus saprophyticus* | A | A | T | C | G | A | C | C |
| 1g | Gram-positive, anaerobic, bacillus, *Eubacterium desmolans* | G | A | A | G | A | T | C | T |
| 1h | Gram-negative, anaerobic, cocci, *Veillonella* dispar | G | A | A | T | G | A | C | C |
| 1i | Gram-positive, anaerobic, bacillus, *Clostridium difficile* | G | A | G | G | G | G | C | C |
| 1j | Gram-positive, *bacillus*, *Erysipelothrix rhusiopathiae* | T | A | C | C | G | A | C | C |
| 1k | Gram-positive, *cocci*, alpha-hemolytic, *Streptococcus bovis*, *Streptococcus mitis*, *Streptococcus mutans*, *Streptococcus oralis*, *Streptococcus pneumoniae*, *Streptococcus sanguinis*, and *Streptococcus sobrinus* | T | A | C | C | G | A | G | G |
| 1l | Gram-positive, anaerobic, cocci, *Peptostreptococcus stomatis* | T | G | T | G | G | G | C | C |

Pathogens classified into Group 2 can be further classified into 9 subgroups by analysing nucleic acid for SNPs in the 16S rRNA gene (or 16S rRNA molecule or DNA copy thereof) at positions corresponding to positions 490, 491, 492, 493, 496, 499 and 501 of the 16S rRNA gene set SEQ ID NO:1, and applying the rules set forth in Table 5, wherein an A, G, A, T, G, G and A at positions 490, 491, 492, 493, 496, 499 and 501, respectively, indicate that the bacterium is the Gram-positive, acid fast *bacillus, Cornebacterium diptheriae*; a G, C, A, G, G, G and A at positions 490, 491, 492, 493, 496, 499 and 501, respectively, indicate that the bacterium is a Gram-positive coccus selected from *Dermatophilus congolensis, Micrococcus luteus* and *Rhodococcus equi*; a G, C, A, G, G, G and G at positions 490, 491, 492, 493, 496, 499 and 501, respectively, indicate that the bacterium is a Gram-positive, acid fast *bacillus*, either *Streptomyces anulatus* or *Streptomyces somaliensis*; a G, C, C, T, A, A and C at positions 490, 491, 492, 493, 496, 499 and 501, respectively, indicate that the bacterium is the Gram-negative spiral bacterium, *Leptospira interrogans*; a G, G, A, G, G, G and A at positions 490, 491, 492, 493, 496, 499 and 501, respectively, indicate that the bacterium is the Gram-positive, acid fast *bacillus, Mycobacterium tuberculosis*; a G, G, A, T, G, G and A at positions 490, 491, 492, 493, 496, 499 and 501, respectively, indicate that the bacterium is a Gram-positive, acid fast *bacillus*, either *Corynebacterium jeikeium* or *Corynebacterium urealyticum*; a G, G, G, G, G, G and G at positions 490, 491, 492, 493, 496, 499 and 501, respectively, indicate that the bacterium is the Gram-positive, anaerobic *bacillus, Mobiluncus curtisii*; a G, G, T, A, G, G and A at positions 490, 491, 492, 493, 496, 499 and 501, respectively, indicate that the bacterium is Gram-negative and either *Chlamydia trachomatis* or *Chlamydophila pneumoniae*; a G, T, A, G, G, G and A at positions 490, 491, 492, 493, 496, 499 and 501, respectively, indicate that the bacterium is a Gram-positive *bacillus*, partially acid fast and either the aerobic *Nocardia* asteroids, *Nocardia brasilensis*; and a G, T, T, G, G, G and A at positions 490, 491, 492, 493, 496, 499 and 501, respectively, indicate that the bacterium is a Gram-positive *bacillus*, partially acid fast and the anaerobe *Actinomyces massiliensis*.

TABLE 5

| Group | Status | 490 | 491 | 492 | 493 | 496 | 499 | 501 |
|---|---|---|---|---|---|---|---|---|
| 2a | Gram-positive, acid fast *bacillus*, *Corynebacterium diptheriae* | A | G | A | T | G | G | A |
| 2b | Gram-positive, *coccus*, *Dermatophilus congolensis*, *Micrococcus luteus*, *Rhodococcus equi* | G | C | A | G | G | G | A |
| 2c | Gram-positive, acid fast *bacillus*, *Streptomyces anulatus*, *Streptomyces somaliensis* | G | C | A | G | G | G | G |
| 2d | Gram-negative, spiral, *Leptospira interrogans* | G | C | C | T | A | A | C |
| 2e | Gram-positive, acid fast *bacillus*, *Mycobacterium tuberculosis* | G | G | A | G | G | G | A |
| 2f | Gram-positive, acid fast *bacillus*, *Corynebacterium jeikeium*, *Corynebacterium urealyticum* | G | G | A | T | G | G | A |
| 2g | Gram-positive, anaerobe, *bacillus*, *Mobiluncus curtisii* | G | G | G | G | G | G | G |
| 2h | Gram-negative, *Chlamydia trachomatis*, *Chlamydophila pneumoniae* | G | G | T | A | G | G | A |
| 2i | Gram-positive, partially acid fast, *bacillus*, aerobes *Nocardia asteroids*, *Nocardia brasilensis*, | G | T | A | G | G | G | A |
| 2j | Gram-positive, partially acid fast, anaerobe *Actinomyces massiliensis* | G | T | T | G | G | G | A |

Pathogens classified into Group 3 can be further classified into 7 subgroups by analysing nucleic acid for SNPs in the 16S rRNA gene (or 16S rRNA molecule or DNA copy thereof) at positions corresponding to positions 490, 491, 496, and 501 of the 16S rRNA gene set SEQ ID NO:1, and applying the rules set forth in Table 6, wherein an A, C, G and A at positions 490, 491, 496, and 501, respectively, indicate that the bacterium is a Gram-negative coccus or coccobacillus, selected from *Actinobacillus hominis, Edwardsiella tarda, Haemophilus ducreyi, Haemophilus influenzae, Haemophilus parahaemolyticus, Haemophilus parainfluenzae, Morganella morganii, Pasteurella multocida, Providentia alcalifaciens* and *Vibrio cholerae*; an A, C, T and A at positions 490, 491, 496, and 501, respectively, indicate that the bacterium is a Gram-negative bacterium with potential extended spectrum beta lactamase resistance, including *Moraxella catarrhalis* and *Psuedomona aeruginosa*; a G, A, T and A at positions 490, 491, 496, and 501, respectively, indicates that the bacterium is a Gram-negative diplococcus, either *Neisseria gonorrhoeae* or *Neisseria meningitides*; a G, C, G and A at positions 490, 491, 496, and 501, respectively, indicate that the bacterium is a Gram-negative bacterium with potential extended spectrum beta lactamase resistance, selected from *Aeromonas hydrophila, Citrobacter freundii, Enterobacter aerogenes, Enterobacter cloacae, Escherichia coli, Klebsiella oxytoca, Klebsiella pneumonia, Proteus mirabilis, Salmonella enterica, Serratia marcescens, Shigella dysenteriae, Shigella sonnei, Yersinia enterocolitica* and *Yersinia pestis*; a G, C, T and A at positions 490, 491, 496, and 501, respectively, indicate that the bacterium is the Gram-negative coccus *Acinetobacter baumannii*, having potential extended spectrum beta lactamase resistant; a G, G, G and C at positions 490, 491, 496, and 501, respectively, indicate that the bacterium is *Brucella abortus*; and a T, A, T and A at positions 490, 491, 496, and 501, respectively, indicate that the bacterium is *Flavibacterium ceti*.

TABLE 6

| Group | Status | 490 | 491 | 496 | 501 |
|---|---|---|---|---|---|
| 3a | Gram-negative, coccus or coccobacilllus, *Actinobacillus hominis, Edwardsiella tarda, Haemophilus ducreyi, Haemophilus influenzae, Haemophilus parahaemolyticus, Haemophilus parainfluenzae, Morganella morganii, Pasteurella multocida, Providentia alcalifaciens, Vibrio cholerae* | A | C | G | A |
| 3b | Gram-negative, potential extended spectrum beta lactamase resistant, *Moraxella catarrhalis, Psuedomona aeruginosa* | A | C | T | A |
| 3c | Gram-negative, diplococcus, *Neisseria gonorrhoeae, Neisseria meningitides* | G | A | T | A |
| 3d | Gram-negative, potential extended spectrum beta lactamase resistant, *Aeromonas hydrophila, Citrobacter freundii, Enterobacter aerogenes, Enterobacter cloacae, Escherichia coli, Klebsiella oxytoca, Klebsiella pneumonia, Proteus mirabilis, Salmonella enterica, Serratia marcescens, Shigella dysenteriae, Shigella sonnei, Yersinia enterocolitica, Yersinia pestis* | G | C | G | A |
| 3e | Gram-negative, cocci, potential extended spectrum beta lactamase resistant, *Acinetobacter baumannii* | G | C | T | A |
| 3f | Gram-negative, coccobacillus, *Brucella abortus* | G | G | G | C |
| 3g | Gram-negative, bacillus, *Flavobacterium ceti* | T | A | T | A |

Pathogens classified into Group 4 can be further classified into 3 subgroups by analysing nucleic acid for SNPs in the 16S rRNA gene (or 16S rRNA molecule or DNA copy thereof) at positions corresponding to positions 490, 491, 496, and 499 of the 16S rRNA gene set SEQ ID NO:1, and applying the rules set forth in Table 7, wherein an A, C, G and C at positions 490, 491, 496, and 499, respectively, indicate that the bacterium is the Gram-negative pleomorphic bacterium, *Legionella pneumophila*; a G, A, T and G at positions 490, 491, 496, and 499, respectively, indicate that the bacterium is the Gram-negative *bacillus, Burkholderia cepacia*; and a G, C, G and G at positions 490, 491, 496, and 499, respectively, indicate that the bacterium is the Gram-negative *bacillus, Cardiobacterium valvarum*.

TABLE 7

| Group | Status | 490 | 491 | 496 | 499 |
|---|---|---|---|---|---|
| 4a | Gram-negative, pleomorphic, *Legionella pneumophila* | A | C | G | C |
| 4b | Gram-negative, *bacillus, Burkholderia cepacia* | G | A | T | G |
| 4c | Gram-negative, *bacillus, Cardiobacterium valvarum* | G | C | G | G |

The pathogen in Group 5, *Stenotropomonas maltophila*, can be identified without the use of further SNPs other than those in Table 3.

Pathogens classified into Group 6 can be further classified into 4 subgroups by analysing nucleic acid for SNPs in the 16S rRNA gene (or 16S rRNA molecule or DNA copy thereof) at positions corresponding to positions 490, 491, and 492 of the 16S rRNA gene set SEQ ID NO:1, and applying the rules set forth in Table 8, wherein a C, A and T at positions 490, 491, and 492, respectively, indicate that the bacterium is the Gram-negative, anaerobic, *bacillus, Prevotella buccae*; a T, A and C at positions 490, 491, and 492, respectively, indicate that the bacterium is the Gram-negative, anaerobic, *bacillus, Prevotella melaninogenica*; a T, A and T at positions 490, 491, and 492, respectively, indicate that the bacterium is the Gram-negative, anaerobic, *bacillus Bacteroides fragilis*; and a T, T and C at positions 490, 491, and 492, respectively indicate that the bacterium is the Gram-negative, anaerobic, *bacillus Prevotella intermedia*.

TABLE 8

| Group | Status | 490 | 491 | 496 |
|---|---|---|---|---|
| 6a | Gram-negative, anaerobic, *bacillus Prevotella buccae* | C | A | T |
| 6b | Gram-negative, anaerobic, *bacillus Prevotella melaninogenica* | T | A | C |
| 6c | Gram-negative, anaerobic, *bacillus, Bacteroides fragilis* | T | A | T |
| 6d | Gram-negative, anaerobic, *bacillus Prevotella intermedia* | T | T | C |

The pathogen in Group 7, *Porphyromonas gingivalis*, can be identified without the use of further SNPs other than those in Table 3.

Thus, a sample, such as a blood sample from a mammalian (e.g., human) subject with sepsis or a mammalian (e.g., human) subject suspected of having sepsis, e.g. a human subject presenting with SIRS, can be analysed using the methods of the present invention to accurately and rapidly determine whether a bacterium is likely to be the causative agent (i.e. whether there is bacteria present in the sample), and also whether that bacterium is Gram-positive or Gram-negative, acid-fast or not acid-fast, aerobic or anaerobic, and/or part of a major potential antibiotic resistance group. Using the information in Tables 3-8, the identity of the bacterial species can also be narrowed down or, in some cases, confirmed.

2.3 Classification of Mammalian (e.g., Human) Pathogens Commonly Causing Sepsis Using 1 or More SNPs in 16S rRNA Bacterial pathogens that commonly cause sepsis in mammals (e.g., humans) include the Gram-positive bacteria *Staphylococcus aureus*, *Staphylococcus epidermidis*, *Staphylococcus haemolyticus*, *Staphylococcus hominis*, *Staphylococcus saprophyticus*, *Enterococcus faecalis*, *Enterococcus faecium*, *Clostridium perfringens*, *Streptococcus viridans* group (*Streptococcus anginosus*, *Streptococcus constellatus*, *Streptococcus intermedius*, *Streptococcus mitis*, *Streptococcus mutans*, *Streptococcus sanguinis*, *Streptococcus sobrinus* and *Streptococcus oralis*), *Streptococcus pneumoniae*, *Streptococcus agalactiae*, *Streptococcus bovis*, *Streptococcus sanguinis*, *Streptococcus dysgalactiae*, *Streptococcus mutans* and *Streptococcus pyogenes*, and the Gram-negative bacteria *Escherichia coli*, *Acinetobacter baumannii*, *Bacteroides fragilis*, *Burkholderia cepacia*, *Klebsiella pneumonia*, *Klebsiella oxytoca*, *Pseudomonas aeruginosa*, *Enterobacter aerogenes*, *Enterobacter cloacae*, *Serratia marcescens*, *Proteus mirabilis*, *Citrobacter freundii*, *Morganella morganii*, *Haemophilus influenzae*, *Neisseria meningitidis*, *Stenotrophomonas maltophila*, *Prevotella buccae*, *Prevotella intermedia* and *Prevotella melaninogenica*. These pathogens can be classified as Gram-positive or Gram-negative by analysing nucleic acid for SNPs in the 16S rRNA gene (or 16S rRNA molecule or DNA copy thereof) at positions corresponding to positions 396 and 398 of the 16S rRNA gene set SEQ ID NO:1, and applying the rules set forth in Table 1, wherein a C at position 396 and a T, A or C at position 398 indicates that the bacterium is a Gram-negative bacterium; and an A, T or G at position 396 and a C at position 398 indicates that the bacterium is a Gram-positive bacterium.

Indeed, the Gram status of this subset of mammalian (e.g., human) sepsis-associated bacteria can be determined on the basis of just a single SNP in the 16S rRNA gene (or 16S rRNA molecule or DNA copy thereof) at a position corresponding to position 396 of the *Escherichia coli* 16S rRNA gene set forth in SEQ ID NO:1. Specifically, a C at the position corresponding to position 396 of SEQ ID NO:1 indicates that the bacterium is a Gram-negative bacterium, and an A, T or G indicates that the bacterium is a Gram-positive bacterium. Thus, the present invention provides methods for determining the Gram status of a bacterium in a sample, by analyzing nucleic acid from the sample for a SNP in the 16S rRNA gene (or 16S rRNA or DNA copy thereof) at the position corresponding to position 396 of the 16S rRNA gene set forth in SEQ ID NO:1, wherein a C at position 396 indicates that the bacterium in the sample is a Gram-negative bacterium; and an A, T or G at position 396 indicates that the bacterium is a Gram-positive bacterium. The bacterium in the sample may be a mammalian (e.g., human) sepsis-associated bacterium, such as *Staphylococcus aureus*, *Staphylococcus epidermidis*, *Staphylococcus haemolyticus*, *Staphylococcus hominis*, *Staphylococcus saprophyticus*, *Enterococcus faecalis*, *Enterococcus faecium*, *Clostridium perfringens*, *Streptococcus viridans* group (*Streptococcus anginosus*, *Streptococcus constellatus*, *Streptococcus intermedius*, *Streptococcus mitis*, *Streptococcus mutans*, *Streptococcus sanguinis*, *Streptococcus sobrinus* and *Streptococcus oralis*), *Streptococcus pneumoniae*, *Streptococcus agalactiae*, *Streptococcus bovis*, *Streptococcus sanguinis*, *Streptococcus dysgalactiae*, *Streptococcus mutans*, *Streptococcus pyogenes*, *Escherichia coli*, *Acinetobacter baumannii*, *Bacteroides fragilis*, *Burkholderia cepacia*, *Klebsiella pneumonia*, *Klebsiella oxytoca*, *Pseudomonas aeruginosa*, *Enterobacter aerogenes*, *Enterobacter cloacae*, *Serratia marcescens*, *Proteus mirabilis*, *Citrobacter freundii*, *Morganella morganii*, *Haemophilus influenzae*, *Neisseria meningitidis*, *Stenotrophomonas maltophila*, *Prevotella buccae*, *Prevotella intermedia* or *Prevotella melaninogenica*. Accordingly, the present invention provides methods for detecting a bacterium in a sample, such as a blood sample, from a mammalian (e.g., human) subject with sepsis or a mammalian (e.g., human) subject suspected of having sepsis, e.g. a mammalian (e.g., human) subject presenting with SIRS and, if so, determining whether the bacterium is Gram-positive or Gram-negative.

Other bacteria that can cause sepsis in mammals (e.g., humans), although less commonly than those described above, include for example the Gram-negative bacteria *Salmonella enterica*, *Haemophilus influenzae*, *Campylobacter coli*, *Campylobacter jejuni*, *Campylobacter lari*, *Campylobacter fetus*, *Helicobacter cinaedi*, *Helicobacter pylori*, *Chlamydophila abortus*, *Veillonella atypica*, *Veillonella parvula*, *Veillonella denticariosi* and *Veillonella rogosae*; and the Gram-positive bacteria *Streptomyces anulatus*, *Streptomyces somaliensis*, and *Mycobacterium tuberculosis*. Of these, *Campylobacter coli*, *Campylobacter jejuni*, *Campylobacter lari*, *Campylobacter fetus*, *Helicobacter cinaedi*, *Helicobacter pylori*, *Chlamydophila abortus*, *Veillonella atypica*, *Veillonella parvula*, *Veillonella denticariosi* and *Veillonella rogosae* do not follow the rules described above and thus are unable to be classified as Gram-positive or Gram-negative using only a SNP at positions 396, or SNPs at positions 396 and 398. To accurately classify these bacterial pathogens that also cause sepsis as Gram-positive or Gram-negative, a further 3 SNPs at positions 278, 286 and 648 (numbering corresponding to the 16S rRNA set forth in SEQ ID NO:1) can be used. Thus, a total of 5 SNPs at positions 396, 398, 278, 286 and 648 can be used to determine the Gram status of the mammalian (e.g., human) sepsis-associated bacterial pathogens *Staphylococcus aureus*, *Staphylococcus epidermidis*, *Staphylococcus haemolyticus*, *Staphylococcus hominis*, *Staphylococcus saprophyticus*, *Enterococcus faecalis*, *Enterococcus faecium*, *Clostridium perfringens*, *Streptococcus viridans* group (*Streptococcus anginosus*, *Streptococcus constellatus*, *Streptococcus intermedius*, *Streptococcus mitis*, *Streptococcus mutans*, *Streptococcus sanguinis*, *Streptococcus sobrinus* and *Streptococcus oralis*), *Streptococcus pneumoniae*, *Streptococcus agalactiae*, *Streptococcus bovis*, *Streptococcus sanguinis*, *Streptococcus dysgalactiae*, *Streptococcus mutans*, *Streptococcus pyogenes*, *Escherichia coli*, *Acinetobacter baumannii*, *Bacteroides fragilis*, *Burkholderia cepacia*, *Klebsiella pneumonia*, *Klebsiella oxytoca*, *Pseudomonas aeruginosa*, *Enterobacter aerogenes*, *Enterobacter cloacae*, *Serratia marcescens*, *Proteus mirabilis*, *Citrobacter freundii*, *Morganella morganii*, *Haemophilus influenzae*, *Neisseria meningitidis*, *Stenotrophomonas maltophila*, *Prevotella buccae*, *Prevotella intermedia*, *Prevotella melaninogenica*, *Salmonella enterica*, *Serratia marcescens*, *Haemophilus influenzae*, *Campylobacter coli*, *Campylobacter jejuni*, *Campylobacter lari*, *Campylobacter fetus*, *Helicobacter cinaedi*, *Helicobacter pylori*, *Chlamydophila abortus*, *Veillonella atypica*, *Veillonella parvula*, *Veillonella denticariosi*, *Veillonella rogosae*, *Streptomyces anulatus*, *Streptomyces somaliensis* and *Mycobacterium tuberculosis*.

The general rules for classifying these Gram-positive and Gram-negative bacteria that may cause mammalian (e.g., human) sepsis using the five SNPs defined above are as follows:

If position 396 is a C then the bacterium is Gram-negative and includes the species in Table 9; and if position 396 is A or G then the bacterium is Gram-positive and includes the species in Table 10.

TABLE 9

| Gram | Species | 396 | 398 | 278 | 286 | 648 |
|---|---|---|---|---|---|---|
| Negative | Prevotella melaninogenica | C | A | A | G | T |
| Negative | Prevotella intermedia | C | A | T | G | G |
| Negative | Prevotella buccae | C | A | T | G | T |
| Negative | Bacteroides fragilis | C | A | T | A | A |
| Negative | Citrobacter freundii | C | T | G | C | A |
| Negative | Enterobacter aerogenes | C | T | G | C | A |
| Negative | Klebsiella oxytoca | C | T | G | C | A |
| Negative | Serratia marcescens | C | T | G | C | A |
| Negative | Morganella morganii | C | T | G | C | C |
| Negative | Stenotrophomonas maltophila | C | T | G | G | C |
| Negative | Acinetobacter baumannii | C | T | G | G | G |
| Negative | Enterobacter cloacae | C | T | G | C | A |
| Negative | Klebsiella pneumoniae | C | T | G | C | A |
| Negative | Salmonella enterica | C | T | G | C | A |
| Negative | Escherichia coli | C | T | G | C | A |
| Negative | Proteus mirabilis | C | T | G | C | T |
| Negative | Neisseria meningitidis | C | T | G | G | T |
| Negative | Pseudomonas aeruginosa | C | T | G | G | T |
| Negative | Haemophilus influenzae | C | T | T | C | T |
| Negative | Burkholderia cepacia | C | T | G | G | A |

TABLE 10

| Gram | Species | 396 | 398 | 278 | 286 | 648 |
|---|---|---|---|---|---|---|
| Positive | Mycobacterium tuberculosis | G | C | G | G | A |
| Positive | Streptomyces somaliensis | G | C | G | G | A |
| Positive | Streptomyces anulatus | G | C | G | G | T |

If positions 396, 398 and 278 are A, C and T (respectively) then the bacterium is Gram-negative and includes the species in Table 11.

If positions 396, 398 and 278 are A, C and C (respectively) then the bacterium is Gram-positive and includes the species in Table 12.

TABLE 11

| Gram | Species | 396 | 398 | 278 | 286 | 648 |
|---|---|---|---|---|---|---|
| Negative | Campylobacter coli | A | C | T | T | A |
| Negative | Campylobact jejuni | A | C | T | T | A |
| Negative | Campylobacter lari | A | C | T | T | A |
| Negative | Campylobacter fetus | A | C | T | A | A |
| Negative | Helicobacter cinaedi | A | C | T | G | T |
| Negative | Helicobacter pylori | A | C | T | G | A |
| Negative | Chlamydophda abortus | A | C | T | T | T |

TABLE 12

| Gram | Species | 396 | 398 | 278 | 286 | 648 |
|---|---|---|---|---|---|---|
| Positive | Enterococcus faecalis | A | C | C | A | A |
| Positive | Enterococcus faecium | A | C | C | A | A |

If positions 396, 398 and 278 are A, C, G and position 286 is an A then the bacterium is Gram-positive and includes the species in Table 13.

TABLE 13

| Gram | Species | 396 | 398 | 278 | 286 | 648 |
|---|---|---|---|---|---|---|
| Positive | Streptococcus bovis | A | C | G | A | A |
| Positive | Streptococcus agalactiae | A | C | G | A | G |
| Positive | Streptococcus dysgalactiae | A | C | G | A | G |
| Positive | Streptococcus pyogenes | A | C | G | A | G |
| Positive | Streptococcus anginosus | A | C | G | A | T |
| Positive | Streptococcus intermedius | A | C | G | A | T |
| Positive | Streptococcus mitis | A | C | G | A | T |
| Positive | Streptococcus mutans | A | C | G | A | T |
| Positive | Streptococcus pneumoniae | A | C | G | A | T |
| Positive | Streptococcus sanguinis | A | C | G | A | T |

If positions 396, 398, 278, 286 are A, C, A, A then the bacterium is Gram-positive and includes the species in Table 14.

TABLE 14

| Gram | Species | 396 | 398 | 278 | 286 | 648 |
|---|---|---|---|---|---|---|
| Positive | Staphylococcus aureus | A | C | A | A | A |
| Positive | Streptococcus sobrinus | A | C | A | A | A |
| Positive | Streptococcus constellatus | A | C | A | A | T |
| Positive | Streptococcus oralis | A | C | A | A | T |

If positions 396, 398, 278, 286 are A, C, A, G and position 648 is a G then the bacterium is Gram-negative and includes the species in Table 15.

If positions 396, 398, 278, 286 are A, C, A, G and position 648 is an A then the bacterium is Gram-positive and includes the species in Table 16.

TABLE 15

| Gram | Species | 396 | 398 | 278 | 286 | 648 |
|---|---|---|---|---|---|---|
| Negative | Veillonella rogosae | A | C | A | G | G |

TABLE 16

| Gram | Species | 396 | 398 | 278 | 286 | 648 |
|---|---|---|---|---|---|---|
| Positive | Staphylococcus epidermidis | A | C | A | G | A |
| Positive | Staphylococcus hominus | A | C | A | G | A |

If positions 396, 398, 278 and 286 are A, C, G and G (respectively) and position 648 is G then the bacterium is Gram-negative and includes the species in Table 17.

If positions 396, 398, 278 and 286 are A, C, G and G and position 648 is A or T then the bacterium is Gram-positive and includes the species in Table 18.

TABLE 17

| Gram | Species | 396 | 398 | 278 | 286 | 648 |
|---|---|---|---|---|---|---|
| Negative | Veillonella atypica | A | C | G | G | G |
| Negative | Veillonella parvula | A | C | G | G | G |
| Negative | Veillonella denticariosi | A | C | G | G | G |

TABLE 18

| Gram | Species | 396 | 398 | 278 | 286 | 648 |
|---|---|---|---|---|---|---|
| Positive | Staphylococcus haemolyticus | A | C | G | G | A |
| Positive | Staphylococcus saprophyticus | A | C | G | G | A |
| Positive | Clostridium perfringens | A | C | G | G | T |

Thus, the Gram status of most mammalian (e.g., human) sepsis-associated bacteria can be determined by analysing nucleic acid for SNPs at positions 396, 398, 278, 386 and 648 of the 16S rRNA (or 16S rRNA or DNA copy thereof), wherein the bacterial pathogen is determined to be a Gram-negative bacterium when there is a C at position 396; or an A at position 396, a C at position 398 and an T at position 278; an A at position 396, a C at position 398, an A at position 278, a G at position 286 and a G at position 648; or an A at position 396, a C at position 398, an G at position 278, a G at position 286 and a G at position 648; and the bacterial pathogen is determined to be a Gram-positive bacterium when there is a G at position 396; or an A at position 396, a C at position 398 and a C at position 278; or an A at position 396, a C at position 398, a G at position 278, and an A at position 286; or an A at position 396, a C at position 398, an A at position 278 and an A at position 286; or an A at position 396, a C at position 398, an A at position 278, a G at position 286 and an A at position 648; or an A at position 396, a C at position 398, a G at position 278, a G at position 286 and a T or A at position 648.

Thus, a sample, such as a blood sample from a mammalian (e.g., human) subject with sepsis or a mammalian (e.g., human) subject suspected of having sepsis, e.g. a mammalian (e.g., human) subject presenting with SIRS, can be analysed using the methods of the present invention to accurately and rapidly determine whether a bacterium is likely to be the causative agent (i.e. whether there is bacteria present in the sample), and also whether that bacterium is Gram-positive or Gram-negative. Using the information in Tables 9-18, the identity of the bacterial species can also be narrowed down or, in some cases, confirmed.

2.4 Differentiation of Fungal Cells from Mammalian Cells and Prokaryotes Using SNPs in 5.8S rRNA 5.8S rRNA molecules are unique to eukaryotes. As determined herein, a number of SNPs within the 5.8S rRNA gene (and thus within the 5.8S rRNA molecule) are unique to fungal eukaryotes (including yeasts), such as mammalian (e.g., human) fungal pathogens *Candida albicans*, *Ajellomyces capsulatus*, *Stachybotrys* sp., *Scedosporium apiospermum*, *Fusarium* sp., *Aspergillus fumigatus* and *Cryptococcus neoformans*, and can thus be used to differentiate such fungal cells from mammalian cells. Because the 5.8S rRNA molecule is not present in prokaryotes, the same SNPs can be used to distinguish fungal cells from prokaryotes such as bacteria. As such, these SNPs can be used to determine the presence of fungal cells in a sample.

SNPs at any one of positions corresponding to positions 142, 144, 146, 147, 148, 154, 157, 164, 167, 185, 187, 188, 194, 197, 213, 215, 216, 219, 223, 231, 232, 236, 245, 251, 256 of the *Candida albicans* 5.8S rRNA gene set forth in SEQ ID NO:2 can be used to identify the presence of fungal cells such as *Candida albicans*, *Ajellomyces capsulatus*, *Stachybotrys* sp., *Scedosporium apiospermum*, *Fusarium* sp., *Aspergillus fumigatus* and *Cryptococcus neoformans* in a sample, and distinguish them from mammalian cells. The SNPs at these positions in the 5.8S rRNA gene of fungi and mammalian cells are shown in Table 19.

TABLE 19

| SNP Position | Fungi | Mammals |
| --- | --- | --- |
| 142 | C | T |
| 144 | A | G |
| 146 | A | G |
| 147 | A | G |

TABLE 19-continued

| SNP Position | Fungi | Mammals |
| --- | --- | --- |
| 148 | C | T |
| 154 | T | A |
| 157 | T | C |
| 164 | C/G | T |
| 167 | A | G |
| 185 | G | T |
| 187 | A | G |
| 188 | A | C |
| 194 | T | G |
| 197 | G | T |
| 213 | A | G |
| 215 | T | C |
| 216 | T | A |
| 219 | G | T |
| 223 | A | Absent |
| 231 | A/G | C |
| 232 | T | A |
| 236 | T | C |
| 245 | A/C | Absent |
| 251 | C | G |
| 256 | T | G |

Thus, the invention provides methods for rapidly detecting the presence of fungal cells in a sample, by analyzing nucleic acid from the sample for SNPs at any one of positions corresponding to positions 142, 144, 146, 147, 148, 154, 157, 164, 167, 185, 187, 188, 194, 197, 213, 215, 216, 219, 223, 231, 232, 236, 245, 251, 256 of the *Candida albicans* 5.8S rRNA gene set forth in SEQ ID NO:2, wherein a C at position 142; an A at position 144; an A at position 146; an A at position 147; a C at position 148; a T at position 154; a T at position 157; a C or G at position 164; an A at position 167; a G at position 185; an A at position 187; an A at position 188; a T at position 194; a G at position 197; an A at position 213; a T at position 215; a T at position 216; a G at position 219; an A at position 223; a G or A at position 231; a T at position 232; a T at position 236; a C or A at position 245; a C at position 251; or a T at position 256 indicates the presence of a fungal cell. In contrast, the 5.8S rRNA gene of mammalian cells contains a T at position 142; a G at position 144; a G at position 146; a G at position 147; a T at position 148; an A at position 154; a C at position 157; a T at position 164; a G at position 167; a T at position 185; a G at position 187; a C at position 188; a G at position 194; a T at position 197; a G at position 213; a C at position 215; an A at position 216; a T at position 219; nothing at position 223; a C at position 231; an A at position 232; a C at position 236; nothing at position 245; a G at position 251; or a G at position 256. The fungal cells identified by this method can include, for example, *Candida albicans*, *Ajellomyces capsulatus*, *Stachybotrys* sp., *Scedosporium apiospermum*, *Fusarium* sp., *Aspergillus fumigatus* and *Cryptococcus neoformans*.

2.5 Identification of Mammalian (e.g., Human) Fungal Pathogens Using SNPs in 5.8S rRNA Several fungal species are known mammalian (e.g., human) pathogens. These include *Candida albicans*, *Candida tropicalis*, *Candida parapsilosis*, *Candida krusei*, *Candida glabrata*, *Ajellomyces capsulatus*, *Stachybotrys* sp., *Scedosporium apiospermum*, *Fusarium* sp., *Aspergillus fumigatus* and *Cryptococcus neoformans*. A combination of 4 SNPs in the 5.8S rRNA gene (and thus a combination of 4 SNPs in the 5.8S rRNA molecule or a DNA copy thereof) can be used to accurately identify and differentiate each of these species.

The combinations of 4 SNPs that can be used to identify and differentiate the eleven mammalian (e.g., human) fungal pathogens include those at position 254; one of positions 160 or 255; and any 2 of positions 163, 164, 165, 196, 202, 223, 224 and 259, with numbering corresponding to the *Candida albicans* 5.8S rRNA gene set forth in SEQ ID NO:2. Table 20 sets forth the SNPs at each position for each pathogen. Thus, the present invention provides methods for determining the identity of a mammalian (e.g., human) fungal pathogen in a sample by analyzing nucleic acid from the sample for at least 4 SNPs in the 5.8S rRNA gene, wherein the SNPs are at position 254; one of positions 160 or 255; and any 2 of positions 163, 164, 165, 196, 202, 223, 224 and 259.

TABLE 20

| | SNP position | | | | | | | | | |
|---|---|---|---|---|---|---|---|---|---|---|
| | 160 | 163 | 164 | 165 | 196 | 202 | 223 | 224 | 254 | 255 | 259 |
| *Candida albicans* | T | T | C | G | C | A | A | T | T | C | T |
| *Candida tropicalis* | T | T | C | G | C | A | A | T | T | T | T |
| *Candida parapsilosis* | T | T | C | G | A | A | A | T | T | T | T |
| *Candida krusei* | T | T | C | G | C | G | A | T | C | T | C |
| *Candida glabrata* | T | T | C | G | C | G | A | T | T | C | T |
| *Ajellomyces capsulatus* | T | C | G | A | A | G | A | T | T | C | T |
| *Stachybotrys* sp. | C | T | G | G | A | G | A | T | G | C | C |
| *Scedosporium apiospermum* | T | T | G | G | A | G | A | T | G | C | T |
| *Fusarium* sp. | C | T | G | G | A | G | A | T | G | C | T |
| *Aspergillus fumigatus* | T | C | G | G | A | G | A | T | C | C | T |
| *Cryptococcus neoformans* | C | C | C | A | A | G | A | T | T | T | T |

Because SNPs 164 and 223 can also be used to differentiate fungi from mammalian cells, combinations using SNPs at positions 164 or 223 are able to completely discriminate the eleven pathogenic fungal species in a mammalian background. Thus in one example, the present invention provides methods for determining the identity of a mammalian (e.g., human) fungal pathogen in a sample by analyzing nucleic acid from the sample for at least 4 SNPs in the 5.8S rRNA gene, wherein the SNPs include those at position 254; one of positions 160 or 255; position 164 and one of positions 163, 165, 196, 202, 223, 224 and 259. In another example, the methods include analyzing nucleic acid from the sample for at least 4 SNPs, wherein the SNPs includes those at position 254; one of positions 160 or 255; position 223 and one of positions 163, 164, 165, 196, 202, 224 and 259. Using such methods, the pathogenic fungal species can be accurately identified in a sample, including biological samples from mammals including human subjects.

Additionally, SNPs 163 and 164 can differentiate *Candida* species from other fungal pathogens. Thus in another example, the present invention provides methods for determining the identity of a mammalian (e.g., human) fungal pathogen in a sample by analyzing nucleic acid from the sample for at least two SNPs in a 5.8S rRNA gene, wherein: the at least two SNPs are at a position corresponding to position 163 of SEQ ID NO:2, and a position corresponding to position 164 of SEQ ID NO:2, wherein the presence of T at position 163 and C at position 164 indicates that the fungal pathogen in the sample is a *Candida* species. In relates examples, the present invention also provides methods for determining the presence or absence of a *Candida* species in a sample by analyzing nucleic acid from the sample for at least two SNPs in a 5.8S rRNA gene, wherein: the at least two SNPs are at a position corresponding to position 163 of SEQ ID NO:2, and a position corresponding to position 164 of SEQ ID NO:2, wherein the presence of T at position 163 and C at position 164 indicates the presence of a *Candida* species in the sample, and wherein the absence of T at position 163 and C at position 164 indicates the absence of a *Candida* species in the sample. In specific embodiments of the above examples, the *Candida* species is selected from *Candida albicans, Candida tropicalis, Candida parapsilosis, Candida krusei* and *Candida glabrata*.

3. Screening for Specific Polymorphisms to Classify Microbes According to the Invention Any method known in the art to detect one or more SNPs can be used in the methods described herein to classify and/or identify microbes in a sample. In particular embodiments, the methods also facilitate quantitation of the microbe in the sample, i.e. the number of bacteria and/or fungi in the sample is determined or estimated. Numerous methods are known in the art for determining the nucleotide occurrence at a particular position corresponding to a single nucleotide polymorphism in a sample. The various tools for the detection of polymorphisms include, but are not limited to, DNA sequencing, scanning techniques, hybridization based techniques, extension based analysis, incorporation based techniques, restriction enzyme based analysis and ligation based techniques.

The methods according to the present invention can identify the polymorphisms described herein within the 16S rRNA and/or 5.8S rRNA genes, within the 16S rRNA and/or 5.8S rRNA molecules or within DNA copies thereof, and for either strand. In some examples, the methods of detecting the polymorphisms utilise a first step of amplification, and amplification can be from the 16S rRNA and/or 5.8S rRNA genes or from DNA copies of the 16S rRNA and/or 5.8S rRNA molecules.

The nucleic acid may be from a biological sample from a subject or from an environmental sample, such as an air, soil or water sample, a filtrate, a food or manufactured product, or swab from a surface, such as from a medical instrument or work place surface. The subject may be a human subject or non-human subject, such as mammalian subject, such as a primate, livestock animal (e.g., sheep, cows, horses, donkeys, pigs, goats), laboratory test animal (e.g., rabbits, mice, rats, guinea pigs, hamsters), companion animal (e.g., cats, dogs) and captive wild animal (e.g., foxes, deer, dingoes). Biological samples from a subject may be from any part of the subject's body, including, but not limited to bodily fluids such as blood, saliva, or sputum, or urine, feces, cells, tissue or biopsies. In other examples, the nucleic acid is obtained from cultured cells. In particular examples, the nucleic acid analyzed is from a biological sample from a mammalian (e.g., human) subject presenting with SIRS. Such a subject may have sepsis and/or may be suspected of having sepsis.

The nucleic acid that is analysed according to the methods of present invention may be analysed while within the sample, or may first be extracted from the sample, e.g. isolated from the sample prior to analysis. Any method for isolating nucleic acid from a sample can be used in the methods of the present invention, and such methods are well known to those of skill in the art. The extracted nucleic acid can include DNA and/or RNA (including mRNA or rRNA). In some examples, a further step of reverse transcription can be included in the methods prior to analysis. Thus, the nucleic acid to be analysed can include the 16S rRNA gene, 16S rRNA, DNA copy of the 16S rRNA, 5.8S rRNA gene, 5.8S rRNA, DNA copy of the 5.8S rRNA, or any combination thereof. The nucleic acid can also contain portions of include the 16S rRNA gene, 16S rRNA, DNA copy of the 16S rRNA, 5.8S rRNA gene, 5.8S rRNA, or DNA copy of the 5.8S rRNA, providing the portions contain the nucleic acid positions that are being analysed for SNPs.

In some instances, the methods include amplification of the nucleic acid. In such instances, suitable nucleic acid amplification techniques are well known to a person of ordinary skill in the art, and include polymerase chain reaction (PCR) as for example described in Ausubel et al., Current Protocols in Molecular Biology (John Wiley & Sons, Inc. 1994-1998) strand displacement amplification (SDA) as for example described in U.S. Pat. No. 5,422,252; rolling circle replication (RCR) as for example described in Liu et al., (1996, J. Am. Chem. Soc. 118: 1587-1594 and International application WO 92/01813) and Lizardi et al., (International Application WO 97/19193); nucleic acid sequence-based amplification (NASBA) as for example described by Sooknanan et al., (1994, Biotechniques 17: 1077-1080); ligase chain reaction (LCR); simple sequence repeat analysis (SSR); branched DNA amplification assay (b-DNA); transcription amplification and self-sustained sequence replication; and Q-β replicase amplification as for example described by Tyagi et al., (1996, Proc. Natl. Acad. Sci. USA 93: 5395-5400).

Such methods can utilize one or more oligonucleotide probes or primers, including, for example, an amplification primer pair, that selectively hybridize to a target polynucleotide, which contains one or more SNPs. Oligonucleotide probes useful in practicing a method of the invention can include, for example, an oligonucleotide that is complementary to and spans a portion of the target polynucleotide, including the position of the SNP, wherein the presence of a specific nucleotide at the polymorphic site (i.e., the SNP) is detected by the presence or absence of selective hybridization of the probe. Such a method can further include contacting the target polynucleotide and hybridized oligonucleotide with an endonuclease, and detecting the presence or absence of a cleavage product of the probe, depending on whether the nucleotide occurrence at the polymorphic site is complementary to the corresponding nucleotide of the probe.

Primers may be manufactured using any convenient method of synthesis. Examples of such methods may be found in "Protocols for Oligonucleotides and Analogues; Synthesis and Properties", Methods in Molecular Biology Series; Volume 20; Ed. Sudhir Agrawal, Humana ISBN: 0-89603-247-7; 1993. The primers may also be labeled to facilitate detection.

Any method useful for the detection of SNPs can be used in the present invention, and many different methods are known in the art for SNP genotyping (for review see Syvänen, A. C. (2001) Nat. Rev. Genet. 2, 930-942 (2001); Kwok, P. Y. (2001) Ann Rev Genomics Hum Genet 2, 235-258; Kim S, Misra A. (2007) Ann Rev Biomed Eng. 9:289-320). Such methodology may consist of the use of three steps in succession, including a "reaction" (e.g. hybridization, ligation, extension and cleavage) followed by "separation" (e.g. solid phase microtitre plates, microparticles or arrays, gel electrophoresis, solution-phase homogenous or semi-homogenous) followed by "detection" (e.g. indirect colorimetric, mass spectrometry, fluorescence, fluorescence resonance energy transfer, fluorescence polarization and chemiluminescence). No single ideal SNP genotyping method exists for all applications, and it is well within the skill of a skilled artisan to determine the most appropriate method given the various parameters, such as sample size and number of SNPs to be analysed.

Example technologies that particularly lend themselves to clinical use and that rely on querying small numbers of SNPs, are fast, sensitive (through amplification of nucleic acid in the sample), one-step, output measured in real-time, able to be multiplexed and automated, comparatively inexpensive, and accurate include, but are not limited to, TaqMan® assays (5' nuclease assay, Applied Biosystems), molecular beacon probes such as LUX® (Invitrogen) or Scorpion® probes (Sigma Aldrich), and Template Directed Dye Incorporation (TDI, Perkin Elmer). For example, TaqMan® (Applied Biosystems) uses a combination of hybridization with allele-specific probes, solution phase homogenous, and fluorescence resonance energy transfer. The TaqMan® assay relies on forward and reverse primers and Taq DNA polymerase to amplify nucleic acid in conjunction with the 5'-nuclease activity of Taq DNA polymerase to degrade a labeled probe designed to bind across the SNP site(s). Reaction, separation and detection can all be performed at the same time and results read in real-time as the reaction proceeds. While such an approach does not lend itself to analyzing large numbers of SNPs simultaneously it is particularly suitable for querying small numbers of SNPs quickly, sensitively and accurately at a reasonable cost.

Although some methods may be more suitable than others, any method known in the art to detect one or more SNPs can be used in the methods described herein to classify and/or identify microbes in a sample Non-limiting examples of such methods are described below.

3.1 Nucleic Acid Sequencing Techniques

In some embodiments, the polymorphism is identified through nucleic acid sequencing techniques. Specifically, amplification products which span a SNP locus can be sequenced using traditional sequence methodologies (e.g., the "dideoxy-mediated chain termination method", also known as the "Sanger Method" (Sanger, F., et al., (1975) J. Molecular, Biol. 94: 441; Prober et al., 1987, Science, 238: 336-340) and the "chemical degradation method", also known as the "Maxam-Gilbert method" (Maxam, A. M., et al., (1977) Proc. Natl. Acad. Sci. (U.S.A.) 74: 560), both references herein incorporated by reference to determine the nucleotide occurrence at the SNP loci.

Boyce-Jacino, et al., U.S. Pat. No. 6,294,336 provides a solid phase sequencing method for determining the sequence of nucleic acid molecules (either DNA or RNA) by utilizing a primer that selectively binds a polynucleotide target at a site wherein the SNP is the most 3' nucleotide selectively bound to the target. Other sequencing technologies such as Denaturing High Pressure Liquid Chromatography or mass spectroscopy may also be employed.

In other illustrative examples, the sequencing method comprises a technique known as Pyrosequencing™. The approach is based on the generation of pyrophosphate whenever a deoxynucleotide is incorporated during polymerization of DNA. The generation of pyrophosphate is coupled to a luciferase-catalysed reaction resulting in light emission if the particular deoxynucleotide added is incorporated, yielding a quantitative and distinctive pyrogram. Sample processing includes PCR amplification with a biotinylated primer, isolation of the biotinylated single strand amplicon on streptavidin coated beads (or other solid phase) and annealing of a sequencing primer. Samples are then analysed by a Pyrosequence™, which adds a number of enzymes and substrates required for the indicator reaction, including sulfurylase and luciferase, as well as a pyrase for degradation of unincorporated nucleotides. The sample is then interrogated by addition of the four deoxynucleotides. Light emission can be detected by a charge coupled device camera (CCD) and is proportional to the number of nucleotides incorporated. Results are automatically assigned by pattern recognition.

Alternatively, methods of the invention can identify nucleotide occurrences at polymorphic sites within a nucleic acid sequence using a "micro-sequencing" method. Micro-sequencing methods determine the identity of only a single nucleotide at a "predetermined" site. Such methods have particular utility in determining the presence and identity of polymorphisms in a target polynucleotide. Such micro-sequencing methods, as well as other methods for determining the nucleotide occurrence at a polymorphic site are discussed in Boyce-Jacino et al., U.S. Pat. No. 6,294,336, incorporated herein by reference.

Micro-sequencing methods include the Genetic Bit Analysis™ method disclosed by Goelet, P. et al. WO 92/15712. Additional, primer-guided, nucleotide incorporation procedures for assaying polymorphic sites in DNA have also been described (Komher, J. S. et al, (1989) Nucl. Acids. Res. 17: 7779-7784; Sokolov, B. P., (1990) Nucl. Acids Res. 18: 3671; Syvanen, A. C, et al., (1990) Genomics, 8: 684-692; Kuppuswamy, M. N. et al., (1991) Proc. Natl. Acad. Sci. (U.S.A.) 88: 1143-1147; Prezant, T. R. et al, (1992) Hum. Mutat. 1: 159-164; Ugozzoli, L. et al., 1992, GATA, 9: 107-112; Nyren, P. et al., (1993) Anal. Biochem. 208: 171-175; and Wallace, WO89/10414). These methods differ from Genetic Bit Analysis™ in that they all rely on the incorporation of labeled deoxynucleotides to discriminate between bases at a polymorphic site. In such a format, since the signal is proportional to the number of deoxynucleotides incorporated, polymorphisms that occur in runs of the same nucleotide can result in signals that are proportional to the length of the run (Syvanen, A. C., et al., (1993) Amer. J. Hum. Genet. 52: 46-59).

Further micro-sequencing methods have been provided by Mundy, C. R. (U.S. Pat. No. 4,656,127) and Cohen, D. et al (French Patent 2,650,840; PCT Publication No. WO91/02087) which involve a solution-based method for determining the identity of a nucleotide of a polymorphic site. As in the Mundy method of U.S. Pat. No. 4,656,127, a primer is employed that is complementary to allelic sequences immediately 3' to a polymorphic site.

In other illustrative examples, Macevicz (U.S. Pat. No. 5,002,867), for example, describes a method for determining nucleic acid sequences via hybridization with multiple mixtures of oligonucleotide probes. In accordance with such methods, the sequence of a target polynucleotide is determined by permitting the target to sequentially hybridize with sets of probes having an invariant nucleotide at one position, and variant nucleotides at other positions. The Macevicz method determines the nucleotide sequence of the target by hybridizing the target with a set of probes, and then determining the number of sites that at least one member of the set is capable of hybridizing to the target (i.e., the number of "matches"). This procedure is repeated until each member of a set of probes has been tested.

Alternatively, the template-directed dye-terminator incorporation assay with fluorescence polarization detection (FP-TDI) assay (Chen et al., 1999) is a version of the primer extension assay that is also called mini-sequencing or the single base extension assay (Syvanen, 1994). The primer extension assay is capable of detecting SNPs. The DNA sequencing protocol ascertains the nature of the one base immediately 3' to the SNP-specific sequencing primer that is annealed to the target DNA immediately upstream from the polymorphic site. In the presence of DNA polymerase and the appropriate dideoxyribonucleoside triphosphate (ddNTP), the primer is extended specifically by one base as dictated by the target DNA sequence at the polymorphic site. By determining which ddNTP is incorporated, the allele(s) present in the target DNA can be inferred.

3.2 Polymorphism Hybridization Based Techniques

Hybridization techniques for detecting polymorphisms within a nucleotide sequence can include, but are not restricted to the TaqMan® assay (Applied Biosystems), dot blots, reverse dot blot, Multiplex-allele-specific diagnostic assays (MASDA), Dynamic allele-specific hybridization (DASH) Jobs et al., (Genome Res (2003) 13: 916-924), molecular beacons and Southern blots.

The TaqMan® assay (also known as a 5' nuclease assay or 5' digestion assay) for identifying SNPs within a nucleotide sequence is based on the nuclease activity of Taq polymerase that displaces and cleaves the oligonucleotide probes hybridized to the target DNA, generating a fluorescent signal. TaqMan® probes specific for a particular SNP are required, with each probe having different fluorescent dyes attached to the 5' end and a quencher attached to the 3' end. When the probes are intact, the quencher interacts with the fluorophore by fluorescence resonance energy transfer (FRET), quenching their fluorescence. During the PCR annealing step, the TaqMan® probes hybridize to the target DNA. In the extension step, the fluorescent dye is cleaved by the nuclease activity of the Taq polymerase, leading to an increase in fluorescence of the reporter dye. Mismatch probes are displaced without fragmentation. The genotype of a sample is determined by measuring the signal intensity of the two different dyes.

Another useful SNP identification method includes DASH (dynamic allele-specific hybridization), which encompasses dynamic tracking of probe (oligonucleotide) to target (PCR product) hybridization as the reaction temperature is steadily increased to identify polymorphisms (Prince, J. A et al., (2001) Genome Res, 11(1): 152-162).

In some embodiments, multiplex-allele-specific diagnostic assays (MASDA) can be used for the analysis of a large number of samples (>500). MASDA utilizes oligonucleotide hybridization to interrogate DNA sequences. Multiplex DNA samples are immobilized on a solid support and a single hybridization is performed with a pool of allele-specific oligonucleotide (ASO) probes. Any probes complementary to specific polymorphisms present in a given sample are in effect affinity purified from the pool by the target DNA. Sequence-specific band patterns (fingerprints), generated by chemical or enzymatic sequencing of the bound ASO(s), easily identify the specific mutation(s).

There are several alternative hybridization-based techniques, including, among others, molecular beacons, and Scorpion® probes (Tyagi, S and Kramer, F. R., (1996) Nat. Biotechnol, 14: 303-308; Thelwell et al., (2000) Nucleic Acid Res. 28(19): 3752-3761). Molecular beacons are comprised of oligonucleotides that have a fluorescent reporter and quencher dyes at their 5' and 3' ends. The central portion of the oligonucleotide hybridizes across the target sequence, but the 5' and 3' flanking regions are complementary to each other. When not hybridised to their target sequence, the 5' and 3' flanking regions hybridise to form a stem-loop structure, and there is little fluorescence because of the proximity of the reporter and quencher dyes. However, upon hybridization to their target sequence, the dyes are separated and there is a large increase in fluorescence. Mismatched probe-target hybrids dissociate at substantially lower temperature than exactly complementary hybrids. There are a number of variations of the "beacon" approach. Scorpion® probes are similar but incorporate a PCR primer sequence as part of the probe. A more recent "duplex" format has also been developed.

In some embodiments, a further method of identifying a SNP comprises the SNP-IT™ method (Orchid BioSciences, Inc., Princeton, N.J.). In general, SNP-IT™ is a 3-step primer extension reaction. In the first step a target polynucleotide is isolated from a sample by hybridization to a capture primer, which provides a first level of specificity. In a second step the capture primer is extended from a terminating nucleotide trisphosphate at the target SNP site, which provides a second level of specificity. In a third step, the extended nucleotide trisphosphate can be detected using a variety of known formats, including: direct fluorescence, indirect fluorescence, an indirect colorimetric assay, mass spectrometry, fluorescence polarization, etc. Reactions can be processed in 384-well format in an automated format using a SNPstream.™ instrument (Orchid BioSciences, Inc., Princeton, N.J.).

In these embodiments, the amplification products can be detected by Southern blot analysis with or without using radioactive probes. In one such method, for example, a small sample of DNA containing a very low level of the nucleic acid sequence of the polymorphic locus is amplified, and analyzed via a Southern blotting technique or similarly, using dot blot analysis. The use of non-radioactive probes or labels is facilitated by the high level of the amplified signal. Alternatively, probes used to detect the amplified products can be directly or indirectly detectably labeled, for example, with a radioisotope, a fluorescent compound, a bioluminescent compound, a chemiluminescent compound, a metal chelator or an enzyme.

Hybridization conditions, such as salt concentration and temperature can be adjusted for the nucleotide sequence to be screened. Southern blotting and hybridizations protocols are described in Current Protocols in Molecular Biology (Greene Publishing Associates and Wiley-Interscience), pages 2.9.1-2.9.10. Probes can be labeled for hybridization with random oligomers and the Klenow fragment of DNA polymerase. Very high specific activity probes can be obtained using commercially available kits such as the Ready-To-Go DNA Labeling Beads (Pharmacia Biotech), following the manufacturer's protocol. Possible competition of probes having high repeat sequence content, and stringency of hybridization and wash down will be determined individually for each probe used. Alternatively, fragments of a candidate sequence may be generated by PCR, the specificity may be verified using a rodent-human somatic cell hybrid panel, and sub-cloning the fragment. This allows for a large prep for sequencing and use as a probe. Once a given gene fragment has been characterized, small probe preparations can be achieved by gel or column purifying the PCR product.

Suitable materials that can be used in the dot blot, reverse dot blot, multiplex, and MASDA formats are well-known in the art and include, but are not limited to nylon and nitrocellulose membranes.

3.3 Polymorphism Scanning Techniques

Scanning techniques contemplated by the present invention for detecting polymorphisms within a nucleotide sequence can include, but are not restricted to, chemical mismatch cleavage (CMC) (Saleeba, J. A et al., (1992) Huma. Mutat, 1: 63-69), mismatch repair enzymes cleavage (MREC) (Lu, A. L and Hsu, I. C., (1992) Genomics, 14(2): 249-255), chemical cleavage techniques, denaturing gradient gel electrophoresis (DGGE) Wartell et al., (1990) Nucl. Acids Res. 18: 2699-2705 and; Sheffield et al., (1989) Proc. Natl. Acad. Sci. USA 86: 232-236), temperature gradient gel electrophoresis (TGGE) (Salimullah, et al., (2005) Cellular and Mol. Biol. Letts, 10: 237-245), constant denaturant gel electrophoresis (CDGE), single strand conformation polymorphism (SSCP) analysis (Kumar, D et al., (2006) Genet. Mol. Biol, 29(2): 287-289), heteroduplex analysis (HA) (Nagamine, C. M et al., (1989) Am. J. Hum. Genet, 45: 337-339), microsatellite marker analysis and single strand polymorphism assays (SSPA).

In some embodiments, the SNPs of the present invention are detected through CMC, wherein a radiolabeled DNA wild type sequence (probe) is hybridized to an amplified sequence containing the putative alteration to form a heteroduplex. A chemical modification, followed by piperidine cleavage, is used to remove the mismatch bubble in the heteroduplex. Gel electrophoresis of the denatured heteroduplex and autoradiography allow visualizing the cleavage product. Osmium tetroxide is used for the modification of mispaired thymidines and hydroxylamine for mismatched cytosines. Additionally, labeling the antisense strand of the probe DNA allows the detection of adenosine and guanosine mismatches. The chemical cleavage of mismatch can be used to detect almost 100% of mutations in long DNA fragments. Moreover, this method provides the precise characterization and the exact location of the mutation within the tested fragment. Recently, the method has been amended to make CMC more suitable for automation by using fluorescent primers also enabling multiplexing and thereby reducing the number of manipulations. Alternatively, fluorescently labeled dUTPs incorporated via PCR allow the internal labeling of both target and probe DNA strands and therefore labeling of each possible hybrid, doubling the chances of mutation detection and virtually guaranteeing 100% detection.

In other embodiments, the mismatch repair enzymes cleavage (MREC) assay is used to identify SNPs of the present invention. MREC relies on nicking enzyme systems specific for mismatch-containing DNA. The sequence of interest is amplified by PCR and homo- and heteroduplex species may be generated at the end of the PCR, by denaturing and allowing to re-anneal the amplified products. These hybrids are treated with mismatch repair enzymes and then analysed by denaturing gel electrophoresis. The MREC assay makes use of three mismatch repair enzymes. The MutY endonuclease removes adenines from the mismatches and is useful to detect both A/T and C/G transversions and G/C and T/A transitions. Mammalian thymine glycosylase removes thymines from T/G, T/C, and T/T mismatches and is useful to detect G/C and A/T transitions as well as A/T and G/C and T/A and A/T transversions. The all-type endonuclease or topoisomerase I from human or calf thymus can recognize all eight mismatches and can be used to scan any nucleotide substitution. MREC can use specific labels which can be incorporated into both DNA strands, thus allowing all four possible nucleotide substitutions in a give site to be identified.

In some embodiments, chemical cleavage analysis as described in U.S. Pat. No. 5,217,863 (by R. G. H. Cotton) is used for identifying SNPs within nucleotide sequences. Like heteroduplex analysis, chemical cleavage detects different properties that result when mismatched allelic sequences hybridize with each other. Instead of detecting this difference as an altered migration rate on a gel, the difference is detected in altered susceptibility of the hybrid to chemical cleavage using, for example, hydroxylamine, or osmium tetroxide, followed by piperidine.

Among the cleavage methods contemplated by the present invention, RNAse A relies on the principle of heteroduplex mismatch analysis. In the RNAse A cleavage method, RNA-DNA heteroduplex between radiolabeled riboprobe and a DNA, obtained by PCR amplification, is enzymatically cleaved by RNAse A, by exploiting the ability of RNAse A to cleave single-stranded RNA at the points of mismatches in RNA:DNA hybrids. This is followed by electrophoresis and autoradiography. The presence and location of a mutation are indicated by a cleavage product of a given size (Meyers, R. M et al., (1985) Science, 230: 1242-1246 and; Gibbs, R. A and Caskey, T, 1987, Science, 236: 303-305).

DNA probes also can be used to detect mismatches, through enzymatic or chemical cleavage. See, e.g., Cotton, et al., (1988) Proc. Natl. Acad. Sci. USA 85: 4397; Shenk et al., (1975) Proc. Natl. Acad. Sci. USA 72: 989; and Novack et al., (1986) Proc. Natl. Acad. Sci. USA 83: 586.

In some embodiments, the Invader® assay (Third Wave™ Technology) is employed to scan for polymorphisms within the 16S rRNA and/or 5.8S rRNA genes of the present invention. For example, the Invader® assay is based on the specificity of recognition, and cleavage, by a Flap endonuclease, of the three dimensional structure formed when two overlapping oligonucleotides hybridize perfectly to a target DNA (Lyamichev, V et al., (1999) Nat Biotechnol, 17: 292-296).

Alternatively, denaturing gradient gel electrophoresis (DGGE) is a useful technique to separate and identify sequence variants. DGGE is typically performed in constant-concentration polyacrylamide gel slabs, cast in the presence of linearly increasing amounts of a denaturing agent (usually formamide and urea, cathode to anode). A variant of DGGE employs temperature gradients along the migration path and is known as TGGE. Separation by DGGE or TGGE is based on the fact that the electrophoretic mobility in a gel of a partially melted DNA molecule is greatly reduced as compared to an unmelted molecule.

In some embodiments, constant denaturant gel electrophoresis (CDGE) is useful for detecting SNPs within a nucleotide sequence, as described in detail in Smith-Sorenson et al., (1993) Human Mutation 2: 274-285 (see also, Anderson & Borreson, (1995) Diagnostic Molecular Pathology 4: 203-211). A given DNA duplex melts in a predetermined, characteristic fashion in a gel of a constant denaturant. Mutations alter this movement. An abnormally migrating fragment is isolated and sequenced to determine the specific mutation.

In other embodiments, single-strand conformation polymorphism (SSCP) analysis provides a method for detecting SNPs of the present invention. SSCP is a method based on a change in mobility of separated single-strand DNA molecules in non-denaturing polyacrylamide gel electrophoresis. Electrophoretic mobility depends on both size and shape of a molecule, and single-stranded DNA molecules fold back on themselves and generate secondary structures, which are determined by intra-molecular interactions in a sequence dependent manner. A single nucleotide substitution can alter the secondary structure and, consequently, the electrophoretic mobility of the single strands, resulting in band shifts on autoradiographs. The ability of a given nucleotide variation to alter the conformation of the single strands is not predictable on the basis of an adequate theoretical model and base changes occurring in a loop or in a long stable stem of the secondary structure might not be detected by SSCP. Standard SSCP reaches maximal reliability in detecting sequence alterations in fragments of 150-200 bp. More advanced protocols, allowing the detection of mutations at sensitivity equal to that of the radioactively-based SSCP analysis, have been developed. These methods use fluorescence-labeled primers in the PCR and analyze the products with a fluorescence-based automated sequencing machine. Multi-colour fluorescent SSCP also allows including an internal standard in every lane, which can be used to compare data from each lane with respect to each other. Other variants to increase the detection rate include a dideoxy sequencing approach based on dideoxy fingerprinting (ddF) and restriction endonuclease fingerprinting (REF).

The ddF method is a combination of SSCP and Sanger dideoxy sequencing, which involves non-denaturing gel electrophoresis of a Sanger sequencing reaction with one dideoxynucleotide. In this way, for example, a 250-bp fragment can be screened to identify a SNP. REF is a more complex modification of SSCP allowing the screening of more than 1 kb fragments. For REF, a target sequence is amplified with PCR, digested independently with five to six different restriction endonucleases and analyzed by SSCP on a non-denaturing gel. In the case of six restriction enzymes being used, a sequence variation will be present in six different restriction fragments, thus generating 12 different single-stranded segments. A mobility shift in any one of these fragments is sufficient to pinpoint the presence of a SNP of the invention. The restriction pattern obtained enables localization of an alteration in the region examined.

In some embodiments, heteroduplex analysis (HA) detects single base substitutions in PCR products or nucleotide sequences. HA can be rapidly performed without radioisotopes or specialized equipment. The HA method takes advantage of the formation of heteroduplexes between sequences with differing nucleotides at one or more positions by heating and renaturing of PCR products. Due to a more open double-stranded configuration surrounding the mismatched bases, heteroduplexes migrate slower than their corresponding homoduplexes, and are then detected as bands of reduced mobility. The ability of a particular single base substitution to be detected by the HA method cannot be predicted merely by knowing the mismatched bases since the adjacent nucleotides have a substantial effect on the configuration of the mismatched region and length-based separation will clearly miss nucleotide substitutions. Optimization of the temperature, gel cross-linking and concentration of acrylamide used as well as glycerol and sucrose enhance the resolution of mutated samples. The HA method can be rapidly performed without radioisotopes or specialized equipment and screens large numbers of samples for known mutations and polymorphisms in sequenced genes. When HA is used in combination with SSCP, up to 100% of all alterations in a DNA fragment can be easily detected.

In some embodiments, the use of proteins that recognize nucleotide mismatches, such as the E. coli mutS protein can be used to detect a polymorphism within 16S rRNA or 5.8S rRNA of the present invention (Modrich, (1991) Ann. Rev. Genet. 25: 229-253). In the mutS assay, the protein binds only to sequences that contain a nucleotide mismatch in a heteroduplex between two sequences.

In further embodiments, polymorphism detection can be performed using microsatellite marker analysis. Microsatellite markers with an average genome spacing, for example of about 10 centimorgans (cM) can be employed using standard DNA isolation methods known in the art.

SSPA analysis and the closely related heteroduplex analysis methods described above may be used for screening for single-base polymorphisms (Orita, M. et al., (1989) Proc Natl Acad Sci USA, 86: 2766).

3.4 Nucleotide Arrays and Gene Chips for Polymorphism Analysis

The invention further contemplates methods of identifying SNPs through the use of an array of oligonucleotides, wherein discrete positions on the array are complementary to one or more of the sequences containing the SNPs of the present invention, e.g. oligonucleotides of at least 12 nt, at least about 15 nt, at least about 18 nt, at least about 20 nt, or at least about 25 nt, or longer, and including the sequence flanking the polymorphic position. Such an array may comprise a series of oligonucleotides, each of which can specifically hybridize to a different polymorphism. For examples of arrays, see Hacia et al. (1996, Nat. Genet. 14: 441-447 and De Risi et al., (1996, Nat. Genet. 14: 457-460).

A nucleotide array can include all or a subset of the polymorphisms of the invention, as required. One or more polymorphic forms may be present in the array. The oligonucleotide sequence on the array is generally at least about 12 nt in length, at least about 15 nt, at least about 18 nt, at least about 20 nt, or at least about 25 nt, or more, such as 100 to 200 nt in length. For examples of arrays, see Ramsay (1998, Nature Biotech. 16: 40-44; Hacia et al., (1996, Nature Genetics 14: 441-447; Lockhart et al., (1996, Nature Biotechnol. 14:1675-1680; and De Risi et al., (1996, Nature Genetics 14: 457-460).

A number of methods are available for creating microarrays of biological samples, such as arrays of DNA samples to be used in DNA hybridization assays. Examples of such arrays are discussed in detail in PCT Application number. WO95/35505 (1995); U.S. Pat. No. 5,445,934, (1995); and Drmanac et al., (1993, Science 260:1649-1652). Yershov et al., (1996, Genetics 93: 4913-4918) describe an alternative construction of an oligonucleotide array. The construction and use of oligonucleotide arrays are reviewed by Ramsay (1998) supra.

Methods of using high-density oligonucleotide arrays for identifying polymorphisms within nucleotide sequences are known in the art. For example, Milosavljevic et al., (1996, Genomics 37: 77-86) describe DNA sequence recognition by hybridization to short oligomers. See also, Drmanac et al., (1998, Nature Biotech. 16: 54-58); and Drmanac and Drmanac, (1999, Methods Enzymol. 303: 165-178). The use of arrays for identification of unknown mutations is proposed by Ginot, (1997, Human Mutation 10: 1-10).

Detection of known mutations is described in Hacia et al. (1996, Nat. Genet. 14: 441-447; Cronin et al., (1996) Human Mut. 7: 244-255; and others. The use of arrays in genetic mapping is discussed in Chee et al., (1996, Science 274: 610-613; Sapolsky and Lishutz, 1996, Genomics 33: 445-456; and Shoemaker et al., 1996, Nat. Genet. 14: 450-456) perform quantitative phenotypic analysis of yeast deletion mutants using a parallel bar-coding strategy.

Quantitative monitoring of gene expression patterns with a complementary DNA microarray is described in Schena et al., (1995, Science 270: 467; DeRisi et al., 1997, Science 270: 680-686) explore gene expression on a genomic scale. Wodicka et al., (1997, Nat. Biotech. 15: 1-15) perform genome wide expression monitoring in S. cerevisiae.

High-density microarrays of oligonucleotides are known in the art and are commercially available. The sequence of oligonucleotides on the array will correspond to a known target sequences. The length of oligonucleotide present on the array is an important factor in how sensitive hybridization will be to the presence of a mismatch. Usually oligonucleotides will be at least about 12 nt in length, more usually at least about 15 nt in length, preferably at least about 20 nt in length and more preferably at least about 25 nt in length, and will be not longer than about 35 nt in length, usually not more than about 30 nt in length.

Methods of producing large arrays of oligonucleotides are described in U.S. Pat. No. 5,134,854 (Pirrung et al.), and U.S. Pat. No. 5,445,934 (Fodor et al.) using light-directed synthesis techniques. Using a computer-controlled system, a heterogeneous array of monomers is converted, through simultaneous coupling at a number of reaction sites, into a heterogeneous array of polymers. Alternatively, microarrays are generated by deposition of pre-synthesized oligonucleotides onto a solid substrate, for example as described in International Publication WO 95/35505.

Microarrays can be scanned to detect hybridization of the labeled genome samples. Methods and devices for detecting fluorescently marked targets on devices are known in the art. Generally such detection devices include a microscope and light source for directing light at a substrate. A photon counter detects fluorescence from the substrate, while an x-y translation stage varies the location of the substrate. A confocal detection device that may be used in the subject methods is described in U.S. Pat. No. 5,631,734. A scanning laser microscope is described in Shalon et al. (1996, Genome Res. 6: 639). A scan, using the appropriate excitation line, is performed for each fluorophore used. The digital images generated from the scan are then combined for subsequent analysis. For any particular array element, the ratio of the fluorescent signal from one nucleic acid sample is compared to the fluorescent signal from the other nucleic acid sample, and the relative signal intensity determined.

Methods for analyzing the data collected by fluorescence detection are known in the art. Data analysis includes the steps of determining fluorescent intensity as a function of substrate position from the data collected, removing outliers, i.e., data deviating from a predetermined statistical distribution, and calculating the relative binding affinity of the targets from the remaining data. The resulting data may be displayed as an image with the intensity in each region varying according to the binding affinity between targets and probes.

Nucleic acid analysis via microchip technology is also applicable to the present invention. In this technique, thousands of distinct oligonucleotide probes can be applied in an array on a silicon chip. A nucleic acid to be analyzed is fluorescently labeled and hybridized to the probes on the chip. It is also possible to study nucleic acid-protein interactions using these nucleic acid microchips. Using this technique one can determine the presence of mutations, sequence the nucleic acid being analyzed, or measure expression levels of a gene of interest. The method is one of parallel processing of many, even thousands, of probes at once and can tremendously increase the rate of analysis.

Alteration of mRNA transcription can be detected by any techniques known to persons of ordinary skill in the art. These include Northern blot analysis, PCR amplification and RNase protection. Diminished mRNA transcription indicates an alteration of the sequence.

The array/chip technology has already been applied with success in numerous cases. For example, the screening of mutations has been undertaken in the BRCA 1 gene, in S. cerevisiae mutant strains, and in the protease gene of HIV-1 virus (Hacia et al., 1996; Shoemaker et al., 1996; Kozal et al., 1996). Chips of various formats for use in detecting SNPs can be produced on a customized basis.

An array-based tiling strategy useful for detecting SNPs is described in EP 785280. Briefly, arrays may generally be "tiled" for a large number of specific polymorphisms. "Tiling" refers to the synthesis of a defined set of oligonucleotide probes that are made up of a sequence complementary to the target sequence of interest, as well as preselected variations of that sequence, e.g., substitution of one or more given positions with one or more members of the basis set of monomers, i.e., nucleotides. Tiling strategies are further described in PCT application No. WO 95/11995. In some embodiments, arrays are tiled for a number of specific SNPs. In particular, the array is tiled to include a number of detection blocks, each detection block being specific for a specific SNP or a set of SNPs. For example, a detection block may be tiled to include a number of probes that span the sequence segment that includes a specific SNP. To ensure probes that are complementary to each allele, the probes are synthesized in pairs differing at the SNP position. In addition to the probes differing at the SNP position, monosubstituted probes are also generally tiled within the detection block. Such methods can readily be applied to the SNP information disclosed herein.

These monosubstituted probes have bases at and up to a certain number of bases in either direction from the polymorphism, substituted with the remaining nucleotides (selected from A, T, G, C and U). Typically, the probes in a tiled detection block will include substitutions of the sequence positions up to and including those that are 5 bases away from the SNP. The monosubstituted probes provide internal controls for the tiled array, to distinguish actual hybridization from artifactual cross-hybridization. Upon completion of hybridization with the target sequence and washing of the array, the array is scanned to determine the position on the array to which the target sequence hybridizes. The hybridization data from the scanned array is then analyzed to identify which allele or alleles of the SNP are present in the sample Hybridization and scanning may be carried out as described in PCT application No. WO 92/10092 and WO 95/11995 and U.S. Pat. No. 5,424,186.

Thus, in some embodiments, the chips may comprise an array of nucleic acid sequences of fragments of about 15 nucleotides in length and the sequences complementary thereto, or a fragment thereof, the fragment comprising at least about 8 consecutive nucleotides, preferably 10, 15, 20, more preferably 25, 30, 40, 47, or 50 consecutive nucleotides and containing a polymorphic base. In some embodiments the polymorphic base is within 5, 4, 3, 2, or 1 nucleotides from the center of the polynucleotide, more preferably at the center of the polynucleotide. In other embodiments, the chip may comprise an array containing any number of polynucleotides of the present invention.

An oligonucleotide may be synthesized on the surface of the substrate by using a chemical coupling procedure and an ink jet application apparatus, as described in PCT application WO95/251116 (Baldeschwieler et al.). In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number which lends itself to the efficient use of commercially available instrumentation.

Using such arrays, the present invention provides methods of identifying the SNPs of the present invention in a sample. Such methods comprise incubating a test sample with an array comprising one or more oligonucleotide probes corresponding to at least one SNP position of the present invention, and assaying for binding of a nucleic acid from the test sample with one or more of the oligonucleotide probes. Such assays will typically involve arrays comprising oligonucleotide probes corresponding to many SNP positions and/or allelic variants of those SNP positions, at least one of which is a SNP of the present invention.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel SNPs disclosed herein. Examples of such assays can be found in Chard, T, An Introduction to Radioimmunoassay and Related Techniques, Elsevier Science Publishers, Amsterdam, The Netherlands (1986); Bullock, G. R. et al., Techniques in Immunocytochemistry, Academic Press, Orlando, Fla. Vol. 1 (I 982), Vol. 2 (1983), Vol. 3 (1985); Tijssen, P., Practice and Theory of Enzyme Immunoassays: Laboratory Techniques in Biochemistry and Molecular Biology, Elsevier Science Publishers, Amsterdam, The Netherlands (1985).

Multicomponent integrated systems may also be used to analyze SNPs. Such systems miniaturize and compartmentalize processes such as PCR and capillary electrophoresis reactions in a single functional device. An example of such technique is disclosed in U.S. Pat. No. 5,589,136, which describes the integration of PCR amplification and capillary electrophoresis in chips.

Integrated systems can be envisaged mainly when microfluidic systems are used. These systems comprise a pattern of micro-channels designed onto a glass, silicon, quartz, or plastic wafer included on a microchip. The movements of the samples are controlled by electric, electro-osmotic or hydrostatic forces applied across different areas of the microchip to create functional microscopic valves and pumps with no moving parts. Varying the voltage controls the liquid flow at intersections between the micro-machined channels and changes the liquid flow rate for pumping across different sections of the microchip.

For genotyping SNPs, the microfluidic system may integrate, for example, nucleic acid amplification, mini-sequencing primer extension, capillary electrophoresis, and a detection method such as laser induced fluorescence detection.

In a first step, the DNA samples are amplified, preferably by PCR. Then, the amplification products are subjected to automated mini-sequencing reactions using ddNTPs (specific fluorescence for each ddNTP) and the appropriate oligonucleotide mini-sequencing primers which hybridize just upstream of the targeted polymorphic base. Once the extension at the 3' end is completed, the primers are separated from the unincorporated fluorescent ddNTPs by capillary electrophoresis. The separation medium used in capillary electrophoresis can be, for example, polyacrylamide, polyethyleneglycol or dextran. The incorporated ddNTPs in the single nucleotide primer extension products are identified by laser-induced fluorescence detection. This microchip can be used to process at least 96 to 384 samples, or more, in parallel.

3.5 Extension Based Techniques for the Detection of Polymorphisms

Extension based techniques for detecting polymorphisms within a nucleotide sequence can include, but are not restricted to allele-specific amplification, also known as the amplification refractory mutation system (ARMS) as disclosed in European Patent Application Publication No. 0332435 and in Newton et al., (1989, Nucl. Acids Res. 17: 2503-2516), and cloning of polymorphisms (COPS) as contemplated by Gibbs et al., (1989, Nucleic Acids Research, 17: 2347).

The extension-based technique, ARMS, uses allele specific oligonucleotide (ASO) PCR primers for genotyping. In this approach, one of the two oligonucleotide primers used for PCR is designed to bind to the polymorphic site, most commonly with the 3' end of the primer targeting the site. Under carefully controlled conditions (annealing temperature, magnesium concentration etc.), amplification only takes place if the nucleotide at the 3' end of the PCR primer is complementary to the base at the polymorphic site, with a mismatch being "refractory" to amplification.

A variation of the ARMS approach, termed mutagenically separated PCR (MS-PCR), comprises two ARMS primers of different lengths, each specific for different polymorphisms at a site. This method yields PCR products of different lengths for the different polymorphisms.

3.6 Ligation Based Assays for Detecting Polymorphisms

Another typical method of SNP detection encompasses the oligonucleotide ligation assay. A number of approaches make use of DNA ligase, an enzyme that can join two adjacent oligonucleotides hybridized to a DNA template. The specificity of the approach comes from the requirement for a perfect match between the hybridized oligonucleotides and the DNA template at the ligation site. In the oligonucleotide ligation assay (OLA), or ligase chain reaction (LCR) assay the sequence surrounding the mutation site is first amplified, and one strand serves as a template for three ligation probes, two of these are allele specific oligonucleotides (ASO) and the third a common probe. Numerous approaches can be used for the detection of the ligated products. For example, the two ASOs can be differentially labeled with fluorescent or hapten labels and ligated products detected by fluorimetric or colorimetric enzyme-linked immunosorbent assays, respectively. For electrophoresis-based systems, use of mobility modifier tags or variation in probe lengths coupled with fluorescence detection enables the multiplex genotyping of several single nucleotide substitutions in a single tube. When used on arrays, ASOs can be spotted at specific locations or addresses on a chip. PCR amplified DNA can then be added and ligation to labeled oligonucleotides at specific addresses on the array can be measured.

3.7 Signal Generating Polymorphism Detection Assays

In some embodiments, fluorescence resonance energy transfer (FRET) is contemplated as a method to identify a polymorphism within the 16S rRNA or 5.8S rRNA genes. FRET occurs due to the interaction between the electronic excited states of two dye molecules. The excitation is transferred from one (the donor) dye molecule to the other (the acceptor) dye molecule without emission of a photon. This is distance-dependent, that is the donor and the acceptor dye must be in close proximity. The hybridization probe system consists of two oligonucleotides labeled with fluorescent dyes. The hybridization probe pair is designed to hybridize to adjacent regions on the target DNA. Each probe is labeled with a different marker dye. Interaction of the two dyes can only occur when both are bound to their target. The donor probe is labeled with fluorophore at the 3' end and the acceptor probe at the 5' end. During PCR, the two different oligonucleotides hybridize to adjacent regions of the target DNA such that the fluorophores, which are coupled to the oligonucleotides, are in close proximity in the hybrid structure. The donor fluorophore (F1) is excited by an external light source, and then passes part of its excitation energy to the adjacent acceptor fluorophore (F2). The excited acceptor fluorophore (F2) emits light at a different wavelength which can then be detected and measured for molecular proximity.

In other embodiments, the MagSNiPer method, based on single base extension, magnetic separation, and chemiluminescence provides a further method for SNP identification in a nucleotide sequence. Single base nucleotide extension reaction is performed with a biotinylated primer whose 3' terminus is contiguous to the SNP site with a tag-labeled ddNTP. Then the primers are captured by magnetic-coated beads with streptavidin, and unincorporated labeled ddNTP is removed by magnetic separation. The magnetic beads are incubated with anti-tag antibody conjugated with alkaline phosphatase. After the removal of excess conjugates by magnetic separation, SNP typing is performed by measuring chemiluminescence. The incorporation of labeled ddNTP is monitored by chemiluminescence induced by alkaline phosphatase.

In some embodiments, fluorescence polarization provides a method for identifying polymorphisms within a nucleotide sequence. For example, amplified DNA containing a polymorphic is incubated with oligonucleotide primers (designed to hybridize to the DNA template adjacent to the polymorphic site) in the presence of allele-specific dye-labeled dideoxyribonucleoside triphosphates and a commercially available modified Taq DNA polymerase. The primer is extended by the dye-terminator specific for the allele present on the template, increasing approximately 10-fold the molecular weight of the fluorophore. At the end of the reaction, the fluorescence polarization of the two dye-terminators in the reaction mixture is analyzed directly without separation or purification. This homogeneous DNA diagnostic method is shown to be highly sensitive and specific and is suitable for automated genotyping of large number of samples.

In other embodiments, surface enhanced Raman scattering can be used as a method for detecting and identifying single base differences in double stranded DNA fragments. Chumanov, G. "Surface Enhanced Raman Scattering (SERS) for Discovering and Scoring Single Based Differences in DNA" Proc. Volume SPIE, 3608 (1999). SERS has also been used for single molecule detection. Kneipp, K, (1997, Physical Review Letters, 78(9): 1667-1670). SERS results in strongly increased Raman signals from molecules that have been attached to nanometer sized metallic structures.

Illustrative examples include a genotyping method discussed by Xiao and Kwok (2003, Genome Research, 13(5): 932-939) based on a primer extension assay with fluorescence quenching as the detection. The template-directed dye-terminator incorporation with fluorescence quenching detection (FQ-TDI) assay is based on the observation that the intensity of fluorescent dye R110- and R6G-labeled acycloterminators is universally quenched once they are incorporated onto a DNA oligonucleotide primer. By comparing the rate of fluorescence quenching of the two allelic dyes in real time, the frequency of SNPs in DNA samples can be measured. The kinetic FQ-TDI assay is highly accurate and reproducible both in genotyping and in allele frequency estimation.

4. Primers, Probes, Kits and Processing Systems

The present invention provides probes and primer that may be used in the methods described herein to determine SNPs at one or more positions of the 16S rRNA and/or 5.8S rRNA genes so as to classify and/or identify microorganisms in a sample. In some instances, use of the primers and probes in the methods of the invention facilitate quantitation of the microorganisms.

The primers and probes of the present invention hybridize to at least a portion of the 16S rRNA or 5.8S rRNA gene (or 16S rRNA or 5.8S rRNA molecules or DNA copies thereof) containing the SNP position(s). For example, the primers may hybridize to a sequence flanking one or more SNPs, and the probe may hybridize to a sequence that includes one or more SNPs. It is well within the skill of a skilled artisan to design appropriate primers and probes for use in the methods of the present invention, based on the known sequences of the 16S rRNA and 5.8S rRNA genes.

Non-limiting examples of primers and probes that are useful for the methods of the present invention, in which SNPs in the 16S rRNA of mammalian (e.g., human) sepsis pathogens at positions corresponding to positions 396, 398, 278, 286 and/or 648 of the 16S rRNA gene set forth in SEQ ID NO:1 are analyzed, include those described in Example 6. For example, to detect SNPs at positions 396 and 398, exemplary probe sequences include GCAACGCCGCGT (SEQ ID NO:4) and GCGACGCCGCGT (SEQ ID NO:5) for Gram-positive bacteria, and GCCAAGTAGCGT (SEQ ID NO:6) and GCCATGCCGCGT (SEQ ID NO:7) for Gram-negative bacteria, an exemplary forward primers from both Gram-positive and -negative bacteria includes ACTCCTACGGGAGGCAGCAGT (SEQ ID NO:8); and exemplary reverse primers include GCCAGCAGCYGCGGTAATACG (SEQ ID NO:9) for Gram-negative and GCCAGCAGCCGCGGTAATACG (SEQ ID NO:10) for Gram-positive bacteria. To detect SNPs at positions 278 and 286, exemplary probe sequences include GCGATGATCAGTAG (SEQ ID NO:11), GCTATGACGCTTAA (SEQ ID NO:12), GCTTTGACGCATAA (SEQ ID NO:13), GCTATGACGGGTAT (SEQ ID NO:14), GCAATGATCAGTAG (SEQ ID:15) and GTTTTGACGTCTAG (SEQ ID:16) for Gram-negative and GCAACGATGCATAG (SEQ ID NO:17), GCAACGATGCGTAG (SEQ ID NO:18) and GCCACGATACATAG (SEQ ID NO:19) for Gram-positive bacteria; exemplary forward primer sequences include: TGWAGGAGGGGATTGCGTC (SEQ ID NO:20), TGTAGGATGAGACTATATW (SEQ ID NO:21) and TAARRGATCAGCCTATGTC (SEQ ID NO:22) for Gram-negative and TGATGGATGGACCCGCGGT (SEQ ID NO:24) for Gram-positive bacteria; and exemplary reverse primer sequences include ATGAACGGCCACATTGG (SEQ ID NO:25), ATGATCAGTCACACTGG (SEQ ID NO:26) and GTGAWCGGACACACTGG (SEQ ID NO:27) for Gram-negative and GTGATCGGCCACACTGGRACT (SEQ ID NO:28) for Gram-positive bacteria. To detect SNPs at position 648, exemplary probes include CTGCTGATCTAGAG (SEQ ID NO:29) for Gram-negative bacteria and CTGGAAAACTTGAG (SEQ ID NO:30) and CTGGGAGACTTGAG (SEQ ID NO:31) for Gram-positive bacteria; exemplary forward primer sequences include TAACCCCGTGAKGGGATGGA (SEQ ID NO:32) for Gram-negative bacteria and CAACCGKGGAGGGTCATTGGA (SEQ ID NO:33) for Gram-positive bacteria; and exemplary reverse primer sequences include TCGGAGAGGAAAGTGGAATTCC (SEQ ID NO:34) for Gram-negative and CARRAGRGGARAGTGGAATTCC (SEQ ID NO:35) for Gram-positive bacteria. Additional non-limiting examples of primers and probes to differentiate Gram-negative bacteria include those in Table 21, and additional non-limiting examples of primers and probes to differentiate Gram-positive bacteria include those in Table 22. Such primers and probes are particularly suitable for assays such as the TaqMan® assay.

TABLE 21

| SNP | Forward primer | Probe | Reverse primer | Bacteria |
|---|---|---|---|---|
| 278 and 286 | TGTAGGATGAGACTATATW (SEQ ID NO: 41) | GCTATGACGCTTAA (SEQ ID NO: 42) | ATGATCAGTCACACTGG (SEQ ID NO: 43) | C. coli, C. jejuni, C. lari |
| | TGTAGGATGAGACTATATW (SEQ ID NO: 44) | GCTTTGACGCATAA (SEQ ID NO: 45) | ATGATCAGTCACACTGG (SEQ ID NO: 46) | C. fetus |
| | TAARRGATCAGCCTATGTC (SEQ ID NO: 47) | GCTATGACGGGTAT (SEQ ID NO: 48) | GTGAWCGGACACACTGG (SEQ ID NO: 49) | H. cinaedi, H. pylori |
| | CATCAGATGTGCCCAGATG (SEQ ID NO: 50) | GCGACGATCCCTAG (SEQ ID NO: 51) | ATGACCAGCCACACTGG (SEQ ID NO: 52) | E. cloacae, S. enterica, K. pneumoniae, S. marcescens, E. coli, |
| | TATCGGATGAACCCATATG (SEQ ID NO: 53) | GCGACGATCTCTAG (SEQ ID NO: 54) | ATGACCAGCCACACTGG (SEQ ID NO: 55) | P. mirabilis |
| | TATTCGAGCGGCCGATATC (SEQ ID NO: 56) | CCTGCGATCTCTAG (SEQ ID NO: 57) | ATGACCAGCCACACTGG (SEQ ID NO: 58) | H. influenzae |
| | TATCAGATGAGCCTAGGTC (SEQ ID NO: 59) | GCGACGATCCGTAA (SEQ ID NO: 60) | ATGATCAGTCACACTGG (SEQ ID NO: 61) | P. aeruginosa |
| | TATTCGAGCGGCCGATATC (SEQ ID NO: 62) | GCGACGATCAGTAG (SEQ ID NO: 63) | ATGACCAGCCACACTGG (SEQ ID NO: 64) | N. meningitidis |
| | TGWAGGAGGGGATTGCGTC (SEQ ID NO: 65) | GCGATGATCAGTAG (SEQ ID NO: 66) | ATGAACGGCCACATTGG (SEQ ID NO: 67) | V. atypica, V. dispar, V. parvula, V. denticariosi, V. montpellierensis |
| | TGWAGGAGGGGATTGCGTC (SEQ ID NO: 68) | GCAATGATCAGTAG (SEQ ID NO: 69) | ATGAACGGCCACATTGG (SEQ ID NO: 70) | V. rogosae |
| | TTAAGGGAGAGTCTATGG (SEQ ID NO: 71) | GTTTTGACGTCTAG (SEQ ID NO: 72) | TTGACCGCCAACACTGG (SEQ ID NO: 73) | C. abortus |
| | TAAAGGATGGGGATGCGT T (SEQ ID NO: 74) | CCTTCGATGGATAG (SEQ ID NO: 75) | AAGGTCCCCCACATTGG (SEQ ID NO: 76) | B. fragilis |
| 396 and 398 | ACTCCTACGGGAGGCAGC AGT (SEQ ID NO: 77) | GCAACGCCGCGT (SEQ ID NO: 78) | GCCAGCAGCYGCGGTAATAC G (SEQ ID NO: 79) | C. coli, C. jejuni, C. lari, C. fetus, H. |

TABLE 21 -continued

| SNP | Forward primer | Probe | Reverse primer | Bacteria |
|---|---|---|---|---|
| | | | | cindaedi, H. pylori, V. atypica, V. rogosae, V. dispar, V. parvula, V. denticariosi, V. montpellierensis, C. abortus, |
| | ACTCCTACGGGAGGCAGC AGT (SEQ ID NO: 80) | GCCAAGTAGCGT (SEQ ID NO: 81) | GCCAGCAGCYGCGGTAATAC G (SEQ ID NO: 82) | B. fragilis |
| | ACTCCTACGGGAGGCAGC AGT (SEQ ID NO: 83) | GCCATGCCGCGT (SEQ ID NO: 84) | GCCAGCAGCYGCGGTAATAC G (SEQ ID NO: 85) | E. cloacae, S. enterica, K. pneumoniae, S. marcescens, E. coli, P. mirabilis, |
| 648 | TAACCATTAAACTGCTTGA GA (SEQ ID NO: 86) | CTGATAATCTAGAG (SEQ ID NO: 87) | DGGGAGAGGYAGRTGGAAT TSG (SEQ ID NO: 88) | C. coli |
| | TAACCGTTGAACTGCTTGG GA (SEQ ID NO: 89) | CTGGTAATCTAGAG (SEQ ID NO: 90) | DGGGAGAGGYAGRTGGAAT TSG (SEQ ID NO: 91) | C. lari |
| | TAACTACAGAACTGCATTT GA (SEQ ID NO: 92) | CTGACTATCTAGAG (SEQ ID NO: 93) | DGGGAGAGGYAGRTGGAAT TSG (SEQ ID NO: 94) | C. jejuni |
| | TAACCATAGAACTGCATTT GA (SEQ ID NO: 95) | CTACTATTCTAGAG (SEQ ID NO: 69) | DGGGAGAGGYAGRTGGAAT TSG (SEQ ID NO: 97) | C. fetus |
| | TAACTACAGAACTGCATTT GA (SEQ ID NO: 98) | CTGACTATCTAGAG (SEQ ID NO: 99) | DGGGAGAGGYAGRTGGAAT TSG (SEQ ID NO: 100) | H. cinaedi |
| | TAACTACAGAACTGCATTT GA (SEQ ID NO: 101) | CTACTATTCTAGAG (SEQ ID NO: 102) | DGGGAGAGGYAGRTGGAAT TSG (SEQ ID NO: 103) | H. pylori |
| | CAACCTGGGAACTGCATTT GA (SEQ ID NO: 104) | CTGGCAGGCTGGAG (SEQ ID NO: 105) | TYGTAGAGGGGGTAGAATT CC (SEQ ID NO: 106) | E. cloacae |
| | CAACCTGGGAACTGCATTC GA (SEQ ID NO: 107) | CTGGCAGGCTTGAG (SEQ ID NO: 108) | TYGTAGAGGGGGTAGAATT CC (SEQ ID NO: 109) | S. enterica, K. pneumoniae |
| | CAACCTGGGAACTGCATTT GA (SEQ ID NO: 110) | CTGGCAAGCTAGAG (SEQ ID NO: 111) | TYGTAGAGGGGGTAGAATT CC (SEQ ID NO: 112) | S. marcescens |
| | CAACCTGGGAACTGCATCT GA (SEQ ID NO: 113) | CTGGCAAGCTTGAG (SEQ ID NO: 114) | TYGTAGAGGGGGTAGAATT CC (SEQ ID NO: 115) | E. coli |
| | CAACCTGGGAACTGCATCC AA (SEQ ID NO: 116) | CTACTGAGCTAGAG (SEQ ID NO: 117) | CGGTAGAGGGTGGTGGAATT TC (SEQ ID NO: 118) | P. aeruginosa |
| | TAACTTGGGAATTGCATCT GA (SEQ ID NO: 119) | CTGGTTGGCTAGAG (SEQ ID NO: 120) | TYGTAGAGGGGGTAGAATT CC (SEQ ID NO: 121) | P. mirabilis |
| | TAACCTAGGAATTGCATTT CA (SEQ ID NO: 122) | CTGGGTAACTAGAG (SEQ ID NO: 123) | CTTTAGGGAGGGGTAGAATT CC (SEQ ID NO: 124) | H. influenzae |
| | CAACCCGGGAACTGCGTTC TG (SEQ ID NO: 125) | CTGGGTGACTCGAG (SEQ ID NO: 126) | TGTCAGAGGGAGGTAGAATT CC (SEQ ID NO: 127) | N. meningitidis |
| | TAACCCCGTGAKGGGATG GA (SEQ ID NO: 128) | CTGCTGATCTAGAG (SEQ ID NO: 129) | TCGGAGAGGAAAGTGGAATT CC (SEQ ID NO: 130) | V. alypica, V. rogosae, V. parvula, V. denticariosi |
| | TAACCCCGTGAKGGGATG GA (SEQ ID NO: 131) | CTGCCAATCTAGAG (SEQ ID NO: 132) | TCGGAGAGGAAAGTGGAATT CC (SEQ ID NO: 133) | V. dispar |
| | CAACCCCAAGCCAGCATCT AA (SEQ ID NO: 134) | CTATCTTTCTAGAG (SEQ ID NO: 135) | TAGATGGAGAAAAGGGAATT CC (SEQ ID NO: 136) | C. abortus |
| | CAACCGTAAAATTGCAGTT GA (SEQ ID NO: 137) | CTGTCAGTCTTGAG (SEQ ID NO: 138) | CAGTAGAGGTGGGCGGAATT CG (SEQ ID NO: 139) | B. fragilis |

TABLE 22

| SNP | Forward primer | Probe | Reverse primer | Bacteria |
|---|---|---|---|---|
| 278 and 286 | TTATAGATGGATCCGCGCY (SEQ ID NO: 140) | GCAACGATGCATAG (SEQ ID NO: 141) | GTGATCGGCCACACTGGRACT (SEQ ID NO: 142) | S. aureus |
| | TTATAGATGGATCCGCGCY (SEQ ID NO: 143) | GCAACGATGCGTAG (SEQ ID NO: 144) | GTGATCGGCCACACTGGRACT (SEQ ID NO: 145) | S. epidermidis |
| | TRTGAGATGGACCTGCGTT (SEQ ID NO: 146) | GCGACGATACATAG (SEQ ID NO: 147) | GTGATCGGCCACACTGGRACT (SEQ ID NO: 148) | S. agalactiae, S. pyogenes |
| | TACCAGATGGACCTGCGTT (SEQ ID NO: 149) | GCGACGATACATAG (SEQ ID NO: 150) | GTGATCGGCCACACTGGRACT (SEQ ID NO: 151) | S. pneumoniae |
| | TGATGGATGGACCCGCGGT (SEQ ID NO: 152) | GCCACGATGCATAG (SEQ ID NO: 153) | GTGATCGGCCACACTGGRACT (SEQ ID NO: 154) | E. faecalis |
| | TGMAGGATGRGCCCGCGGC (SEQ ID NO: 155) | GCGACGACGGGTAG (SEQ ID NO: 156) | GCGACCGGCCACACTGGGAC T (SEQ ID NO: 157) | S. anulatus, S. somaliensis |

TABLE 22 -continued

| SNP | Forward primer | Probe | Reverse primer | Bacteria |
|---|---|---|---|---|
| | TGTGGGATGAGCCCGCGGC (SEQ ID NO: 158) | GCGACGACGGGTAG (SEQ ID NO: 159) | GTGTCCGGCCACACTGGGACT (SEQ ID NO: 160) | M. tuberculosis |
| | TATGAGATGGACCCGCGGC (SEQ ID NO: 161) | GCGACGATGCTGTAG (SEQ ID NO: 162) | GTGATCGGCCACATTGGGACT (SEQ ID NO: 163) | C. perfringens |
| 396 and 398 | ACTCCTACGGGAGGCAGCA GT (SEQ ID NO: 164) | GCAACGCCGCGT (SEQ ID NO: 165) | GCCAGCAGCCGCGGTAATAC G (SEQ ID NO: 166) | E. faecalis, C. perfringens |
| | ACTCCTACGGGAGGCAGCA GT (SEQ ID NO: 167) | GCGACGCCGCGT (SEQ ID NO: 168) | GCCAGCAGCCGCGGTAATAC G (SEQ ID NO: 169) | S. anulatus, S. somaliensis, M. tuberculosis |
| 648 | CAACCGKGGAGGGTCATTG GA (SEQ ID NO: 170) | CTGGAAAACTTGAG (SEQ ID NO: 171) | CARRAGRGGARAGTGGAATT CC (SEQ ID NO: 172) | S. aureus, S. epidermidis |
| | CAACCGKGGAGGGTCATTG GA (SEQ ID NO: 173) | CTGGGAGACTTGAG (SEQ ID NO: 174) | CARRAGRGGARAGTGGAATT CC (SEQ ID NO: 175) | E. faecalis |
| | TAACCATTGTACGCTTTGGACTGGAGGACTTGAG (SEQ ID NO: 176) | (SEQ ID NO: 177) | CARRAGRGGARAGTGGAATT CC (SEQ ID NO: 178) | S. agalactiae |
| | CAACCAATGTACGCTTTGG A (SEQ ID NO: 179) | CTGGAGAACTTGAG (SEQ ID NO: 180) | CARRAGRGGARAGTGGAATT CC (SEQ ID NO: 181) | S. pyogenes |
| | TAACCATAGTAGGCTTTGG A (SEQ ID NO: 182) | CTGTTTAACTTGAG (SEQ ID NO: 183) | CARRAGRGGARAGTGGAATT CC (SEQ ID NO: 184) | S. pneumoniae |
| | TAACCCGGGTCTGCATTC GA (SEQ ID NO: 185) | CGGGCTAGCTAGAG (SEQ ID NO: 186) | YGGTAGGGGAGATCGGAATT CC (SEQ ID NO: 187) | S. anulatus, S. somaliensis |
| | TAACTGTGAGCGTGCGGGC GA (SEQ ID NO: 188) | CGGGCAGACTAGAG (SEQ ID NO: 189) | CTGCAGGGGAGACTGGAATT CC (SEQ ID NO: 190) | M tuberculosis |
| | CAACTTGGGTGCTGCATTC CA (SEQ ID NO: 191) | CTGGTTATCTAGAG (SEQ ID NO: 192) | CAGGAGAGGAGAGTGGAATT CC (SEQ ID NO: 193) | C. perfringens |

Non-limiting examples of primers and probes that are useful for the methods of the present invention, in which SNPs in the 16S rRNA of mammalian (e.g., human) sepsis pathogens at positions corresponding to positions 396, 398, 399, 400 and 401, and positions 490, 491, 492, 493, 495, 496, 500 and 501 of the 16S rRNA gene set forth in SEQ ID NO:1 are analyzed, include those described in Example 6 and set forth in Table 23.

TABLE 23

| SNP | Forward primer | Reverse primer | Probe | Species |
|---|---|---|---|---|
| 396, 398, 399, 400, 401 | ACTCCTACGGGAGGC AGCAGT (SEQ ID NO: 8) | GTATTACCGCGGCTGCT GGCAC (SEQ ID NO: 278) | AGCAACGCCGCGT (SEQ ID NO: 281) | Group 1 bacteria |
| | | | AGCGACGCCGCGT (SEQ ID NO: 282) | Group 2 bacteria (except Chlamydia and Chlamydophila spp) |
| | | | AGCCATGCCGCGT (SEQ ID NO: 283) | Group 3 bacteria |
| | | | AGCAATGCCGCGT (SEQ ID NO: 284) | Group 4 bacteria |
| | | | AGCCATACCGCGT (SEQ ID NO: 285) | Group 5 bacteria |
| | | | AGCCAAGTAGCGT (SEQ ID NO: 286) | Group 6 bacteria |
| | | | AGCCAAGTCGCGT (SEQ ID NO: 287) | Group 7 bacteria |
| | ACTCCTACGGGAGGC TGCAGT (SEQ ID NO: 279) | GTATTACCGCGGCAGC TGGCAC (SEQ ID NO: 280) | AGCGACGCCGCGT (SEQ ID NO: 282) | Chlamydia and Chlamydophila spp (part of Group 2 bacteria) |
| 490, 491, 492, 493, 495, 496, 500, 501 | ACTCCTACGGGAGGC AGCAGT (SEQ ID NO: 8) | GTATTACCGCGGCTGCT GGCAC (SEQ ID NO: 278) | AACCAGAAAGCC (SEQ ID NO: 288) | Group 1a bacteria B. anthracis; E. faecalis; E. faeciutn; L. monocytogenes |
| | | | AACCAGAAAGGG (SEQ ID NO: 289) | Group 1b bacteria S. agalactiae; S. anginosus; S. constellatus; S. dysgalactiae; S. intermedius; S. pyogenes |
| | | | AACCAGAAAGTC (SEQ ID NO: 290) | Group 1c bacteria L. intestinalis |
| | | | AACGAATAAGCA (SEQ ID NO: 291) | Group 1d bacteria H. pylori; C. coli |
| | | | AAGGAGGAAGCC (SEQ ID NO: 292) | Group 1e bacteria C. perfringens |

TABLE 23 -continued

| SNP | Forward primer | Reverse primer | Probe | Species |
|---|---|---|---|---|
| | | | AATCAGAAAGCC (SEQ ID NO: 293) | Group 1f bacteria S. aureus; S. epidermidis; S. haemolyticus; S. hominis; S. saprophyticus |
| | | | GAAGAATAAGCT (SEQ ID NO: 294) | Group 1g bacteria E. desmolans |
| | | | GAATAGAAAGCC (SEQ ID NO: 295) | Group 1h bacteria V. dispar |
| | | | GAGGAGGAAGCC (SEQ ID NO: 296) | Group 1i bacteria C. difficile |
| | | | TACCAGAAAGCC (SEQ ID NO: 297) | Group 1j bacteria E. rhusiopathiae |
| | | | TACCAGAAAGGG (SEQ ID NO: 298) | Group 1k bacteria S. bovis; S. mitis; S. mutans; S. oralis; S. pneumonia; S. sanguinis; S. sobrinus |
| | | | TGTGAGGAAGCC (SEQ ID NO: 299) | Group 1l bacteria P. stomatic |
| 490, 491, 492, 493, 496, 499 and 501 | ACTCCTACGGGAGGC AGCAGT (SEQ ID NO: 8) | GTATTACCGCGGCTGCT GGCAC (SEQ ID NO: 278) | AGATAAGAAGCA (SEQ ID NO: 300) | Group 2a bacteria C. diphtheria |
| | | | GCAGAAGAAGCA (SEQ ID NO: 301) | Group 2b bacteria D. congolensis; M. luteus; R. equi |
| | | | GCAGAAGAAGCG (SEQ ID NO: 302) | Group 2c bacteria S. anulatus; S. somaliensis |
| | | | GCCTAAAGCACC (SEQ ID NO: 303) | Group 2d bacteria L. interrogans |
| | | | GGAGAAGAAGCA (SEQ ID NO: 304) | Group 2e bacteria M. tuberculosis |
| | | | GGATAAGAAGCA (SEQ ID NO: 305) | Group 2f bacteria C. jeikeium C. urealyticutn |
| | | | GGGGAAGAAGCG (SEQ ID NO: 306) | Group 2g bacteria M. curtisii |
| | ACTCCTACGGGAGGC TGCAGT (SEQ ID NO: 279) | GTATTACCGCGGCAGC TGGCAC (SEQ ID NO: 280) | GGTAAAGAAGCA (SEQ ID NO: 307) | Group 2h bacteria C. trachomatis; C. pneumoniae |
| | ACTCCTACGGGAGGC AGCAGT (SEQ ID NO: 8) | GTATTACCGCGGCTGCT GGCAC (SEQ ID NO: 278) | GTAGAAGAAGCA (SEQ ID NO: 308) | Group 2i bacteria N. asteroids; N. brasiliensis |
| | | | GTTAATGAAGCG (SEQ ID NO: 309) | Group 2j bacteria A. massiliensi |
| 490, 491, 496, and 501 | ACTCCTACGGGAGGC AGCAGT (SEQ ID NO: 8) | GTATTACCGCGGCTGCT GGCAC (SEQ ID NO: 278) | ACAGAAGAAGCA (SEQ ID NO: 310) | Group 3a bacteria A. hominis; E. tarda; H. ducreyi; H. influenza; H. parahaemolyticus; H. parainfluenzae M. morganii P. multocida P. alcalifaciens V. cholerae |
| | | | ACAGAATAAGCA (SEQ ID NO: 311) | Group 3b bacteria M. catarrhalis; P. aeruginosa |
| | | | GAAGAATAAGCA (SEQ ID NO: 312) | Group 3c bacteria N. gonorrhoeae; N. meningitides |
| | | | GCAGAAGAAGCA (SEQ ID NO: 313) | Group 3d bacteria A. hydrophile C. freundii E. aerogenes E. cloacae E. coli K. oxytoca K. pneumonia P. mirabilis |

TABLE 23 -continued

| SNP | Forward primer | Reverse primer | Probe | Species |
|---|---|---|---|---|
| | | | | S. enterica |
| | | | | S. marcescens |
| | | | | S. dysenteriae |
| | | | | S. sonnei |
| | | | | Y. enterocolitica |
| | | | | Y. pestis |
| | | | GCAGAATAAGCA (SEQ ID NO: 314) | Group 3e bacteria A. baumannii |
| | | | GGAGAAGAAGCC (SEQ ID NO: 315) | Group 3f bacteria B. abortus |
| | | | TAAGAATAAGGA (SEQ ID NO: 316) | Group 3g bacteria F. ceti |
| 490, 491, 496, and 499 | ACTCCTACGGGAGGC AGCAGT (SEQ ID NO: 8) | GTATTACCGCGGCTGCT GGCAC (SEQ ID NO:278) | ACAGAAGAACCA (SEQ ID NO: 317) | Group 4a bacteria L. pneumophila |
| | | | GAAGAATAAGCA (SEQ ID NO: 318) | Group 4b bacteria B. cepacia |
| | | | GCAGAAGAAGCA (SEQ ID NO: 319) | Group 4c bacteria C. valvarum |
| 490, 491, and 492 | ACTCCTACGGGAGGC AGCAGT (SEQ ID NO: 8) | GTATTACCGCGGCTGCT GGCAC (SEQ ID NO: 278) TACGAATAAGGA | CATGAATAAGGA (SEQ ID NO: 320) | Group 6a bacteria P. buccae |
| | | | Group 6b bacteria (SEQ ID NO: 321) | P. melaninogenica |
| | | | TATGAATAAGGA (SEQ ID NO: 322) | Group 6c bacteria B. fragilis |
| | | | TTCGAATAAGGA (SEQ ID NO: 323) | Group 6d bacteria P. intermedia |

Non-limiting examples of primers and probes that are useful for the methods of the present invention in which 30 SNPs in the 5.8S rRNA of fungi are analysed include those set forth in Table 24.

TABLE 24

| SNP | Forward primer | Probe | Reverse primer | Species |
|---|---|---|---|---|
| 160, 163, 164, 165 | TATGCAGTCTGAGTT GATTATCGTAATC (SEQ ID NO: 194) | CTCTTGGTTCCGGCAT CGA (SEQ ID NO: 195) | GCATTTCGCTGCGTTCT TC (SEQ ID NO: 196) | A. fumigatus |
| 160, 163, 164, 166 | CAGAGGTCTAAACTT ACAACCAATTTTTT (SEQ ID NO: 197) | CTCTTGGTTCTCGCAT CGA (SEQ ID NO: 198) | GCATTTCGCTGCGTTCT TC (SEQ ID NO: 199) | C.albicans |
| 160, 163, 164, 167 | GGCAAACGCAAAAT AAATCAAAA (SEQ ID NO: 200) | CTCTTGGCTCTGGCAT CGA (SEQ ID NO: 201) | GCATTTCGCTGCGTTCT TC (SEQ ID NO: 202) | Stachybottys sp. |
| 160, 163, 164, 168 | AATTAAAACTTTCAA CAAC (SEQ ID NO: 203) | CTCTTGGCTCTGGCAT CGA (SEQ ID NO: 204) | ACTTATCGCATTTCG (SEQ ID NO: 205) | Fusarium sp. |
| 160, 163, 164, 169 | GAAAACAAAAAAAA CAAGTTAAAAC (SEQ ID NO: 206) | CTCTTGGTTCTGGCAT CGA (SEQ ID NO: 207) | CACATTACTTATCGCAT TTCG (SEQ ID NO: 208) | Scedosporium apiospermum |
| 160, 163, 164, 170 | TCCAGTCAAAACTTT CAACAAC (SEQ ID NO: 209) | CTCTTGGTTCCGACAT CGA (SEQ ID NO: 210) | GCATTTCGCTGCGTTCT (SEQ ID NO: 211) | Ajellomyces capsulatus |
| 160, 163, 164, 171 | CAATAATAAAACTTT CAACAAC (SEQ ID NO: 212) | CTCTTGGCTTCCACAT CGA (SEQ ID NO: 213) | CGCTGCGTTCTTCA (SEQ ID NO: 214) | Cryptococcus neoformans |
| 163, 164 | CAAAACTTTCAACAA CGGATCTC (SEQ ID NO: 326) | TTCTCGCATCGA (SEQ ID NO: 325) | GACGCTCAAACAGGCA TG (SEQ ID NO: 329) | Candida sp |
| 163, 164 | TAAAACTTTCAACAA CGGATCTC (SEQ ID NO: 327) | TTCCGGCATCGA (SEQ ID ID NO: 324) | GACCGTCGGACAGGCA TG (SEQ ID NO: 328) | Aspergillus fumigatus |

TABLE 24 -continued

| SNP | Forward primer | Probe | Reverse primer | Species |
|---|---|---|---|---|
| 196, 202 | GGTTCCGGCATCGA (SEQ ID NO: 215) | CGATAAGTAATGTG (SEQ ID NO: 216) | GATTCACTGAATTCTGC AAT (SEQ ID NO: 217) | *A. fumigatus* |
| 196, 202 | TGGTTCTCGCATCGA (SEQ ID NO: 218) | CGATACGTAATATG (SEQ ID NO: 219) | CACGAATATCTGCACAA TT (SEQ ID NO: 220) | *C. albicans* |
| 196, 202 | GGCTCTGGCATCGA (SEQ ID NO: 221) | CGATAAGTAATGTG (SEQ ID NO: 222) | TTCACTGAATTCTGCAA T (SEQ ID NO: 223) | *Stachybotlys sp.* |
| 196, 202 | AACGCAGCGAAAT (SEQ ID NO: 224) | CGATAAGTAATGTG (SEQ ID NO: 225) | ATGATTCACTGAATTCT G (SEQ ID NO: 226) | *Fusarium* sp. |
| 196, 202 | TGGTTCTGGCATCGA (SEQ ID NO: 227) | CGATAAGTAATGTG (SEQ ID NO: 228) | ATTCACTGAATTCTGCA AT (SEQ ID NO: 229) | *Scedosporium apiospermum* |
| 196, 202 | TGGTTCCGACATCGA (SEQ ID NO: 230) | CGATAAGTAATGTG (SEQ ID NO: 231) | CACGGAATTCTGCAAT (SEQ ID NO: 232) | *Ajellomyces capsulatus* |
| 196, 202 | AAGAACGCAGCGAA AT (SEQ ID NO: 233) | CGATAAGTAATGTG (SEQ ID NO: 234) | ATTCACTGAATTCTGCA AT (SEQ ID NO: 235) | *Cryptococcus neoformans* |
| 196 | AACTTTCAACAACGG ATCTCTTGG (SEQ ID NO: 330 | AAATGCGATACGTAA (SEQ ID NO: 334) | GCGTTCAAAGATTCGAT GATTCAC (SEQ ID NO: 332) | Forward: *Candida* spp, *Ajellomyces capsulatus*, *Scedosporium apiospermum*, *Fusarium* sp, *Aspergillus fumigatus*, *Cryptococcus neoformans*. Reverse: *Candida* spp versus *Ajellomyces capsulatus*, *Scedosporium apiospermum*, *Fusarium* sp, *Stachybottys* sp, Probe: *Candida* sp. |
| 196 | AACTTTTAACAACGG ATCTCTTGG (SEQ ID NO: 331) | ATGCGATAAGTAA (SEQ ID NO: 335) | GCGTTCAAAGACTCGAT GATTCAC (SEQ ID NO: 333) | Forward: *Stachybottys* sp. Reverse: *Aspergillus fumigatus*, *Cryptococcus neoformans*. Probe: Fungal pathogen species other than *Candida* sp. |
| 223, 224, 226 | AAGTAATGTGAATTG CAGAA (SEQ ID NO: 236) | GTGAATCATCGAG (SEQ ID NO: 237) | CCCCCGGAATACCA (SEQ ID NO: 238) | *A. fumigatus* |
| 223, 224, 226 | CGTAATATGAATTGC AGATATTC (SEQ ID NO: 239) | GTGAATCATCGAA (SEQ ID NO: 240) | GAGGGCGCAATGTG (SEQ ID NO: 241) | *C. albicans* |
| 223, 224, 226 | GCGAAATGCGATAA GTAA (SEQ ID NO: 242) | GTGAATTGCAGAA (SEQ ID NO: 243) | GATTCGATGATTCACTG AA (SEQ ID NO: 244) | *Stachybottys* sp. |
| 223, 224, 226 | AATGTGAATTGCAG AA (SEQ ID NO: 245) | GTGAATCATCGAA (SEQ ID NO: 246) | GGGCGCAATGTG (SEQ ID NO: 247) | *Fusarium* sp. |
| 223, 224, 226 | *AAGTAATGTGAATTG CAGAA (SEQ ID NO: 248)* | *GTGAATCATCGAA (SEQ ID NO: 249)* | *CGGGCGCAATGT (SEQ ID NO: 250)* | *Scedosporium apiospermum* |
| 223, 224, 226 | *AAGTAATGTGAATTG CAGAA (SEQ ID NO: 251)* | *GTGAATCATCGAA (SEQ ID NO: 252)* | *GAGGGCGCAATGTG (SEQ ID NO: 253)* | *Ajellomyces capsulatus* |
| 223, 224, 226 | *AAGTAATGTGAATTG CAGAA (SEQ ID NO: 254)* | *GTGAATCATCGAG (SEQ ID NO: 255)* | *CAAGTTGCGTTCAAAGA (SEQ ID NO: 256)* | *Cryptococcus neoformans* |

TABLE 24 -continued

| SNP | Forward primer | Probe | Reverse primer | Species |
|---|---|---|---|---|
| 254, 255, 259 | TCAGTGAATCATCGA GTCTTTGAAC (SEQ ID NO: 257) | CCCCCTGGTATTCC (SEQ ID NO: 258) | TGCTTGAGGGCAGCAAT G (SEQ ID NO: 259) | A. fumigatus |
| 254, 255, 260 | TCGTGAATCATCGAA TCTTTGAA (SEQ ID NO: 260) | CCCTCTGGTATTCC (SEQ ID NO: 261) | GGAGAAACGACGCTCA AACAG (SEQ ID NO: 262) | C. albicans |
| 254, 255, 261 | TTCAGTGAATCATCG AATCTTTGAA (SEQ ID NO: 263) | CCCGCCAGGCTCT (SEQ ID NO: 264) | GCATTTCGCTGCGTTCT TC (SEQ ID NO: 265) | Stachyboays sp. |
| 254, 255, 262 | TCAGTGAATCATCGA ATCTTTGAAC (SEQ ID NO: 266) | CCCGCCAGTATTCT (SEQ ID NO: 267) | GGTTGTAATGACGCTCG AACAG (SEQ ID NO: 268) | Fusarium sp. |
| 254, 255, 263 | GCAGAATTCAGTGA ATCATCGAAT (SEQ ID NO: 269) | CCCGGCAGTAATCT (SEQ ID NO: 270) | GAGGTTCGAGGGTTGA AATGAC (SEQ ID NO: 271) | Scedosporium apiospermum |
| 254, 255, 264 | CCGTGAATCATCGAA TCTTTGA (SEQ ID NO: 272) | CCCTCTGGTATTCC (SEQ ID NO: 273) | GCGCTTGAGGGTTGCAA T (SEQ ID NO: 274) | Ajellomyces capsulatus |
| 254, 255, 265 | TCGAGTCTTTGAACG CAACTTG (SEQ ID NO: 275) | CCCTTTGGTATTCC (SEQ ID NO: 276) | CGAGGGATTGAGATTTT CATGAC (SEQ ID NO: 277) | Cryptococcus neoformans |

All the essential materials and reagents required for detecting one or more SNPs in the 16S rRNA and/or 5.8S rRNA genes according to the invention may be assembled together in a kit. The kits may also optionally include appropriate reagents for detection of labels, positive and negative controls, washing solutions, blotting membranes, microtitre plates dilution buffers and the like. For example, a nucleic acid-based detection kit for the identification of polymorphisms may include one or more of the following: (i) nucleic acid from A Gram-positive, Gram-negative, fungal and/or mammalian cell (which may be used as a positive control); and (ii) a primer and/or probe that specifically hybridizes to at least a portion of the 16S rRNA or 5.8S rRNA gene containing the SNP position(s) to be analysed, and optionally one or more other AS markers, at or around the suspected SNP site. Also included may be enzymes suitable for amplifying nucleic acids including various polymerases (Reverse Transcriptase, Taq, Sequenase™ DNA ligase etc. depending on the nucleic acid amplification technique employed), deoxynucleotides and buffers to provide the necessary reaction mixture for amplification. Such kits also generally will comprise, in suitable means, distinct containers for each individual reagent and enzyme as well as for each primer or probe. The kit can also feature various devices and reagents for performing one of the assays described herein; and/or printed instructions for using the kit to identify the presence of a SNP as defined herein.

In some embodiments, the methods described generally herein are performed, at least in part, by a processing system, such as a suitably programmed computer system. A stand-alone computer, with the microprocessor executing applications software allowing the above-described methods to be performed, may be used. Alternatively, the methods can be performed, at least in part, by one or more processing systems operating as part of a distributed architecture. For example, a processing system can be used to detect the presence of an SNP at a position by detecting the hybridization of a probe to a nucleic acid molecule. A processing system also can be used to determine the Gram status, identity or grouping of a bacterium, or the identity or grouping of a fungus, on the basis of detection of one or more SNPs. In some examples, commands inputed to the processing system by a user assist the processing system in making these determinations.

In one example, a processing system includes at least one microprocessor, a memory, an input/output device, such as a keyboard and/or display, and an external interface, interconnected via a bus. The external interface can be utilised for connecting the processing system to peripheral devices, such as a communications network, database, or storage devices. The microprocessor can execute instructions in the form of applications software stored in the memory to allow the SNP detection and/or microorganism identification or classification process to be performed, as well as to perform any other required processes, such as communicating with the computer systems. The applications software may include one or more software modules, and may be executed in a suitable execution environment, such as an operating system environment, or the like.

5. Applications of the Methods of the Present Invention

The methods of the present invention are useful for classifying and/or identifying microbes in a sample, such as a sample from a subject or an environmental sample such as a soil or water sample or a sample taken from the surface of equipment or instruments (e.g. medical or surgical instruments) or a work surface. Such classification or identification can then be used to determine a course of treatment to remove, eradicate or reduce the number the microbes. Any two or more of the methods of the present invention can be combined. For example, nucleic acid from a sample can be analysed for the presence of SNPs in a 16SrRNA gene and for the presence of SNPs in a 5.8S rRNA using the methods of the present invention. This can be done so as to determine whether Gram-positive bacteria, Gram-negative bacteria and/or fungi are present in the sample. In some instances, the identity of the fungi can also be determined as taught herein. The bacteria can be further grouped or the identity of the bacteria may also be determined or narrowed down to one of a few possibilities. For example, as would be apparent from the disclosure above, SNPs at positions corresponding to positions 396 and 398 of the 16S rRNA gene set forth in SEQ ID NO:1, in combination with SNPs at positions corresponding to 399, 400 and 401 or positions corresponding to 278, 286 and 648 of the 16S rRNA gene set forth in SEQ ID NO:1, can be assessed so as to classify or even identify a mammalian (e.g., human) sepsis-associated bacterium in a sample. For example, if SNPs at positions 396, 398, 399, 400 and 401 are assessed, a mammalian (e.g., human) sepsis-associated bacterium in a sample can be classified into one of 7 pathogen groups, as described above. Additional SNPs can then be assessed to further classify or even identify the mammalian (e.g., human) sepsis-associated bacterium. If SNPs at positions 278, 286, 396, 398 and 648 are assessed, a mammalian (e.g., human) sepsis-associated bacterium can be classified as Gram-positive or Gram-negative, and can also be further identified or identified as one of a group of species, as described above. In some instances, the number of bacteria or fungi in the sample is determined or estimated.

Subjects with infections or suspected infections (e.g. subjects with SIRS) often present to clinicians in clinics, emergency rooms, general wards and intensive care units. Such patients often have non-diagnostic clinical signs of abnormal temperature, increased heart and respiratory rates and abnormal white cells counts. A clinician must decide whether the patient has an infection or not, the severity of the infection, whether to admit the patient to hospital (if not already in hospital), the source of infection, whether to use antibiotics, and if so, the type, route and dose of antibiotics. The presence of an infection in a patient has most typically been assessed by taking a sample from the patient and growing an organism in culture broth. Once an organism has grown it can be Gram stained, identified and its antibiotic resistance determined. However, in many infected patients (>50%) it is not possible to culture an organism. Without an identified organism a clinician must rely on clinical judgment and the use of broad spectrum, and often combination, antibiotics. The indiscriminate use of broad-spectrum antibiotics, without knowledge of the pathogenic organism's identity or sensitivity, results in the development of antibiotic resistance, overuse of antibiotics, and potentially toxic side effects in patients. Further, inadequate use of antibiotic in sepsis patients leads to higher mortality and longer hospital stays (Garnacho-Montero, J. et al. (2008) Journal of Antimicrobial Chemotherapy 61, 436-441). Blood culture is a sensitive method (1-100 cfu/mL) but only when the blood sample taken contains a viable organism, which is not always the case in sepsis (Coburn B, Morris A M, Tomlinson G, Detsky A S (2012) Does this adult patient with suspected bacteremia require blood cultures? JAMA 308: 502-511. doi:10.1001/jama.2012.8262.)

Thus, the methods of the present invention are particularly useful in assisting clinicians in determining whether the subject, such as a subject presenting with SIRS, has an infection (e.g. sepsis) and if so, an appropriate course of treatment based on the classification of the microorganism causing the infection. As demonstrated in Example 6, in an exemplary method of the present invention, the limit of detection is 10-100 fold more sensitive than culturing of the microbe. Furthermore, the methods of the present invention facilitate discrimination of Gram-positive and Gram-negative organisms and fungi within three hours of taking a whole blood sample (in suspected sepsis for instance) from a subject. The methods of the present invention also can be performed in a time-efficient manner, so that the results are available to the clinician within hours rather than days. Such attributes allow a clinician to sensitively detect and quantitate the presence of a microorganism and to make an informed decision on the use of antibiotics specific to the Gram status or further grouping or identification of the bacteria, or anti-fungals specific to the fungus. These improvements can result in a reduced number of patients admitted to hospital unnecessarily, sensitive detection of microorganisms, severity of infection assessed on load (and other factors), reduced use of broad-spectrum antibiotics, reduced patient time on broad spectrum antibiotics, reduced toxicity from antibiotics, reduced development of antibiotic resistance. Tables 25 and 26 show examples of timelines for decision making available to the clinician based on detection and differentiation of microbial infections using methods of the prior art and the methods of the present invention (referred to in the table as "SNP assay").

TABLE 25

Decision timeline using classification of microorganisms based on culture

| Action | Elapsed time (hours) | Possible adverse outcomes |
|---|---|---|
| Assess patient | 1 | |
| Admit patient with suspected infection | 2 | Patients admitted unnecessarily |
| Assess severity | 3 | Severity and bacterial load not determined properly Patient over-treated or under-treated |
| Take clinical samples for culture | 3 | Insufficient sample collected to grow organism |
| Treat with intravenous, combination, empirical antibiotics Perform culture and sensitivity | 4 | Infection missed in some patients Antibiotic resistance develops Wrong antibiotic choice Toxicity to the use of empirical antibiotics Takes 48 hours to complete. Organism does not grow. |
| Receive culture results | 48 | Culture positive - wrong antibiotic choice initially has led to toxicity and adds to resistance development, patient may have died. Culture negative - patient left on broad-spectrum antibiotics, which leads to toxicity and resistance development. |
| Treat with narrow spectrum antibiotics | 50 | Only possible if culture results are positive. |

TABLE 26

Decision timeline using classification of microorganisms based on methods of the present invention

| Action | Elapsed time (hours) | Possible adverse outcomes |
|---|---|---|
| Assess patient | 1 | |
| Take clinical samples for SNP analysis and culture in | 2 | Patient not admitted unnecessarily |

TABLE 26-continued

Decision timeline using classification of microorganisms based on methods of the present invention

| Action | Elapsed time (hours) | Possible adverse outcomes |
|---|---|---|
| suspected infection (as outpatient) | | |
| Treat with combination, empirical antibiotics | | Broad spectrum antibiotics used for a short period |
| Perform SNP assay | 2 | Takes approximately 3 hours to complete |
| Receive SNP assay results | 5 | Infection diagnosed more sensitively. Load determines severity. |
| Admit patient with known infection based on results | 6 | Only those patients with known infection and severity are admitted. |
| Treat with narrow spectrum antibiotics | 7 | Narrow spectrum antibiotics used lowering the likelihood of resistance development and toxicity. Patient treated within 5 hours with narrow spectrum antibiotic. |

Thus, the present invention also extends to the diagnosis of sepsis in a subject, and the management of sepsis following the positive diagnosis. The methods described herein that analyse one or more SNPs within a 5.8S rRNA and/or one or more SNPs within a 16S rRNA can be used to determine whether a subject has a fungal and/or bacterial infection in their blood and further to classify the bacteria as Gram-positive or Gram-negative, and/or identify the group or species of bacteria and/or fungi in the blood. The bacterial and/or fungal load (i.e. the number of bacteria or fungi) can also be determined.

In instances where the subject presents with SIRS and a diagnosis of sepsis can not be made using the methods provided herein, i.e. bacterial or fungal cells are not identified in the sample from the subject using the methods provided herein, then a diagnosis of inSIRS can be made by elimination. In some instances, additional testing to confirm the diagnosis can be performed. Thus, the present invention also extends to the diagnosis of inSIRS in a subject, and the management of inSIRS following the diagnosis.

5.1 Additional Assay and Tests

In some instances, the methods of the present invention are performed in combination with other methods for identifying or classifying microbes, or characterizing microbes. For example, the antibiotic sensitivity of the bacteria or the presence of virulence factors can be assessed once its grouping or identity is determined using the methods of the present invention.

Antibiotic sensitivity assays can be performed using culture methods or molecular methods, and such methods are well known to those skilled in the art. Various commercial systems that require initial culturing of the bacteria are available, including the Etest® by Biomerieux. Such systems allow for the determination of minimum inhibitory concentrations of a wide variety of antibiotics.

Molecular tests have also been developed to identify the presence of antibiotic resistance genes (see e.g. Huletsky, A. et al. (2004) Journal of Clinical Microbiology 42, 1875-1884; Watterson et al. (1998) Journal of Clinical Microbiology 36, 1969-1973). Molecular testing for ORSA can be achieved using a PCR assay designed to detect the presence of mecR1 (or mecA or the protein PBP2a). Various approaches include those described in Fang & Hedin (2006) Journal of Clinical Microbiology 44, 675; Huletsky, A. et al. (2004) Journal of Clinical Microbiology 42, 1875-1884; and U.S. Pat. No. 8,362,228. Molecular testing for VRE can be achieved using a PCR assay designed to detect the presence of VanA and/or VanB. Particular test include those described in Cantarelli. et al. (2011) Revista da Sociedade Brasileira de Medicina Tropical 44, 631-632; Fang et al. (2012) Eur J Clin Microbiol Infect Dis 31, 261-265; and US Pat. Pub. No. 20050058985 A1. Molecular testing for QREC (fluoroquinalone resistance) can be achieved using a PCR assay designed to detect mutations in gyrA and parC. Various approaches include those described in Jurado et al. (2008) J. Vet. Diagn. Invest. 20, 342-345; Karczmarczyk et al. (2011) Appl. Environ. Microbiol. 77, 7113-7120; US Pat Pub. No. 20100136523A1; and International Pat. Pub. No. WO 2000024932. Molecular testing for ESBL (ceftazidime resistance) can be performed using a PCR assay designed to detect bla(SHV) and mutations (see e.g., Alfaresi et al. (2010) Indian J Med Microbiol 28, 332; Randegger et al. (2001) Antimicrob. Agents Chemother. 45, 1730-1736; and US Pat. Pub. No. 20130065790A1.

Many antibiotic resistance genes and mechanisms are well known in the art (see e.g. Liu B, Pop M. ARDB-Antibiotic Resistance Genes Database. Nucleic Acids Res. 2009 January; 37 (Database issue): D443-7; http://ardb.cb-cb.umd.edu/). Some of the more common antibiotic resistance mechanisms are detailed in Table 27.

TABLE 27

| Type | Subtype |
|---|---|
| Aminoglycoside Resistance | Aac (Acetylation) |
| | Aph (Phosphorylation) |
| | Ant (Adenylylation) |
| Beta Lactamase (beta-lactam resistance) | beta-lactamase class A |
| | beta-lactamase class B |
| | beta-lactamase class C |
| | beta-lactamase class D |
| Macrolide-Lincosamide-Streptogramin B (MLSB) Resistance | erm rRNA methylases |
| | ATP-binding transporters (ABC) |
| | Major facilitator family transporters |
| | Esterases |
| | Hydrolases |
| | transferases |
| | phosphorylases |
| Multidrug Transporters | Major Facilitator Superfamily (MFS) transporter |
| | ATP-Binding Cassette transporter |
| | Resistance-Nodulation-Cell Division (RND) transporter |
| | Small Multidrug Resistance (SMR) transporter |
| Tetracycline Resistance | Tetracycline Efflux Resistance |
| | Ribosome Protection Resistance |
| Vancomycin Resistance | VanA Type Operon |
| | VanB Type Operon |
| | VanC Type Operon |
| | VanD Type Operon |
| | VanE Type Operon |
| | VanG Type Operon |

The major mechanisms of resistance in each of the key, known resistant bacterial genera are listed in Table 28 with the main mechanism(s) underlined.

TABLE 28

| Genus | Resistance gene | Description | Resistance |
|---|---|---|---|
| Staphylococcus | mecr1 | Methicillin-resistance regulatory protein for mecA | methicillin |
| Staphylococcus | aac6ie | Aminoglycoside N-acetyltransferase, which modifies aminoglycosides by acetylation. | amikacin dibekacin isepamicin netilmicin sisomicin tobramycin |
| Staphylococcus | aad9ib | Aminoglycoside O-nucleotidylyltransferase, which modifies aminoglycosides by adenylylation. | spectomycin streptomycin |
| Staphylococcus | aadd | Aminoglycoside O-nucleotidylyltransferase, which modifies aminoglycosides by adenylylation. | kanamycin tobramycin |
| Staphylococcus | aph3iiia | Aminoglycoside O-phosphotransferase, which modifies aminoglycosides by phosphorylation. | amikacin butirosin gentamincin_b isepamicin kanamycin lividomycin neomycin paromomycin ribostamycin |
| Staphylococcus | baca | Undecaprenyl pyrophosphate phosphatase, which consists in the sequestration of Undecaprenyl pyrophosphate. | bacitracin |
| Staphylococcus | bcra, (bcrc) | ABC transporter system, bacitracin efflux pump. | bacitracin |
| Staphylococcus | bl2a_pc | Class A beta-lactamase. This enzyme breaks the beta-lactam antibiotic ring open and deactivates the molecule's antibacterial properites. | penicillin |
| Staphylococcus | bl2b_tem | Class A beta-lactamase. This enzyme breaks the beta-lactam antibiotic ring open and deactivates the molecule's antibacterial properites. | cephalosporin penicillin |
| Staphylococcus | bl2_len | Class A beta-lactamase. This enzyme breaks the beta-lactam antibiotic ring open and deactivates the molecule's antibacterial properites. | penicillin |
| Staphylococcus | ble | Binding protein with a strong affinity to the bleomycin family of antibiotics, which confers resistance to these antibiotics by preventing the bleomycin-induced DNA breakage | bleomycin |
| Staphylococcus | cata7 | Group A chloramphenicol acetyltransferase, which can inactivate chloramphenicol. | chloramphenicol |
| Staphylococcus | cata8 | Group A chloramphenicol acetyltransferase, which can inactivate chloramphenicol. | chloramphenicol |
| Staphylococcus | cata9 | Group A chloramphenicol acetyltransferase, which can inactivate chloramphenicol. | chloramphenicol |
| Staphylococcus | cml_e1 | Major facilitator superfamily transporter, chloramphenicol efflux pump. | chloramphenicol |
| Staphylococcus | cml_e4 | Major facilitator superfamily transporter, chloramphenicol efflux pump. | chloramphenicol |
| Staphylococcus | dfra12 | Group A drug-insensitive dihydrofolate reductase, which can not be inhibited by trimethoprim. | trimethoprim |
| Staphylococcus | dfra17 | Group A drug-insensitive dihydrofolate reductase, which can not be inhibited by trimethoprim. | trimethoprim |
| Staphylococcus | erma | rRNA adenine N-6-methyltransferase, which can methylate adenine at position 2058 of 23S rRNA, conferring resistance to erythromycin. | lincosamide macrolide streptogramin_b |
| Staphylococcus | ermb | rRNA adenine N-6-methyltransferase, which can methylate adenine at position 2058 of 23S rRNA, conferring resistance to erythromycin. | lincosamide macrolide streptogramin_b |
| Staphylococcus | ermc | rRNA adenine N-6-methyltransferase, which can methylate adenine at position 2058 of 23S rRNA, conferring resistance to erythromycin. | lincosamide macrolide streptogramin_b |
| Staphylococcus | ermy | rRNA adenine N-6-methyltransferase, which can methylate adenine at | lincosamide macrolide |

TABLE 28-continued

| Genus | Resistance gene | Description | Resistance |
|---|---|---|---|
| | | position 2058 of 23S rRNA, conferring resistance to erythromycin. | streptogramin_b |
| Staphylococcus | fosb | Glutathione transferase, metalloglutathione transferase which confers resistance to fosfomycin by catalyzing the addition of glutathione to fosfomycin | fosfomycin |
| Staphylococcus | fusb | Involved in the resistance (detoxification) of the fungal toxin fusaric acid. | fusaric_acid |
| Staphylococcus | lnua | Lincosamide nucleotidyltransferase. | lincomycin |
| Staphylococcus | meca | Penicillin binding protein, which has a low affinity for beta-lactams and catalyze a penicillin-insensitive transpeptidation. | beta_lactam |
| Staphylococcus | mefa | Major facilitator superfamily transporter, Macrolide-Lincosamide-Streptogramin B efflux pump. | macrolide |
| Staphylococcus | mphc | Macrolide phosphotransferase | macrolide |
| Staphylococcus | msra | ABC transporter system, Macrolide-Lincosamide-Streptogramin B efflux pump. | lincosamide macrolide streptogramin_b nora |
| Staphylococcus | qac | Small Multidrug Resistance (SMR) protein family. Multidrug resistance efflux pump, which consists of two proteins. | qa_compound |
| Staphylococcus | qaca, (qacb) | Multidrug efflux pump from bacterial pathogen staphylococcus aureus. Including QacA and QacB, both of which confer resistance to various toxic organic cations but differ in that QacB mediates lower levels of resistance to divalent cations. They differed by seven nucleotide substitutions. | qa_compound |
| Staphylococcus | qacb, (qaca) | Multidrug efflux pump from bacterial pathogen staphylococcus aureus. Including QacA and QacB, both of which confer resistance to various toxic organic cations but differ in that QacB mediates lower levels of resistance to divalent cations. They differed by seven nucleotide subsititutions. | qa_compound |
| Staphylococcus | str | Streptomycin resistance protein. | streptomycin |
| Staphylococcus | tet38 | Major facilitator superfamily transporter, tetracycline efflux pump. | tetracycline |
| Staphylococcus | teta | Major facilitator superfamily transporter, tetracycline efflux pump. | tetracycline |
| Staphylococcus | tetk | Major facilitator superfamily transporter, tetracycline efflux pump. | tetracycline |
| Staphylococcus | tetl | Major facilitator superfamily transporter, tetracycline efflux pump. | tetracycline |
| Staphylococcus | tetm | Ribosomal protection protein, which protects ribosome from the translation inhibition of tetracycline. | tetracycline |
| Staphylococcus | vana, (vanra vanha vansa vanya vanxa) | VanA type vancomycin resistance operon genes, which can synthesize peptidoglycan with modified C-terminal D-Ala-D-Ala to D-alanine--D-lactate. | teicoplanin vancomycin |
| Staphylococcus | vanha (vanra vansa vana vanya vanxa) | VanA type vancomycin resistance operon genes, which can synthesize peptidoglycan with modified C-terminal D-Ala-D-Ala to D-alanine--D-lactate. | teicoplanin vancomycin |
| Staphylococcus | vanra (vanha vansa vana vanya vanxa) | VanA type vancomycin resistance operon genes, which can synthesize peptidoglycan with modified C-terminal D-Ala-D-Ala to D-alanine--D-lactate. | teicoplanin vancomycin |
| Staphylococcus | vansa (vanra | VanA type vancomycin resistance operon genes, which can synthesize | teicoplanin vancomycin |

TABLE 28-continued

| Genus | Resistance gene | Description | Resistance |
|---|---|---|---|
| | vanha vana vanya vanxa) | peptidoglycan with modified C-terminal D-Ala-D-Ala to D-alanine--D-lactate. | |
| Staphylococcus | vanxa (vanra vanha vansa vana vanya) | VanA type vancomycin resistance operon genes, which can synthesize peptidoglycan with modified C-terminal D-Ala-D-Ala to D-alanine--D-lactate. | teicoplanin vancomycin |
| Staphylococcus | vanya (vanra vanha vansa vana vanxa) | VanA type vancomycin resistance operon genes, which can synthesize peptidoglycan with modified C-terminal D-Ala-D-Ala to D-alanine--D-lactate. | teicoplanin vancomycin |
| Staphylococcus | vanz | VanZ confers low-level to the glycopeptide antibiotic teicoplanin. | teicoplanin |
| Staphylococcus | vata | Virginiamycin A acetyltransferase, which can inactivate the target drug. | streptogramin_a |
| Staphylococcus | vatb | Virginiamycin A acetyltransferase, which can inactivate the target drug. | streptogramin_a |
| Staphylococcus | vatc | Virginiamycin A acetyltransferase, which can inactivate the target drug. | streptogramin_a |
| Staphylococcus | vgaa | ABC transporter system, Macrolide-Lincosamide-Streptogramin B efflux pump. | streptogramin_a |
| Staphylococcus | vgab | ABC transporter system, Macrolide-Lincosamide-Streptogramin B efflux pump. | streptogramin_a |
| Staphylococcus | vgba | Streptogramin B Lyase, which can deactivate the target drug by hydrolysis. | streptogramin_b |
| Staphylococcus | vgbb | Streptogramin B Lyase, which can deactivate the target drug by hydrolysis. | streptogramin_b |

Microbial virulence genes and mechanisms are also well known and there are online databases of virulence mechanisms and factors of known pathogens, e.g. Virulence Factors of Pathogenic Bacteria (http://www.mgc.ac.cnNFs/main.htm) and LLNL Virulence Database (http://mvirdb.llnl.gov/). Thus, having identified a causative pathogen using the methods described herein, those skilled in the art can design and/or perform specific detection assays for virulence factor genetic determinants easy. Exemplary assays for detecting various virulence factors in Staphylococcus spp., Enterococcus spp., Escherichia coli and Klebsiella spp. include those described in US Pat. Pub. Nos. US2008012473 and US20060194206; Int. Pat. Pub. No. WO2003052143; EP Pat. Pub. No. 2231851; Pichon, B. et al. (2012) J. Antimicrob. Chemother. 67, 2338-2341; Lenz et al. (2010) Food Microbiol 27, 317-326 (2010); Margot et al. (2013) J Food Prot 76, 871-873; and Huang et al. (2012) BMC Microbiol. 12, 148. Non-limiting examples of important virulence factors of some key mammalian (e.g., human) pathogens are listed in Table 29.

TABLE 29

| Bacteria | Virulence Mechanism | Factor(s) |
|---|---|---|
| Staphylococcus | Adherence | CNA Clumping factor Eap/Map EbpS FnBPs Intercellular adhesion proteins SDr |
| Staphylococcus | Antiphagocytosis | Capsule |
| Staphylococcus | Exoenzyme | Aureolysin Hyaluronate lyase Lipase Staphopain Staphylocoagulase V8 protease vWbp |
| Staphylococcus | Immune evasion | AdsA CHIPS SCIN Sbi SpA |
| Staphylococcus | Iron uptake | Isd |
| Staphylococcus | Plasminogen activator | Staphylokinase |
| Staphylococcus | Secretion system | Type VII secretion system |
| Staphylococcus | Toxin | α-hemolysin β-hemolysin δ-hemolysin γ-hemolysin Exfoliative toxin PVL SE TSST-1 |
| Enterococcus | Adherence | AS Ace Acm EfaA Esp Scm |

TABLE 29-continued

| Bacteria | Virulence Mechanism | Factor(s) |
|---|---|---|
| *Enterococcus* | Antiphagocytosis | Capsule |
| *Enterococcus* | Biofilm formation | BopD |
| | | Fsr |
| *Enterococcus* | Exoenzyme | Gelatinase |
| | | Hyaluronidase |
| | | SprE |
| *Enterococcus* | Toxin | Cytolysin |
| *Escherichia coli* (EHEC and EAEC) | Adherence | AAFs |
| | | Dispersin |
| | | ECP |
| | | Efa-1/LifA |
| | | Intimin |
| | | Paa |
| | | ToxB |
| *Escherichia coli* (EHEC and EAEC) | Toxin | EAST1 |
| | | Pet |
| | | Pic |
| | | ShET1 |
| | | Hemolysin |
| | | Stx |
| *Escherichia coli* (EHEC and EAEC) | Iron uptake | Chu |
| *Escherichia coli* (EHEC and EAEC) | Protease | EspP |
| | | StcE |
| *Escherichia coli* (EHEC and EAEC) | Regulation | Ler |
| *Escherichia coli* (EHEC and EAEC) | Secretion system | TTSS |
| *Escherichia coli* (EHEC and EAEC) | Type III translocated protein | Cif |
| | | EspA |
| | | EspB |
| | | EspD |
| | | EspF |
| | | EspG |
| | | EspH |
| | | Map |
| | | NleA/EspI |
| | | NleC |
| | | NleD |
| | | Tir |
| *Klebsiella* | Capsule | CPS |
| | | LPS |
| *Klebsiella* | Adhesins | Fimbrial |
| | | Non-fimbrial |
| *Klebsiella* | Iron-binding/scavenging | Yersiniabactin |

5.2 Management and Therapy

Based on the results of the methods of the present invention, the subject can be appropriately managed and administered therapy where required. For example, the management of inSIRS can include, for example, administration of therapeutic agents such as vasoactive compounds, steroids and anti tumour necrosis factor agents. In addition, palliative therapies as described for example in Cohen and Glauser (1991, Lancet 338: 736-739) aimed at restoring and protecting organ function can be used such as intravenous fluids and oxygen and tight glycemic control.

Where sepsis is diagnosed and further classification, grouping or identification of the microbe is made, a practitioner can then determine an appropriate regimen to manage the infection. This may include the administration of one or more therapeutic agents such as antibiotics, anti-fungals or antibodies to endotoxin. Appropriate therapies for sepsis are well known to those skilled in the art and are reviewed in, for example, Healy (2002, Ann. Pharmacother. 36(4): 648-54) and Brindley (2005, CJEM. 7(4): 227) and Jenkins (2006, J Hosp Med. 1(5): 285-295).

Typically, therapeutic agents will be administered in pharmaceutical (or veterinary if the subject is a non-human subject) compositions together with a pharmaceutically acceptable carrier and in an effective amount to achieve their intended purpose. The dose of active compounds administered to a subject should be sufficient to achieve a beneficial response in the subject over time such as a reduction in, or relief from, the symptoms of sepsis or inSIRS, and/or the reduction or elimination of microorganisms from the blood. The quantity of the pharmaceutically active compounds(s) to be administered may depend on the subject to be treated inclusive of the age, sex, weight and general health condition thereof. In this regard, precise amounts of the active compound(s) for administration will depend on the judgment of the practitioner. In determining the effective amount of the active compound(s) to be administered in the treatment or prevention of sepsis or inSIRS, the practitioner may evaluate severity of infection in the case of sepsis, and severity of any symptom associated with sepsis or inSIRS including, inflammation, blood pressure anomaly, tachycardia, tachypnea fever, chills, vomiting, diarrhoea, skin rash, headaches, confusion, muscle aches, seizures. In any event, those of skill in the art may readily determine suitable dosages of the therapeutic agents and suitable treatment regimens without undue experimentation.

The therapeutic agents may be administered in concert with adjunctive (palliative) therapies to increase oxygen supply to major organs, increase blood flow to major organs and/or to reduce the inflammatory response. Illustrative examples of such adjunctive therapies include non steroidal-anti inflammatory drugs (NSAIDs), intravenous saline and oxygen.

In order that the invention may be readily understood and put into practical effect, particular preferred embodiments will now be described by way of the following non-limiting examples.

EXAMPLES

Example 1

Identification of 16S rRNA SNPs that Differentiate Gram-Negative and Gram-Positive Prokaryotes Representative genes encoding 16S rRNA molecules were downloaded from GenBank and aligned using CLUSTALW to determine the conserved sequence regions. Variable sequences, as determined by the CLUSTALW alignment, were removed, the sequences were re-aligned using CLUSTALW and checked for any further variable regions. This process was repeated several times. Subsequently, a final conserved mega-alignment of all genes encoding 16S rRNA was generated, consisting of an approximately 702 base pair conserved sequence region. The gene encoding an exemplary 16S rRNA from *Escherichia coli* (GenBank accession NR_074891) is set forth in SEQ ID NO:1, and the 702 base pair conserved regions extends from nucleotides 254-955 of SEQ ID NO:1.

The aligned sequences were analysed, and it was determined that two SNPs were sufficient to differentiate most Gram-positive and Gram-negative bacteria. The two SNPs identified are at positions 396 and 398 in the *Escherichia coli* 16S rRNA set forth in SEQ ID NO:1, and are referred to as SNP 396 and SNP 398. The general rules for differentiating most Gram-positive and Gram-negative prokaryotes using these two SNPs are depicted in Table 30.

TABLE 30

| Gram Status | SNP 396 | SNP 398 |
|---|---|---|
| Negative | C | T/A/C |
| Positive | A/T/G | C |

Example 2

In Silico Differentiation of Gram-Negative and Gram-Positive Prokaryotes Using SNP 396 and SNP 398

In silico analysis was used to assess which prokaryotes could be classified on the basis of their Gram status using SNPs 396 and 398 only. Twelve 12 base pair probes (GC(A/C/G/T)A(A/C/G/T)G(CC/TA)GCGT; SEQ ID NO:2) were used in BLAST searches to identify the prokaryotic 16S rRNA regions spanning positions 396 and 398 (numbering corresponding to *Escherichia coli* 16S rRNA set forth in SEQ ID NO:1), and the results were analysed to determine which species could be classified correctly as Gram-positive or Gram-negative on the basis of the SNPs.

Table 31 table lists the most common mammalian pathogens typed into Gram-negative or Gram-positive based only on SNP positions 396 and 398. Most pathogens can be typed as Gram-negative or Gram-positive based on these two SNPs, with the exception of some Gram-negative bacteria that have A and C or G and C at SNP loci 396 and 398, respectively, such as *Helicobacter*, *Veillonella*, some *Bacteroides*, *Campylobacter*, *Chlamydiophila* spp.

TABLE 31

| | SNP Position | | Example Pathogens |
|---|---|---|---|
| Gram Stain | 396 | 398 | Genera and Comments |
| Negative | C | T | *Escherichia* <br> *Enterobacter* <br> *Brucella* <br> *Cardiobacterium* <br> *Edwardsiella* <br> *Haemophilus* <br> *Klebsiella* <br> *Moraxella* <br> *Providentia* <br> *Pseudomonas* <br> *Salmonella* <br> *Vibrio* <br> *Yersinia* <br> *Flavobacterium* <br> *Neisseria* (some) <br> *Shigella* <br> *Plesiomonas* <br> *Pasteurella* <br> *Actinobaccillus* <br> *Aeromonas* <br> *Burkholderia* <br> *Citrobacter* <br> *Morganella* <br> *Proteus* <br> *Serratia* <br> *Acinetobacter* <br> *Legionella* <br> 3416 BLAST hits, 12 bp probe, 100% identity. |
| Negative | C | A | *Neisseria* <br> *Porphyromonas* <br> *Bacteroides* <br> *Prevotella* <br> 97 BLAST hits, 12 bp probe, 100% identity. |

TABLE 31-continued

| | SNP Position | | Example Pathogens |
|---|---|---|---|
| Gram Stain | 396 | 398 | Genera and Comments |
| Negative | C | C | *Bacteroides* (some) <br> 51 BLAST hits, 12 bp probe, 100% identity |
| Positive | A | C | *Dermatophilus* <br> *Enterococcus* <br> *Listeria* <br> *Mycobacterium* <br> *Proprionibacterium* <br> *Rhodococcus* <br> *Streptomyces* <br> *Micrococcus* <br> *Bacillus* <br> *Eubacterium* <br> *Lactobacillus* <br> *PeptoStreptococcus* <br> *Streptococcus* <br> *Actinomyces* <br> *Erysipelothrix* <br> *Staphylococcus* <br> *Corynebacterium* <br> *Clostridium* <br> *Nocardia* <br> 3208 BLAST hits, 12 bp probe, 100% identity <br> Includes some Gram-negative species including *Helicobacter*, *Veillonella*, some *Bacteriodes*, *Campylobacter*, *Chlamydiophila*. |
| Positive | T | C | *Lactobacillus* <br> *Streptomyces* (some) <br> *Steptococcus* (some) <br> *Actinomyces* (some) <br> 294 BLAST hits, 12 bp probe, 100% identity |
| Positive | G | C | *Mycobacterium* <br> *Rhodococcus* <br> *Streptomyces* <br> *Micrococcus* (some) <br> *Bacillus* (some) <br> *Eubacterium* <br> *Actinomyces* <br> *Corynebacterium* (some) <br> *Mobiluncus* <br> *Nocardia* <br> *Lactobacillus* (some) <br> 2240 BLAST hits, 12 bp probe, 100% identity. <br> Mostly Gram-positive but includes the negative spp *Chlamydia* and *Chlamydiophilus*. |

Table 32 shows the SNPs at positions 396 and 398 for the most common soil bacteria as identified in Janssen et al. (Appl. Environ. Microbiol. (2006) 72, 1719-1728).

TABLE 32

| | SNP Position | | Most Common |
|---|---|---|---|
| Gram Stain | 396 | 398 | Soil Organisms |
| Negative | C | T | *Agrobacterium* <br> *Flavobacterium* <br> *Hyphomicrobium* <br> *Pseudomonas* <br> *Ralstonia* |
| Positive | A/G | C | *Actinomadura* <br> *Actinoplanes* <br> *Arthrobacter* <br> *Bacillus* <br> *Clostridium* <br> *Micromonospora* <br> *Mycobacterium* <br> *Nocardia* |

TABLE 32-continued

| Gram Stain | SNP Position 396 | SNP Position 398 | Most Common Soil Organisms |
|---|---|---|---|
| | | | Paenibacillus |
| | | | Rhodococcus |
| | | | Streptomyces |

Table 33 shows the SNPs at positions 396 and 398 for a range of Gram-positive and Gram-negative prokaryotes found in work environments as identified in Hewitt et al. (PLoS ONE (2012) 7, e37849).

TABLE 33

| Gram Stain | SNP Position 396 | SNP Position 398 | Common Environmental Organisms |
|---|---|---|---|
| Negative | C | T | Escherichia |
| | | | Klebsiella |
| | | | Pseudomonas |
| | | | Salmonella |
| | | | Yersinia |
| | | | Shigella |
| | | | Burkholderia |
| | | | Sphingomonas |
| | | | Methylobacterium |
| Negative | C | A | Neisseria |
| | | | Bacteroides |
| | | | Prevotella |
| Negative | C | C | Bacteroides (further typed using other SNPs) |
| Positive | A | C | Bacillus |
| | | | Lactobacillus |
| | | | Streptococcus |
| | | | Actinomyces |
| | | | Staphlococcus |
| | | | Corynebacterium |
| | | | Planomicrobium |
| | | | Planococcus |
| Positive | T | C | Lactobacillus |
| Positive | G | C | Mycobacterium |
| | | | Actinomyces |
| | | | Lactobacillus (some) |

Table 34 shows the SNPs at positions 396 and 398 for common bacteria found contaminating red blood cell and platelet preparations as identified in Brecher et al. (2005) Clinical Microbiology Reviews 18, 195-204).

TABLE 34

| Gram Stain | SNP Position 396 | SNP Position 398 | Common Blood Preparation Contaminants |
|---|---|---|---|
| Negative | C | T | Escherichia |
| | | | Klebsiella |
| | | | Providentia |
| | | | Pseudomonas |
| | | | Salmonella |
| | | | Yersinia |
| | | | Shigella |
| | | | Proteus |
| | | | Serratia |
| | | | Acinetobacter |
| Positive | A | C | Enterococcus |
| | | | Propionibacterium |
| | | | Bacillus |
| | | | Streptococcus |
| | | | Staphylococcus |

Table 35 shows the SNPs at positions 396 and 398 for common bacteria found in human blood stream infections (sepsis) as identified in Son et al. (J Korean Med Sci (2010) 25, 992 (2010); and the SeeGene website (www.seegene.com) and the Septifast website (www.roche.com).

TABLE 35

| Gram Stain | SNP Position 396 | SNP Position 398 | Common Human Sepsis Blood Pathogens |
|---|---|---|---|
| Negative | C | T | Escherichia |
| | | | Enterobacter |
| | | | Citrobacter |
| | | | Haemophilus |
| | | | Klebsiella |
| | | | Pseudomonas |
| | | | Salmonella |
| | | | Yersinia |
| | | | Shigella |
| | | | Burkholderia |
| | | | Morganella |
| | | | Proteus |
| | | | Serratia |
| | | | Acinetobacter |
| | | | Stenotrophomonas |
| Negative | C | A | Neisseria |
| | | | Bacteroides |
| | | | Prevotella |
| Negative | C | C | Bacteroides (some) |
| Positive | A | C | Enterococcus |
| | | | Streptococcus |
| | | | Staphylococcus |
| | | | Clostridium |

Table 36 shows the SNPs at positions 396 and 398 for the most common bacteria found in human faecal samples when using next generation sequencing technologies as identified in Claesson et al. (Nucl Acids Res (2010) 38(22), e200).

TABLE 36

| Gram Stain | SNP Position 396 | SNP Position 398 | Most Common Human Faecal Organism Genera |
|---|---|---|---|
| Negative | C | T | Alistipes |
| Negative | C | A | Parabacteroides |
| | | | Bacteroides (s) |
| Positive | A/G | C | Dorea |
| | | | PeptoStreptococcus |
| | | | Anaerococcus |
| | | | Filifactor |
| | | | Finegoldia |
| | | | Gallicola |
| | | | Helcococcus |
| | | | Peptoniphilus |
| | | | Sedimentibacter |
| | | | Sporanaerobacter |
| | | | Tissierella |
| | | | Roseburia (variable but ultrastructure is Gram-positive) |
| | | | Ruminococcus |
| | | | Erysipelothrix |
| | | | Bulleidia |
| | | | Holdemania |
| | | | Solobacterium |
| | | | Faecalibacterium (further typed using other SNPs) |
| | | | Bacteroides (further typed using other SNPs) |

Thus, SNPs at positions 396 and 398 were able to differentiate a large number of Gram-positive from Gram-negative prokaryotes including the most common bacterial organisms found in soil, office environments, as blood product contaminants, in mammalian (e.g., human) faecal material, most mammalian (e.g., human) bacterial pathogens and most pathogens commonly found in mammalian (e.g., human) sepsis.

Example 3

In Silico Differentiation of Gram-Negative and Gram-Positive Sepsis-Associated Bacteria Using SNPs As indicated in Example 2 (Table 31), there are a few instances where the Gram status of mammalian (e.g., human) pathogens cannot be determined using SNPs at positions 396 and 398. These pathogens include the Gram-negative genera of *Helicobacter, Veillonella*, some *Bacteroides, Campylobacter*, and *Chlamydiophila*. Although the most common mammalian (e.g., human) sepsis-associated bacteria (e.g. *Staphylococcus aureus, Staphylococcus epidermidis, Staphylococcus haemolyticus, Staphylococcus hominis, Staphylococcus saprophyticus, Enterococcus faecalis, Enterococcus faecium, Clostridium perfringens, Streptococcus viridans* group (*Streptococcus anginosus, Streptococcus constellatus, Streptococcus intermedius, Streptococcus mitis, Streptococcus mutans, Streptococcus sanguinis, Streptococcus sobrinus* and *Streptococcus oralis*), *Streptococcus pneumoniae, Streptococcus agalactiae, Streptococcus bovis, Streptococcus sanguinis, Streptococcus dysgalactiae, Streptococcus mutans, Streptococcus pyogenes, Escherichia coli, Acinetobacter baumannii, Bacteroides fragilis, Burkholderia cepacia, Klebsiella pneumoniae, Klebsiella oxytoca, Pseudomonas aeruginosa, Enterobacter aerogenes, Enterobacter cloacae, Serratia marcescens, Proteus mirabilis, Citrobacter freundii, Morganella morganii, Haemophilus influenzae, Neisseria meningitidis, Stenotrophomonas maltophila, Prevotella buccae, Prevotella intermedia* or *Prevotella melaninogenica*) can be classified as Gram-negative or Gram-positive using SNPs at positions 396 and 398, other bacteria that can cause sepsis in mammals (e.g., humans), such as *Campylobacter coli, Campylobacter jejuni, Campylobacter lari, Campylobacter fetus, Helicobacter cinaedi, Helicobacter pylori, Chlamydophila abortus, Veillonella atypica, Veillonella parvula, Veillonella denticariosi* and *Veillonella rogosa*, cannot be classified using SNPs at positions 396 and 398.

Sequence analysis was performed to determine which SNPs could classify the common and less-common mammalian (e.g., human) sepsis-associated bacteria (*Staphylococcus aureus, Staphylococcus epidermidis, Staphylococcus haemolyticus, Staphylococcus hominis, Staphylococcus saprophyticus, Enterococcus faecalis, Enterococcus faecium, Clostridium perfringens, Streptococcus viridans* group (*Streptococcus anginosus, Streptococcus constellatus, Streptococcus intermedius, Streptococcus mitis, Streptococcus mutans, Streptococcus sanguinis, Streptococcus sobrinus* and *Streptococcus oralis*), *Streptococcus pneumoniae, Streptococcus agalactiae, Streptococcus bovis, Streptococcus sanguinis, Streptococcus dysgalactiae, Streptococcus mutans, Streptococcus pyogenes, Escherichia coli, Acinetobacter baumannii, Bacteroides fragilis, Burkholderia cepacia, Klebsiella pneumonia, Klebsiella oxytoca, Pseudomonas aeruginosa, Enterobacter aerogenes, Enterobacter cloacae, Serratia marcescens, Proteus mirabilis, Citrobacter freundii, Morganella morganii, Haemophilus influenzae, Neisseria meningitidis, Stenotrophomonas maltophila, Prevotella buccae, Prevotella intermedia, Prevotella melaninogenica, Salmonella enterica, Serratia marcescens, Haemophilus influenzae, Campylobacter coli, Campylobacter jejuni, Campylobacter lari, Campylobacter fetus, Helicobacter cinaedi, Helicobacter pylori, Chlamydophila abortus, Veillonella atypica, Veillonella parvula, Veillonella denticariosi, Veillonella rogosae, Streptomyces anulatus, Streptomyces somaliensis* and *Mycobacterium tuberculosis*) on the basis of their Gram status. It was found that another three SNPs at positions 278, 286 and 648 (numbering corresponding to the 16SrRNA set forth in SEQ ID NO:1) could be used to classify the 33 mammalian (e.g., human) sepsis pathogens. Thus, a total of 5 SNPs at positions 396, 398, 278, 286 and 648 can be used to determine the Gram status of these mammalian (e.g., human) sepsis pathogens.

The general rules for differentiating 33 Gram-positive and Gram-negative prokaryotes causing mammalian (e.g., human) sepsis using the five SNPs are as follows:

If position 396 is a C then the bacterium is Gram-negative and includes the species in Table 37; and if position 396 is A or G then the bacterium is Gram-positive and includes the species in Table 38.

TABLE 37

| Gram | Species | 396 | 398 | 278 | 286 | 648 |
|---|---|---|---|---|---|---|
| Negative | Prevotella melaninogenica | C | A | A | G | T |
| Negative | Prevotella intermedia | C | A | T | G | G |
| Negative | Prevotella buccae | C | A | T | G | T |
| Negative | Bacteroides fragilis | C | A | T | A | A |
| Negative | Citrobacter freundii | C | T | G | C | A |
| Negative | Enterobacter aerogenes | C | T | G | C | A |
| Negative | Klebsiella oxytoca | C | T | G | C | A |
| Negative | Serratia marcescens | C | T | G | C | A |
| Negative | Morganella morganii | C | T | G | C | C |
| Negative | Stenotrophomonas maltophila | C | T | G | G | C |
| Negative | Acinetobacter baumannii | C | T | G | G | G |
| Negative | Enterobacter cloacae | C | T | G | C | A |
| Negative | Klebsiella pneumoniae | C | T | G | C | A |
| Negative | Salmonella enterica | C | T | G | C | A |
| Negative | Escherichia coli | C | T | G | C | A |
| Negative | Proteus mirabilis | C | T | G | C | T |
| Negative | Neisseria meningitidis | C | T | G | G | T |
| Negative | Pseudomonas aeruginosa | C | T | G | G | T |
| Negative | Haemophilus influenzae | C | T | T | C | T |
| Negative | Burkholderia cepacia | C | T | G | G | A |

TABLE 38

| Gram | Species | 396 | 398 | 278 | 286 | 648 |
|---|---|---|---|---|---|---|
| Positive | Mycobacterium tuberculosis | G | C | G | G | A |
| Positive | Streptomyces somaliensis | G | C | G | G | A |
| Positive | Streptomyces anulatus | G | C | G | G | T |

If positions 396, 398 and 278 are A, C and T (respectively) then the bacterium is Gram-negative and includes the species in Table 39; and if positions 396, 398 and 278 are A, C and C (respectively) then the bacterium is Gram-positive and includes the species in Table 40.

TABLE 39

| Gram | Species | 396 | 398 | 278 | 286 | 648 |
|---|---|---|---|---|---|---|
| Negative | Campylobacter coli | A | C | T | T | A |
| Negative | Campylobact jejuni | A | C | T | T | A |
| Negative | Campylobacter lari | A | C | T | T | A |
| Negative | Campylobacter fetus | A | C | T | A | A |
| Negative | Helicobacter cinaedi | A | C | T | G | T |
| Negative | Helicobacter pylori | A | C | T | G | A |
| Negative | Chlamydophila abortus | A | C | T | T | T |

TABLE 40

| Gram | Species | 396 | 398 | 278 | 286 | 648 |
|---|---|---|---|---|---|---|
| Positive | Enterococcus faecalis | A | C | C | A | A |
| Positive | Enterococcus faecium | A | C | C | A | A |

If positions 396, 398 and 278 are A, C, G and position 286 is an A then the bacterium is Gram-positive and includes the species in Table 41.

TABLE 41

| Gram | Species | 396 | 398 | 278 | 286 | 648 |
|---|---|---|---|---|---|---|
| Positive | Streptococcus bovis | A | C | G | A | A |
| Positive | Streptococcus agalactiae | A | C | G | A | G |
| Positive | Streptococcus dysgalactiae | A | C | G | A | G |
| Positive | Streptococcus pyogenes | A | C | G | A | G |
| Positive | Streptococcus anginosus | A | C | G | A | T |
| Positive | Streptococcus intermedius | A | C | G | A | T |
| Positive | Streptococcus mitis | A | C | G | A | T |
| Positive | Streptococcus mutans | A | C | G | A | T |
| Positive | Streptococcus pneumoniae | A | C | G | A | T |
| Positive | Streptococcus sanguinis | A | C | G | A | T |

If positions 396, 398, 278, 286 are A, C, A, A then the bacterium is Gram-positive and includes the species in Table 42.

TABLE 42

| Gram | Species | 396 | 398 | 278 | 286 | 648 |
|---|---|---|---|---|---|---|
| Positive | Staphylococcus aureus | A | C | A | A | A |
| Positive | Streptococcus sobrinus | A | C | A | A | A |
| Positive | Streptococcus constellatus | A | C | A | A | T |
| Positive | Streptococcus oralis | A | C | A | A | T |

If positions 396, 398, 278, 286 are A, C, A, G and position 648 is a G then the bacterium is Gram-negative and includes the species in Table 43.

If positions 396, 398, 278, 286 are A, C, A, G and position 648 is an A then the bacterium is Gram-positive and includes the species in Table 44.

TABLE 43

| Gram | Species | 396 | 398 | 278 | 286 | 648 |
|---|---|---|---|---|---|---|
| Negative | Veillonella rogosae | A | C | A | G | G |

TABLE 44

| Gram | Species | 396 | 398 | 278 | 286 | 648 |
|---|---|---|---|---|---|---|
| Positive | Staphylococcus epidermidis | A | C | A | G | A |
| Positive | Staphylococcus hominus | A | C | A | G | A |

If positions 396, 398, 278 and 286 are A, C, G and G (respectively) and position 648 is G then the bacterium is Gram-negative and includes the species in Table 45.

If positions 396, 398, 278 and 286 are A, C, G and G and position 648 is A or T then the bacterium is Gram-positive and includes the species in Table 46.

TABLE 45

| Gram | Species | 396 | 398 | 278 | 286 | 648 |
|---|---|---|---|---|---|---|
| Negative | Veillonella atypica | A | C | G | G | G |
| Negative | Veillonella parvula | A | C | G | G | G |
| Negative | Veillonella denticariosi | A | C | G | G | G |

TABLE 46

| Gram | Species | 396 | 398 | 278 | 286 | 648 |
|---|---|---|---|---|---|---|
| Positive | Staphylococcus haemolyticus | A | C | G | G | A |
| Positive | Staphylococcus saprophyticus | A | C | G | G | A |
| Positive | Clostridium perfringens | A | C | G | G | T |

Example 4

Identification and Location of 5.8S rRNA SNPs that Differentiates Fungal Eukaryotes from Prokaryotes and Other Eukaryotes To identify SNPs in 5.8S rRNA that could differentiate fungal (including yeast) eukaryotes from other eukaryotes and also prokaryotes, representative 5.8S rRNA sequences from *Candida albicans, Ajellomyces capsulatus, Stachybotrys* sp, *Scedosporium apiospermum, Fusarium* sp, *Aspergillus fumigatus* and *Cryptococcus neoformans* were downloaded from GenBank and aligned using CLUSTALW to determine the conserved sequence regions. Variable sequences, as determined by the CLUSTALW alignment, were removed and the sequences were re-aligned using CLUSTALW and checked for any further variable regions. This process was repeated several times. A final conserved mega-alignments of fungi and four mammalian 5.8S rRNA was generated, which consisted of approximately 126 base pair conserved sequences. This 126-base pair sequence corresponds to nucleotides 134-259 of the *Candida albicans* 5.8S rRNA gene set forth in SEQ ID NO:2 and nucleotides 1-222 of the human 5.8S rRNA gene set forth in SEQ ID NO:3. Different fungal, yeast and mammalian species have slightly different lengths and base pair composition across this region.

By analysis of the sequences, it was determined that SNPs at any one of positions 142, 144, 146, 147, 148, 154, 157, 164, 167, 185, 187, 188, 194, 197, 213, 215, 216, 219, 223, 231, 232, 236, 245, 251, 256 (numbering corresponding to the *Candida albicans* 5.8S rRNA set forth in SEQ ID NO:2) will differentiate common fungal and yeast human pathogen nucleic acid from mammalian host nucleic acid. The general rules for differentiating fungi from mammals using these SNPs in 5.8S rRNA is depicted in Table 47.

TABLE 47

| SNP Position | Fungi | Mammals |
|---|---|---|
| 142 | C | T |
| 144 | A | G |
| 146 | A | G |
| 147 | A | G |
| 148 | C | T |
| 154 | T | A |
| 157 | T | C |
| 164 | C/G | T |
| 167 | A | G |
| 185 | G | T |
| 187 | A | G |
| 188 | A | C |

TABLE 47-continued

| SNP Position | Fungi | Mammals |
|---|---|---|
| 194 | T | G |
| 197 | G | T |
| 213 | A | G |
| 215 | T | C |
| 216 | T | A |
| 219 | G | T |
| 223 | A | Absent |
| 231 | A/G | C |
| 232 | T | A |
| 236 | T | C |
| 245 | A/C | Absent |
| 251 | C | G |
| 256 | T | G |

Example 5

Differentiation of Mammalian (e.g., Human) Fungal Pathogens

Seven fungal species, *Candida albicans*, *Ajellomyces capsulatus*, *Stachybotrys* sp., *Scedosporium apiospermum*, *Fusarium* sp., *Aspergillus fumigatus* and *Cryptococcus neoformans*, are known mammalian (e.g., human) pathogens. 5.8S rRNA sequences of these pathogens were downloaded from GenBank and the ~126 bp conserved regions described in Example 4, above, were aligned using CLUSTALW.

Sequence analysis was performed to determine that a minimum of 4 SNPs could be used to differentiate these pathogens and identify them. These SNPs include those at the position corresponding to position 254 of the *Candida albicans* 5.8S rRNA gene set forth in SEQ ID NO:2; one of positions corresponding to position 160 or 255 of SEQ ID NO:2; and two of positions corresponding to positions 163, 164, 165, 196, 202, 223, 224 or 259 of SEQ ID NO:2.

Thus, various combinations of 4 SNPs will discriminate the seven mammalian (e.g., human) fungal pathogens, wherein the 4 SNPs include those at position 254; one of positions 160 or 255; and any 2 of positions 163, 164, 165, 196, 202, 223, 224, 259. Table 48 sets forth the SNPs at each position for each pathogen. Because SNPs 164 and 223 can also be used to differentiate yeast/fungi from mammals, combinations using 164 or 223 are able to completely discriminate the seven pathogenic fungal species in a mammalian background.

TABLE 48

| | SNP position | | | | | | | | | |
|---|---|---|---|---|---|---|---|---|---|---|
| | 160 | 163 | 164 | 165 | 196 | 202 | 223 | 224 | 254 | 255 | 259 |
| *Candida albicans* | T | T | C | G | C | A | A | T | T | C | T |
| *Ajellomyces capsulatus* | T | C | G | A | A | G | A | T | T | C | T |
| *Stachybotrys* sp. | C | T | G | G | A | G | A | T | G | C | C |
| *Scedosporium apiospermum* | T | T | G | G | A | G | A | T | G | C | T |
| *Fusarium* sp. | C | T | G | G | A | G | A | T | G | C | T |
| *Aspergillus fumigatus* | T | C | G | G | A | G | A | T | C | C | T |
| *Cryptococcus neoformans* | C | C | C | A | A | G | A | T | T | T | T |

Example 6

Differentiation and Quantitation of Gram-Negative and Gram-Positive Prokaryotes and Fungal Eukaryotes Commonly Found in Mammal (e.g., Human) Sepsis An assay was performed to differentiate and quantify Gram-negative and Gram-positive prokaryotes and fungal eukaryotes commonly found in mammalian (e.g., human) sepsis.

A. Primers, Probes and Standards for detecting 16S rRNA SNPs and Quantifying Bacteria Primer Express 2.0 (Applied Biosystems) software was used to design TaqMan® MGB probes and primers to determine SNPs at positions 396, 398, 278, 286 and 648 of 16S rRNA of prokaryotes. In total, 8 pairs of forward and reverse primers and 16 probes were designed for these SNPs. The combination of primers and probes below can be used to classify the mammalian (e.g., human) sepsis pathogens described in Example 3 on the basis of their Gram status.

Primers and Probes to Detect SNPs at Positions 396 and 398 of 16S rRNA of Mammalian (e.g., Human) Sepsis Pathogens:

Probe sequences: GCAACGCCGCGT (SEQ ID NO:4) and GCGACGCCGCGT (SEQ ID NO:5) for Gram-positive bacteria; and GCCAAGTAGCGT (SEQ ID NO:6) and GCCATGCCGCGT (SEQ ID NO:7) for Gram-negative bacteria.

Forward Primer sequences: ACTCCTACGGGAGGCAGCAGT (SEQ ID NO:8) for Gram-negative and Gram-positive bacteria. Reverse primer sequences: GCCAGCAGCYGCGGTAATACG (SEQ ID NO:9) for Gram-negative and GCCAGCAGCCGCGGTAATACG (SEQ ID NO:10) for Gram-positive bacteria.

Primers and Probes to Detect SNPs at Positions 278 and 286 of 16S rRNA of Mammalian (e.g., Human) Sepsis Pathogens:

Probe sequences: GCGATGATCAGTAG (SEQ ID NO:11), GCTATGACGCTTAA (SEQ ID NO:12), GCTTTGACGCATAA (SEQ ID NO:13), GCTATGACGGGTAT (SEQ ID NO:14), GCAATGATCAGTAG (SEQ ID:15) and GTTTTGACGTCTAG (SEQ ID:16) for Gram-negative bacteria; and GCAACGATGCATAG (SEQ ID NO:17), GCAACGATGCGTAG (SEQ ID NO:18) and GCCACGATACATAG (SEQ ID NO:19) for Gram-positive bacteria.

Forward primer sequences: TGWAGGAGGGGATTGCGTC (SEQ ID NO:20), TGTAGGATGAGACTATATW (SEQ ID NO:21) and TAARRGATCAGCCTATGTC (SEQ ID NO:22) for Gram-negative bacteria; and TTATAGATGGATCCGCGCY (SEQ ID NO:23) and TGATGGATGGACCCGCGGT (SEQ ID NO:24) for Gram-positive bacteria.

Reverse primer sequences: ATGAACGGCCACATTGG (SEQ ID NO:25), ATGATCAGTCACACTGG (SEQ ID NO:26) and GTGAWCGGACACACTGG (SEQ ID NO:27) for Gram-negative; and GTGATCGGCCACACTGGRACT (SEQ ID NO:28) for Gram-positive.

Primers and Probes to Detect SNPs at Position 648 of 16S rRNA of Mammalian (e.g., Human) Sepsis Pathogens:

Probe sequences: CTGCTGATCTAGAG (SEQ ID NO:29) for Gram-negative; and CTGGAAAACTTGAG (SEQ ID NO:30) and CTGGGAGACTTGAG (SEQ ID NO:31) for Gram-positive.

Forward primer sequences: TAACCCCGTGAK-GGGATGGA (SEQ ID NO:32) for Gram-negative; and CAACCGKGGAGGGTCATTGGA (SEQ ID NO:33) for Gram-positive.

Reverse primer sequences: TCGGAGAGGAAAGTG-GAATTCC (SEQ ID NO:34) for Gram-negative; and CARRAGRGGARAGTGGAATTCC (SEQ ID NO:35) for Gram-positive.

Primers and probes were synthesized as Custom TaqMan® gene expression assays by Applied Biosystems (Life Technologies, USA). All Gram-negative probes were labelled with the VIC™ fluorescent label and all Gram-positive probes were labelled with FAM™ fluorescent label, so as to enable discrimination between Gram-negative and Gram-positive bacterial species in one single reaction.

For quantitative Real-Time PCR, reactions were prepared for each Gram-positive and Gram-negative probe and primer set. To generate the standard curve for each major bacterial group, the ATCC controls set forth in Table 49 were prepared.

TABLE 49

| PCR Master mix | ATCC control strain used |
| --- | --- |
| 396398 GRPOS1 | Staphylococcus aureus ATCC25923 |
| 396398 GRPOS2 | Staphylococcus aureus ATCC25923 |
| 396398 GRNEG1 | Escherichia coli ATCC25922 |
| 396398 GRNEG2 | Escherichia coli ATCC25922 |
| 278286 GRNEG | Escherichia coli ATCC25922 |
| 278286 GRPOS1 | Staphylococcus aureus ATCC25923 |
| 278286GRPOS2 | Staphylococcus epidermidis ATCC35983 |
| 648GRNEG | Veillonella atypica ATCC12641 |
| 648GRPOS1 | Staphylococcus aureus ATCC25923 |
| 648GRPOS2 | Enterococcus faecalis ATCC29212 |

Each standard was prepared in duplicate, and a typical PCR run format was prepared as follows: Tubes 1-16: 396398 GRPOS1, 278286 GRPOS1 and 648GRPOS1 Mastermix with S. aureus ATCC25923 DNA serially diluted 1:10. This generates the standard curve. Tubes 17-32: 396398 GRPOS1, 278286 GRPOS1 and 648GRPOS1 Mastermix with serially diluted blood spiked bacterial DNA. Tubes 33-48: 396398 GRPOS2, 278286GRPOS2 and 648GRPOS2 Mastermix with S. aureus ATCC25923 DNA serially diluted 1:10. This generates the standard curve. Tubes 49-64: 396398GRPOS2, 278286GRPOS2 and 648GRPOS2 Mastermix with serially diluted blood spiked bacterial DNA. Tubes 65-66: 396938 GRPOS1, 278286 GRPOS1 and 648GRPOS1 Mastermix no template control. Tubes 67-68: 396398 GRPOS2, 278286GRPOS2 and 648GRPOS2 Mastermix no template control. This protocol was followed for all Gram-positive and Gram-negative probes.

PCR reactions (in duplicate) were prepared as follows: 1 µL 20× TaqMan Gene Expression Assay; 10 µL 2× TaqMan Gene Expression Master Mix; 4 µL DNA template (1-100 ng); 5 µL DNase and RNase-free water. The PCR reactions were transferred to a Rotor-Gene Q Real-Time PCR instrument (Qiagen, Australia) and PCR was performed at the following conditions: 50° C. for 2 min; 95° C. for 10 min; then 45 cycles of 95° C. for 15 sec and 60° C. for 1 min.

The Rotor-Gene Q v.2.1.0.9 software was used to generate a standard curve for the following controls, each serially diluted. Gram-positive control: Staphylococcus aureus ATCC25923; Gram-negative control: Escherichia coli ATCC25922.

B. Primers and Probes for Detecting 5.8S rRNA SNPs 5.8S rDNA sequences for Candida and Aspergillus species were downloaded from GenBank and aligned as described above. The Primer Express 2.0 (Applied Biosystems) was used to design TaqMan® MGB probes and primers specific for the identification of yeast and fungal species using SNPs at positions 164 and 165

The TaqMan® MGB FAM probe sequence was CTCT-TGGTTCCGGCATCGA (SEQ ID NO:36) and the TaqMan® MGB VIC probe sequence was CTCTTGGT-TCTCGCATCGA (SEQ ID NO:37) the forward primer sequence was TATGCAGTCTGAGTTGATTATCGTAATC (SEQ ID NO:38) and CAGAGGTCTAAACTTACAAC-CAATTTTTT (SEQ ID NO:39); and the reverse primer sequence was GCATTTCGCTGCGTTCTTC (SEQ ID NO:40). The primers and probes were synthesised as Custom TaqMan® gene expression assays by Applied Biosystems (Life Technologies, USA).

Example 7

Classification and Quantitation of Common Mammalian (e.g., Human) Pathogenic Bacteria Using SNPs Classification and quantification of common mammalian (e.g., human) pathogens into broad groups that allows for downstream decisions to be made, such as antibiotic choice, enrichment media choice, which antibiotic resistance tests to perform, and which microbial virulence tests to perform, can be achieved by first extracting DNA from a biological sample and performing a multiplex RT-PCR reaction to amplify a 181 base pair region of bacterial 16S rRNA covering positions 396, 398, 399, 400 and 401, using probes to classify the bacterium into one of Groups 1-7, as described above. If bacterial DNA is detected, a second reaction can be performed to further classify the bacterium into a subgroup, thereby providing additional information as to the identity and/or characteristics of the bacterium, which can be used by a clinician to determine an appropriate course of treatment. Further investigations to determine the precise identity of the bacteria and/or antibiotic resistance and/or virulence can be performed using standard and well-known molecular techniques as described in the art.

In the first step, any bacterial DNA is extracted from the biological sample using any method known in the art, including but not limited to the use of automated systems from Biomerieux (NucleSENS EasyMAG®) and Becton Dickinson (BD MAX®). Specialised kits/systems are also available for concentration and extraction of bacterial DNA from whole blood including Polaris® (Biocartis), and MolYsis® (MolZym). The multiplex RT-PCR reaction (Reaction 1) is then performed using two pairs of forward and reverse primers that amplify the same 181 base pair region of bacterial 16S rDNA: the forward primer having the sequence ACTCCTACGGGAGGCAGCAGT (SEQ ID NO:8) and the reverse primer having the sequence GTAT-TACCGCGGCTGCTGGCAC (SEQ ID NO:278), which amplify the region corresponding to nucleotides 338 to 536 of the 16S rRNA of SEQ ID NO:2 from the majority of Gram-positive and Gram-negative bacteria, and the forward primer having the sequence ACTCCTACGGGAGGCT-GCAGT (SEQ ID NO:279) and reverse primer having the sequence GTATTACCGCGGCAGCTGGCAC (SEQ ID NO:280), which amplify the same region from Chlamydia spp. and Chlamydophila spp. Reaction 1 also includes seven 12 base-pair probes, with each probe having different dyes, covering positions 396, 398, 399, 400 and 401. The probes are as follows, in a 5' to 3' direction with the SNPs underlined:

```
                                         (SEQ ID NO: 281)
         Probe 1 = AGCAACGCCGCGT (SEQ ID NO: 282)
         Probe 2 = AGCGACGCCGCGT (SEQ ID NO: 283)
         Probe 3 = AGCCATGCCGCGT (SEQ ID NO: 284)
         Probe 4 = AGCAATGCCGCGT (SEQ ID NO: 285)
         Probe 5 = AGCCATACCGCGT (SEQ ID NO: 286)
         Probe 6 = AGCCAAGTAGCGT (SEQ ID NO: 287)
         Probe 7 = AGCCAAGTCGCGT
```

If bacterial DNA is present in the sample at sufficient concentration, these primers will amplify nucleic acid from over 7000 bacterial species present in the Genbank database, including Chlamydial species. The seven probes broadly classify bacteria into seven groups: Group 1 contains mostly Gram-positive organisms and the 12 base pair probe, in combination with the forward and reverse primers, will identify the presence of over 1800 bacetrial species in this group; Group 2 contains mostly Gram-positive organisms and the 12 base pair probe, in combination with the forward and reverse primers, will identify the presence of over 2200 species in this group; Group 3 contains Gram-negative organisms and the 12 base pair probe, in combination with the forward and reverse primers, will identify the presence of over 2300 species in this group; Group 4 contains Gram-negative organisms and the 12 base pair probe, in combination with the forward and reverse primers, will identify the presence of over 800 species in this group; Group 5 contains Gram-negative organisms and the 12 base pair probe, in combination with the forward and reverse primers, will identify 46 species this group (mostly *Stenotrophmonas* spp); Group 6 contains Gram-negative anaerobic organisms and the 12 base pair probe, in combination with the forward and reverse primers, will identify 82 species in this group (mostly *Bacteroides* and *Prevotella* spp); Group 7 contains Gram-negative anaerobic organisms and the 12 base pair probe, in combination with the forward and reverse primers, will identify 33 species in this group (mostly *Porphyromonas* spp).

If Reaction 1 yields a positive result, a second step is performed that includes diluting the product of Reaction 1 by 1:100 and adding it to multiplex Reaction 2, which contains the same forward and reverse primers as Reaction 1 and the probes listed in Table 7 for each mammalian (e.g., human) pathogen group. For example, if Reaction 1 is positive for Group 1 bacteria, then the reaction product is diluted 1:100 and added to a reaction containing the forward and reverse primer pairs set forth in SEQ ID NOs: 8 and 278 and Gram-positive probes 1a (SEQ ID NO: 288), 1b (SEQ ID NO: 289), 1c (SEQ ID NO: 290), 1d (SEQ ID NO: 291), 1e (SEQ ID NO: 292), 1f (SEQ ID NO: 293), 1g (SEQ ID NO: 294), 1h (SEQ ID NO: 295), 1i (SEQ ID NO: 296), 1j (SEQ ID NO: 297), 1k (SEQ ID NO: 298), 1l (SEQ ID NO: 299). Because of the limitations of multiplexing and the number of dyes available, each reaction can be limited to the appropriate number of probes. For example, two reactions can be performed, one containing Probes 1a-1g and the other containing probes 1h-1l. A positive result with any of the probes indicates the grouping and possible identity of the bacterium in the sample. For example, should a positive result be obtained using Probe 1a, then the bacterium present in the sample is a Gram-positive bacterium with possible vancomycin resistance, selected from among *Bacillus anthracia, Enterococcus faecalis, Enterococcus faecium* and *Listeria monocytogenes*. Table 50 sets forth the probes that can be used to categorize bacteria, and the grouping and characteristics of the identified bacteria identified using each probe, in a sample using the above method.

TABLE 50

| Reaction 1 Probe (Seq ID #) | Gp | Reaction 2 Probes (Seq ID #) | Gp | Bacterial Species | Characteristics | Possible resistance |
|---|---|---|---|---|---|---|
| AGCAACGCCGCGT (SEQ ID NO: 281) | 1 | AACCAGAAAGCC (SEQ ID NO: 288) | 1a | B. anthracis; E. faecalis; E. faecium; L. monocytogenes | Gm + ve | VRE |
| AGCAACGCCGCGT (SEQ ID NO: 281) | 1 | AACCAGAAAGGG (SEQ ID NO: 289) | 1b | S. agalactiae; S. anginosus; S. constellatus; S. dysgalactiae; S. intermedius; S. pyogenes | Gm + ve cocci | |
| AGCAACGCCGCGT (SEQ ID NO: 281) | 1 | AACCAGAAAGTC (SEQ ID NO: 290) | 1c | L. intestinalis | Gm + ve bacillus | |
| AGCAACGCCGCGT (SEQ ID NO: 281) | 1 | AACGAATAAGCA (SEQ ID NO: 291) | 1d | H. pylori; C. coli | Gm − ve spiral | |
| AGCAACGCCGCGT (SEQ ID NO: 281) | 1 | AAGGAGGAAGCC (SEQ ID NO: 292) | 1e | C. perfringens | Gm + ve anaerobe bacillus | |
| AGCAACGCCGCGT (SEQ ID NO: 281) | 1 | AATCAGAAAGCC (SEQ ID NO: 293) | 1f | S. aureus; S. epidermidis; S. haemolyticus; | Gm + ve cocci | ORSA |

TABLE 50 -continued

| Reaction 1 Probe (Seq ID #) | Gp | Reaction 2 Probes (Seq ID #) | Gp | Bacterial Species | Characteristics | Possible resistance |
|---|---|---|---|---|---|---|
| | | | | S. hominis; S. saprophyticus | | |
| AGCAACGCCGCGT (SEQ ID NO: 281) | 1 | GAAGAATAAGCT (SEQ ID NO: 294) | 1g | E. desmolans | Gm + ve anaerobe bacillus | |
| AGCAACGCCGCGT (SEQ ID NO: 281) | 1 | GAATAGAAAGCC (SEQ ID NO: 295) | 1h | V. dispar | Gm – ve anaerobe cocci | |
| AGCAACGCCGCGT (SEQ ID NO: 281) | 1 | GAGGAGGAAGCC (SEQ ID NO: 296) | 1i | C. difficile | Gm + ve anaerobe bacillus | |
| AGCAACGCCGCGT (SEQ ID NO: 281) | 1 | TACCAGAAAGCC (SEQ ID NO: 297) | 1j | E. rhusiopathiae | Gm + ve bacillus | |
| AGCAACGCCGCGT (SEQ ID NO: 281) | 1 | TACCAGAAAGGG (SEQ ID NO: 298) | 1k | S. bovis; S. mitis; S. mutans; S. orates; S. pneumonia; S. sanguinis; S. sobrinus | Gm + ve cocci | |
| AGCAACGCCGCGT (SEQ ID NO: 281) | 1 | TGTGAGGAAGCC (SEQ ID NO: 299) | 1l | P. stomatis | Gm + ve anaerobe cocci | |
| AGCGACGCCGCGT (SEQ ID NO: 282) | 2 | AGATAAGAAGCA (SEQ ID NO: 300) | 2a | C. diphtheria | Gm + ve acid fast bacillus | |
| AGCGACGCCGCGT (SEQ ID NO: 282) | 2 | GCAGAAGAAGCA (SEQ ID NO: 301) | 2b | D. congolensis; M. luteus; R. equi | Gm + ve coccus filamentous | |
| AGCGACGCCGCGT (SEQ ID NO: 282) | 2 | GCAGAAGAAGCG (SEQ ID NO: 302) | 2c | S. anulatus; S. somaliensis | Gm + ve acid fast bacillus | |
| AGCGACGCCGCGT (SEQ ID NO: 282) | 2 | GCCTAAAGCACC (SEQ ID NO: 303) | 2d | L interrogans | Gm – ve spiral | |
| AGCGACGCCGCGT (SEQ ID NO: 282) | 2 | GGAGAAGAAGCA (SEQ ID NO: 304) | 2e | M. tuberculosis | Gm + ve acid fast bacillus | |
| AGCGACGCCGCGT (SEQ ID NO: 282) | 2 | GGATAAGAAGCA (SEQ ID NO: 305) | 2f | C. jeikeium C. urealyticum | Gm + ve acid fast bacillus | |
| AGCGACGCCGCGT (7) | 2 | GGGGAAGAAGCG (SEQ ID NO: 306) | 2g | M. curtisii | Gm + ve anaerobe bacillus | |
| AGCGACGCCGCGT (7) | 2 | GGTAAAGAAGCA (SEQ ID NO: 307) | 2h | C. trachomatis; C. pneumoniae | Gm -ve | |
| AGCGACGCCGCGT (SEQ ID NO: 282) | 2 | GTAGAAGAAGCA (SEQ ID NO: 308) | 2i | N. asteroids;; N. brasiliensis | Gm + ve Acid fast, bacillus | |
| AGCGACGCCGCGT (SEQ ID NO: 282) | 2 | GTTAATGAAGCG (SEQ ID NO: 309) | 2j | A. massiliensi | Gm + ve anaerobe bacillus | |
| AGCCATGCCGCGT (SEQ ID NO: 283) | 3 | ACAGAAGAAGCA (SEQ ID NO: 310) | 3a | A. hominis; E. tarda; H. ducreyi; H. influenza; H. parahaemolyticus; H. parainfluenzae; M. morganii; P. multocida | Gm – ve cocci- bacillus | |

TABLE 50 -continued

| Reaction 1 Probe (Seq ID #) | Gp | Reaction 2 Probes (Seq ID #) | Gp | Bacterial Species | Characteristics | Possible resistance |
|---|---|---|---|---|---|---|
| | | | | P. alcalifaciens  V. cholerae | | |
| AGCCATGCCGCGT (SEQ ID NO: 283) | 3 | ACAGAATAAGCA (SEQ ID NO: 311) | 3b | M. catarrhalis; P. aeruginosa | Gm – ve diplococcus | ESBL |
| AGCCATGCCGCGT (SEQ ID NO: 283) | 3 | GAAGAATAAGCA (SEQ ID NO: 312) | 3c | N. gonorrhoeae; N. meningitides | Gm – ve diplococcus | |
| AGCCATGCCGCGT (SEQ ID NO: 283) | 3 | GCAGAAGAAGCA (SEQ ID NO: 313) | 3d | A. hydrophila  C. freundii  E. aerogenes  E. cloacae  E. coli  K. oxytoca  K. pneumonia  P. mirabilis  S. enterica  S. marcescens  S. dysenteriae  S. sonnei  Y. enterocolitica  Y. pestis | Gm – ve bacillus | ESBL |
| AGCCATGCCGCGT (SEQ ID NO: 283) | 3 | GCAGAATAAGCA (SEQ ID NO: 314) | 3e | A. baumannii | Gm – ve cocci | ESBL |
| AGCCATGCCGCGT (SEQ ID NO: 283) | 3 | GGAGAAGAAGCC (SEQ ID NO: 315) | 3f | B. abortus | Gm – ve coccibacillus | |
| AGCCATGCCGCGT (SEQ ID NO: 283) | 3 | TAAGAATAAGGA (SEQ ID NO: 316) | 3g | F. ceti | Gm – ve bacillus | |
| AGCAATGCCGCGT (SEQ ID NO: 284) | 4 | ACAGAAGAACCA (SEQ ID NO: 317) | 4a | L. pneumophila | Gm – ve pleo-morphic | |
| AGCAATGCCGCGT (SEQ ID NO: 284) | 4 | GAAGAATAAGCA (SEQ ID NO: 318) | 4b | B. cepacia | Gm – ve bacillus | ESBL |
| AGCAATGCCGCGT (SEQ ID NO: 284) | 4 | GCAGAAGAAGCA (SEQ ID NO: 319) | 4c | C. valva rum | Gm – ve bacillus | |
| AGCCAAGTAGCGT (SEQ ID NO: 286) | 6 | CATGAATAAGGA (SEQ ID NO: 321) | 6a | P. buccae | Gm – ve anaerobe bacillus | |
| AGCCAAGTAGCGT (SEQ ID NO: 286) | 6 | TACGAATAAGGA (SEQ ID NO: 322) | 6b | P. melaninogenica | Gm – ve anaerobe bacillus | |
| AGCCAAGTAGCGT (SEQ ID NO: 286) | 6 | TATGAATAAGGA (SEQ ID NO: 323) | 6c | B. fragilis | Gm – ve anaerobe bacillus | |
| AGCCAAGTAGCGT (SEQ ID NO: 286) | 6 | TTCGAATAAGGA (SEQ ID NO: 324) | 6d | P. intermedia | Gm – ve anaerobe bacillus | |

Gm + ve = Gram-positive
Gm – ve = Gram-negative
VRE = vancomycin resistant enterococci
ORSA = oxacillin-resistant *Staphylococcus aureus*.
ESBL = extended spectrum beta-lactamase A third step can be performed that includes specific testing for bacterial species and/or antibiotic resistance and/or virulence, which can be achieved using standard molecular techniques as described in the art.

Once the results of steps 1 and 2 are known (and step 3 if performed), then bacterial quantification can be performed as described above using an appropriate bacterial species control DNA of known quantity and the generation of a standard curve.

Thus, a three or four step series of reactions can classify bacteria into groups, determine bacterial species, determine antibiotic resistance, determine bacterial virulence and quantify the amount of bacterial DNA in the original sample without having to grow or enrich the organism first. Such a process can be achieved in less time than it currently takes to grow an organism in culture broth.

Example 8

Differentiation and Quantitation of Gram-Negative and Gram-Positive Prokaryotes and Fungal Eukaryotes Found in the Airways and Respiratory Fluids of Immunocompromised, Pneumonia and Cystic Fibrosis Patients An assay was performed to differentiate and quantify Gram-negative and Gram-positive prokaryotes and fungal eukaryotes commonly found in the airways and respiratory fluids from human patients that are immunocompromised, have pneumonia with sepsis complications, and cystic fibrosis. Common micro-organisms isolated from BAL fluid from immunocompromised patients include; *Staphylococcus, Enterococcus, Streptococcus, Staphylococcus aureus, Acinetobacter, Capnocytophaga, Enterobacteriaca, Haemophilus, Legionella, Pseudomonas, Mycobacterium, Candida* and *Aspergillus* (see Table 2, p 118, Hohenadel I A, et al., (2001) Role of bronchoalveolar lavage in immunocompromised patients with pneumonia treated with a broad spectrum antibiotic and antifungal regimen. Thorax 56: 115-120). Example micro-organisms commonly found in the lower respiratory tract of patients with acute bronchitis, community acquired pneumonia and hospital acquired pneumonia include; *Bordetella, Streptococcus, Haemophilus, Legionella, Klebsiella, Enterobacteriaca, Staphylococcus aureus, Moraxella, Psuedomonas, Acinetobacter, Candida* and *Aspergillus* (Carroll K C (2002) Laboratory Diagnosis of Lower Respiratory Tract Infections: Controversy and Conundrums. Journal of Clinical Microbiology 40: 3115-3120). Example micro-organisms commonly found in the airways of cystic fibrosis patients include: *Haemophilus, Staphylococcus, Psuedomonas, Burkholderia, Stenotrophomonas, Klebsiella, Candida* and *Aspergillus* (Harrison F (2007) Microbial ecology of the cystic fibrosis lung. Microbiology (Reading, Engl) 153: 917-923).

A. Primers, Probes and Standards for Detecting 16S rRNA SNPs and Quantifying Bacteria Primer Express 2.0 (Applied Biosystems) software was used to design TaqMan® MGB probes and primers to determine SNPs at positions 396 and 398 of prokaryotes. In total, 1 pair of forward and reverse primers and 3 probes were designed for these SNPs. The combination of primers and probes below can be used to classify the most common human respiratory bacterial pathogens.

Primers and Probes to Detect SNPs at Positions 396 and 398 of 16S rRNA of Mammalian (e.g., Human) Sepsis Pathogens:

Probe sequences: GCAACGCCGCGT (SEQ ID NO:4) and GCGACGCCGCGT (SEQ ID NO:5) for Gram-positive bacteria; and GCCATGCCGCGT (SEQ ID NO:7) for Gram-negative bacteria.

Forward Primer sequences: ACTCCTACGGGAGGCAGCAGT (SEQ ID NO:8) for Gram-negative and Gram-positive bacteria. Reverse primer sequence: GTATTACCGCGGCTGCTGGCAC (SEQ ID NO:278) for Gram-negative and Gram-positive bacteria.

Primers and probes were synthesized as Custom TaqMan® gene expression assays by Applied Biosystems (Life Technologies, USA). All Gram-negative probes were labelled with the VIC™ fluorescent label and all Gram-positive probes were labelled with FAM™ fluorescent label, so as to enable discrimination between Gram-negative and Gram-positive bacterial species in one single reaction.

For quantitative Real-Time PCR, reactions were prepared for each Gram-positive and Gram-negative probe and primer set. To generate the standard curve for each major bacterial group, the ATCC controls set forth in Table 51 were prepared.

TABLE 51

| PCR Master mix | ATCC control strain used |
|---|---|
| 396398 GRPOS1 | *Staphylococcus aureus* ATCC25923 |
| 396398 GRPOS2 | *Staphylococcus aureus* ATCC25923 |
| 396398 GRNEG1 | *Escherichia coli* ATCC25922 |
| 396398 GRNEG2 | *Escherichia coli* ATCC25922 |
| 278286 GRNEG | *Escherichia coli* ATCC25922 |

TABLE 51-continued

| PCR Master mix | ATCC control strain used |
|---|---|
| 278286 GRPOS1 | *Staphylococcus aureus* ATCC25923 |
| 278286GRPOS2 | *Staphylococcus epidermidis* ATCC35983 |
| 648GRNEG | *Veillonella atypica* ATCC12641 |
| 648GRPOS1 | *Staphylococcus aureus* ATCC25923 |
| 648GRPOS2 | *Enterococcus faecalis* ATCC29212 |

Each standard was prepared in duplicate, and a typical PCR run format was prepared as follows: Tubes 1-16: 396398 GRPOS1, 278286 GRPOS1 and 648GRPOS1 Mastermix with *S. aureus* ATCC25923 DNA serially diluted 1:10. This generates the standard curve. Tubes 17-32: 396398 GRPOS1, 278286 GRPOS1 and 648GRPOS1 Mastermix with serially diluted blood spiked bacterial DNA. Tubes 33-48: 396398 GRPOS2, 278286GRPOS2 and 648GRPOS2 Mastermix with *S. aureus* ATCC25923 DNA serially diluted 1:10. This generates the standard curve. Tubes 49-64: 396398GRPOS2, 278286GRPOS2 and 648GRPOS2 Mastermix with serially diluted blood spiked bacterial DNA. Tubes 65-66: 396938 GRPOS1, 278286 GRPOS1 and 648GRPOS1 Mastermix no template control. Tubes 67-68: 396398 GRPOS2, 278286GRPOS2 and 648GRPOS2 Mastermix no template control. This protocol was followed for all Gram-positive and Gram-negative probes.

PCR reactions (in duplicate) were prepared as follows: 1 µL 20× TaqMan Gene Expression Assay; 10 µL 2× TaqMan Gene Expression Master Mix; 4 µL DNA template (1-100 ng); 5 µL DNase and RNase-free water. The PCR reactions were transferred to a Rotor-Gene Q Real-Time PCR instrument (Qiagen, Australia) and PCR was performed at the following conditions: 50° C. for 2 min; 95° C. for 10 min; then 45 cycles of 95° C. for 15 sec and 60° C. for 1 min.

The Rotor-Gene Q v.2.1.0.9 software was used to generate a standard curve for the following controls, each serially diluted. Gram-positive control: *Staphylococcus aureus* ATCC25923; Gram-negative control: *Escherichia coli* ATCC25922.

B. Primers and Probes for Detecting 5.8S rRNA SNPs 5.8S rDNA sequences for *Candida* and *Aspergillus* species were downloaded from GenBank and aligned as described above. The Primer Express 2.0 (Applied Biosystems) was used to design TaqMan® MGB probes and primers specific for the identification of yeast and fungal species using SNPs at positions 163 and 164.

The TaqMan® MGB FAM probe sequence was TTCCGGCATCGA (SEQ ID NO:324) and the TaqMan® MGB VIC probe sequence was TTCTCGCATCGA (SEQ ID NO:325) the forward primer sequences were CAAAACTTTCAACAACGGATCTC (SEQ ID NO:326) and TAAAACTTTCAACAACGGATCTC (SEQ ID NO:327); and the reverse primer sequences were GACGCTCGGACAGGCATG (SEQ ID NO:328) and GACGCTCAAACAGGCATG (SEQ ID NO:329). The primers and probes were synthesised as Custom TaqMan® gene expression assays by Applied Biosystems (Life Technologies, USA).

TABLE 52

Common bacterial species from BAL of immunocompromised patients.

| | SNP Position | | Example Pathogens |
|---|---|---|---|
| Gram Stain | 396 | 398 | Genera and Comments |
| Negative | C | T | Escherichia<br>Enterobacter<br>Haemophilus<br>Klebsiella<br>Psuedomonas<br>Salmonella<br>Yersinia<br>Shigella<br>Citrobacter<br>Proteus<br>Serratia<br>Acinetobacter<br>Legionella<br>Capnocytophaga |
| Positive | A | C | Enterococcus<br>Mycobacterium<br>Streptococcus<br>Staphylococcus |
| Positive | G | C | Mycobacterium |

TABLE 53

Common fungal/yeast species from BAL of immunocompromised patients

| | SNP Position | | Example Pathogens |
|---|---|---|---|
| Gram Stain | 163 | 164 | Genera and Comments |
| Fungal | T | C | Candida albicans<br>Candida tropicalis<br>Candida glabrata<br>Candida krusei<br>Candida parapsilosis |
| Fungal | C | G | Aspergillus fumigatus |

TABLE 54

Common microbial species isolated from the lower respiratory tract of patients with acute bronchitis, community acquired pneumonia, and hospital acquired pneumonia.

| | SNP Position | | Example Pathogens |
|---|---|---|---|
| Gram Stain | 396 | 398 | Genera and Comments |
| Negative | C | T | Escherichia<br>Enterobacter<br>Haemophilus<br>Klebsiella<br>Moraxella<br>Pseudomonas<br>Salmonella<br>Yersinia<br>Shigella<br>Citrobacter<br>Proteus<br>Serratia<br>Acinetobacter<br>Legionella<br>Bordetella |
| Positive | A | C | Enterococcus<br>Streptococcus<br>Staphylococcus |

TABLE 55

Common fungal/yeast species isolated from the lower respiratory tract of patients with acute bronchitis, community acquired pneumonia, and hospital acquired pneumonia.

| | SNP Position | | Example Pathogens |
|---|---|---|---|
| Gram Stain | 163 | 164 | Genera and Comments |
| Fungal | T | C | Candida albicans<br>Candida tropicalis<br>Candida glabrata<br>Candida krusei<br>Candida parapsilosis |
| Fungal | C | G | Aspergillus fumigatus |

TABLE 56

Common microorganisms found in airways of patients with cystic fibrosis.

| | SNP Position | | Example Pathogens |
|---|---|---|---|
| Gram Stain | 396 | 398 | Genera and Comments |
| Negative | C | T | Haemophilus<br>Pseudomonas<br>Klebsiella<br>Stenotrophomonas<br>Burkholderia |
| Positive | A | C | Staphylococcus |

TABLE 57

Common fungal/yeast species found in airways of patients with cystic fibrosis.

| | SNP Position | | Example Pathogens |
|---|---|---|---|
| Gram Stain | 163 | 164 | Genera and Comments |
| Fungal | T | C | Candida albicans<br>Candida tropicalis<br>Candida glabrata<br>Candida krusei<br>Candida parapsilosis |
| Fungal | C | G | Aspergillus fumigatus |

Example 9

Differentiation of Mammalian (e.g., Human) *Candida* Fungal Pathogens from Other Fungal Pathogens in a Mammalian Background Eleven fungal species, *Candida albicans*, *Candida tropicalis*, *Candida parapsilosis*, *Candida krusei*, *Candida glabrata*, *Ajellomyces capsulatus*, *Stachybotrys* sp., *Scedosporium apiospermum*, *Fusarium* sp., *Aspergillus fumigatus* and *Cryptococcus neoformans*, are known mammalian (e.g., human) pathogens. 5.8S rRNA sequences of these pathogens were downloaded from GenBank and the ~126 bp conserved regions described in Example 4, above, were aligned using CLUSTALW.

Sequence analysis was performed to determine that a minimum of 2 SNPs could be used to differentiate common *Candida* pathogens from other fungal pathogens in a mammalian genomic background. Such a distinction is important clinically with respect to determining an appropriate treatment regimen and in determining prognosis. Such a test could be used on any clinical sample but it is particularly relevant to blood and bronchioalveolar lavage samples for sepsis and pneumonia diagnoses respectively. The two SNPs include those at positions corresponding to 163, 164 of the *Candida albicans* 5.8S rRNA gene set forth in SEQ ID NO:2.

Table 58 sets forth the SNPs at each position for each pathogen and for a number of mammals. Because SNPs 163 and 164 can also be used to differentiate yeast/fungi from mammals, the combination of these two SNPs is able to completely discriminate *Candida* pathogenic species from other pathogenic fungal species in a mammalian background.

Primers and probes are as for those described in Example 8 above.

TABLE 58

| Fungal Species | SNP Position | |
|---|---|---|
| | 163 | 164 |
| *Candida albicans* | T | C |
| *Candida tropicalis* | T | C |
| *Candida parapsilosis* | T | C |
| *Candida krusei* | T | C |
| *Candida glabrata* | T | C |
| *Ajellomyces capsulatus* | C | G |
| *Stachybotrys* sp. | T | G |
| *Scedosporium apiospermum* | T | G |
| *Fusarium* sp. | T | G |
| *Aspergillus fumigatus* | C | G |
| *Cryptococcus neoformans* | C | C |
| *Homo sapiens* (human) | G | T |
| *Sus scrofa* (pig) | G | T |
| *Gorilla gorilla* (gorilla) | G | T |
| *Mus musculus* (mouse) | G | T |
| *Bos taurus* (cow) | G | T |

Example 10

Antibiotic Choices Based on Broad Categorization of Microbial Pathogens

Using the invention detailed herein, and the resultant broad categorization of microbial pathogens, more informed decisions can be made with respect to the choice of appropriate empirical and targeted antibiotic therapies as provided in Tables 59 and 60 below (by example). The use of antibiotics more directed towards the causative pathogen leads to reduced costs (narrow spectrum antibiotics are much less expensive than broad spectrum antibiotics), better patient outcomes, less likelihood of the development of adverse side-effects (including *Clostridium difficile* infection) and less likelihood of the development of antibiotic resistances.

TABLE 59

Example Choices of Empiric Antibiotic Based on Gram and Group Determination for Common Sepsis Causing Organisms

| Organism | Group | Antibiotic | Alternative |
|---|---|---|---|
| Gram Positive Organisms | | | |
| *Staphylococcus aureus* | 1f | Cefazolin or Vancomycin | Linezolid |
| Coagulase Negative *Staphylococcus* | 1f | Vancomycin | Linezolid |
| *Streptococcus pneumoniae* | 1k | Ceftriaxone | Moxifloxacin |
| *Enterococcus faecalis* | 1a | Ampicillin +/− Gentamicin | Vancomycin +/− Gentamicin |
| *Enterococcus faecium* | 1a | Linezolid | Quinupristin/ dalfopristin |
| Gram Negative Organisms | | | |
| *Serratia* | 3d | Piperacillin/ tazobactam/ gentamicin | Beta lactam/ ciprofloxacin or ciprofloxacin/ aminoglycoside |
| *Acinetobacter* | 3e | Piperacillin/ tazobactam/ gentamicin | |
| *Pseudomonas aeruginosa* | 3b | Cefepime/ Gentamicin | |
| *Citrobacter* | 3d | Cefepime/ Gentamicin | |
| *Enterobacter* | 3d | Piperacillin/ tazobactam/ Gentamicin | |
| *E. coli* | 3d | Cefazolin/ Meropenem | Gentamicin |
| *Klebsiella* | 3d | Cefazolin/ Meropenem | Gentamicin or quinolone |
| *Haemophilus influenzae* | 3a | Azithromycin | Cefuroxime |
| *Stenotrophomonas maltophilia* | 5 | Trimethoprim/ sulfamethooxazole | Ticarcillin/ claulanic acid |

TABLE 60

Example Choices of Narrow Spectrum Antibiotic Based on Gram and Group Determination for Organisms Able to be Grouped

| Group | Species | Bacterial Type | Example Antibiotic Choice(s)* |
|---|---|---|---|
| 1a | *Bacillus anthracis* *Enterococcus faecalis* *Enterococcus faecium* *Listeria monocytogenes* | Positive | Ciprofloxacin, penicillin, doxycycline, ampicillin, ampicillin/gentamicin |
| 1b | *Streptococcus agalactiae* *Streptococcus anginosus* *Streptococcus constellatus* *Streptococcus dysgalactiae* *Streptococcus intermedius* *Streptococcus pyogenes* | Positive, cocci | Penicillin |
| 1c | *Lactobacillus intestinalis* | Positive, *bacillus* | Penicillin |
| 1d | *Helicobacter pylori* *Campylobacter coli* | Negative, spiral | Erythromycin Metronidazole |

TABLE 60-continued

Example Choices of Narrow Spectrum Antibiotic Based on Gram
and Group Determination for Organisms Able to be Grouped

| Group | Species | Bacterial Type | Example Antibiotic Choice(s)* |
|---|---|---|---|
| 1e | *Clostridium perfringens* | Positive, Anaerobe, *bacillus* | Metronidazole |
| 1f | *Staphylococcus aureus* | Positive, cocci | Oxacillin |
|  | *Staphylococcus epidermidis* |  | Vancomycin |
|  | *Staphylococcus haemolyticus* |  | Linezolid |
|  | *Staphylococcus hominis* |  |  |
|  | *Staphylococcus saprophyticus* |  |  |
| 1g | *Eubacterium desmolans* | Positive, Anaerobe, *bacillus* | Cefoxitin |
| 1h | *Veillonella dispar* | Negative, Anaerobe, cocci | Penicillin |
| 1i | *Clostridium difficile* | Positive, Anaerobe, *bacillus* | Metronidazole |
| 1j | *Erysipelothrix rhusiopathiae* | Positive, *bacillus* | Penicillin |
| 1k | *Streptococcus bovis* | Positive, cocci | Penicillin |
|  | *Streptococcus mitis* |  |  |
|  | *Streptococcus mutans* |  |  |
|  | *Streptococcus oralis* |  |  |
|  | *Streptococcus pneumonia* |  |  |
|  | *Streptococcus sanguinis* |  |  |
|  | *Streptococcus sobrinus* |  |  |
| 1l | *Peptostreptococcus stomatis* | Positive, Anaerobe, cocci | Penicillin |
| 2a | *Corynebacterium diphtheria* | Positive, Acid fast, *bacillus* | Metronidazole |
| 2b | *Dermatophilus congolensis* | Positive, coccus filamentous | Penicillin |
|  | *Micrococcus luteus* |  |  |
|  | *Rhodococcus equi* |  |  |
| 2c | *Streptomyces anulatus* | Positive, Acid fast, *bacillus* |  |
|  | *Streptomyces somaliensis* |  |  |
| 2d | *Leptospira interrogans* | Negative, spiral | Doxycycline |
| 2e | *Mycobacterium tuberculosis* | Positive, Acid fast, *bacillus* | Isoniazid + Rifampin + Pyrazinamide |
| 2f | *Corynebacterium jeikeium* | Positive, Acid fast, *bacillus* | Vancomycin |
|  | *Corynebacterium urealyticum* |  |  |
| 2g | *Mobiluncus curtisii* | Positive, Anaerobe, *bacillus* | Vancomycin |
| 2h | *Chlamydia trachomatis* | Negative | Doxycycline |
|  | *Chlamydophila pneumoniae* |  |  |
| 2i | *Nocardia asteroids* | Positive, Acid fast, *bacillus* | Trimethoprim/ sulfamethooxazole |
|  | *Nocardia brasiliensis* |  |  |
| 2j | *Actinomyces massiliensis* | Positive, Anaerobe, *bacillus* | Trimethoprim/ sulfamethooxazole |
| 3a | *Actinobacillus hominis* | Negative, coccibacillus | Cefotaxime |
|  | *Edwardsiella tarda* |  |  |
|  | *Haemophilus ducreyi* |  |  |
|  | *Haemophilus influenza* |  |  |
|  | *Haemophilus parahaemolyticus* |  |  |
|  | *Haemophilus parainfluenzae* |  |  |
|  | *Morganella morganii* |  |  |
|  | *Pasteurella multocida* |  |  |
|  | *Providencia alcalifaciens* |  |  |
|  | *Vibrio cholerae* |  |  |
| 3b | *Moraxella catarrhalis* | Negative, diplococcus | Penicillin |
|  | *Pseudomonas aeruginosa* |  |  |
| 3c | *Neisseria gonorrhoeae* | Negative, diplococcus | Ceftriaxone |
|  | *Neisseria meningitides* |  |  |
| 3d | *Aeromonas hydrophila* | Negative, *bacillus* | Meropenem |
|  | *Citrobacter freundii* |  |  |
|  | *Enterobacter aerogenes* |  |  |
|  | *Enterobacter cloacae* |  |  |
|  | *Escherichia coli* |  |  |
|  | *Klebsiella oxytoca* |  |  |
|  | *Klebsiella pneumonia* |  |  |
|  | *Proteus mirabilis* |  |  |
|  | *Salmonella enterica* |  |  |
|  | *Serratia marcescens* |  |  |
|  | *Shigella dysenteriae* |  |  |
|  | *Shigella sonnei* |  |  |
|  | *Yersinia enterocolitica* |  |  |
|  | *Yersinia pestis* |  |  |
| 3e | *Acinetobacter baumannii* | Negative, cocci | Tigecycline |
| 3f | *Brucella abortus* | Negative, coccibacillus | Doxycycline |
| 3g | *Flavobacterium ceti* | Negative, *bacillus* | Ciprofloxacin |
| 4a | *Legionella pneumophila* | Negative, pleomorphic | Azithromycin |
| 4b | *Burkholderia cepacia* | Negative, *bacillus* | Trimethoprim/ sulfamethooxazole |
| 4c | *Cardiobacterium valvarum* | Negative, *bacillus* | Azithromycin |
| 5 | *Stenotrophomonas maltophilia* | Negative, *bacillus* | Trimethoprim/ sulfamethooxazole |
| 6a | *Prevotella buccae* | Negative Anaerobe, *bacillus* | Penicillin |

TABLE 60-continued

Example Choices of Narrow Spectrum Antibiotic Based on Gram
and Group Determination for Organisms Able to be Grouped

| Group | Species | Bacterial Type | Example Antibiotic Choice(s)* |
|---|---|---|---|
| 6b | *Prevotella melaninogenica* | Negative Anaerobe, *bacillus* | Penicillin |
| 6c | *Bacteroides fragilis* | Negative, Anaerobe, *bacillus* | Metronidazole |
| 6d | *Prevotella intermedia* | Negative Anaerobe, *bacillus* | Penicillin |
| 7 | *Porphyromonas gingivalis* | Negative, Anaerobe, *bacillus* | Amoxycillin |

*Example only - often antibiotic choice depends on other factors such as source of infection (e.g. respiratory vs skin vs abdominal vs urinary), hospital antibiogram, patient co-morbidities and allergies.

The disclosure of every patent, patent application, and publication cited herein is hereby incorporated herein by reference in its entirety.

The citation of any reference herein should not be construed as an admission that such reference is available as "Prior Art" to the instant application.

Throughout the specification the aim has been to describe the preferred embodiments of the invention without limiting the invention to any one embodiment or specific collection of features. Those of skill in the art will therefore appreciate that, in light of the instant disclosure, various modifications and changes can be made in the particular embodiments exemplified without departing from the scope of the present invention. All such modifications and changes are intended to be included within the scope of the appended claims.

What is claimed is:

1. A method of treating a sepsis-associated bacterial infection in a mammalian subject, the method comprising:
   1) determining that a subject has an infection with a sepsis-associated Gram positive or Gram negative bacterium by detecting a single nucleotide polymorphism (SNP) in a 16S rRNA gene in nucleic acid from a blood sample from the subject, wherein the SNP is at a position corresponding to position 396 of the 16S rRNA gene set forth in SEQ ID NO:1, and wherein the bacterium is determined to be a Gram-negative bacterium only when there is a C at position 396 and the bacterium is determined to be a Gram-positive bacterium only when there is an A, T or G at position 396; wherein the bacterium is selected from among Salmonella enterica, Staphylococcus aureus, Staphylococcus epidermidis, Staphylococcus haemolyticus, Staphylococcus hominis, Staphylococcus saprophyticus, Enterococcus faecalis, Enterococcus faecium, Clostridium perfringens, Streptococcus anginosus, Streptococcus constellatus, Streptococcus intermedius, Streptococcus mitis, Streptococcus mutans, Streptococcus sanguinis, Streptococcus sobrinus, Streptococcus oralis, Streptococcus pneumoniae, Streptococcus agalactiae, Streptococcus bovis, Streptococcus sanguinis, Streptococcus dysgalactiae, Streptococcus mutans, Streptococcus pyogenes, Escherichia coli, Acinetobacter baumannii, Bacteroides fragilis, Burkholderia cepacia, Klebsiella pneumoniae, Klebsiella oxytoca, Pseudomonas aeruginosa, Enterobacter aerogenes, Enterobacter cloacae, Serratia marcescens, Proteus mirabilis, Citrobacter freundii, Morganella morganii, Haemophilus influenzae, Neisseria meningitidis, Stenotrophomonas maltophila, Prevotella buccae, Prevotella intermedia, Prevotella melaninogenica, Mycobacterium tuberculosis, Streptomyces somaliensis and Streptomyces anulatus; and
   2) administering to the subject a therapy when the subject is determined in step 1) to have an infection with a sepsis-associated Gram positive or Gram negative bacterium, wherein the therapy comprises administration of an antibiotic and/or an antibody to endotoxin.

2. The method of claim 1, further comprising determining whether the sepsis-associated bacterium is resistant to a therapeutic agent, wherein the therapy administered to the subject is other than the therapeutic agent to which the bacterium is resistant.

3. The method of claim 1, wherein the mammalian subject is human.

4. The method of claim 1, wherein method comprises extracting the nucleic acid from the sample prior to detecting the SNP in the 16S rRNA gene.

5. The method of claim 1, wherein the nucleic acid is analyzed by a method comprising amplification of the nucleic acid so as to detect the SNP in the 16S rRNA gene.

6. The method of claim 1, wherein the nucleic acid is analyzed by a method comprising sequencing, 5' nuclease digestion, molecular beacons, oligonucleotide ligation, microarray, or any combination thereof, so as to detect the SNP in the 16S rRNA gene.

7. A method of treating a subject having sepsis, comprising:
   1) determining that a subject has sepsis resulting from an infection with a sepsis-associated Gram positive bacterium, a sepsis-associated Gram negative bacterium, or a fungus by detecting a single nucleotide polymorphism (SNP) in a 16S rRNA gene and a SNP in a 5.8s rRNA gene is detected in nucleic acid from a blood sample from the subject, wherein:
   the SNP in the 16S rRNA gene is at a position corresponding to position 396 of the 16S rRNA gene set forth in SEQ ID NO:1 and wherein sepsis resulting from an infection with a Gram-negative bacterium is determined only when there is a C at position 396, and sepsis resulting from an infection with a Gram-positive bacterium is determined only when there is an A, T or G at position 396; and
   the SNP in the 5.8S rRNA gene is at a position corresponding to position 142, 144, 146, 147, 148, 154, 157, 164, 167, 185, 187, 188, 194, 197, 213, 215, 216, 219, 223, 231, 232, 236, 245, 251, or 256 of the 5.8S rRNA gene set forth in SEQ ID NO:2, and sepsis resulting from an infection with a fungus is determined when there is a C at position 142; an A at position 144; an A at position 146; an A at position 147; a C at position 148; a T at position 154; a T at position 157; a C or G at position 164; an A at position 167; a G at position 185; an A at position 187; an A at position 188; a T at position 194; a G at position 197; an A at position 213; a T at position 215; a Tat position 216; a G at position 219; an A at position 223; a G or A at position 231; a T at position 232; a T at position 236; a C or A at position 245; a C at position 251; or a T at position 256;
   wherein the bacterium selected from among Salmonella enterica, Staphylococcus aureus, Staphylococcus epidermidis, Staphylococcus haemolyticus, Staphylococcus hominis, Staphylococcus saprophyticus, Enterococcus faecalis, Enterococcus faecium, Clostridium perfringens, Streptococcus anginosus, Streptococcus constellatus, Streptococcus intermedius, Streptococcus mitis, Streptococcus mutans, Streptococcus sanguinis, Streptococcus sobrinus, Streptococcus oxalis, Streptococcus pneumoniae, Streptococcus agalactiae, Streptococcus bovis, Streptococcus sanguinis, Streptococcus dysgalactiae, Streptococcus mutans, Streptococcus pyogenes, Escherichia coli, Acinetobacter baumannii, Bacteroides fragilis, Burkholderia cepacia, Klebsiella pneumoniae, Klebsiella oxytoca, Pseudomonas aeruginosa, Enterobacter aerogenes, Enterobacter cloacae, Serratia marcescens, Proteus mirabilis, Citrobacter freundii, Morganella morganii, Haemophilus influenzae, Neisseria meningitidis, Stenotrophomonas maltophila, Prevotella buccae, Prevotella intermedia, Prevotella melaninogenica, Mycobacterium tuberculosis, Streptomyces somaliensis and Streptomyces anulatus; and
   2) administering to the subject a therapy for treating sepsis when the subject is determined in step 1) to have sepsis resulting from an infection with a sepsis-associated Gram positive bacterium, a sepsis-associated Gram negative bacterium, or a fungus, wherein the therapy comprises administration of an anti-fungal agent when the subject is determined to have sepsis resulting from infection with a fungus, or an antibiotic and/or an antibody to endotoxin when the subject is determined to have sepsis resulting from an infection with a sepsis-associated Gram positive bacterium, or a sepsis-associated Gram negative bacterium.

8. The method of claim 7, wherein the method comprises extracting the nucleic acid from the sample prior to detecting the SNP in the 16S rRNA gene or the SNP in the 5.8S rRNA gene.

9. The method of claim 7, wherein the nucleic acid is analysed by a method comprising amplification of the nucleic acid so as to detect the SNP in the 16S rRNA gene or the SNP in the 5.8S rRNA gene.

10. The method of claim 7, wherein the nucleic acid is analysed by a method comprising sequencing, 5' nuclease digestion, molecular beacons, oligonucleotide ligation, microarray, or any combination thereof, so as to detect the SNP in the 16S rRNA gene or the SNP in the 5.8S rRNA gene.

11. The method of claim 7, wherein the therapy comprises administration of an anti-fungal agent when the subject has sepsis resulting from an infection with a fungus or an antibiotic when the subject has sepsis resulting from an infection with a sepsis-associated Gram positive bacterium, or a sepsis-associated Gram negative bacterium.

12. The method of claim 1, wherein the antibiotic is selected from one or more of cefazolin, doxycycline, erythromycin, vancomycin, metronidazole, ciprofloxacin, linezolid, ceftriaxone, cefoxitin, azithromycin, moxifloxacin, ampicillin, gentamicin, oxacillin, quinupristin, dalfopristin, piperacillin, tazobactam, ciprofloxacin, isoniazid, cefepime, rifampin, meropenem, quinolone, azithromycim, cefuroxime, cefotaxime, trimethoprim, sulfamethoxazole, ticarcillin, tigecycline and claulanic acid.

13. The method of claim 7, wherein the antibiotic is selected from one or more of cefazolin, doxycycline, erythromycin, vancomycin, metronidazole, ciprofloxacin, linezolid, ceftriaxone, cefoxitin, azithromycin, moxifloxacin, ampicillin, gentamicin, oxacillin, quinupristin, dalfopristin, piperacillin, tazobactam, ciprofloxacin, isoniazid, cefepime, rifampin, meropenem, quinolone, azithromycim, cefuroxime, cefotaxime, trimethoprim, sulfamethoxazole, ticarcillin, tigecycline and claulanic acid.

* * * * *